(12) United States Patent
Chaturvedula et al.

(10) Patent No.: US 7,544,680 B2
(45) Date of Patent: Jun. 9, 2009

(54) CONSTRAINED COMPOUNDS AS CGRP-RECEPTOR ANTAGONISTS

(75) Inventors: Prasad V. Chaturvedula, Cheshire, CT (US); Stephen E. Mercer, Middletown, CT (US); Haiquan Fang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/105,434

(22) Filed: Apr. 18, 2008

(65) Prior Publication Data

US 2008/0287422 A1 Nov. 20, 2008

Related U.S. Application Data

(62) Division of application No. 11/247,697, filed on Oct. 11, 2005, now Pat. No. 7,384,930.

(60) Provisional application No. 60/678,099, filed on May 5, 2005, provisional application No. 60/624,655, filed on Nov. 3, 2004.

(51) Int. Cl.
C07D 487/00 (2006.01)
C07D 491/00 (2006.01)
A61K 31/55 (2006.01)
A61P 25/06 (2006.01)

(52) U.S. Cl. .................. 514/212.07; 540/523
(58) Field of Classification Search .......... 540/523; 514/212.07
See application file for complete search history.

(56) References Cited

U.S. PATENT DOCUMENTS

| | | | |
|---|---|---|---|
| 6,313,097 B1 | 11/2001 | Eberlein et al. |
| 6,344,449 B1 | 2/2002 | Rudolf et al. |
| 6,521,609 B1 | 2/2003 | Doods et al. |
| 6,552,043 B1 | 4/2003 | Patchett et al. |
| 2001/0036946 A1 | 11/2001 | Rudolf et al. |
| 2003/0139417 A1 | 7/2003 | Eberlein et al. |
| 2003/0181462 A1 | 9/2003 | Doods et al. |
| 2003/0191068 A1 | 10/2003 | Trunk et al. |
| 2003/0212057 A1 | 11/2003 | Rudolf et al. |
| 2003/0236282 A1 | 12/2003 | Hurnaus et al. |
| 2004/0002495 A1 | 1/2004 | Sher et al. |
| 2004/0014679 A1 | 1/2004 | Trunk et al. |
| 2004/0063735 A1 | 4/2004 | Chaturvedula et al. |
| 2004/0076587 A1 | 4/2004 | Kruss et al. |
| 2004/0132716 A1 | 7/2004 | Rudolf et al. |
| 2004/0192729 A1 | 9/2004 | Rudolf et al. |
| 2004/0204397 A1 | 10/2004 | Chaturvedula et al. |
| 2004/0214819 A1 | 10/2004 | Rudolf et al. |
| 2004/0229861 A1 | 11/2004 | Burgey et al. |
| 2004/0248816 A1 | 12/2004 | Doods et al. |
| 2005/0032783 A1 | 2/2005 | Doods et al. |
| 2005/0065094 A1 | 3/2005 | Davidai |
| 2005/0153959 A1 | 7/2005 | Luo et al. |
| 2005/0215546 A1 | 9/2005 | Hurnaus et al. |
| 2005/0215576 A1 | 9/2005 | Degnan et al. |
| 2005/0227968 A1 | 10/2005 | Lustenberger et al. |
| 2005/0233980 A1 | 10/2005 | Doods et al. |
| 2005/0234054 A1 | 10/2005 | Mueller et al. |
| 2005/0234067 A1 | 10/2005 | Mueller et al. |
| 2005/0250763 A1 | 11/2005 | Mueller et al. |
| 2005/0256098 A1 | 11/2005 | Burgey et al. |
| 2005/0256099 A1 | 11/2005 | Mueller et al. |
| 2005/0272955 A1 | 12/2005 | Zimmer et al. |
| 2006/0094707 A1 | 5/2006 | Chaturvedula et al. |

FOREIGN PATENT DOCUMENTS

| | | |
|---|---|---|
| CA | 2 387 613 | 5/2001 |
| CA | 2 503 455 | 4/2005 |
| EP | 1 227 090 A1 | 7/2002 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 99/52875 | 10/1999 |
| WO | WO 00/18764 | 4/2000 |
| WO | WO 00/55154 | 9/2000 |
| WO | WO 01/32648 | 3/2001 |
| WO | WO 01/25228 | 4/2001 |
| WO | WO 01/32649 | 5/2001 |
| WO | WO 01/49676 | 7/2001 |
| WO | WO 02/10140 | 2/2002 |

(Continued)

OTHER PUBLICATIONS

U.S. Appl. No. 11/291,670, filed Dec. 1, 2005, Chaturvedula, et al.

(Continued)

*Primary Examiner*—Bruck Kifle
(74) *Attorney, Agent, or Firm*—James Epperson

(57) ABSTRACT

The invention encompasses constrained bicyclic and tricyclic CGRP-receptor antagonists, methods for identifying them, pharmaceutical compositions comprising them, and methods for their use in therapy for treatment of migraine and other headaches, neurogenic vasodilation, neurogenic inflammation, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

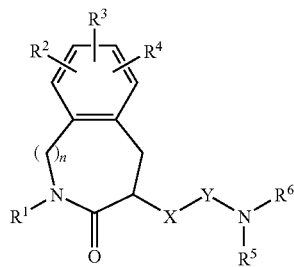

9 Claims, No Drawings

FOREIGN PATENT DOCUMENTS

| WO | WO 03/027252 | 4/2003 |
|---|---|---|
| WO | WO 03/070753 | 8/2003 |
| WO | WO 03/076432 | 9/2003 |
| WO | WO 03/104236 | 12/2003 |
| WO | WO2004/002960 A1 | 1/2004 |
| WO | WO 2004/037810 | 5/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2005/000807 | 1/2005 |
| WO | WO 2005/009962 | 2/2005 |
| WO | WO 2005/013894 | 2/2005 |
| WO | WO 2005/056550 | 6/2005 |
| WO | WO2005/065779 | 7/2005 |
| WO | WO 2005/072308 | 8/2005 |
| WO | WO2005/084672 | 9/2005 |
| WO | WO 2005/092880 | 10/2005 |
| WO | WO 2005/095383 | 10/2005 |
| WO | WO/2005/100343 | 10/2005 |
| WO | WO/2005/100352 | 10/2005 |
| WO | WO/2005/100360 | 10/2005 |
| WO | WO 2005/102322 | 11/2005 |
| WO | WO 2005/103037 | 11/2005 |
| WO | WO/2005/121078 | 12/2005 |
| WO | WO 2006/052378 | 5/2006 |
| WO | WO 2006/060678 | 6/2006 |
| WO | WO 2008/085317 | 7/2008 |

OTHER PUBLICATIONS

Ashina, M., et al., "Evidence for increased plasma levels of calcitonin gene-related peptide in migraine outside of attacks", *Pain*, 2000, 86(1-2):133-138.

Brain, S.D., et al., "CGRP receptors: a headache to study, but will antagonists prove therapeutic in migraine?", *TiPS*, 2002, 23(2): 51-53.

Carlström, A.-S. and Frejd, T., Palladium-Catalyzed Synthesis of Didehydroamino Acid Derivatives, *Synthesis*, 1989, 6, 414-418.

Carlström, A.-S. and Frejd, T., "Palladium-Catalyzed Bis-coupling of Dihaloaromatics with 2-Amidoacrylates", *J. Org. Chem.*, 1991, 56: 1289-1293.

Chu, D.Q., et al., "The calcitonin gene-related peptide (CGRP) antagonist CGRP8-37 blocks vasodilation in inflamed rat skin: involvement of adrenomedullin in addition to CGRP," *Neuroscience Letters*, 2001, 310:169-172.

De Vries, P., et al., "Pharmacological aspects of experimental headache models in relation to acute antimigraine therapy," *European Journal of Pharmacology*, 1999, 375: 61-74.

Doods, H., et al., "Pharmacological profile of BIBN4096BS, the first selective small molecule CGRP antagonist," *British Journal of Pharmacology*, 2000, 129: 420-423.

Dygos, J.H., "A Convenient Asymmetric Synthesis of the Unnatural Amino Acid 2,6-Dimethyl-L-tyrosine", *Synthesis*, 1992, 741-743.

Edvinsson, L., "Calcitonin Gene-Related Peptide (CGRP) and the Pathophysiology of Headache", *CNS Drugs*, 2001, 15(10):745-753.

Escott, K.J., et al., "Trigeminal ganglion stimulation increases facial skin blood flow in the rat: a major role for calcitonic gene-related peptide", *Brain Research*, 1995, 669: 93-99.

Escott, K.J., et al., "Effect of a calcitonin gene-related peptide antagonist (CGRP8-37) on skin vasodilation and oedema induced by stimulation of the rat saphenous nerve", *British Journal of Pharmacology*, 1993, 110, 772-776.

Evans, B.N. et al., "CGRP-RCP, a Novel Protein Required for Signal Transduction at Calcitonin Gene-related Peptide and Adrenomedullin Receptors", *J. Biol. Chem.*, 2000, 275(4): 31438-31443.

Gallai, V., et al. "Vasoactive peptide levels in the plasma of young migraine patients with and without aura assessed both interictally and ictally", *Cephalalgia*, 1995;15: 384-390.

Goadsby, P.J., et al., "Vasoactive peptide release in the extracerebral circulation of humans during migraine headache", *Annals of Neurology*, 1990, 28(2):183-187.

Grant, A.D., "Evidence of a role for NK1 and CGRP receptors in mediating neurogenic vasodilation in the mouse ear", *British Journal of Pharmacology*, 2002, 135: 356-362.

Hall, J.M. and Brain, S.D., "Interaction of amylin with calcitonin gene-related peptide receptors in the microvasculature of the hamster cheek pouch in vivo," *British Journal of Pharmacology*, 1999, 126: 280-284.

Hall, J.M., et al., "Interaction of human adrenomedullin 13-52 with calcitonin gene-related peptide receptors in the microvasculature of the rat and hamster," *British Journal of Pharmacology*, 1995, 114: 592-597.

Juaneda, C. et al. "The molecular pharmacology of CGRP and related peptide receptor subtypes", *TiPS*, 2000, 21: 432-438.

Lassen, L.H. et al. "CGRP may play a causative role in migraine", *Cephalalgia*, 2002, 22(1): 54-61.

Mallee, J.J., et al. "Receptor Activity-modifying Protein 1 Determines the Species Selectivity of Non-peptide CGRP Receptor Antagonist", *J. Biol. Chem.*, 2002, 277(16): 14294-14298.

McLatchie, L.M. et al., "RAMPs regulate the transport and ligand specificity of the calcitonin-receptor-like receptor", *Nature*, 1998, 393: 333-339.

Olesen, J. et al., "Calcitonin Gene-Related Peptide Receptor Antagonist BIBN 4096 BS for the Acute Treatment of Migraine", *New England J. of Medicine*, 2004, 350 (11): 1104-1110.

Pasternak, A., et al., "Potent, orally bioavailable somatostatin agonists: good absorption achieved by urea backbone cyclization", *Bioorganic & Medicinal Chemistry Letters*, Oxford GB, vol. 9, No. 3, Feb. 8, 1999, p. 491-496.

Poyner, D.R. et al., "Pharmacological characterization of a receptor for calcitonin gene-related peptide on rat, L6 myocytes", *British Journal of Pharmacology*, 1992, 105: 441-447.

Rosenfeld, M.G., et al., "Production of a novel neuropeptide encoded by the calcitonin gene via tissue-specific RNA processing", *Nature*, 1983, 304:129-135.

Rudolf, K., et al., "Development of Human Calcitonin Gene-Related Peptide (CGRP) Receptor Antagonists. 1. Potent and Selective Small Molecule CGRP Antagonists. 1-[$N^2$-[3,5-Dibromo-$N$-[[4-(3,4-dihydro-2(1$H$)-oxoquinazolin-3-yl)-1-piperidinyl]carbonyl]-D-tyrosyl] L-lysyl]-4-(4-pyridinyl)piperazine: The First CGRP Antagonist for Clinical Trials in Acute Migraine", *J. Med. Chem.* 2005, 48: 5921-5931.

Shen, Y-T. et al., "Functional Role of α-Calcitonin Gene-Related Peptide in the Regulation of the Cardiovascular System", *J. Pharm. Exp. Ther.*, 2001, 298: 551-558.

Van Valen, F. et al., "Calcitonin gene-related peptide (CGRP) receptors are linked to cyclic adenosine monophosphate production in SK-N-MC human neuroblastoma cells", *Neuroscience Letters*, 1990, 119: 195-198.

Williamson, D.J. and Hargreaves, R.J., "Neurogenic Inflammation in the Context of Migraine", *Microsc. Res. Tech.*, 2001, 53: 167-178.

Williamson, D.J., et al., "Intravital microscope studies on the effects of neurokinin agonists and calcitonin gene-related peptide on dural vessel diameter in the anaesthetized rat," *Cephalalgia*, 1997, 17: 518-524.

Williamson, D.J., et al., "Sumatriptan inhibits neurogenic vasodilation of dural blood vessels in the anaesthetized rat-intravital microscope studies," *Cephalalgia*, 1997, 17: 525-531.

Xin, Z., et al., "Potent, Selective Inhibitors of Protein Tyrosine Phosphatase IB", *Bioorg. Med. Chem. Lett.*, 2003, 13: 1887-1890.

CONSTRAINED COMPOUNDS AS CGRP-RECEPTOR ANTAGONISTS

CROSS-REFERENCE TO RELATED APPLICATIONS

This application claims the benefit of U.S. non-provisional application Ser. No. 11/247,697 filed Oct. 11, 2005 and provisional application Ser. Nos. 60/624,655 filed Nov. 3, 2004 and 60/678,099 filed May 5, 2005.

BACKGROUND OF THE INVENTION

Calcitonin gene-related peptide (CGRP) is a naturally occurring 37-amino-acid peptide first identified in 1982 (Amara, S. G. et al, *Science* 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, *Br J Pharmacol* 1992, 105, 441-7; Van Valen, F. et al, *Neurosci Lett* 1990, 119, 195-8). Two classes of CGRP receptors, $CGRP_1$ and $CGRP_2$, have been proposed based on the antagonist properties of the peptide fragment CGRP(8-37) and the ability of linear analogues of CGRP to activate $CGRP_2$ receptors (Juaneda, C. et al. *TiPS* 2000, 21, 432-438). However, there is lack of molecular evidence for the $CGRP_2$ receptor (Brain, S. D. et al, *TiPS* 2002, 23, 51-53). The $CGRP_1$ receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., *J Biol Chem.* 2000, 275, 31438-43). RAMP1 is required for transport of CRLR to the plasma membrane and for ligand binding to the CGRP-receptor (McLatchie, L. M. et al, *Nature* 1998, 393, 333-339). RCP is required for signal transduction (Evans B. N. et al., *J Biol Chem.* 2000, 275, 31438-43). There are known species-specific differences in binding of small molecule antagonists to the CGRP-receptor with typically greater affinity seen for antagonism of the human receptor than for other species (Brain, S. D. et al, *TiPS* 2002, 23, 51-53). The amino acid sequence of RAMP1 determines the species selectivity, in particular, the amino acid residue Trp74 is responsible for the phenotype of the human receptor (Mallee et al. *J Biol Chem* 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001; 15(10): 745-53; Williamson, D. J. *Microsc. Res. Tech.* 2001, 53, 167-178; Grant, A. D. *Brit. J. Pharmacol.* 2002, 135, 356-362). Serum levels of CGRP are elevated during migraine (Goadsby P J, et al. *Ann Neurol* 1990; 28:183-7) and treatment with anti-migraine drugs returns CGRP levels to normal coincident with alleviation of headache (Gallai V. et al. *Cephalalgia* 1995; 15: 384-90). Migraineurs exhibit elevated basal CGRP levels compared to controls (Ashina M, et al., *Pain* 2000, 86(1-2):133-8.2000). Intravenous CGRP infusion produces lasting headache in migraineurs (Lassen L H, et al. *Cephalalgia* 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, *J Pharmacol Exp Ther* 2001, 298, 551-8). Thus, CGRP-receptor antagonists may present a novel treatment for migraine that avoids the cardiovascular liabilities of active vasoconstriction associated with non-selective $5\text{-}HT_{1B/1D}$ agonists, 'triptans' (e.g., sumatriptan).

A number of non-peptidic, small molecule CGRP-receptor antagonists have been recently reported. WO 04/091514, WO 04/092166 and WO 04/092168 disclose cyclic compounds containing an amide bond in the ring as CGRP antagonists. WO 97/09046 and equivalents disclose inter alia quinine and quinidine related compounds which are ligands, in particular antagonists, of CGRP-receptor. WO 98/09630 and WO 98/56779 and equivalents disclose inter alia variously substituted, nitrobenzamide compounds as CGRP-receptor antagonists. WO 01/32649, WO 01/49676, and WO 01/32648 and equivalents disclose inter alia a series of 4-oxobutanamides and related cyclopropane derivatives as CGRP-receptor antagonists. WO 00/18764, WO 98/11128 and WO 00/55154 and equivalents disclose inter alia benzimidazolinyl piperidines as antagonists to CGRP-receptor. Unrelated to CGRP, a series of somatostatin antagonists have been disclosed in WO 99/52875 and WO 01/25228 and equivalents. See also U.S. Pat. No. 6,344,449, U.S. Pat. No. 6,313,097, U.S. Pat. No. 6,521,609, U.S. Pat. No. 6,552,043, US 20030181462, US20030191068 and WO 03/076432 and related applications. Thus, novel CGRP-receptor antagonists effective for the treatment of neurogenic inflammation, migraine and other disorders would be greatly advantageous.

DESCRIPTION OF THE INVENTION

The invention encompasses compounds of Formula I and II which are CGRP antagonists. The invention also encompasses compositions incorporating these compounds and methods of using these compounds in therapeutic treatment.

One aspect of the invention is a compound of Formula I

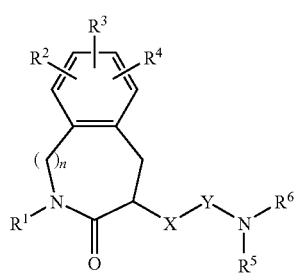

I wherein:
$R^1$ is $C_{1-6}$alkyl, $C_{2-6}$alkenyl, $C_{3-7}$cycloalkyl, $C_{5-7}$cycloalkenyl, $C_{1-6}(C_{3-7}$cycloalkyl)alkyl, $C_{1-6}$haloalkyl, $C_{1-6}(C_{1-6}$alkoxy)alkyl, $C_{1-6}(Ar^1)$alkyl, $C_{1-6}(NR^7R^8)$alkyl, N—$(R^9)$-pyrrolidinyl or N—$(R^9)$-piperidinyl;

R² is hydrogen, halo, hydroxy, $C_{1-6}$alkyl, $C_{2-6}$alkenyl, benzyloxy, or $NR^7R^8$;

R³ is hydrogen, hydroxy, halo, $C_{1-6}$alkyl, or $C_{2-6}$alkenyl;

or R² and R³ taken together are CHNNR⁵;

R⁴ is hydrogen, halo or $C_{1-6}$alkyl, or $C_{2-6}$alkenyl;

R⁵ is hydrogen or $C_{1-6}$alkyl;

R⁶ is hydrogen, $C_{1-6}$alkyl, $NR^7R^8$ taken together is selected from the group consisting of pyrrolidinyl, piperidinyl, N—(R⁹)-piperazinyl, morpholinyl, and thiomorpholinyl;

R⁹ is hydrogen, $C_{1-6}$alkyl, $C_{1-6}$alkylcarbonyl, or $C_{1-6}$alkoxycarbonyl;

R¹⁰ is phenyl, naphthyl, pyridinyl, pyridinyl N-oxide, quinolinyl, quinolinyl N-oxide, isoquinolinyl, or isoquinolinyl N-oxide, and is substituted with 0-2 substituents selected from the group consisting of halo, $C_{1-6}$alkyl, $C_{1-6}$haloalkyl, $C_{1-6}$alkoxy, hydroxy, and phenyl;

or R¹⁰ is selected from the group consisting of

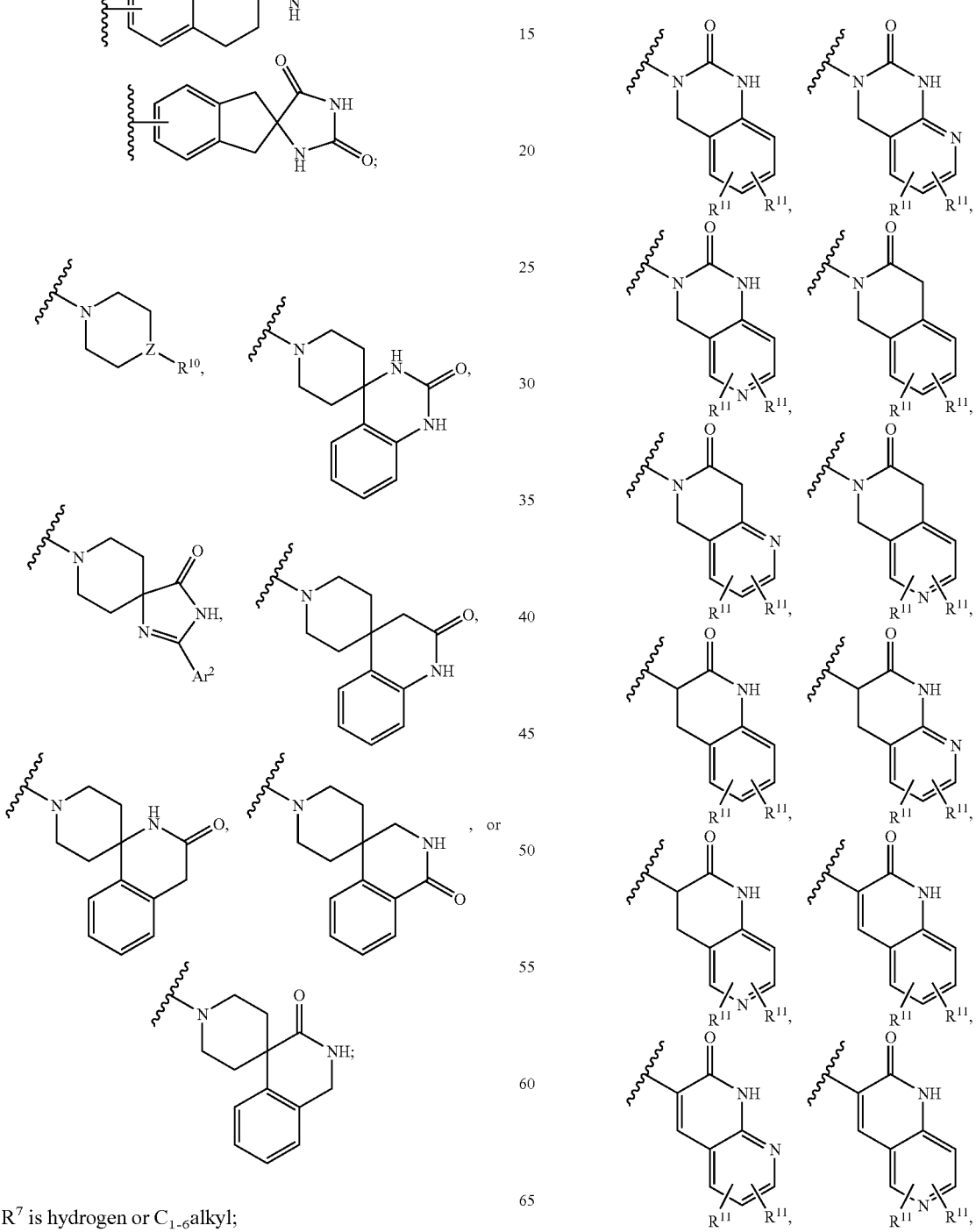

R⁷ is hydrogen or $C_{1-6}$alkyl;

R⁸ is hydrogen or $C_{1-6}$alkyl; or

-continued

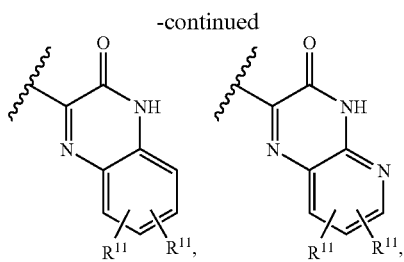

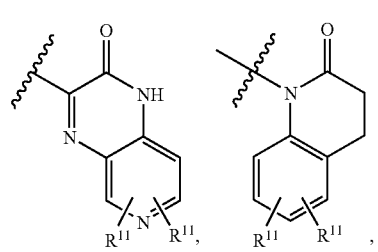

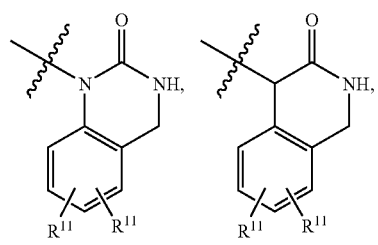

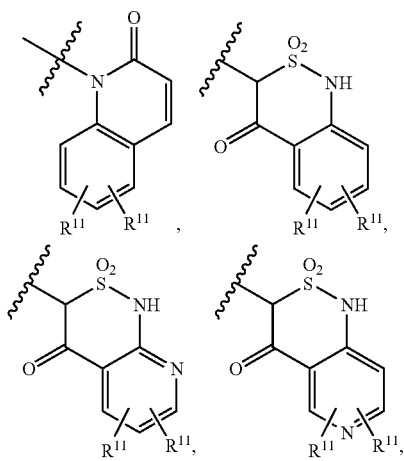

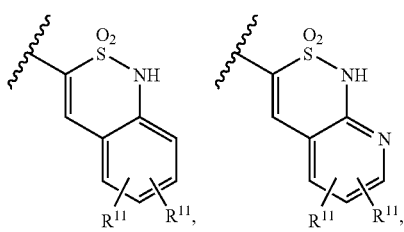

-continued

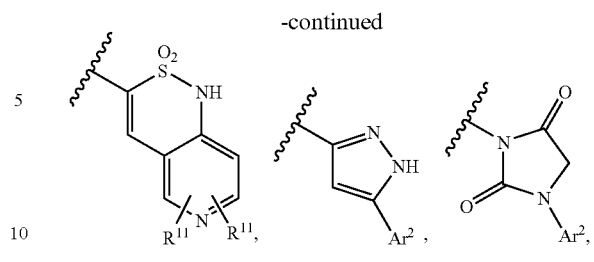

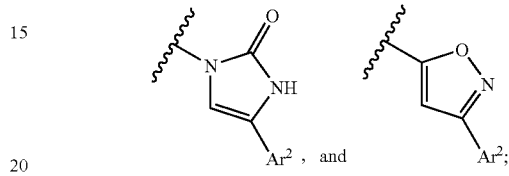

$R^{11}$ is hydrogen, halo, $C_{1-6}$alkyl, $C_{1-6}$haloalkyl, or $C_{1-6}$alkoxy;

$Ar^1$ is phenyl, naphthyl, pyridinyl, or imidazolyl, and is substituted with 0-2 substituents selected from the group consisting of halo, $C_{1-6}$alkyl, and $C_{1-6}$haloalkyl;

$Ar^2$ is phenyl, naphthyl, or pyridinyl, and is substituted with 0-2 substituents selected from the group consisting of halo, $C_{1-6}$alkyl, and $C_{1-6}$haloalkyl;

X—Y is aminocarbonyl, oxycarbonyl, methylenecarbonyl, ethylene, or amino(cyano)iminomethyl;

Z is N or CH; and n is 0 or 1;

or a pharmaceutically acceptable salt or solvate thereof.

Another aspect of the invention is a compound of Formula Ia.

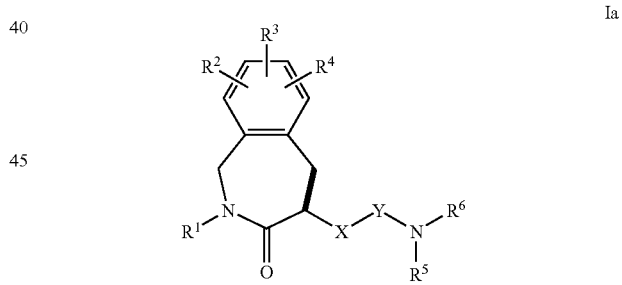

Another aspect of the invention is a compound of Formula Ib.

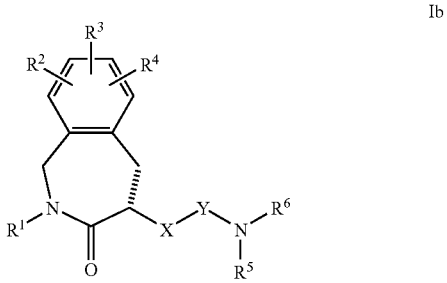

Another aspect of the invention is a compound of Formula II.

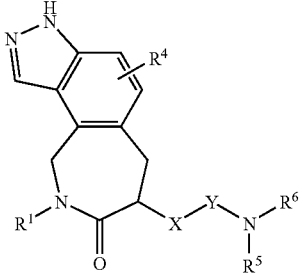

II

Another aspect of the invention is a compound of Formula IIa.

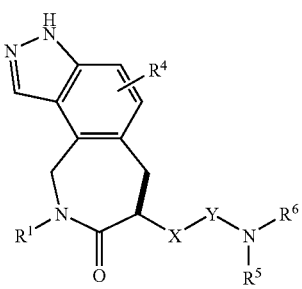

IIa

Another aspect of the invention is a compound of Formula IIb.

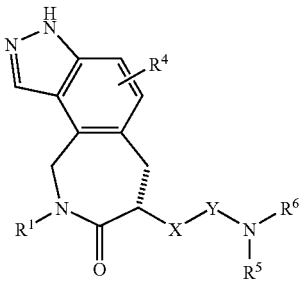

IIb

Another aspect of the invention is a compound of Formula I or II where $R^4$ is chloro, fluoro, or methyl.

Another aspect of the invention is a compound of Formula I or II where $NR^5R^6$ taken together is

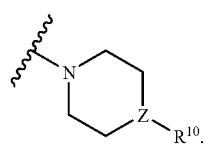

Another aspect of the invention is a compound of Formula I or II where $NR^5R^6$ taken together is

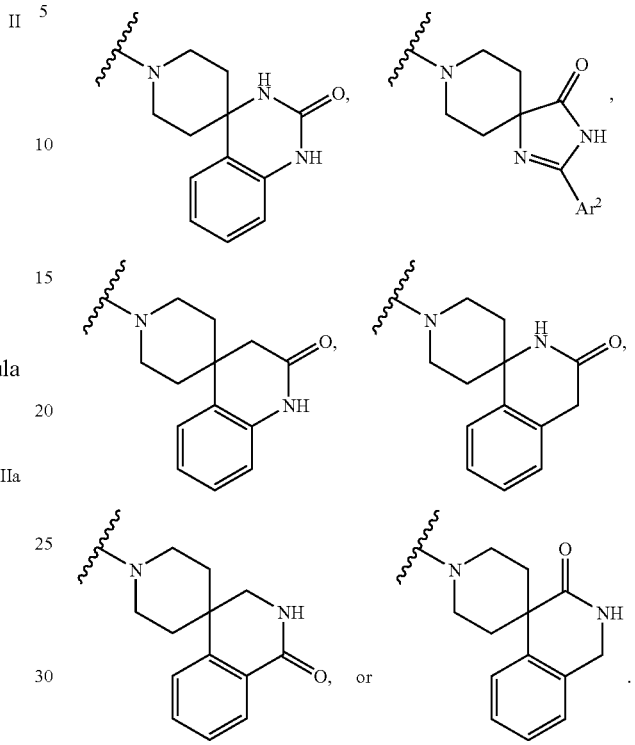

Another aspect of the invention is a compound of Formula I or II where $R^{10}$ is selected from the group consisting of

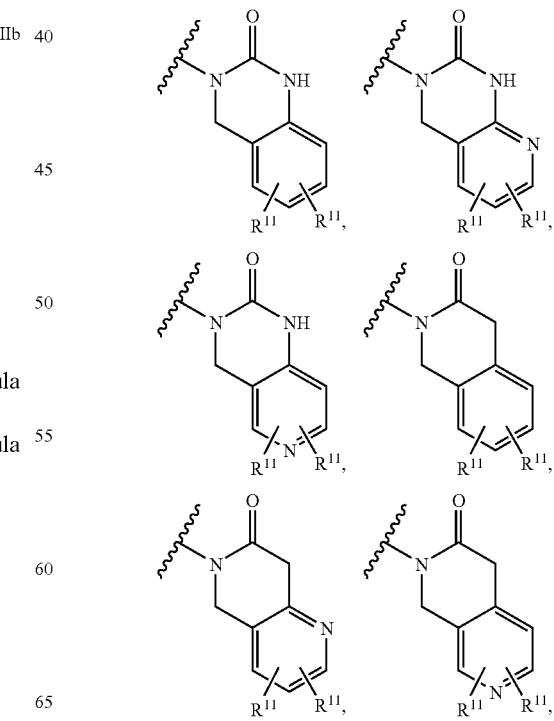

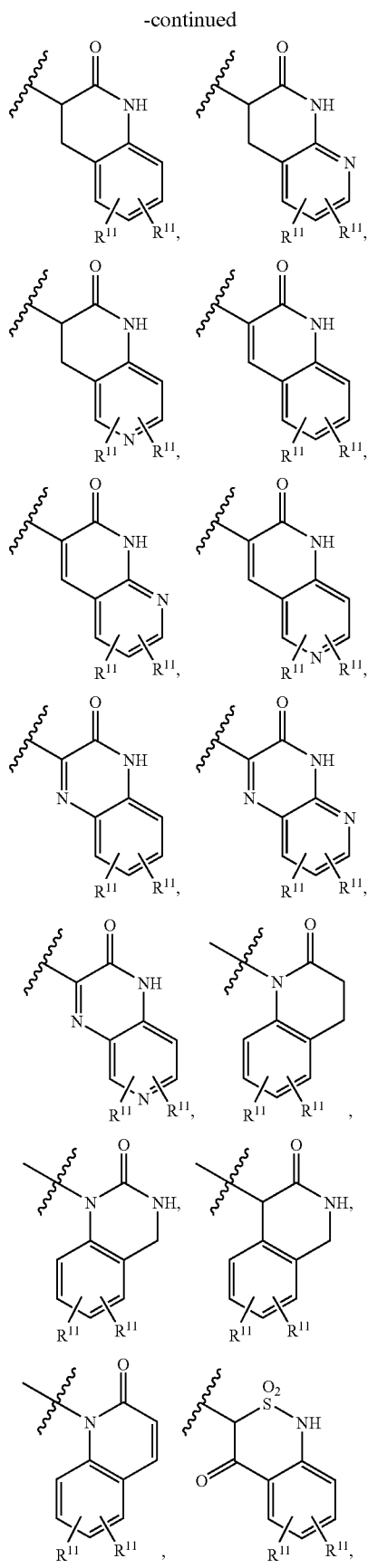
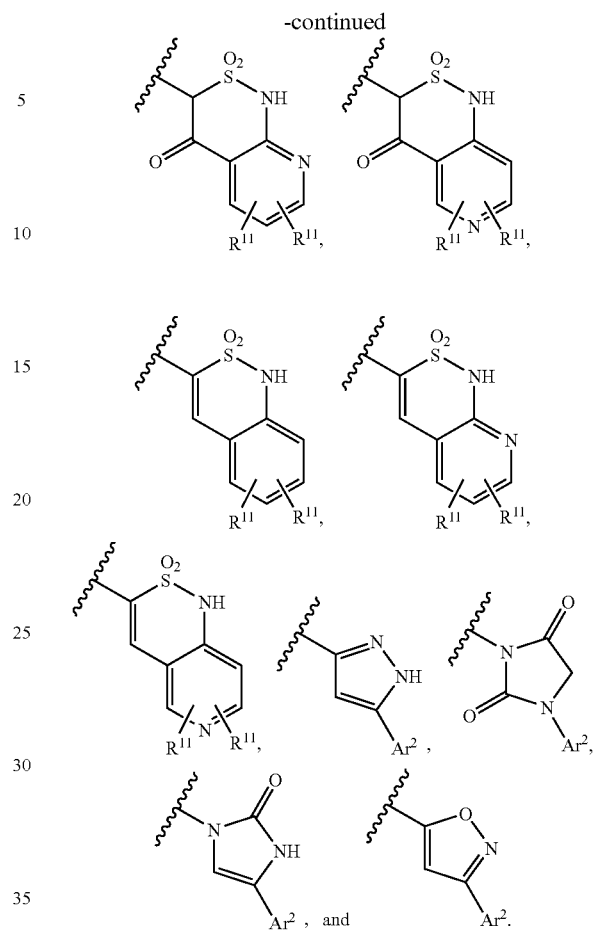

Another aspect of the invention is a compound of Formula I or II where $R^{11}$ is hydrogen, chloro, fluoro, or methyl.

Another aspect of the invention is a compound of Formula I or II where Z is CH.

Another aspect of the invention is a compound of Formula I where n is 1.

Another aspect of the invention is that any scope of variables $R^1$, $R^2$, $R^3$, $R^4$, $R^5$, $R^6$, $R^7$, $R^8$, $R^9$, $R^{10}$, $R^{11}$, $Ar^1$, $Ar^2$, X—Y, Z, and n can be used with any scope of the remaining variables "Alkyl," "hydroxyalkyl," "alkoxy" and related terms with an alkyl moiety include straight and branched isomers. "Alkenyl" means a straight or branched alkyl group with at least one double bond. A term such as $C_{1-6}(R)$alkyl means a straight or branched alkyl group of one to six carbons substituted with the substituent R. A term such as N—(R)-pyrrolidinyl indicates that the nitrogen is substituted with the substituent R. "Haloalkyl" and "haloalkoxy" include all halogenated isomers from monohalo substituted alkyl to perhalo substituted alkyl. "Aryl" includes carbocyclic and heterocyclic aromatic ring systems. "Amino" includes primary, secondary, and tertiary moieties. "Carbonyl" means CO. "Oxy" means —O—. "Aminocarbonyl" means —N(R)C(=O)—. "Oxycarbonyl" means —OC(=O)—. "Methylenecarbonyl" means —$CH_2$C(=O)—. "Amino(cyano)iminomethyl" means —NHC(=NCN)—.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Some compounds of the invention may exist in stereoisomeric forms, one example of which is shown below. The invention includes all stereoisomeric and tautomeric forms of the compounds.

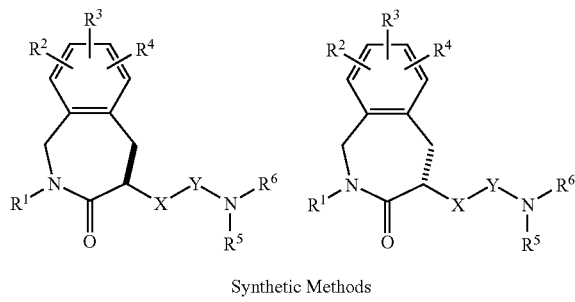

Synthetic Methods

The compounds described in the present invention can be synthesized according to Schemes 1-4 as well as other procedures known in the art. Starting materials are commercially available or synthesized by common synthetic procedures. Variations of the compounds and the procedures to make them which are not illustrated are within the skill of the art.

Scheme 1 describes how to make certain compounds of the invention. Regiospecific introduction of iodine on a appropriately substituted aromatic ring can be accomplished using iodine monochloride. Aryl iodides (II) are good coupling partners in palladium-mediated Heck reactions. The Heck products (III) can be reduced with hydrogen mediated by number of asymmetric catalysts to produce enantiomerically pure materials (IV). Subsequent hydrolysis of acetate functionality with methanolic potassium carbonate followed by treatment of alcohol (V) with thionyl chloride can produce benzylic chlorides (VI). Treatment of benzylic chlorides with various amines in acetonitrile can deliver requisite amines (VII).

The amines (VII) can be converted into desired azepinones (VIII) in refluxing toluene mediated by catalytic acetic acid. The azepinone intermediates VIII (X=NH, $CH_2$, O) can in turn be elaborated into final products. Hydrogenolysis of VIII (X=NH) under 10% Pd on carbon produces amine intermediate IX (Scheme II). The amine functionality can be transformed to the desired urea functionality (X) with the assistance of phosgene or N,N'-disuccinimyl dicarbonate and various amines (Scheme 2). Alternatively, the succinic ester VIII (X=$CH_2$) can be converted to carboxylic acid (XI) with lithium hydroxide, followed by reaction with an appropriate amine under TBTU coupling conditions to give desired amides (XII) (Scheme 3).

Scheme 1.

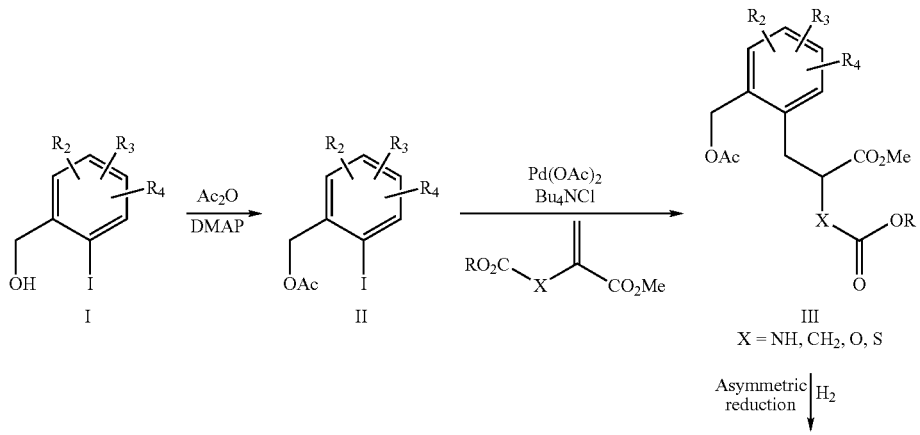

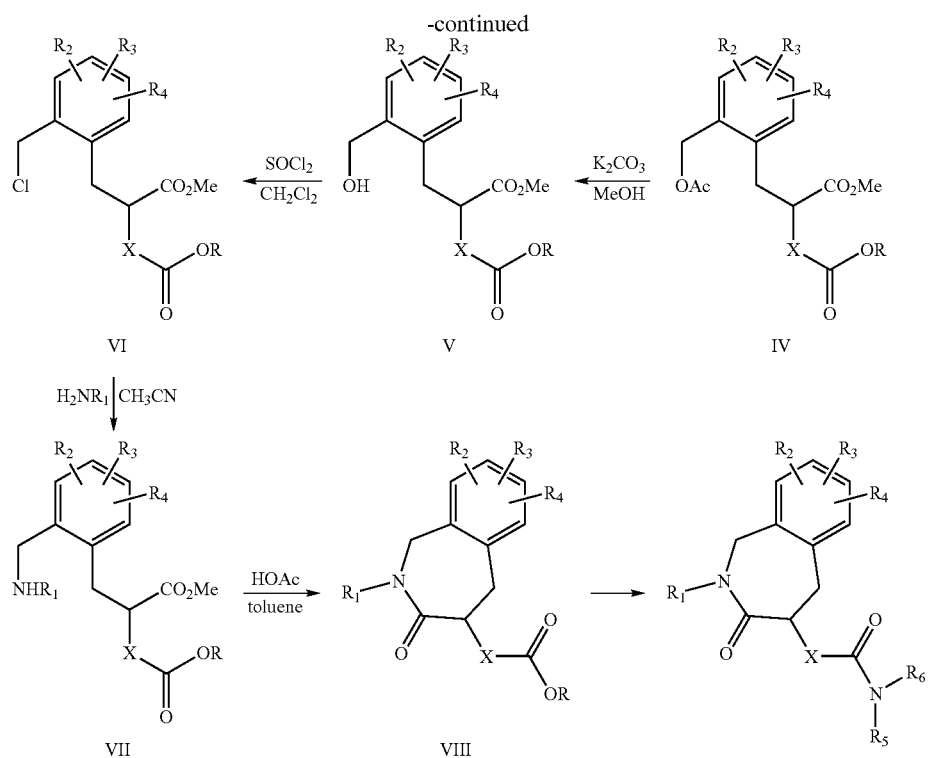
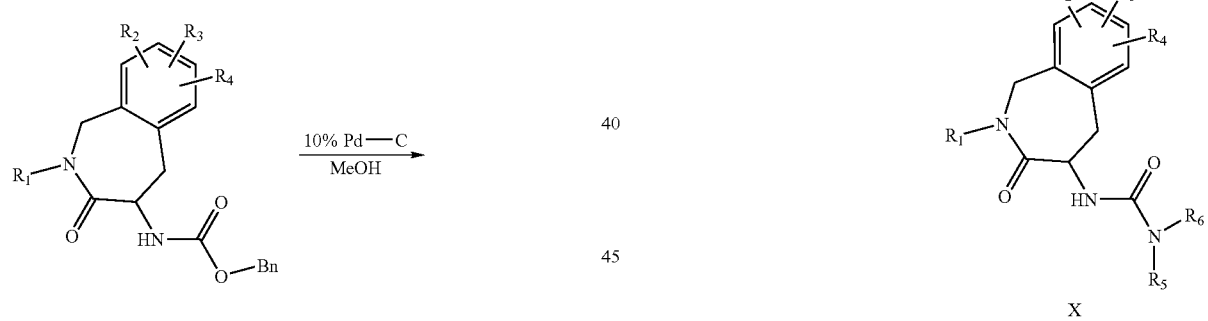
Scheme 2.
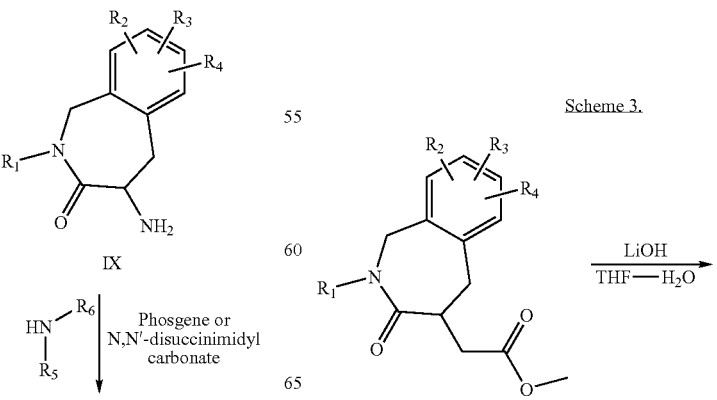
Scheme 3.

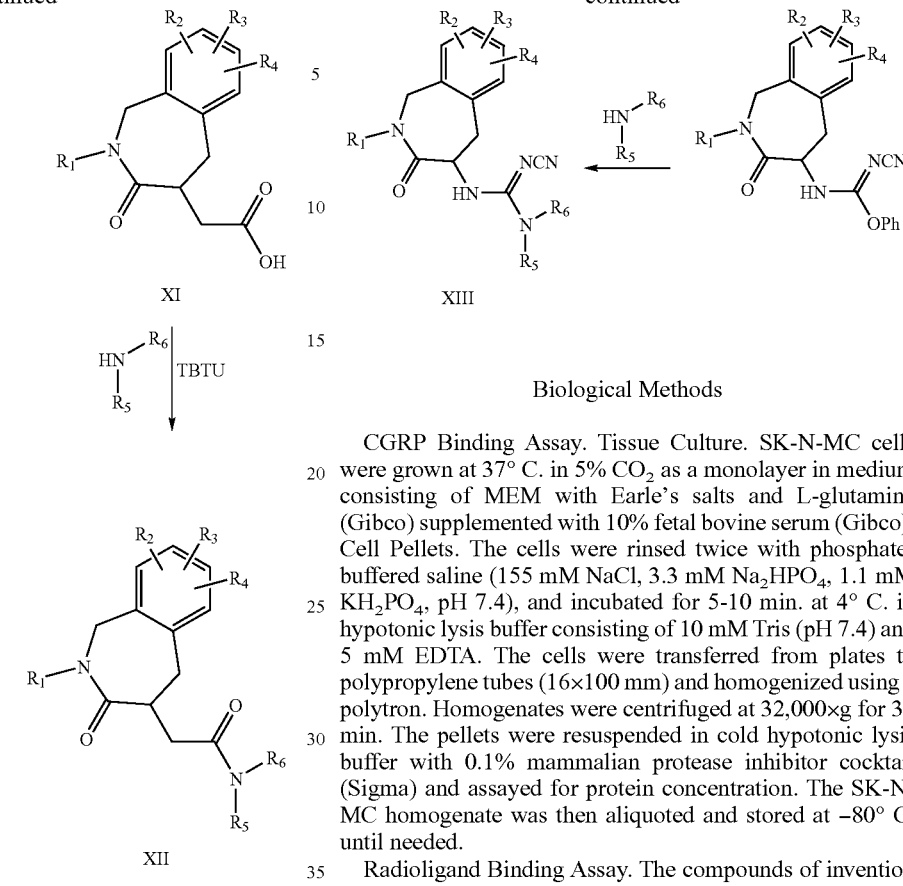

In a manner similar to urea formation, cyanoguanidine XIII can be prepared using diphenyl N-cyanocarboimidate and various substituted amines (Scheme 4).

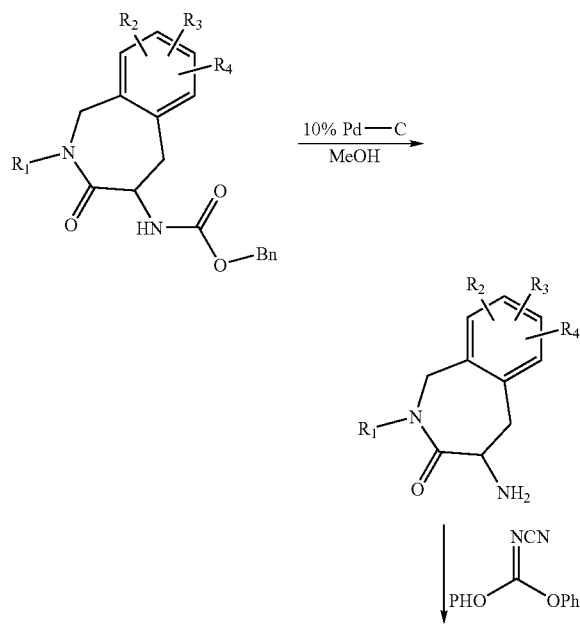

Biological Methods

CGRP Binding Assay. Tissue Culture. SK-N-MC cells were grown at 37° C. in 5% $CO_2$ as a monolayer in medium consisting of MEM with Earle's salts and L-glutamine (Gibco) supplemented with 10% fetal bovine serum (Gibco). Cell Pellets. The cells were rinsed twice with phosphate-buffered saline (155 mM NaCl, 3.3 mM $Na_2HPO_4$, 1.1 mM $KH_2PO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was then aliquoted and stored at −80° C. until needed.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 μl) into 96 well assay plates. [$^{125}I$]-CGRP (Amersham Biosciences) was diluted to 60 pM in assay buffer and a volume of 50 μl was added to each well. SK-N-MC pellets were thawed, diluted in assay buffer with fresh 0.1% mammalian protease inhibitor cocktail (Sigma), and homogenized again. SK-N-MC homogenate (5 μg/well) was added in a volume of 100 μl. The assay plates were then incubated at room temperature for 2 h. Assays were stopped by addition of excess cold wash buffer (20 mM Tris-Cl pH 7.5, 0.1% BSA) immediately followed by filtration over glass fiber filters (Whatman GF/B) previously soaked in 0.5% PEI. Non-specific binding was defined with 1 μM beta-CGRP. Protein bound radioactivity was determined using a gamma or scintillation counter. The $IC_{50}$ was defined as the concentration of a compound of invention required to displace 50% of radioligand binding.

Cyclic AMP Functional Antagonism Assay. Antagonism of the compounds of invention was determined by measuring the formation of cyclic AMP (adenosine 3'5'-cyclic monophosphate) in SK-N-MC cells that endogenously express the human CGRP receptor. CGRP receptor complex is coupled with Gs protein and CGRP binding to this complex leads to the cyclic AMP production via Gs—dependent activation of an adenylate cyclase (Juaneda C et al., TiPS, 2000; 21:432-438; incorporated by reference herein). Consequently, CGRP receptor antagonists inhibit CGRP—induced cyclic AMP formation in SK-N-MC cells (Doods H et al., Br J Pharmacol, 2000; 129(3):420-423); incorporated by reference herein).

For cyclic AMP measurements SK-N-MC cells were incubated with 0.3 nM CGRP alone or in the presence of various concentrations of the compounds of invention for 30 min at room temperature. Compounds of invention were pre-incubated with SK-N-MC cells for 15 min before the addition of CGRP to allow receptor occupancy (Edvinsson et al., Eur J Pharmacol, 2001, 415:39-44; incorporated by reference herein). Cyclic AMP was extracted using the lysis reagent and its concentration was determined by radioimmunoassay using RPA559 cAMP SPA Direct Screening Assay Kit (Amersham Pharmacia Biotech). IC50 values were calculated using Excel fit. The tested compounds of invention were determined to be antagonists as they exhibited a dose—dependent inhibition of the CGRP—induced cyclic AMP production.

In the Table 4, results are denoted as follows: A 0.1-10 nM; B=10-100 nM; C=100-1000 nM; D>1000 nM.

TABLE 4

CGRP Binding and cAMP Functional Data

| Example | CGRP binding[1] IC$_{50}$ (nM) | cAMP Function[2] IC$_{50}$ (nM) |
|---|---|---|
| 1 | B | B |
| 2 | C | * |
| 3 | C | * |
| 4 | C | * |
| 5 | C | * |
| 6 | B | B |
| 7 | B | * |
| 8 | D | * |
| 9 | C | * |
| 10 | B | B |
| 11 | B | B |
| 12 | A | A |
| 13 | B | * |
| 14 | C | * |
| 15 | B | * |
| 16 | A | A |
| 17 | B | * |
| 18 | C | * |
| 19 | B | A |
| 20 | A | A |
| 21 | A | A |
| 22 | A | A |
| 23 | B | * |
| 24 | B | B |
| 25 | C | * |
| 26 | A | A |
| 27 | C | * |
| 28 | B | B |
| 29 | C | * |
| 30 | B | B |
| 31 | D | * |
| 32 | C | * |
| 33 | D | * |
| 34 | C | * |
| 35 | B | * |
| 36 | B | B |
| 37 | A | B |
| 38 | C | * |
| 39 | B | B |
| 40 | A | A |
| 41 | A | A |
| 42 | B | B |
| 43 | A | A |
| 44 | A | A |
| 45 | A | A |
| 46 | A | A |
| 47 | B | B |
| 48 | B | * |
| 49 | A | A |
| 50 | A | A |
| 51 | A | * |
| 52 | A | A |
| 53 | A | A |
| 54 | A | A |
| 55 | C | * |
| 56 | C | * |
| 57 | C | * |
| 58 | C | * |
| 59 | C | * |
| 60 | D | * |
| 61 | D | * |
| 62 | B | * |
| 63 | C | * |
| 64 | D | * |
| 65 | D | * |
| 66 | B | * |
| 67 | B | * |
| 68 | C | * |
| 69 | B | * |
| 70 | C | * |
| 71 | C | * |
| 72 | D | * |
| 73 | D | * |
| 74 | D | * |
| 75 | A | * |
| 76 | B | * |
| 77 | B | * |
| 78 | A | * |
| 79 | A | * |
| 80 | B | B |
| 81 | B | * |
| 82 | A | * |
| 83 | C | * |
| 84 | C | * |
| 85 | B | B |
| 86 | A | * |
| 87 | B | * |
| 88 | A | * |
| 89 | A | * |
| 90 | A | * |
| 91 | A | * |
| 92 | B | * |
| 93 | C | * |
| 94 | A | * |
| 95 | B | * |
| 96 | A | * |
| 97 | A | * |
| 98 | B | * |
| 99 | A | * |
| 100 | A | * |
| 101 | B | * |
| 102 | A | * |
| 103 | B | * |
| 104 | B | * |
| 105 | B | * |
| 106 | B | * |
| 107 | C | * |
| 108 | B | * |
| 109 | C | * |
| 110 | B | * |
| 111 | A | * |
| 112 | B | * |
| 113 | A | * |
| 114 | B | * |
| 115 | B | * |
| 116 | A | * |
| 117 | C | * |
| 118 | B | * |
| 119 | D | * |
| 120 | A | * |

Pharmaceutical Compositions and Methods of Treatment

The compounds of Formula I inhibit the CGRP receptor. As such, they are useful for treating disorders associated with aberrant CGRP levels or where modulating CGRP levels may have therapeutic benefit.

Accordingly, another aspect of the invention is a pharmaceutical composition comprising a compound of Formula I with a pharmaceutically acceptable adjuvant, carrier, or diluent.

Compounds are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001, 15(10), 745-53; Williamson, D. J. *Microsc. Res. Tech.* 2001, 53, 167-178; Grant, A. D. *Brit. J. Pharmacol.* 2002, 135, 356-362). Serum levels of CGRP are elevated during migraine (Goadsby P. J. et al. *Ann. Neurol.* 1990, 28, 183-7) and treatment with anti-migraine drugs returns CGRP levels to normal coincident with alleviation of headache (Gallai V. et al. *Cephalalgia* 1995, 15, 384-90). Migraineurs exhibit elevated basal CGRP levels compared to controls (Ashina M. et al., *Pain* 2000, 86(1-2), 133-8). Intravenous CGRP infusion produces lasting headache in migraineurs (Lassen L. H. et al. *Cephalalgia.* 2002, 22(1), 54-61). Preclinical studies in dog and rat report that systemic CGRP blockade with the peptide antagonist CGRP(8-37) does not alter resting systemic hemodynamics nor regional blood flow (Shen, Y-T. et al. *J. Pharmacol. Exp. Ther.* 2001, 298, 551-8). Thus, CGRP-receptor antagonists may present a novel treatment for migraine that avoids the cardiovascular liabilities of active vasoconstriction associated with non-selective 5-HT$_{1B/1D}$ agonists, "triptans" (e.g., sumatriptan).

Another aspect of the invention is a method of treating migraine or headache.

"Migraine," "headache," and related terms are as understood by medical practitioners. Migraine encompasses all classes of migraine including common, classic, cluster, fulgurating, hemiplegic, opthalmoplegic, and opthomalmic.

"Therapeutically effective" means there is a meaningful patient benefit as understood by medical practitioners.

"Patient" means a person who may benefit from treatment as determined by medical practitioners.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

Another aspect of the invention relates to methods selected from the group consisting of (a) immune regulation in gut mucosa (b) protective effect against cardiac anaphylactic injury (c) stimulating or preventing interleukin-1b (IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin1 receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5, Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef, Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218 all incorporated by reference herein.

Another aspect of this invention relates to a method of treatment using combinations of Formula I compounds with one or more agents selected from the group consisting of COX-2 inhibitors, NSAIDS, aspirin, acetaminophen, triptans, ergotamine and caffeine for the treatment of migraine.

DESCRIPTION OF SPECIFIC EMBODIMENTS

Proton magnetic resonance (1H NMR) spectra were recorded on a Bruker AC 300 or AC 500. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak. Low resolution mass spectra (MS) and the apparent molecular (MH+) or (M–H)+ was determined on a Micromass platform. The elemental analysis are reported as percent by weight. The products were purified by Prep HPLC using the column YMC S5 ODS (30×100 mm) at a flow rate of 40.0 mL/min and gradient time of 8.0 min. starting from solvent composition of 40% MeOH-60% H2O-0.1% TFA and ending with solvent composition 95% MeOH-5% H2O-0.1% TFA. The products were analyzed by a HPLC instrument using an XTERA column (3.0×50 mm S7) starting from solvent A (10% MeOH-90% water-0.1% trifluoroacetic acid (TFA)) and reaching solvent B (10% water-90% methanol-0.1% TFA) over a gradient time of 2 min. The flow rate is 5 mL/min. and retention time (Rf) of product was measured at 220 nm wavelength.

Intermediate 1

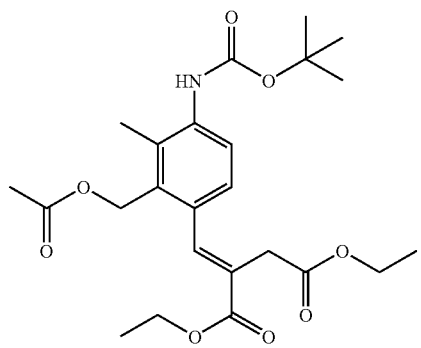

2-(Acetoxymethyl-4-tert-butoxycarbonylamino-3-methyl-benzylidene)-succinic acid diethyl ester. Nitrogen gas was bubbled through a solution of acetic acid 3-tert-butoxycarbonylamino-6-iodo-2-methyl-benzyl ester (3.85 g, 9.5 mmol), itaconic acid diethyl ester (2.2 mL, 12 mmol), tetrabutylammonium chloride (3.4 g, 12 mmol), and triethylamine (4.0 mL, 29 mmol) in N,N-dimethylformamide (25 mL) for 5 minutes. Palladium (II) acetate (0.32 g, 1.4 mmol) was added. Mixture was heated at 100° C. for 45 minutes. Mixture was cooled to room temperature then diluted with diethyl ether (100 ml). Mixture was washed successively with water (3×50 mL), and brine (25 mL). Organic was dried (MgSO4), filtered and concentrated in vacuo. Silica gel purification yielded the desired product in 99% yield as an amber oil. $^1$H NMR (300 MHz, CDCl$_3$): δ=8.0 (s, 1H), 7.78 (d, J=8.4, 1H), 7.08 (d, J=8.4, 1H), 6.32 (s, 1H), 5.11 (s, 2H), 4.27 (q, J=7.3, 2H), 4.11 (q, J=7.1, 2H), 3.30 (s, 2H), 2.24 (s, 3H), 2.04 (s, 3H), 1.55 (s, 3H), 1.51 (s, 9H), 1.32 (t, J=7.1, 3H), 1.23 (t, J=7.3, 3H). MS m/e (M−H)$^−$=462.0.

Intermediate 2

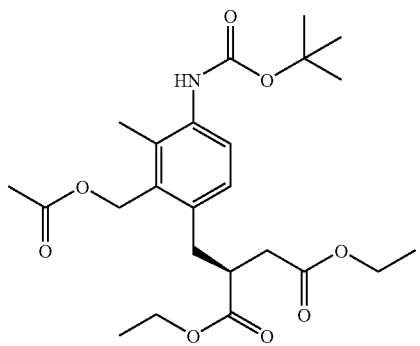

2-(S)-(Acetoxymethyl-4-tert-butoxycarbonylamino-3-methyl-benzyl)-succinic acid diethyl ester. 2-(S)-(Acetoxymethyl-4-tert-butoxycarbonylamino-3-methyl-benzylidene)-succinic acid diethyl ester (4.4 g, 9.5 mmol) and (−)-1,2-bis((2R,5R)-diethylphospholano)benzene(cyclooctadiene)rhodium (I) trifluoromethane sulfonate (100 mg) was dissolved in ethanol (80 mL). Mixture was placed on a Parr hydrogenation apparatus. Reaction vessel was charged with 60 psi of hydrogen gas. Reaction mixture was allowed to shake at room temperature for 18 hours. Reaction mixture was concentrated in vacuo. Residue was passed through a plug of silica gel eluting 80% ethyl acetate-hexanes (250 mL). Filtrate was concentrated in vacuo to afford the desired product in 97% yield as an amber oil. $^1$H NMR (300 MHz, CDCl$_3$): δ=7.62 (d, J=8.1, 1H), 7.01 (d, J=8.4, 1H), 6.20 (s, 1H), 5.20 (m, 2H), 4.09 (m, 4H), 3.14 (m, 1H), 2.69 (m, 2H), 2.38 (dd, J1=16.8, J2=4.8, 1H), 2.23 (s, 3H), 2.07 (s, 3H), 1.56 (3, 3H), 1.50 (s, 9H), 1.22 (m, 6H). MS m/e (M−H)$^−$=464.0.

Intermediate 3

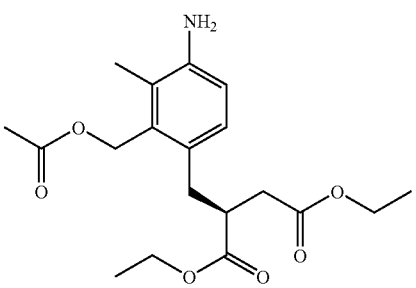

2-(S)-(2-Acetoxymethyl-4-amino-3-methyl-benzyl)-succinic acid diethyl ester. Trifluoroacetic acid (10 mL) was added to a solution of 2-(S)-(acetoxymethyl-4-tert-butoxycarbonylamino-3-methyl-benzyl)-succinic acid diethyl ester (4.6 g, 9.9 mmol) in dichloromethane (40 mL). Reaction mixture was stirred at room temperature for 1.5 hours. Mixture was concentrated in vacuo. Residue was dissolved in dichloromethane (75 mL) and washed successively with saturated aqueous sodium bicarbonate (2×50 mL) and brine (30 mL). Organic was dried (magnesium sulfate), filtered and concentrated in vacuo to yield the desired product in 99% yield as an amber oil. $^1$H NMR (300 MHz, CDCl$_3$): δ=6.85 (d, J=8.1, 1H), 6.67 (d, J=8.4, 1H), 5.18 (m, 2H), 4.09 (m, 4H), 3.09 (dd, J1=6.2, J2=13.9, 1H), 2.96 (m, 1H), 2.66 (m, 2H), 2.37 (dd, J1=4.6, J2=16.7, 1H), 2.15 (s, 3H), 2.06 (s, 3H), 1.20 (m, 6H). MS m/e (M–C$_2$H$_4$O$_2$+H)$^+$=306.2.

Intermediate 4

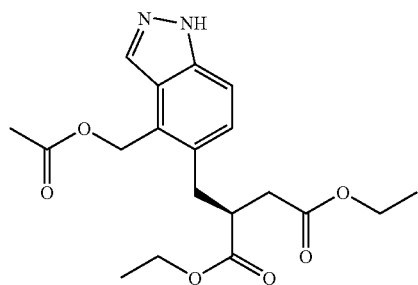

2-(S)-(4-Acetoxymethyl-1H-indazol-5-ylmethyl)-succinic acid diethyl ester. Isoamyl nitrite (1.6 mL, 12 mmol) was added dropwise to a cooled (water ice bath) solution of 2-(S)-(2-acetoxymethyl-4-amino-3-methyl-benzyl)-succinic acid diethyl ester in carbontetrachloride (80 mL) and acetic acid (4 mL). Mixture was stirred at 0° C. for 2 hours. Mixture was warmed and stirred at ambient temperature for 14 hours. Mixture was concentrated in vacuo. Residue was dissolved in dichloromethane (75 mL) then washed successively with saturated aqueous sodium bicarbonate (2×50 mL), and brine (30 mL). Organic was dried (magnesium sulfate), filtered and concentrated in vacuo. Silica gel chromatography (ethyl acetate-hexanes) afforded the product in 55% yield as an amber oil. $^1$H NMR (300 MHz, CDCl$_3$): δ=8.19 (s, 1H), 7.44 (d, J=8.8, 1H), 7.24 (d, J=8.8, 1H), 5.49 (s, 2H), 4.06 (m, 4H), 3.25 (m, 1H), 3.11 (m, 1H), 2.97 (m, 1H), 2.72 (dd, J1=8.8, J2=16.5, 1H) 2.43 (dd, J1=5.1, J2=16.5), 2.09 (s, 3H), 1.19 (m, 6H). MS m/e (M+H)$^+$=377.1.

Intermediate 5

2-(S)-(4-Hydroxymethyl-1H-indazol-5-ylmethyl)-succinic acid dimethyl ester. Potassium carbonate (1.6 g, 11.6 mmol) was added to a solution of 2-(S)-(4-acetoxymethyl-1H-indazol-5-ylmethyl)-succinic acid diethyl ester (2.0 g, 5.5 mmol) in methanol (60 mL). Mixture was stirred at room temperature for 1.5 hours. Reaction was quenched with the addition of 1N hydrochloric acid (30 mL). Methanol was removed from the mixture in vacuo. Remaining aqueous was basified with sodium bicarbonate. Mixture was extracted with ethyl acetate (2×40 mL). Combined organic layers were washed successively with water (30 mL) and brine (30 mL). Organic was dried (magnesium sulfate), filtered then concentrated in vacuo. Desired product was obtained in 92% yield as an amber oil. $^1$H NMR (300 MHz, CDCl$_3$): δ=8.21 ((s, 1H), 7.34 (d, J=9.2, 1H), 7.17 (d, J=8.8, 1H), 5.02 (dd, J1=12.4, J2=17.9, 1H) 3.63 (s, 6H), 3.23 (m, 1H), 2.98 (m, 1H), 2.77 (dd, J1=7.7, J2=16.8, 1H), 2.53 (dd, J1=6.4, J2=16.7, 1H). MS m/e (M+H)$^+$=307.0.

Intermediate 6

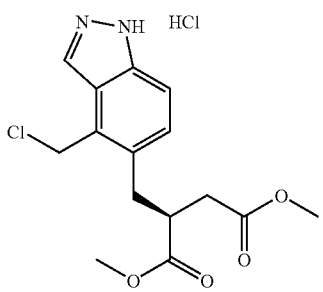

2-(S)-(4-Chloromethyl-1H-indazol-5-ylmethyl)-succinic acid dimethyl ester hydrochloride. Thionyl chloride (5.0 mL) was added to a solution of 2-(S)-(4-hydroxymethyl-1H-indazol-5-ylmethyl)-succinic acid dimethyl ester (1.53 g, 5.0 mmol) in dichloromethane (30 mL). Reaction mixture was stirred at ambient temperature for 2 hours. Mixture was concentrated in vacuo. Residue was triturated in toluene (30 mL), then concentrated in vacuo. Residue was treated with dichloromethane (30 mL) then concentrated in vacuo. Desired product was obtained in 96% yield as an orange solid. $^1$H NMR (300 MHz, CDCl$_3$): δ=8.22 (s, 1H), 7.49 (d, J=8.8, 1H), 7.15 (d, J=8.8, 1H), 5.12 (s, 2H), 3.56 (s, 3H), 3.52 (s, 3H), 3.05 (m, 3H), 2.69 (dd, J1=8.1, J2=16.5), 2.54 (m, 1H). MS m/e (M+H)$^+$=325.2.

Intermediate 7

[9-(2,2-Dimethyl-propyl)-8-oxo-3,6,7,8,9,10-hexahydro-2,3,9-triaza-(S)-cyclohepta[e]inden-7-yl]-acetic acid methyl ester. Neopentylamine (2.0 mL, 17 mmol) was added to a mixture of potassium carbonate (1.2 g, 8.7 mmol) and 2-(S)-(4-chloromethyl-1H-indazol-5-ylmethyl)-succinic acid dimethyl ester hydrochloride (1.56 g, 4.3 mmol) in acetonitrile (30 mL). Reaction mixture was heated at reflux until starting material was deemed to be consumed by HPLC (1.5 hours). Mixture was cooled to room temperature then filtered. Filtrate was concentrated in vacuo. Residue was dissolved in a mixture of toluene (40 mL) and acetic acid (2 mL). Reaction mixture was heated at reflux until judged complete by HPLC (44 hours). Mixture was concentrated in vacuo. Residue was dissolved in ethyl acetate (50 mL) and washed with saturated aqueous sodium bicarbonate (2×25 mL). Organic was dried (magnesium sulfate), filtered and concentrated in vacuo. Silica gel chromatography (ethyl acetate-hexanes) yielded the desired product in 90% yield as a yellow foam. $^1$H NMR (300 MHz, CDCl$_3$): δ=8.01 (s, 1H), 7.35 (d, J=8.4, 1H), 7.13 (d, J=8.4, 1H), 5.41 (d, J=16.8, 1H), 4.50 (d, J=16.8, 1H), 3.90 (m, 1H), 3.70 (s, 3H), 3.62 (m, 1H), 3.50 (d, J=13.9, 1H), 3.18 (d, J=13.5, 1H), 3.05 (m, 2H), 2.43 (dd, J1=16.7, J2=5.3, 1H), 0.83 (s, 9H). MS m/e (M−H)$^-$=342.0.

Intermediate 8

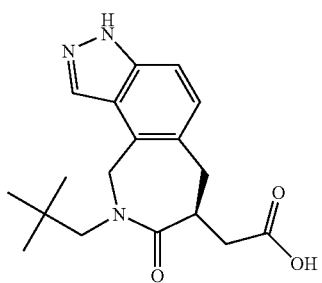

[9-(2,2-Dimethyl-propyl)-8-oxo-3,6,7,8,9,10-hexahydro-2,3,9-triaza-(S)-cyclohepta[e]inden-7-yl]-acetic acid. Lithium hydroxide monohydrate (335 mg, 8.0 mmol) was added to a solution of [9-(2,2-dimethyl-propyl)-8-oxo-3,6,7,8,9,10-hexahydro-2,3,9-triaza-(S)-cyclohepta[e]inden-7-yl]-acetic acid methyl ester (1.32 g, 3.8 mmol) in methanol (15 mL), tetrahydrofuran (15 mL) and water (15 mL). Reaction mixture was heated at 50° C. for 1 hour. The organic solvents were removed from the mixture in vacuo. Remaining aqueous was diluted with water (25 mL). Mixture was neutralized with 1 N hydrochloric acid (8.0 mL). Mixture was extracted with ethyl acetate (2×30 mL). Combined organic layers were washed with brine (20 mL) then dried (magnesium sulfate), filtered and concentrated in vacuo. Desired product was obtained in 88% yield as a light yellow solid. $^1$H NMR (300 MHz, CDCl$_3$): δ=7.98 (s, 1H), 7.36 (d, J=8.8, 1H), 7.10 (d, J=8.8, 1H), 5.38 (d, J=16.8, 1H), 4.48 (d, J=16.8, 1H), 3.85 (m, 1H), 3.49 (d, J=13.5, 1H), 3.18 (d, J=13.9, 1H), 3.08 (s, 2H), 2.92 (dd, J1=8.2, J2=16.3, 1H), 2.55 (dd, J1=16.5, J2=4.8, 1H) 0.81 (s, 9H). MS m/e (M−H)$^-$=328.0.

Intermediate 9

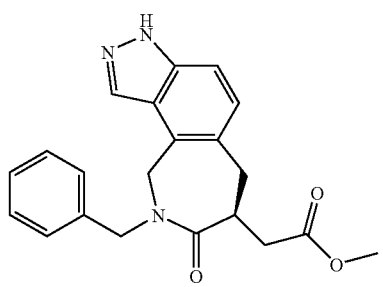

(9-Benzyl-8-oxo-3,6,7,8,9,10-hexahydro-2,3,9-triaza-(S)-cyclohepta[e]inden-7-yl)-acetic acid methyl ester. Benzylamine (250 μL, 2.3 mmol) and 2-(S)-(4-Chloromethyl-1H-indazol-5-ylmethyl)-succinic acid dimethyl ester hydrochloride were converted following a procedure analogous to the preparation of [9-(2,2-Dimethyl-propyl)-8-oxo-3,6,7,8,9,10-hexahydro-2,3,9-triaza-(S)-cyclohepta[e]inden-7-yl]-acetic acid methyl ester. Silica gel chromatography (ethyl acetate-hexanes) afforded the desired product in 62% yield as an amber oil. $^1$H NMR (300 MHz, CDCl$_3$): δ=7.77 (s, 1H), 7.28 (m, 6H), 7.09 (d, J=8.4, 1H), 5.18 (d, J=16.8, 1H), 4.99 (d, J=15.0, 1H), 4.43 (d, J=5.9, 1H), 4.39 (d, J=1.8, 1H), 4.34 (d, J=4.0, 1H), 3.74 (s, 3H), 3.13 (m, 2H), 2.51 (dd, J1=5.5, J2=16.8, 1H). MS m/e (M+H)$^+$=364.0.

Intermediate 10

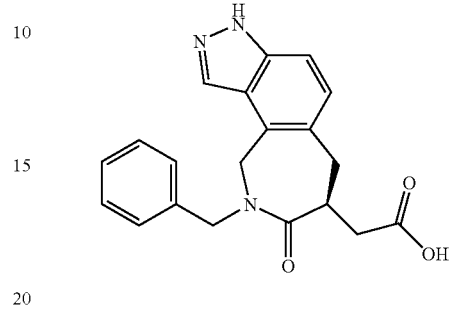

(9-Benzyl-8-oxo-3,6,7,8,9,10-hexahydro-2,3,9-triaza-(S)-cyclohepta[e]inden-7-yl)-acetic acid. Lithium hydroxide (32 mg, 0.76 mmol) and (9-benzyl-8-oxo-3,6,7,8,9,10-hexahydro-2,3,9-triaza-(S)-cyclohepta[e]inden-7-yl)-acetic acid methyl ester were reacted in a manner analogous to the preparation of [9-(2,2-dimethyl-propyl)-8-oxo-3,6,7,8,9,10-hexahydro-2,3,9-triaza-(S)-cyclohepta[e]inden-7-yl]acetic acid. Desired product was obtained as a yellow oil in 99% yield. $^1$H NMR (300 MHz, DMSO, D$_6$): δ=7.72 (s, 1H), 7.28 (m, 4H), 7.16 (m, 2H), 7.06 (d, J=8.8, 1H), 5.15 (d, J=16.8, 1H), 4.95 (d, J=15.0, 1H), 4.37 (m, 4H), 3.09 (m, 2H), 2.59 (dd, J1=5.1, J2=16.5, 1H). MS m/e (M+H)$^+$=350.0.

Intermediate 11

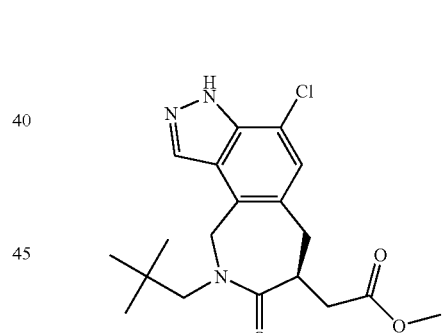

[4-Chloro-9-(2,2-dimethyl-propyl)-8-oxo-3,6,7,8,9,10-hexahydro-2,3,9-triaza-(S)-cyclohepta[e]inden-7-yl]-acetic acid methyl ester. Potassium carbonate (190 mg, 1.4 mmol) was added to a solution of 2-(S)-(4-acetoxymethyl-7-chloro-1H-indazol-5-ylmethyl)-succinic acid diethyl ester (240 mg, 0.58 mmol) in methanol (10 mL) and ethanol (5 mL). Mixture was stirred at room temperature for 1.5 hours. Reaction was quenched with the addition of 1 N hydrochloric acid (10 mL). Organic solvents were removed from the mixture in vacuo. Remaining aqueous was basified with sodium bicarbonate. Mixture was extracted 2× ethyl acetate (15 mL). Combined organic layers were dried (magnesium sulfate), filtered and concentrated. Residue was dissolved in dichloromethane (6 mL). Thionyl chloride (2 mL) was added to the mixture.

Reaction was stirred at room temperature for 1.5 hours. Mixture was concentrated in vacuo. Residue was treated with dichloromethane (25 mL) then concentrated in vacuo. Residue was suspended in acetonitrile (5 mL). Potassium carbonate (200 mg, 1.4 mmol) was added to the mixture followed by neopentylamine (150 μL, 1.3 mmol). Reaction mixture was heated at reflux for 1 hour. Mixture was cooled to room temperature then filtered through a 0.45 μm PTFE membrane. Filtrate was concentrated. Residue was dissolved in a mixture of toluene (5 mL) and acetic acid (250 μL). Reaction mixture was heated at 100° C. for 15 hours then warmed to reflux for 7 hours. Mixture was cooled to room temperature then diluted with ethyl acetate (15 mL). Mixture was washed successively 2× saturated aqueous sodium bicarbonate (20 mL), water (15 mL) and brine (10 mL). Organic was dried (magnesium sulfate), filtered and concentrated in vacuo. Silica gel chromatography (ethyl acetate-hexanes) afforded the desired product in 48% yield as a yellow oil. $^1$H NMR (300 MHz, CDCl$_3$): δ=8.02 (s, 1H), 7.13 (s, 1H), 5.37 (m, 1H), 4.42 (d, J=17.2, 1H), 3.88 (m, 1H), 3.70 (s, 3H), 3.53 (d, J=13.9, 1H), 3.12 (d, J=13.9, 1H), 3.03 (m, 3H), 2.44 (dd, J1=5.9, J2=16.9, 1H), 0.81 (s, 9H). MS m/e (M+H)$^+$=378.1.

Intermediate 12

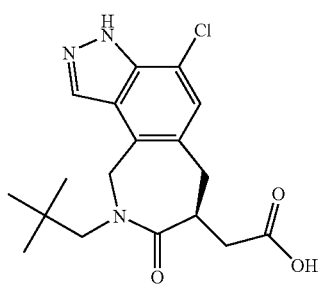

[4-Chloro-9-(2,2-dimethyl-propyl)-8-oxo-3,6,7,8,9,10-hexahydro-2,3,9-triaza-(S)-cyclohepta[e]inden-7-yl]-acetic acid. Lithium hydroxide monohydrate (30 mg, 0.71 mmol) was added to a solution of [4-chloro-9-(2,2-dimethyl-propyl)-8-oxo-3,6,7,8,9,10-hexahydro-2,3,9-triaza-(S)-cyclohepta[e]inden-7-yl]-acetic acid methyl ester (100 mg, 0.26 mmol) in methanol (2 mL), tetrahydrofuran (2 mL) and water (2 mL). Reaction mixture was stirred at ambient temperature for two hours followed by heating at 50° C. for 40 minutes. Organic solvents were removed from the mixture in vacuo. Remaining aqueous was neutralized with 1N hydrochloric acid (750 μL). Mixture was extracted 2× ethyl acetate (10 mL). Combined organic layers were washed with brine (10 mL) then dried (magnesium sulfate), filtered and concentrated in vacuo. Desired product was obtained in 93% yield as an orange solid. $^1$H NMR (300 MHz, CDCl$_3$): δ=7.98 (s, 1H), 7.09 (s, 1H), 5.35 (d, J=17.2, 1H), 4.41 (d, J=17.2, 1H), 3.82 (m, 1H), 3.48 (d, J=13.9, 1H), 3.12 (d, J=13.9, 1H), 3.02 (m, 2H), 2.92 (dd, J1=8.4, J2=16.8, 1H), 2.45 (dd, J1=5.1, J2=16.8, 1H), 0.78 (s, 9H). MS m/e (M–H)$^-$=362.0.

Intermediate 13

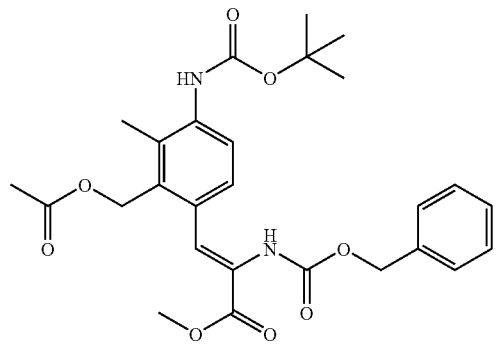

3-(2-Acetoxymethyl-4-tert-butoxycarbonylamino-3-methyl-phenyl)-2-benzyloxycarbonylamino-acrylic acid methyl ester. Palladium (II) acetate (105 mg, 0.43 mmol) was added to a mixture of acetic acid 3-tert-butoxycarbonylamino-6-iodo-2-methyl-benzyl ester (2.89 g, 7.1 mmol), Z-dehydroalanine methyl ester (2.20 g, 9.4 mmol), tetrabutylammonium chloride hydrate (2.70 g, 9.7 mmol), and sodium bicarbonate (1.80 g, 21.4 mmol) in THF (100 mL). Reaction was heated at reflux for 3.75 hours. Mixture was cooled to room temperature then filtered through a plug of silica gel eluting 70% ethyl acetate-hexanes (500 mL). Filtrate was concentrated in vacuo. Silica gel chromatography afforded the title compound as a yellow solid in 69% yield. $^1$H NMR (300 MHz, CDCl$_3$): δ=7.79 (d, J=8.4, 1H), 7.42 (s, 1H), 7.27 (m, 6H), 6.30 (s, 1H), 5.11 (s, 2H), 5.02 (s, 2H), 3.81 (s, 3H), 2.21 (s, 3H), 2.02 (s, 3H), 1.51 (s, 9H). MS m/e (M–H)$^-$=511.0.

Intermediate 14

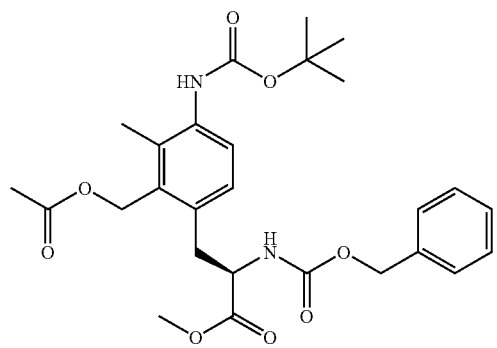

3-(2-Acetoxymethyl-4-tert-butoxycarbonylamino-3-methyl-phenyl)-2-(R)-benzyloxycarbonylamino-propionic acid methyl ester. A solution of 3-(2-acetoxymethyl-4-tert-butoxycarbonylamino-3-methyl-phenyl)-2-benzyloxycarbonylamino-acrylic acid methyl ester (2.51 g, 4.9 mmol) in methanol (50 mL) and ethyl acetate (15 mL) was reacted in a manner similar to the preparation of 2-(S)-(acetoxymethyl-4-tert-butoxycarbonylamino-3-methyl-benzyl)-succinic acid diethyl ester. Title compound was obtained as an off-white solid in 97% yield. $^1$H NMR (300 MHz, CDCl$_3$): δ=7.66 (d, J=7.9, 1H), 7.31 (m, 5H), 6.99 (d, J=8.5, 1H), 6.21 (s, 1H), 5.31 (d, J=7.6, 1H), 5.17 (d, J=3.7, 2H), 5.04 (d, J=5.80, J2H), 4.56 (m, 1H), 3.71 (s, 3H), 3.23 (dd, J1=5.80, J2=14.7, 1H), 3.07 (dd, J1=7.8, J2=14.2, 1H), 2.21 (s, 3H), 2.00 (s, 3H), 1.50 (s, 9H). MS m/e (M−H)⁻=513.0.

Intermediate 15

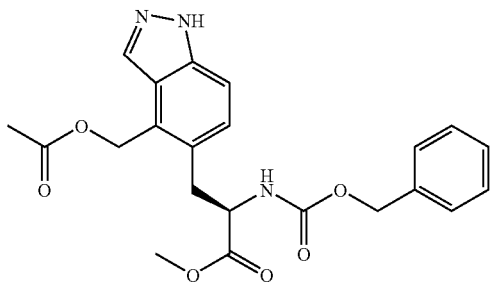

3-(4-Acetoxymethyl-1H-indazol-5-yl)-2-(R)-benzyloxycarbonylamino-propionic acid methyl ester. Trifluoroacetic acid (2.5 mL) was added to a solution of 3-(2-acetoxymethyl-4-tert-butoxycarbonylamino-3-methyl-phenyl)-2-(R)-benzyloxycarbonylamino-propionic acid methyl ester (770 mg, 1.5 mmol) in dichloromethane (10 mL). Reaction mixture was stirred at room temperature for 1.5 hours. Mixture was concentrated in vacuo. Residue was treated with chloroform (40 mL) then concentrated in vacuo. Residue was dissolved in 5% acetic acid in chloroform (10 mL). Isoamyl nitrite (240 μL, 1.8 mmol) was added to the mixture. Reaction mixture was stirred at ambient temperature for 20 minutes. Potassium acetate (690 mg, 7.0 mmol) was added to the mixture. Reaction mixture was stirred at ambient temperature for 45 minutes. Mixture was washed successively with water (10 mL), and 2× saturated aqueous sodium bicarbonate (15 mL). Organic was dried (magnesium sulfate), filtered and concentrated. Crude product was obtained in 81% yield as an amber oil and was used without further purification. $^1$H NMR (300 MHz, CDCl$_3$): δ=8.17 (s, 1H), 7.41 (d, J=8.4, 1H), 7.25 (m, 6H), 5.54 (d, J=8.1, 1H), 5.44 (s, 2H), 5.03 (s, 2H), 4.67 (m, 1H), 3.78 (s, 3H), 3.37 (dd, J1=5.9, J2=14.3, 1H), 3.22 (dd, J1=8.1, J2=14.3, 1H), 1.98 (s, 3H). MS m/e (M+H)⁺=426.0.

Intermediate 16

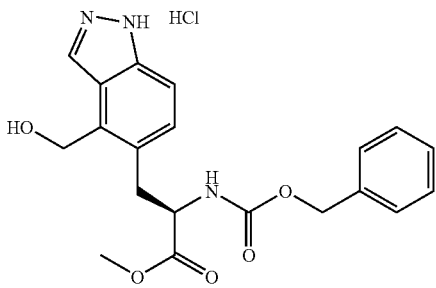

2-(R)-Benzyloxycarbonylamino-3-(4-tert-butoxycarbonylamino-2-hydroxymethyl-3-methyl-phenyl)-propionic acid methyl ester hydrochloride. Potassium carbonate (1.65 g, 12 mmol) was added to a solution of 3-(4-acetoxymethyl-1H-indazol-5-yl)-2-benzyloxycarbonylamino-propionic acid methyl ester (2.30 g, 5.4 mmol) in methanol (70 mL). Reaction mixture was stirred at room temperature for 2 hours. Reaction was quenched with 1N hydrochloric acid (50 mL). Methanol was removed from the mixture in vacuo. Remaining aqueous was basified with sodium bicarbonate. Aqueous was extracted with ethyl acetate (2×50 mL). Combined extracts were washed with water (30 mL) and brine (20 mL). Organic was dried (magnesium sulfate), filtered and concentrated. Residue was dissolved in 1:1 ethyl acetate:hexanes (50 mL). 1N hydrochloric acid in 1,4 dioxane (1.4 mL), was added to the mixture dropwise causing a precipitate to form. Mixture was stirred at room temperature for 1 hour. Solids were filtered, washed with 1:1 ethyl acetate:hexanes, then dried in vacuo. Product was obtained in 61% yield as a tan solid. $^1$H NMR (300 MHz, DMSO-D$_6$): δ=8.67 (s, 1H), 7.49 (s, 2H), 7.22 (m, 5H), 4.99 (m, 4H), 4.50 (m, 1H), 3.73 (s, 3H), 3.41 (m, 1H), 3.13 (dd, J1=9.9, J2=13.9, 1H). MS m/e (M+H)⁺=384.0.

Intermediate 17

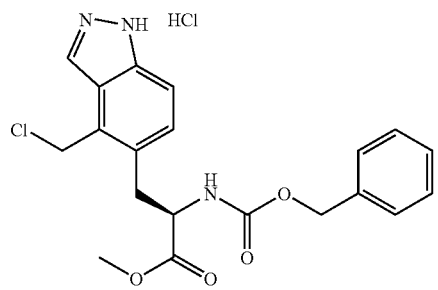

2-(R)-Benzyloxycarbonylamino-3-(4-chloromethyl-1H-indazol-5-yl)-propionic acid methyl ester hydrochloride. 2-(R)-Benzyloxycarbonylamino-3-(4-tert-butoxycarbonylamino-2-hydroxymethyl-3-methyl-phenyl)-propionic acid methyl ester hydrochloride was reacted in a manner analogous to the preparation of 2-(S)-(4-chloromethyl-1H-indazol-5-ylmethyl)-succinic acid dimethyl ester hydrochloride. Title compound was obtained as an orange solid in 99% yield. $^1$H NMR (300 MHz, CD$_3$OD): δ=8.43 (s, 1H), 7.50 (d, J=8.8, 1H), 7.38 (d, J=8.4, 1H), 7.24 (m, 5H), 5.06 (d, J=11.0, 1H), 4.98 (d, J=4.8, 2H), 4.56 (dd, J1=5.7, J2=9.3, 1H), 3.71 (s, 3H), 3.42 (dd, J1=5.5, J2=14.3, 1H), 3.17 (dd, J1=9.3, J2=14.1, 1H). MS m/e (M+H)⁺=402.0.

Intermediate 18

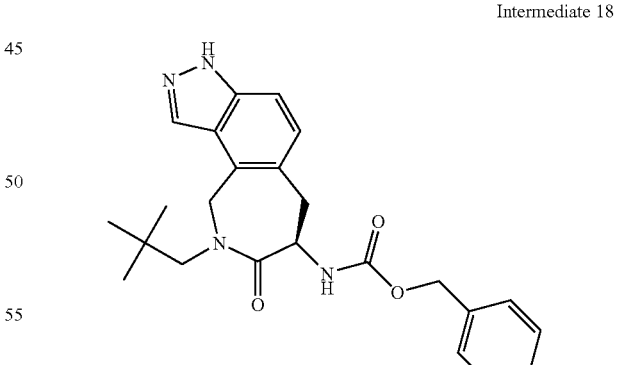

[9-(2,2-Dimethyl-propyl)-8-oxo-3,6,7,8,9,10-hexahydro-2,3,9-triaza-(R)-cyclohepta[e]inden-7-yl]-carbamic acid benzyl ester. Neopentylamine (600 μL, 4.5 mmol) and 2-(R)-benzyloxycarbonylamino-3-(4-chloromethyl-1H-indazol-5-yl)-propionic acid methyl ester hydrochloride were reacted in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Silica gel chromatography afforded the title compound as a lightly colored oil in 88% yield. $^1$H NMR (300 MHz, CDCl$_3$): δ=7.97 (d, J=2.9, 1H), 7.38 (d, J=4.0, 3H), 7.31 (m, 3H), 7.06 (dd, J1=3.7, J2=8.8, 6.32 (d, J=6.3, 1H), 5.24 (m, 2H), 5.15 (s, 2H), 4.42 (dd, J1=5.5, J2=17.2, 1H), 3.56 (d, J=13.9, 1H), 3.45 (d, J=16.5, 1H), 3.07 (m, 2H), 0.82 (s, 9H). (M+H)$^+$=421.0.

Intermediate 19

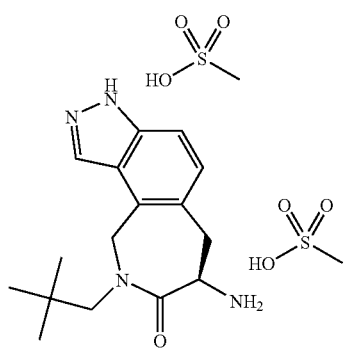

7-(R)-Amino-9-(2,2-dimethyl-propyl)-6,7,9,10-tetrahydro-3H-2,3,9-triaza-cyclohepta[e]inden-8-one bismethanesulfonate. Methanesulfonic acid (1 mL) was added to a solution of [9-(2,2-dimethyl-propyl)-8-oxo-3,6,7,8,9,10-hexahydro-2,3,9-triaza-(R)-cyclohepta[e]inden-7-yl]-carbamic acid benzyl ester (145 mg, 0.34 mmol) and anisole (100 μL, 0.92 mmol) in dichloromethane (4 mL). Reaction mixture was stirred at room temperature for 2.5 hours. Mixture was diluted with diethyl ether (25 mL). Mixture was allowed to stand at room temperature for 30 minutes. Solvents were decanted off. Remaining residue was washed with diethyl ether (25 mL) then dried in vacuo. Crude product was obtained as an orange oil in quantitative yield, and was used without further purification. $^1$H NMR (300 MHz, CD$_3$OD): δ=8.50 (s, 1H), 7.56 (d, J=8.8, 1H), 7.39 (s, J=8.8, 1H), 5.42 (d, J=17.9, 1H), 5.10 (dd, J1=4.4, J2=12.4, 1H), 4.75 (d, J=17.6, 1H), 3.84 (d, J=13.5, 1H), 3.42 (m, 3H), 3.10 (d, J=13.9, 1H), 2.71 (s, 6H), 0.82 (s, 9H). (M+H)$^+$=287.1.

Intermediate 20

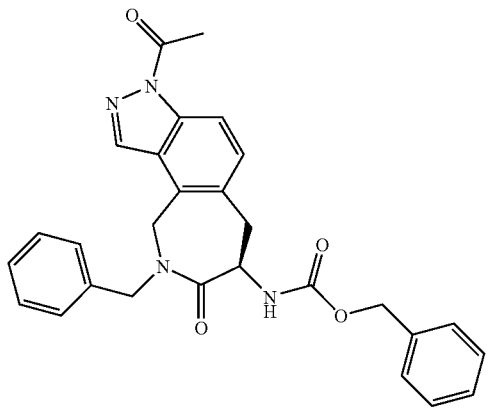

(3-Acetyl-9-benzyl-8-oxo-3,6,7,8,9,10-hexahydro-2,3,9-triaza-(R)-cyclohepta[e]inden-7-yl)-carbamic acid benzyl ester. Benzylamine (53 μL, 0.49 mmol) was added to a mixture of 2-(R)-benzyloxycarbonylamino-3-(4-chloromethyl-1H-indazol-5-yl)-propionic acid methyl ester (125 mg, 0.31 mmol) and potassium carbonate (50 mg, 0.36 mmol) in acetonitrile (5 mL). Reaction was heated at reflux for 1 hour. Mixture was cooled to room temperature then filtered. Filtrate was concentrated. Residue was dissolved in a mixture of toluene (5 mL) and acetic acid (50 μL). Mixture was heated at reflux for 2 hours. Mixture was cooled to room temperature. Acetic anhydride (500 μL) was added to the mixture. Reaction was stirred at room temperature for 2 hours. Mixture was diluted with ethyl acetate (20 mL). Mixture was washed successively with water (15 mL), 1N hydrochloric acid (2×10 mL), and brine (10 mL). Organic was dried (magnesium sulfate), filtered and concentrated. Silica gel chromatography (ethyl acetate-hexanes) yielded the title compound in 43% yield as an amber oil. $^1$H NMR (300 MHz, CDCl$_3$): δ=8.33 (s, 1H), 7.47 (d, J=8.8, 1H), 7.33 (m, 5H), 7.17 (m, 5H), 7.02 (d, J=9.2, 1H), 6.28 (d, J=6.6, 1H), 5.34 (m, 1H), 5.16 (s, 2H), 5.00 (m, 1H), 4.84 (m, 1H), 5.43 (t, J=14.5, 1H), 4.43 (d, J=5.9, 1H), 4.32 (d, J=16.8, 1h), 4.11 (m, 1H), 2.02 (s, 3H). MS m/e (M+H)$^+$=483.2.

Intermediate 21

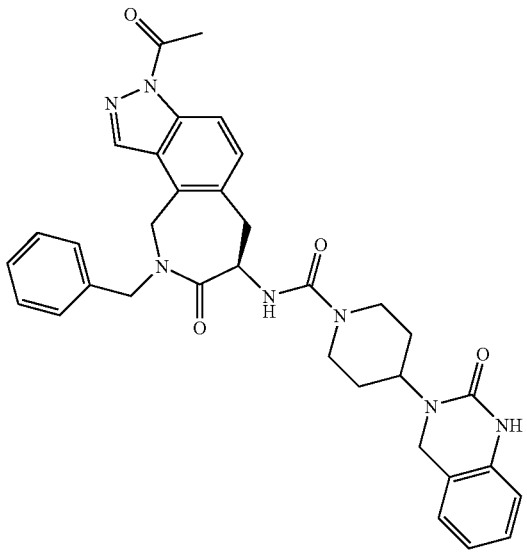

4-(2-Oxo-1,4-dihydro-2H-quinazolin-3-yl)-piperidine-1-carboxylic acid (3-acetyl-9-benzyl-8-oxo-3,6,7,8,9,10-hexahydro-2,3,9-triaza-(R)-cyclohepta[e]inden-7-yl)-amide. A catalytic amount of 10% palladium on carbon was added to a mixture of acetic acid (200 μL) and (3-acetyl-9-benzyl-8-oxo-3,6,7,8,9,10-hexahydro-2,3,9-triaza-(R)-cyclohepta[e]inden-7-yl)-carbamic acid benzyl ester (65 mg, 0.13 mmol) in methanol (10 mL). Reaction vessel was charged with 50 psi of hydrogen gas and placed on a Parr hydrogenation apparatus. Reaction mixture was shaken at room temperature for 2 hours. Mixture was filtered. Filtrate was concentrated. Residue was partitioned between dichloromethane (10 mL) and saturated aqueous sodium bicarbonate (5 mL). 20% phosgene in toluene (170 μL, 0.32 mmol) was added to the mixture with vigorous stirring. 4-(2-Oxo-1,4-dihydro-2H-quinazolin-3-yl)piperidinium acetate (110 mg, 0.38 mmol) was added to the mixture. Reaction mixture was stirred vigorously for 45 minutes. Layers were separated.

Organic was washed with brine (10 mL) then dried (magnesium sulfate) and concentrated in vacuo. Preparatory reverse phase HPLC (acetonitrile—water, 0.2% trifluoroacetic acid) followed by removal of the acetonitrile in vacuo yielded an aqueous solution containing the title compound. Extracted from the aqueous solution with dichloromethane (20 mL). Combined extracts were washed with brine (20 mL). Organic was dried (magnesium sulfate), filtered and concentrated. Desired product was obtained as a white solid in 23% yield. MS m/e (M+H)$^+$=606.4. rf=2.09 min.

Intermediate 22

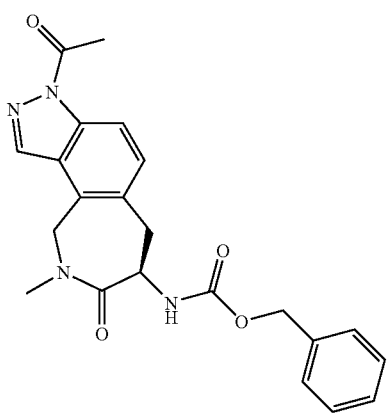

(3-Acetyl-9-methyl-8-oxo-3,6,7,8,9,10-hexahydro-2,3,9-triaza-(R)-cyclohepta[e]inden-7-yl)-carbamic acid benzyl ester. Methylamine solution in methanol (2M, 2 mL, 4 mmol) was added to a mixture of potassium carbonate (130 mg, 0.94 mmol) and 2-(R)-benzyloxycarbonylamino-3-(4-chloromethyl-1H-indazol-5-yl)-propionic acid methyl ester (165 mg, 0.41 mmol) in acetonitrile (5 mL). Mixture was heated at 40° C. for 1 hour. Mixture was cooled to room temperature. Mixture was filtered. Filtrate was concentrated. Residue was treated with a mixture of toluene (5 mL) and acetic acid (200 µL). Mixture was heated at reflux for 45 minutes. Mixture was cooled to room temperature then acetic anhydride was added (2 mL). Reaction was stirred at room temperature for 16 hours. Mixture was diluted with ethyl acetate (10 mL) then washed successively with water (10 mL), saturated aqueous sodium bicarbonate (2×15 mL) and brine (10 mL). Organic was dried (magnesium sulfate), filtered and concentrated. Silica gel chromatography (ethyl Acetate-hexanes) yielded the desired product as a yellow solid in 18% yield. $^1$H NMR (300 MHz, CDCl$_3$): δ=8.70 (s, 1H), 7.51 (d, J=9.2, 1H), 7.34 (m, 5H), 7.05 (d, J=9.2, 1H), 6.19 (m, 1H), 5.23 (s, 2H), 5.13 (s, 2H), 4.18 (d, J=17.2, 1H), 3.46 (d, J=17.2, 1H), 3.11 (s, 3H), 2.95 (m, 1H), 2.89 (s, 3H). MS m/e (M+H)$^+$=407.2.

Intermediate 23

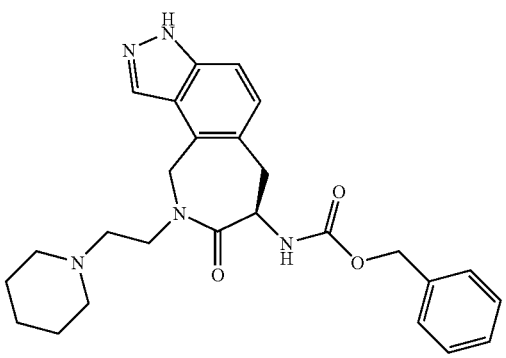

[8-Oxo-9-(2-piperidin-1-yl-ethyl)-3,6,7,8,9,10-hexahydro-2,3,9-triaza-(R)-cyclohepta[e]inden-7-yl]-carbamic acid benzyl ester. 1-(2-Aminoethyl)piperidine (150 µL, 1.1 mmol) was added to a mixture of potassium carbonate (150 mg, 1.1 mmol) and 2-(R)-benzyloxycarbonylamino-3-(4-chloromethyl-1H-indazol-5-yl)-propionic acid methyl ester hydrochloride (220 mg, 0.50 mmol) in acetonitrile (5 mL). Reaction was heated at reflux for 1 hour. Mixture was cooled to room temperature then concentrated. Residue was dissolved in a mixture of dichloromethane (10 mL) and acetic acid (200 µL). Mixture was heated at 40° C. for 32 hours and heated at reflux for 8 hours. Mixture was cooled to room temperature then washed successively with saturated aqueous sodium bicarbonate (2×10 mL), water (10 mL) and brine (10 mL). Organic was dried (magnesium sulfate), filtered and concentrated. Crude product was obtained as a maroon solid in 86% yield. Material was carried forward without further purification. MS m/e (M+H)$^+$=462.4. HPLC rf=1.19 min.

Intermediate 24

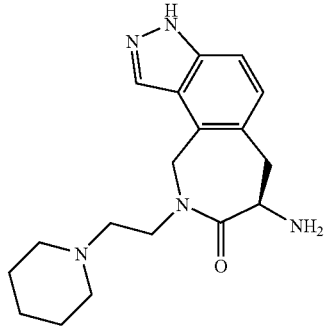

7-(R)-Amino-9-(2-piperidin-1-yl-ethyl)-6,7,9,10-tetrahydro-3H-2,3,9-triaza-cyclohepta[e]inden-8-one. Methanesulfonic acid (1 mL) was added to a mixture of anisole (100 µL, 0.92 mmol) and [8-oxo-9-(2-piperidin-1-yl-ethyl)-3,6,7,8,9,10-hexahydro-2,3,9-triaza-(R)-cyclohepta[e]inden-7-yl]-carbamic acid benzyl ester (200 mg, 0.43 mmol) in dichloromethane (4 mL). Reaction was stirred at ambient temperature for 1 hour. Mixture was diluted with diethyl ether (30 mL). Mixture was allowed to stand at room temperature for 15 minutes. Solvents were decanted off. Remaining residue was dissolved in water (5 mL). Mixture was washed with diethyl ether (2×10 mL). Aqueous was basified with 1N sodium hydroxide (2 mL). Mixture was extracted with ethyl acetate (2×15 mL). Combined extracts were washed with brine (5 mL). Organic was dried (magnesium sulfate), filtered and concentrated. Title compound was obtained as an amber oil in 42% yield. Material was carried forward without further purification. $^1$H NMR (300 MHz, CDCl$_3$): δ=8.06 (S, 1H), 7.35 (d, J=8.4, 1H), 7.11 (d, J=8.4, 1H), 5.16 (d, J=16.8, 1H), 4.57 (d, J=16.8, 1H), 4.40 (dd, J1=12.8, J2=4.4, 1H), 3.77 (m, 1H), 3.54 (m, 1H), 3.29 (m, 1H), 3.03 (m, 1H), 2.36 (m, 6H), 2.14 (m, 2H), 1.38 (m, 4H). MS m/e (M+H)$^+$=328.3.

Intermediate 25

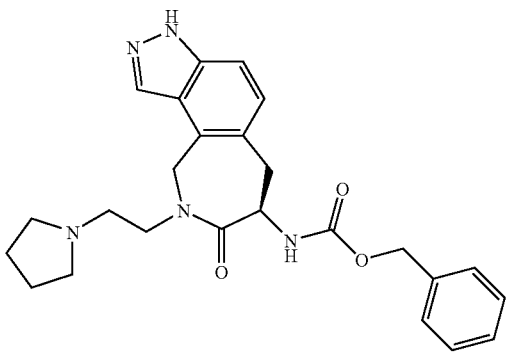

[8-Oxo-9-(2-pyrrolidin-1-yl-ethyl)-3,6,7,8,9,10-hexahydro-2,3,9-triaza-(R)-cyclohepta[e]inden-7-yl]-carbamic acid benzyl ester. 1-(2-Aminoethyl)pyrrolidine (90 µL, 0.71 mmol) was added to a mixture of 2-(R)-benzyloxycarbonylamino-3-(4-chloromethyl-1H-indazol-5-yl)-propionic acid methyl ester (100 mg, 0.23 mmol) and potassium carbonate (120 mg, 0.87 mmol) in acetonitrile (5 mL). Reaction was heated at reflux until HPLC suggested the starting material had been consumed (2 hours). Mixture was cooled to room temperature then filtered. Acetic acid (200 µL) was added to the filtrate. Reaction was heated at reflux until judged complete by HPLC (1 hour). Mixture was diluted with ethyl acetate (20 mL) then washed successively with saturated aqueous sodium bicarbonate (15 mL), water (10 mL) and brine (10 mL). Organic was dried (magnesium sulfate), filtered and concentrated. Crude product was obtained in 69% yield as a yellow oil. Material was carried forward without further purification. $^1$H NMR (300 MHz, CDCl$_3$): δ=8.04 (s, 1), 7.38 (m, 5H), 7.28 (d, J=8.4, 1H), 7.02 (d, J=8.8, 1H), 6.25 (d, J=6.2, 1H), 5.25 (m, 1H), 5.15 (s, 2H), 4.56 (d, J=16.8, 1H), 3.70 (m, 2H), 3.47 (dd, J1=3.5, J2=16.7, 1H), 3.01 (m, 1H), 2.62 (m, 2H), 2.48 (m, 3H), 1.74 (m, 4H). MS m/e (M+H)$^+$=448.4.

Intermediate 26

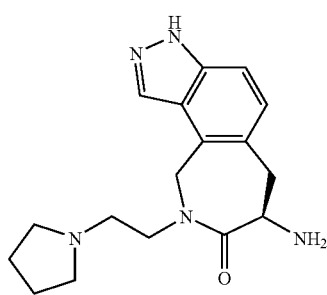

7-(R)-Amino-9-(2-pyrrolidin-1-yl-ethyl)-6,7,9,10-tetrahydro-3H-2,3,9-triaza-cyclohepta[e]inden-8-one. Title compound was obtained from [8-oxo-9-(2-pyrrolidin-1-yl-ethyl)-3,6,7,8,9,10-hexahydro-2,3,9-triaza-(R)-cyclohepta[e]inden-7-yl]-carbamic acid benzyl ester following a procedure analogous to the preparation of 7-(R)-amino-9-(2-piperidin-1-yl-ethyl)-6,7,9,10-tetrahydro-3H-2,3,9-triaza-cyclohepta[e]inden-8-one. Material was obtained as an amber oil in 52% yield and used without further purification. $^1$H NMR (300 MHz, DMSO-D$_6$): δ=8.06 (s, 1H), 7.33 (d, J=8.8, 1H), 7.10 (d, J=8.8, 1H), 5.16 (d, J=16.8, 1H), 5.48 (d, J=16.8, 1H), 4.40 (dd, J1=13.0, J2=4.2, 1H), 3.67 (m, 2H), 3.29 (dd, J1=3.11, J2=17.0, 1H), 3.01 (dd, J1=16.8, J2=12.8, 1H), 2.58 (m, 2H) m 1.87 (m, 4H), 1.67 (m, 4H). MS m/e (M+H)$^+$=422.4.

Intermediate 27

[9-(2-Dimethylamino-ethyl)-8-oxo-3,6,7,8,9,10-hexahydro-2,3,9-triaza-(R)-cyclohepta[e]inden-7-yl]-carbamic acid benzyl ester. N,N-Ethylenediamine (70 µL, 0.66 mmol) and 2-(R)-benzyloxycarbonylamino-3-(4-chloromethyl-1H-indazol-5-yl)-propionic acid methyl ester (100 mg, 0.23 mmol) were converted to the title compound following a procedure analogous to the preparation of [8-oxo-9-(2-pyrrolidin-1-yl-ethyl)-3,6,7,8,9,10-hexahydro-2,3,9-triaza-(R)-cyclohepta[e]inden-7-yl]-carbamic acid benzyl ester. Crude product was obtained as an amber oil in 52% yield. Material was carried forward without further purification. $^1$H NMR (300 MHz, CDCl$_3$): δ=7.99 (s, 1H), 7.36 (m, 6H), 6.27 (d, J=6.2, 1H), 5.25 (m, 1H), 5.16 (s, 2H), 5.13 (m, 1H), 5.06 (d, J=18.7, 1H), 4.52 (d, J=17.2, 1H), 3.61 (t, J=6.8, 2H), 3.45 (dd, J1=2.4, J2=16.7, 1H), 3.01 (m, 1H), 2.38 (m, 2H), 2.11 (s, 6H). MS m/e (M+H)$^+$=422.4.

Intermediate 28

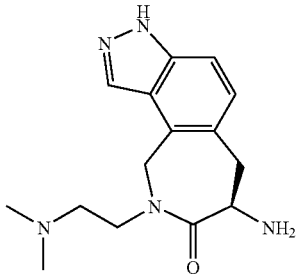

7-(R)-Amino-9-(2-dimethylamino-ethyl)-6,7,9,10-tetrahydro-3H-2,3,9-triaza-cyclohepta[e]inden-8-one. [9-(2-Dimethylamino-ethyl)-8-oxo-3,6,7,8,9,10-hexahydro-2,3,9-triaza-(R)-cyclohepta[e]inden-7-yl]-carbamic acid benzyl ester (65 mg, 0.15 mmol) was converted to the desired product in a manner analogous to the preparation of 7-(R)-amino-9-(2-pyrrolidin-1-yl-ethyl)-6,7,9,10-tetrahydro-3H-2,3,9-triaza-cyclohepta[e]inden-8-one. Crude material was obtained as a yellow oil in 25% yield. Material was carried forward without further purification. $^1$H NMR (300 MHz, CDCl$_3$): δ=8.07 (s, 1H), 7.35 (d, J=8.4, 1H), 7.12 (d, J=8.4, 1H), 5.15 (d, J=16.8, 1H), 4.58 (d, J=16.8, 1H), 4.42 (dd, J1=4.8, J2=12.8, 1H), 3.62 (m, 2H), 3.30 (m, 1H), 3.01 (dd, J1=13.0, J2=16.7, 1H), 2.37 (m, 2H), 2.15 (s, 6H). MS m/e (M+H)$^+$=288.3.

Intermediate 29

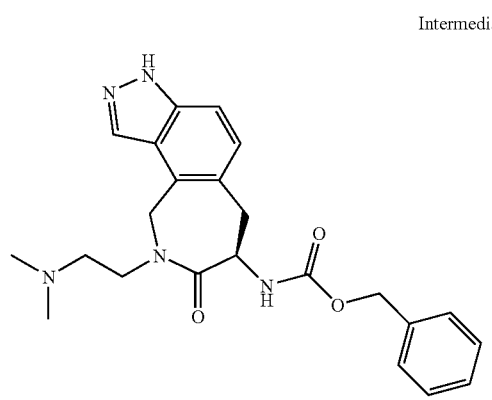

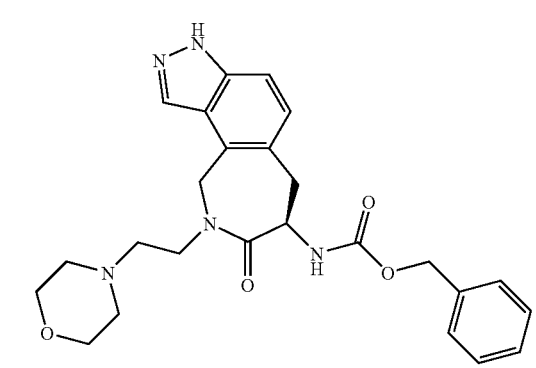

[9-(2-Morpholin-4-yl-ethyl)-8-oxo-3,6,7,8,9,10-hexahydro-2,3,9-triaza-(R)-cyclohepta[e]inden-7-yl]-carbamic acid benzyl ester. 4-(2-Aminoethyl)morpholine (90 µL, 0.69 mmol) and 2-(R)-benzyloxycarbonylamino-3-(4-chloromethyl-1H-indazol-5-yl)-propionic acid methyl ester (100 mg, 0.23 mmol) were converted into the title compound following a procedure analogous to the preparation of [8-oxo-9-(2-piperidin-1-yl-ethyl)-3,6,7,8,9,10-hexahydro-2,3,9-triaza-(R)-cyclohepta[e]inden-7-yl]-carbamic acid benzyl ester. Crude material was obtained as an amber oil in 92% yield. Product was carried forward without further purification. MS m/e (M+H)$^+$=464.4. HPLC rf=1.15 min.

Intermediate 30

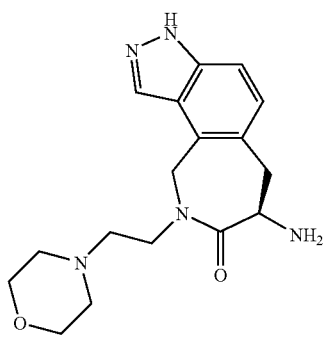

7-(R)-Amino-9-(2-morpholin-4-yl-ethyl)-6,7,9,10-tetrahydro-3H-2,3,9-triaza-cyclohepta[e]inden-8-one. [9-(2-Morpholin-4-yl-ethyl)-8-oxo-3,6,7,8,9,10-hexahydro-2,3,9-triaza-(R)-cyclohepta[e]inden-7-yl]-carbamic acid benzyl ester (95 mg, 0.20 mmol) was converted into the title compound following a procedure analogous to the preparation of 7-(R)-amino-9-(2-piperidin-1-yl-ethyl)-6,7,9,10-tetrahydro-3H-2,3,9-triaza-cyclohepta[e]inden-8-one. Crude product was obtained as an amber oil in 62% yield. Material was carried forward without further purification. $^1$H NMR (300 MHz, CDCl$_3$): δ=8.06 (s, 1H), 7.34 (d, J=8.4, 1H), 7.15 (d, J=8.8, 1H), 5.22 (d, J=16.8, 1H), 4.51 (d, J=17.2, 2H), 4.44 (m, 1H), 4.02 (m, 1H), 3.40 (t, J=4.8, 4H), 3.31 (m, 3H), 3.07 (m, 1H), 2.32 (m, 4H), 1.95 (m, 2H). MS m/e (M+H)$^+$=330.3.

Intermediate 31

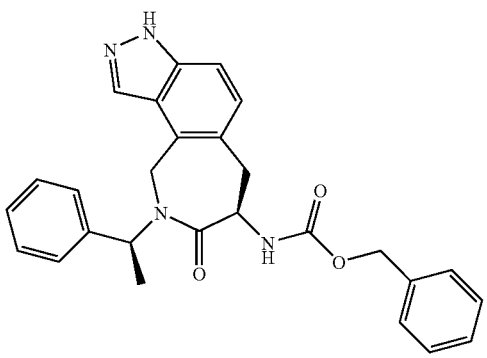

[8-Oxo-9-(1-(S)-phenyl-ethyl)-3,6,7,8,9,10-hexahydro-2,3,9-triaza-(R)-cyclohepta[e]inden-7-yl]-carbamic acid benzyl ester. (S)-(−)-α-Methylbenzylamine (85 µL, 0.67 mmol) and 2-(R)-benzyloxycarbonylamino-3-(4-chloromethyl-1H-indazol-5-yl)-propionic acid methyl ester (100 mg, 0.23 mmol) were converted into the desired product following a procedure analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude product was obtained as a dark oil in quantitative yield. Material was carried forward without further purification. MS m/e (M+H)$^+$=455.3. HPLC rf=1.68 min.

Intermediate 32

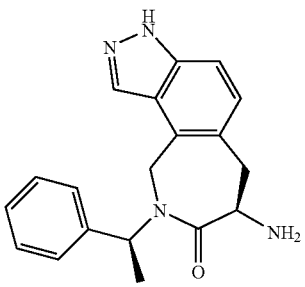

7-Amino-9-(1-(S)-phenyl-ethyl)-6,7,9,10-tetrahydro-3H-2,3,9-triaza-(R)-cyclohepta[e]inden-8-one. [8-Oxo-9-(1-(S)-phenyl-ethyl)-3,6,7,8,9,10-hexahydro-2,3,9-triaza-(R)-cyclohepta[e]inden-7-yl]-carbamic acid benzyl ester (105 mg, 0.23 mmol) was reacted in a manner analogous to the preparation of 7-(R)-amino-9-(2-piperidin-1-yl-ethyl)-6,7,9,10-tetrahydro-3H-2,3,9-triaza-cyclohepta[e]inden-8-one. Crude product was obtained as a dark oil in 82% yield. Material was carried forward without further purification. MS m/e (M−H)$^−$=319.3. HPLC rf=1.49 min.

Intermediate 33

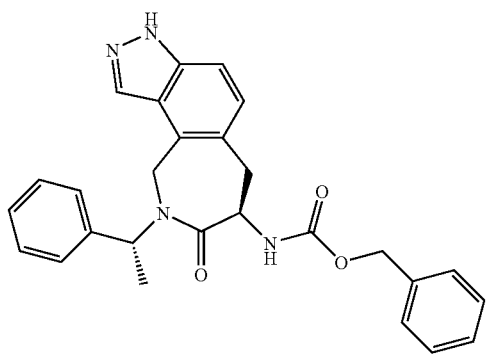

[8-Oxo-9-(1-(R)-phenyl-ethyl)-3,6,7,8,9,10-hexahydro-2,3,9-triaza-(R)-cyclohepta[e]inden-7-yl]-carbamic acid benzyl ester. (R)-(+)-α-Methylbenzylamine (85 µL, 0.67 mmol) and 2-(R)-benzyloxycarbonylamino-3-(4-chloromethyl-1H-indazol-5-yl)-propionic acid methyl ester (100 mg, 0.23 mmol) were converted into the title compound in a manner similar to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude material was obtained as a dark foam in quantitative yield. Material was carried forward without further purification. MS m/e (M−H)$^−$=453.4. HPLC rf=1.98 min.

Intermediate 34

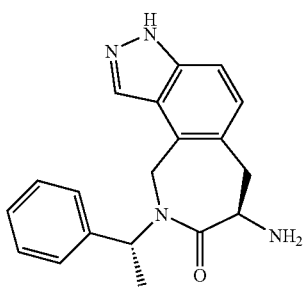

Intermediate 36

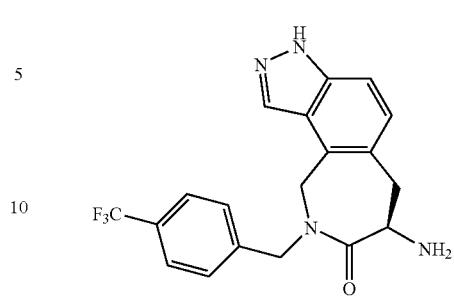

7-Amino-9-(1-(R)-phenyl-ethyl)-6,7,9,10-tetrahydro-3H-2,3,9-triaza-(R)-cyclohepta[e]inden-8-one. [8-Oxo-9-(1-(R)-phenyl-ethyl)-3,6,7,8,9,10-hexahydro-2,3,9-triaza-(R)-cyclohepta[e]inden-7-yl]-carbamic acid benzyl ester (105 mg, 0.23 mmol) was reacted in a manner analogous to the preparation of 7-(R)-amino-9-(2-piperidin-1-yl-ethyl)-6,7,9,10-tetrahydro-3H-2,3,9-triaza-cyclohepta[e]inden-8-one. Crude product was obtained as a maroon solid in 78% yield. Material was carried forward without further purification. $^1$H NMR (300 MHz, CDCl$_3$): δ=7.88 (s, 1H), 7.40 (m, 6H), 7.14 (d, J=8.8, 1H), 6.85 (m, 1H), 6.09 (m, 1H), 4.67 (d, J=16.8, 1H), 4.47 (dd, J1=4.6, J2=12.6, 1H), 4.25 (d, J=17.2, 1H), 1.48 (d, J=7.0, 3H). MS m/e (M−H)$^−$=319.3.

7-Amino-9-(4-trifluoromethyl-benzyl)-6,7,9,10-tetrahydro-3H-2,3,9-triaza-(R)-cyclohepta[e]inden-8-one bismethanesulfonate. [8-Oxo-9-(4-trifluoromethyl-benzyl)-3,6,7,8,9,10-hexahydro-2,3,9-triaza-(R)-cyclohepta[e]inden-7-yl]-carbamic acid benzyl ester was converted into the title compound in a manner analogous to the preparation of 7-(R)-amino-9-(2,2-dimethyl-propyl)-6,7,9,10-tetrahydro-3H-2,3,9-triaza-cyclohepta[e]inden-8-one bismethanesulfonate. Crude material was obtained as a dark foam in quantitative yield. Material was carried forward without further purification. MS m/e (M+H)$^+$=375.2. HPLC rf=1.00 min.

Intermediate 37

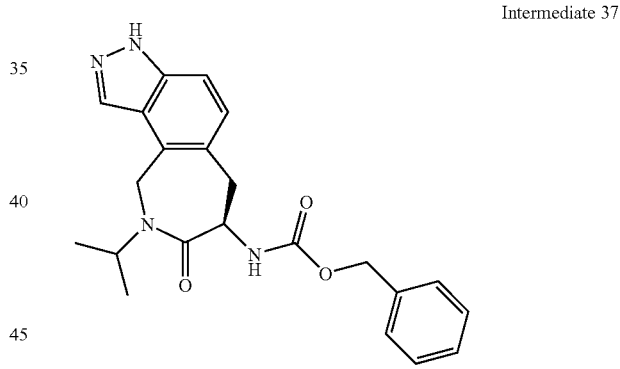

Intermediate 35

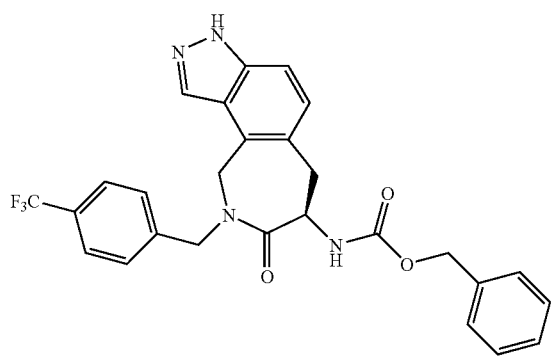

[8-Oxo-9-(4-trifluoromethyl-benzyl)-3,6,7,8,9,10-hexahydro-2,3,9-triaza-(R)-cyclohepta[e]inden-7-yl]-carbamic acid benzyl ester. 4-Trifluoromethylbenzylamine (72 μL, 0.51 mmol) and 2-(R)-benzyloxycarbonylamino-3-(4-chloromethyl-1H-indazol-5-yl)-propionic acid methyl ester (100 mg, 0.23 mmol) were converted into the title compound in a manner similar to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude material was obtained as a dark brown solid in quantitative yield. Material was carried forward without further purification. MS m/e (M+H)$^+$=509.4. HPLC rf=1.67 min.

(9-Isopropyl-8-oxo-3,6,7,8,9,10-hexahydro-2,3,9-triaza-(R)-cyclohepta[e]inden-7-yl)-carbamic acid benzyl ester. Isopropylamine (300 μL, 3.5 mmol) and 2-(R)-benzyloxycarbonylamino-3-(4-chloromethyl-1H-indazol-5-yl)-propionic acid methyl ester were converted into the title compound following a procedure analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude product was obtained as a dark oil in quantitative yield. Material was carried forward without further purification. $^1$H NMR (500 MHz, CDCl$_3$): δ=8.09 (s, 1H), 7.39 (m, 3H), 7.23 (m, 2H), 7.17 (m, 1H), 6.32 (d, J=5.8, 1H), 5.25 (m, 1H), 5.15 (m, 2H), 4.90 (m, 1H), 4.82 (d, J=17.4, 1H), 4.51 (m, 1H), 3.51 (m, 1H), 3.05 (t, J=13.6, 1H), 1.56 (s, 6H). MS m/e (M+H)$^+$=393.4.

Intermediate 38

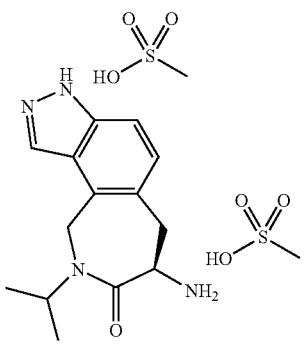

7-(R)-Amino-9-isopropyl-6,7,9,10-tetrahydro-3H-2,3,9-triaza-cyclohepta[e]inden-8-one bismethanesulfonate. (9-Isopropyl-8-oxo-3,6,7,8,9,10-hexahydro-2,3,9-triaza-(R)-cyclohepta[e]inden-7-yl)-carbamic acid benzyl ester (90 mg, 0.23 mmol) was converted into the title compound following a procedure analogous to the synthesis of 7-(R)-amino-9-(2,2-dimethyl-propyl)-6,7,9,10-tetrahydro-3H-2,3,9-triaza-cyclohepta[e]inden-8-one bismethanesulfonate. Crude product was obtained as a dark oil in quantitative yield. Crude material was carried forward without further purification. MS m/e (M+H)$^+$=259.2. HPLC rf=0.60 min.

Intermediate 39

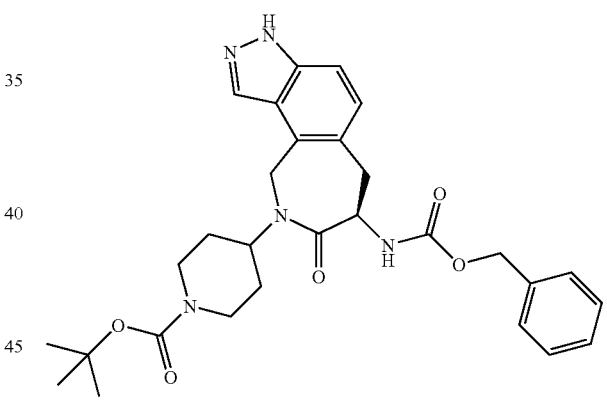

[9-(3,3-Dimethyl-butyl)-8-oxo-3,6,7,8,9,10-hexahydro-2,3,9-triaza-(R)-cyclohepta[e]inden-7-yl]-carbamic acid benzyl ester. 3,3-Dimethylbutylamine (100 μL, 0.74 mmol) and 2-(R)-benzyloxycarbonylamino-3-(4-chloromethyl-1H-indazol-5-yl)-propionic acid methyl ester were converted into the title compound following a procedure analogous to the preparation of [8-oxo-9-(2-piperidin-1-yl-ethyl)-3,6,7,8,9,10-hexahydro-2,3,9-triaza-(R)-cyclohepta[e]inden-7-yl]-carbamic acid benzyl ester. Crude material was obtained as a dark oil in quantitative yield. Material was carried forward without further purification. $^1$H NMR (300 MHz, CDCl$_3$): δ=8.03 (m, 1H), 4.38 (m, 4H), 7.31 (m, 2H), 7.06 (d, J=8.4, 1H), 6.26 (d, J=6.2, 1H), 5.23 (m, 1H), 5.14 (s, 2H), 5.08 (m, 1H), 4.35 (dd, J1=8.8, J2=17.2, 1H), 3.50 (m, 2H), 1.33 (dd, J1=6.2, J2=11.0, 2H), 0.91 (m, 2H), 0.85 (s, 9H). MS m/e (M+H)$^+$=435.1.

Intermediate 40

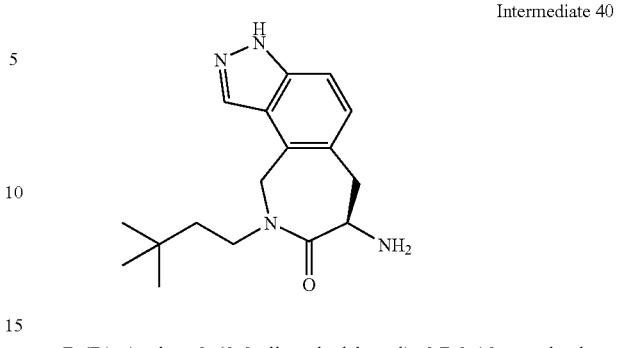

7-(R)-Amino-9-(3,3-dimethyl-butyl)-6,7,9,10-tetrahydro-3H-2,3,9-triaza-cyclohepta[e]inden-8-one bismethanesulfonate. [9-(3,3-Dimethyl-butyl)-8-oxo-3,6,7,8,9,10-hexahydro-2,3,9-triaza-(R)-cyclohepta[e]inden-7-yl]-carbamic acid benzyl ester (100 mg, 0.23 mmol) was converted into the title compound following a procedure analogous to the preparation of 7-(R)-amino-9-(2,2-dimethyl-propyl)-6,7,9,10-tetrahydro-3H-2,3,9-triaza-cyclohepta[e]inden-8-one bismethanesulfonate. Crude material was obtained as a dark oil in quantitative yield. Material was carried forward without further purification. MS m/e (M+H)$^+$=301.2. HPLC rf=1.11 min.

Intermediate 41

4-(7-(R)-Benzyloxycarbonylamino-8-oxo-6,7,8,10-tetrahydro-3H-2,3,9-triaza-cyclohepta[e]inden-9-yl)-piperidine-1-carboxylic acid tert-butyl ester. 4-Amino-1-N-Boc-piperidine (110 mg, 0.55 mmol) and 2-(R)-benzyloxycarbonylamino-3-(4-chloromethyl-1H-indazol-5-yl)-propionic acid methyl ester (150 mg, 0.34 mmol) was converted into the title compound in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Crude product was obtained as a dark foam in quantitative yield. Material was carried forward without further purification. $^1$H NMR (300 MHz, CDCl$_3$): δ=8.05 (m, 1H), 7.35 (m, 6H), 7.15 (m, 1H), 6.27 (m, 1H), 5.28 (m, 1H), 5.15 (s, 2H), 4.87 (d, J=16.5, 1H), 4.63 (m, 1H), 4.47 (m, 1H), 4.24 (m, 1H), 3.99 (m, 1H), 3.49 (m, 1H), 3.04 (m, 1H), 2.83 (m, 2H), 2.63 (m, 1H), 1.90 (m, 1H), 1.74 (m, 2H), 1.58 (s, 9H). MS m/e (M−H)$^-$=532.1.

Intermediate 42

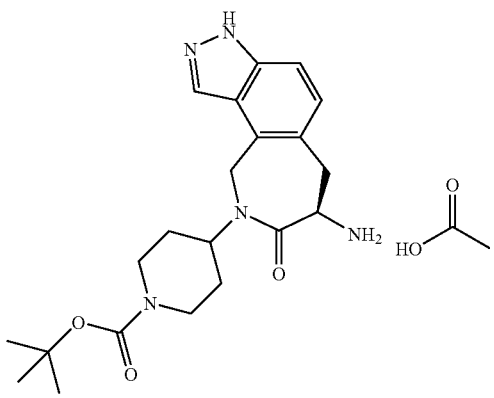

4-(7-(R)-Amino-8-oxo-6,7,8,10-tetrahydro-3H-2,3,9-triaza-cyclohepta[e]inden-9-yl)-piperidine-1-carboxylic acid tert-butyl ester acetate. A catalytic amount of 10% palladium on carbon was added to a solution of 4-(7-(R)-Benzyloxycarbonylamino-8-oxo-6,7,8,10-tetrahydro-3H-2,3,9-triaza-cyclohepta[e]inden-9-yl)-piperidine-1-carboxylic acid tert-butyl ester (200 mg, 0.37 mmol) and acetic acid (100 μL, 1.7 mmol) in methanol (10 mL). Reaction vessel was placed on a Parr apparatus and charged with 30 psi of hydrogen gas. Mixture was allowed to shake at room temperature for 3 hours. Mixture was filtered. Filtrate was concentrated in vacuo. Crude compound was obtained as a dark oil in quantitative yield. Material was carried forward without further purification. $^1$H NMR (300 MHz, CDCl$_3$): δ=8.06 (s, 1H), 7.36 (d, J=8.8, 1H), 7.12 (d, J=8.8, 1H), 4.92 (d, J=17.6, 1H), 4.67 (m, 1H), 4.49 (d, J=17.2, 1H), 4.26 (m, 1H), 3.98 (m, 2H), 3.05 (m, 1H), 2.83 (m, 2H), 2.64 (m, 1H), 1.89 (m, 1H), 1.73 (m, 1H), 1.45 (d, J=2.9, 9H), 1.25 (m, 2H). MS m/e (M−C$_4$H8+H)$^+$=344.2.

Intermediate 43

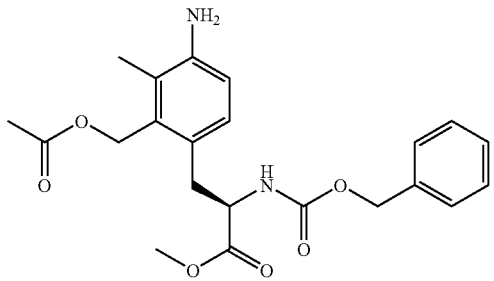

3-(2-Acetoxymethyl-4-amino-3-methyl-phenyl)-2-(R)-benzyloxycarbonylamino-propionic acid methyl ester. 3-(2-Acetoxymethyl-4-tert-butoxycarbonylamino-3-methyl-phenyl)-2-(R)-benzyloxycarbonylamino-propionic acid methyl ester was converted into 3-(2-Acetoxymethyl-4-amino-3-methyl-phenyl)-2-benzyloxycarbonylamino-(R)-propionic acid methyl ester following an analogous procedure to the synthesis of 2-(2-Acetoxymethyl-4-amino-3-methyl-benzyl)-(S)-succinic acid diethyl ester. Desired product was obtained as an yellow oil in 95% yield. $^1$H NMR (300 MHz, CDCl$_3$): δ=7.31 (m, 5H); 6.81 (d, J=8.1, 1H); 6.65 (d, J=8.4, 1H); 5.35 (d, J=8.1, 1H); 5.15 (s, 2H); 5.04 (s, 2H); 4.53 (m, 1H); 3.71 (s, 3H); 3.16 (m, 1H); 3.01 (m, 1H); 2.12 (s, 3H); 1.99 (s, 3H). MS m/e (M+H)$^+$=415.2.

Intermediate 44

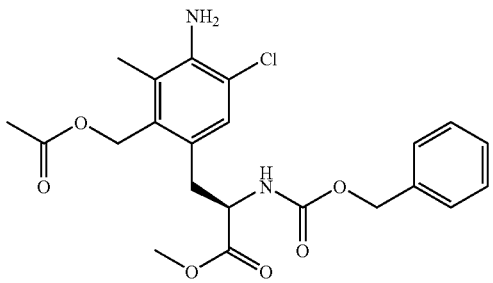

3-(2-Acetoxymethyl-4-amino-5-chloro-3-methyl-phenyl)-2-(R)-benzyloxycarbonylamino-propionic acid methyl ester. Desired product was obtained from 3-(2-Acetoxymethyl-4-amino-3-methyl-phenyl)-2-(R)-benzyloxycarbonylamino-propionic acid methyl ester in a manner analogous to the preparation of 2-(2-Acetoxymethyl-4-amino-5-chloro-3-methyl-benzyl)-(S)-succinic acid diethyl ester. Silica gel chromatography (ethyl acetate-hexanes) afforded the product as an yellow oil in 40% yield. $^1$H NMR (300 MHz, CDCl$_3$): δ=7.31 (m, 5H); 6.96 (s, 1H); 5.36 (d, J=8.4, 1H); 5.12 (s, 2H); 5.05 (s, 2H), 4.53 (m, 1H); 3.72 (s, 3H); 3.15 (m, 1H), 2.99 (m, 1H); 2.15 (s, 3H); 1.99 (s, 3H). MS m/e (M−C$_2$H$_4$O$_2$+H)$^+$=398.3.

Intermediate 45

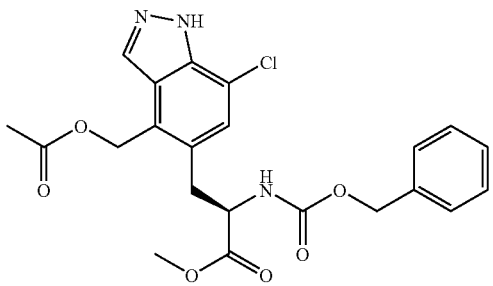

3-(4-Acetoxymethyl-7-chloro-1H-indazol-5-yl)-2-(R)-benzyloxycarbonylamino-propionic acid methyl ester. Trifluoroacetic acid (70 μL, 0.91 mmol) was added to a solution of 3-(2-acetoxymethyl-4-amino-5-chloro-3-methyl-phenyl)-2-(R)-benzyloxycarbonylamino-propionic acid methyl ester (345 mg, 0.77 mmol) in 5% acetic acid in chloroform (5.2 mL). Isoamyl nitrite (120 μL, 0.89 mmol) was added to the mixture drop-wise. Reaction mixture was stirred at room temperature for 40 minutes. Potassium acetate (300 mg, 3.1 mmol) was added to the mixture. Reaction mixture was stirred at room temperature for 45 minutes. Mixture was diluted with dichloromethane (10 mL) then washed successively with water (2×10 mL), and saturated aqueous sodium bicarbonate (2×10 mL). Organic was dried (magnesium sulfate), filtered and concentrated in vacuo. Crude product was obtained as an orange solid in 83% yield. Material was carried forward without further purification. $^1$H NMR (300 MHz, CDCl$_3$): δ=8.20 (s, 1H); 7.29 (m, 5H); 7.21 (s, 1H); 5.53 (d, J=7.7, 1H); 5.40 (s, 2H); 5.04 (s, 2H); 4.67 (m, 1H); 3.74 (s, 3H); 3.34 (m, 1H); 3.21 (m, 1H); 2.02 (s, 3H). MS m/e (M+H)$^+$=460.1.

Intermediate 46

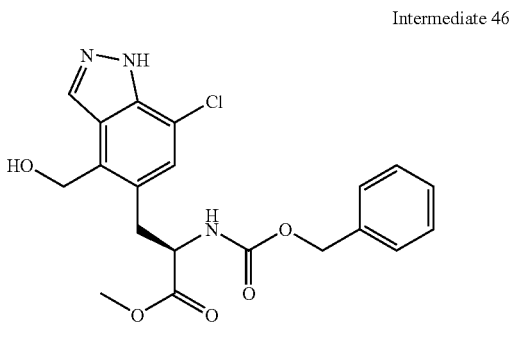

2-(R)-Benzyloxycarbonylamino-3-(7-chloro-4-hydroxymethyl-1H-indazol-5-yl)-propionic acid methyl ester. 3-(4-Acetoxymethyl-7-chloro-1H-indazol-5-yl)-2-(R)-benzyloxycarbonylamino-propionic acid methyl ester (290 mg, 0.63 mmol) was converted into the desired product in a manner analogous to the preparation of 2-(R)-benzyloxycarbonylamino-3-(4-tert-butoxycarbonylamino-2-hydroxymethyl-3-methyl-phenyl)-propionic acid methyl ester. Crude product was obtained as an orange solid in 95% yield. Material was carried forward without further purification. $^1$H NMR (300 MHz, CDCl$_3$): δ=8.15 (s, 1H); 7.27 (m, 5H); 7.14 (s, 1H); 6.10 (m, 1H); 5.01 (d, J=4.8, 2H); 4.95 (s, 2H); 4.75 (m, 1H); 3.79 (s, 3H); 3.34 (m, 1H); 3.09 (m, 1H). MS m/e (M+H)$^+$= 418.0.

Intermediate 47

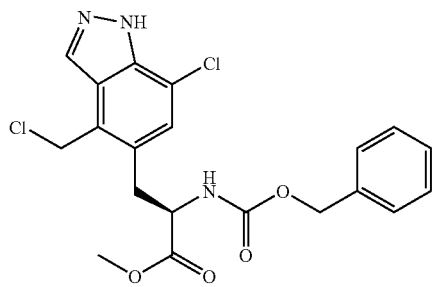

2-(R)-Benzyloxycarbonylamino-3-(7-chloro-4-chloromethyl-1H-indazol-5-yl)-propionic acid methyl ester. Thionyl chloride (2 mL) was added to a solution of 2-(R)-benzyloxycarbonylamino-3-(7-chloro-4-hydroxymethyl-1H-indazol-5-yl)-propionic acid methyl ester (245 mg, 0.59 mmol) in dichloromethane (3 mL). Mixture was stirred at room temperature for 1.5 hours. Mixture was concentrated. Residue was dissolved in dichloromethane (15 mL) then washed with saturated aqueous sodium bicarbonate (2×10 mL). Organic was dried (magnesium sulfate), filtered and concentrated. Title compound was obtained as an orange solid in 86% yield. Material was carried forward without further purification. $^1$H NMR (300 MHz, CDCl$_3$): δ=8.19 (s, 1H), 7.32 (m, 5H), 7.16 (s, 1H), 5.49 (d, J=7.3, 2H), 5.07 (d, J=4.4, 2H), 4.85 (s, 2H), 4.68 (d, J=7.0, 1H), 3.72 (s, 3H), 3.27 (m, 2H). MS m/e (M+H)$^+$=436.1.

Intermediate 48

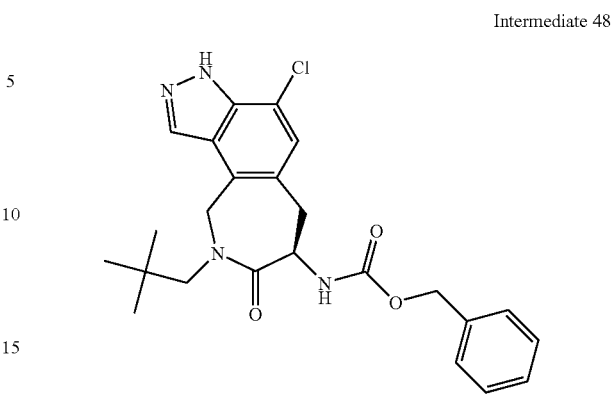

[4-Chloro-9-(2,2-dimethyl-propyl)-8-oxo-3,6,7,8,9,10-hexahydro-2,3,9-triaza-(R)-cyclohepta[e]inden-7-yl]-carbamic acid benzyl ester. Neopentylamine (200 μL, 1.7 mmol) was added to a mixture of 2-(R)-benzyloxycarbonylamino-3-(7-chloro-4-chloromethyl-1H-indazol-5-yl)-propionic acid methyl ester (180 mg, 0.41 mmol) and potassium carbonate (160 mg, 1.2 mmol) in acetonitrile (5 mL). Reaction was heated at reflux for 1 hour. Mixture was cooled to room temperature then filtered through a 0.45 μm PTFE syringeless filter system. Filtrate was concentrated. Residue was dissolved in a mixture of toluene (5 mL) and acetic acid (200 μL). Mixture was heated at 110° C. overnight. Mixture was diluted with ethyl acetate (15 mL) then washed successively with water (15 mL), saturated aqueous sodium bicarbonate (2×15 mL) and brine (10 mL). Organic was dried (magnesium sulfate), filtered and concentrated. Silica gel chromatography afforded the title compound in 52% yield as a yellow solid. $^1$H NMR (300 MHz, CDCl$_3$): δ=7.89 (d, J=10.6, 1H), 7.38 (m, 5H), 6.96 (d, J=10.3, 1H), 6.35 (d, J=5.9, 1H), 5.25 (m, 1H), 5.19 m, 2H), 4.28 (m, 1H), 3.66 (m, 1H), 3.40 (m, 1H), 2.96 (dd, J1=13.9, J2=5.5, 2H), 0.76 (d, J=2.6, 9H). MS m/e (M+H)$^+$=455.2.

Intermediate 49

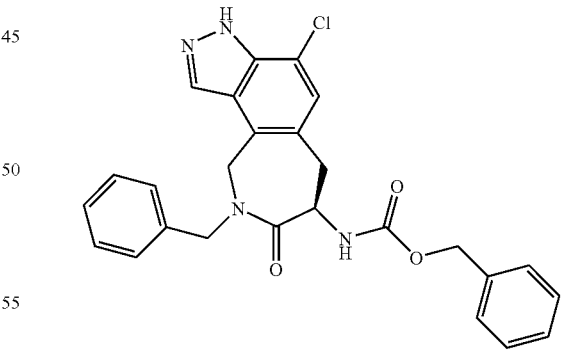

(9-Benzyl-4-chloro-8-oxo-3,6,7,8,9,10-hexahydro-2,3,9-triaza-(R)-cyclohepta[e]inden-7-yl)-carbamic acid benzyl ester. Title compound was obtained from benzylamine (100 μL, 0.92 mmol) and 2-(R)-Benzyloxycarbonylamino-3-(7-chloro-4-chloromethyl-1H-indazol-5-yl)-propionic acid methyl ester (210 mg, 0.48 mmol) following a procedure analogous to the preparation of [4-Chloro-9-(2,2-dimethyl-propyl)-8-oxo-3,6,7,8,9,10-hexahydro-2,3,9-triaza-(R)-cyclohepta[e]inden-7-yl]-carbamic acid benzyl ester. Silica gel chromatography (ethyl acetate-hexanes) afforded the desired product as a yellow solid in 52% yield. ¹H NMR (300 MHz, CDCl₃): δ=7.64 (s, 1H), 7.38 (m, 5H), 7.19 (m, 3H), 7.12 (m, 2H), 7.00 (s, 1H), 6.36 (d, J=6.21H), 5.28 (m, 1H), 5.21 (s, 2H), 5.19 (m, 1H), 4.88 (m, 1H), 4.75 (d, J=16.8, 1H), 4.34 (d, J=14.6, 1H), 3.49 (m, 1H), 3.03 (m, 1H). MS m/e (M+H)⁺= 475.0.

Intermediate 50

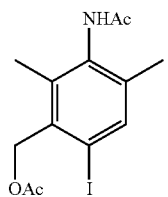

Acetic acid 3-acetylamino-6-iodo-2,4-dimethyl-benzyl ester. To a well stirred solution of (3-amino-2,4-dimethyl-phenyl)-methanol (1.5 g) in methanol (70 mL) and solid sodium hydrogen carbonate (4.0 eq) was added a 1.0 M solution of iodine monochloride dropwise over a period of 5 min at 0° C. The cooling bath was removed after the addition of iodine monochloride. The reaction mixture was brought to room temperature and stirring continued for another 1 h. The reaction mixture was concentrated to remove most of methanol, diluted with dichloromethane (50 mL) and washed with 10% solution of sodium thiosulfate and dried (Na2SO4). The desired compound was purified by trituration with dichloromethane and hexane to give in 1.9 g of iodide. The iodide was then treated with dichloromethane (100 mL) followed by acetic anhydride (4 eq) and catalytic amount of dimethylaminopyridine and stirred for a period of 12 h at room temperature. The reaction mixture was then washed with aqueous sodium hydrogen carbonate, 1.0 M hydrochloric acid and dried (Na2SO4). The desired compound was triturated with dichloromethane and hexane to give acetic acid 3-acetylamino-6-iodo-2,4-dimethyl-benzyl ester in 95% yield. ¹H NMR (300 MHz, CDCl₃): in δ 7.68 (s, 1H), 6.68 (s, 1H), 2.28 (s, 3H), 2.25 (s, 3H), 2.18 (s, 3H), 2.07 (s, 3H); MS (ESI) 384 (M+Na); $R_f$=1.12.

Intermediate 51

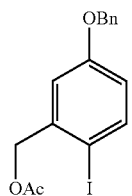

Acetic acid 5-benzyloxy-2-iodo-benzyl ester. To a well stirred solution of 3-benzyloxybenzyl alcohol (5.5 g, 25.7 mmol) in methanol (100 mL) and sodium hydrogencarbonate (8.4 g, 100 mmol) was added a 1.0 M solution of iodine monochloride in dichloromethane (30 mL) at 0° C. The reaction mixture was brought to room temperature and stirring continued for additional 1 h. The reaction mixture was concentrated and then diluted with dichloromethane (150 mL), washed with 10% aqueous sodium thiosulfate and dried (Na₂SO₄). The desired compound was purified by flash chromatography (silica) using 20% ethyl acetate in hexane to give 5-benzyloxy-2-iodobenzyl alcohol (6.2 g, 71% yield). The alcohol (4.2 g, 12.4 mmol) was dissolved in dichloromethane (100 mL) added acetic anhydride (2.52 g, 24.7 mmol) and catalytic amount of 4-dimethylaminopyridine. The reaction mixture was then stirred for 12 h, washed with aqueous sodium hydrogencarbonate and then dried (Na₂SO₄) to give acetic acid 5-benzyloxy-2-iodo-benzyl ester in quantitative yield. MS (ESI) 405 (M+Na); $R_f$=2.27.

Intermediate 52

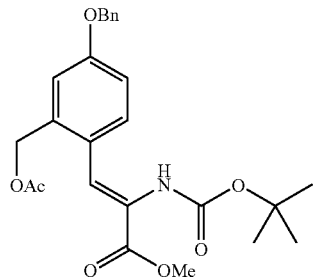

3-(2-Acetoxymethyl-4-benzyloxy-phenyl)-2-tert-butoxycarbonylamino-acrylic acid methyl ester. In a manner similar to 2-(acetoxymethyl-4-tert-butoxycarbonylamino-3-methyl-benzylidene)-succinic acid diethyl ester, 3-(2-acetoxymethyl-4-benzyloxy-phenyl)-2-tert-butoxycarbonylamino-acrylic acid methyl ester was prepared by reacting acetic acid 5-benzyloxy-2-iodo-benzyl ester with 2-tert-butoxycarbonylamino-acrylic acid methyl ester in 74% yield. MS (ESI) 456 (M+H); $R_f$=1.87.

Intermediate 53

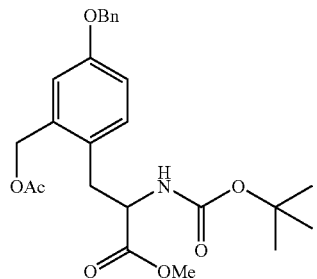

3-(2-Acetoxymethyl-4-benzyloxy-phenyl)-2-tert-butoxycarbonylamino-propionic acid methyl ester. To a solution of 3-(2-acetoxymethyl-4-benzyloxy-phenyl)-2-tert-butoxycarbonylamino-acrylic acid methyl ester (1.9 g, 4.2 mmol) in anhydrous methanol under nitrogen atmosphere was added 1,2-bis((2R,5R)-2,5-diethylphospholano)benzene(cyclootadiene)rhodium (I) trifluoromethanesulfonate (50 mg) and stirred on a Parr shaker at 50 psi of hydrogen atmosphere for 18 h. The solvent was evaporated and the desired product was crystallized from ethyl acetate-hexane in 90% yield. MS (ESI) 458 (M+H); $R_f$=1.81.

Intermediate 54

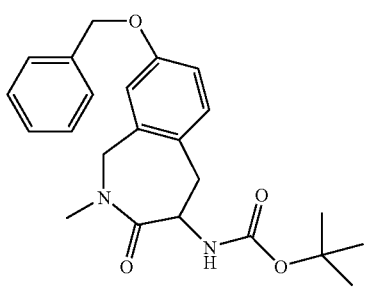

(8-Benzyloxy-2-methyl-3-oxo-2,3,4,5-tetrahydro-1H-benzo[c]azepin-4-yl)-carbamic acid tert-butyl ester. To a solution of 3-(2-acetoxymethyl-4-benzyloxy-phenyl)-2-tert-butoxycarbonylamino-propionic acid methyl ester (1.85 g, 4.0 mmol) in methanol (40 mL) was added potassium carbonate (560 mg, 4.0 mmol) at room temperature and stirred for 1 h. The reaction mixture was diluted with dichloromethane (150 mL), washed with 1.0 M aqueous hydrogen chloride and dried ($Na_2SO_4$) to give the pure 3-(4-benzyloxy-2-hydroxymethyl-phenyl)-2-tert-butoxycarbonylamino-propionic acid methyl ester in almost quantitative yield. To the alcohol (800 mg, 1.93 mmol) in dichloromethane (50 mL) was added methanesulfonyl chloride (0.18 mL, 2.3 mmol) followed by triethylamine (0.38 mL, 2.70 mmol) at 0° C. and then brought to room temperature. After 1 h, the reaction mixture was washed with aqueous sodium hydrogencarbonate, dried ($Na_2SO_4$). The solvent was removed, dissolved the crude product in anhydrous THF (20 mL) followed by addition of 2.0 M solution of methylamine in THF (10 mL) in a sealed tube. The sealed tube was heated at 80° C. for a period of 12 h and then removed the solvent. The crude product was purified by flash chromatography using 30% ethyl acetate in hexane to give (8-benzyloxy-2-methyl-3-oxo-2,3,4,5-tetrahydro-1H-benzo[c]azepin-4-yl)-carbamic acid tert-butyl ester in 39% overall yield. $^1$H NMR (500 MHz, $CDCl_3$): in δ 7.40-7.31 (m, 5H), 7.01-7.00 (m, 1H), 6.83-6.82 (m, 1H), 6.66 (s, 1H), 5.91-5.90 (m, 1H), 5.13-5.01 (m, 4H), 3.50-3.46 (m, 1H), 3.03 (s, 3H), 2.85-2.78 (m, 1H), 1.45 (s, 9H).

Intermediate 55

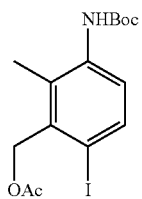

Acetic acid 3-tert-butoxycarbonylamino-6-iodo-2-methyl-benzyl ester. To a well stirred solution of 3-amino-2-methylbenzyl alcohol (10 g, 72.9 mmol) in methanol (250 mL) was added a 1.0 M solution of iodine monochloride in dichloromethane (76.6 mL) dropwise over a period of 5 min at 0° C. The reaction mixture was then brought to room temperature and stirring continued for additional 2 h. The reaction mixture was then concentrated, diluted with dichloromethane (250 mL), washed with 10% aqueous sodium thiosulphate and dried (Na2SO4). The solvent was evaporated and the crude product was dissolved in THF (200 mL). Di-tert-butyl dicarbonate (15.9 g, 72.9 mmol) was added and the reaction mixture was refluxed for 48 h. The reaction mixture was then diluted with ether (400 mL) washed with 1 M HCl (2×100 mL) followed by brine and dried (Na2SO4). The solvent was removed and the desired product was crystallized from 20% ethyl acetate in hexane to give (3-hydroxymethyl-4-iodo-2-methyl-phenyl)-carbamic acid tert-butyl ester (12.5 g). The filtrate was then concentrated and the desired product was purified by flash chromatography (silica) using 30% ethyl acetate to give additional 2.5 g of (3-hydroxymethyl-4-iodo-2-methyl-phenyl)-carbamic acid tert-butyl ester. To a stirred solution of 3-hydroxymethyl-4-iodo-2-methyl-phenyl)-carbamic acid tert-butyl ester (14.5 g, 40 mmol) in dichloromethane (150 mL) was added acetic anhydride (7.5 mL, 80 mmol) and catalytic amount of 4-dimethylaminopyridine and stirred for 12 h at room temperature. The reaction mixture was then quenched with aqueous sodium hydrogencarbonate, brine and dried ($Na_2SO_4$). The solvent was removed and the crude product was purified by crystallization from dichloromethane and hexane to give acetic acid 3-tert-butoxycarbonylamino-6-iodo-2-methyl-benzyl ester (15.5 g, 94%). $^1$H NMR (500 MHz, $CDCl_3$): in δ 7.71 (d, J=8.5 Hz, 1H), 7.25 (d, J=8.5 Hz, 1H), 5.30 (s, 2H), 2.28 (s, 3H), 2.08 (s, 3H), 1.50 (s, 9H); MS (ESI) 428 (M+Na); $R_f$=1.59.

Intermediate 56

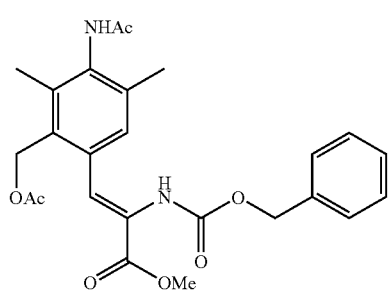

3-(2-Acetoxymethyl-4-acetylamino-3,5-dimethyl-phenyl)-2-benzyloxycarbonylamino-acrylic acid methyl ester. In a manner similar to 2-(acetoxymethyl-4-tert-butoxycarbonylamino-3-methyl-benzylidene)-succinic acid diethyl ester, 3-(2-acetoxymethyl-4-acetylamino-3,5-dimethyl-phenyl)-2-benzyloxycarbonylamino-acrylic acid methyl ester was prepared by reacting acetic acid 3-acetylamino-6-iodo-2,4-dimethyl-benzyl ester with 2-benzyloxycarbonylamino-acrylic acid methyl ester in 74% yield. MS (ESI) 491 (M+H); $R_f$=1.87.

Intermediate 57

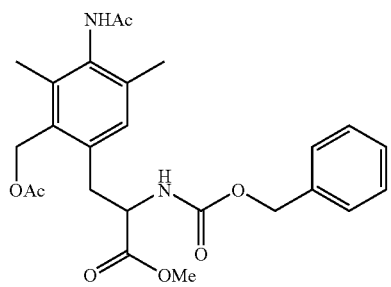

3-(2-Acetoxymethyl-4-acetylamino-3,5-dimethyl-phenyl)-2-benzyloxycarbonylamino-propionic acid methyl ester. In a manner similar to 3-(2-acetoxymethyl-4-benzyloxy-phenyl)-2-tert-butoxycarbonylamino-acrylic acid methyl ester, 3-(2-acetoxymethyl-4-acetylamino-3,5-dimethyl-phenyl)-2-benzyloxycarbonylamino-propionic acid methyl ester was prepared from 3-(2-acetoxymethyl-4-acetylamino-3,5-dimethyl-phenyl)-2-benzyloxycarbonylamino-acrylic acid methyl ester (1.5 g) using 1,2-bis((2R,5R)-2,5-diethylphospholano)benzene(cyclooctadiene)rhodium (I) trifluoromethanesulfonate (25 mg) in 98% yield. MS (ESI) 491 (M+H); $R_f$=1.87.

Intermediate 58

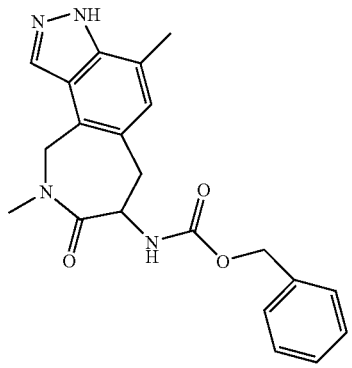

(8-Acetylamino-2,7,9-trimethyl-3-oxo-2,3,4,5-tetrahydro-1H-benzo[c]azepin-4-yl)-carbamic acid benzyl ester. In a manner similar to 2-(R)-benzyloxycarbonylamino-3-(4-tert-butoxycarbonylamino-2-hydroxymethyl-3-methyl-phenyl)-propionic acid methyl ester hydrochloride, the title compound was prepared by hydrolyzing 3-(2-acetoxymethyl-4-acetylamino-3,5-dimethyl-phenyl)-2-benzyloxycarbonylamino-propionic acid methyl ester (1.84 g, 3.78 mmol) with potassium carbonate (525 mg, 3.8 mmol) in MeOH (40 mL). The alcohol was dissolved in dichloromethane (100 mL) and then treated with methanesulfonyl chloride (0.35 mL, 4.5 mmol) and triethylamine (0.68 mL, 4.9 mmol). The reaction mixture was stirred for 12 h, washed with aqueous sodium hydrogencarbonate, 1.0 M aqueous hydrogen chloride and dried ($Na_2SO_4$). The solvent was removed to give pure 3-(4-acetylamino-2-chloromethyl-3,5-dimethyl-phenyl)-2-benzyloxycarbonylamino-propionic acid methyl ester in almost quantitative yield. The chloride (480 mg, 1.08 mmol) was treated with 1.0 M methylamine solution in THF in a sealed tube for 3 h at 90° C. The solvent was removed and the crude product was dissolved in toluene and acetic acid (0.5 mL) and refluxed for 2 h to give (8-acetylamino-2,7,9-trimethyl-3-oxo-2,3,4,5-tetrahydro-1H-benzo[c]azepin-4-yl)-carbamic acid benzyl ester in 68% yield. To the acetate in chloroform (20 mL) was added acetic acid (0.5 mL) followed by isoamylnitrite (1.0 mL) and 18-crown-6 (50 mg). The reaction mixture was refluxed for 12 h and removed the solvent. The crude product was purified by flash chromatography using ethyl acetate as eluent to give (4,9-dimethyl-8-oxo-3,6,7,8,9,10-hexahydro-2,3,9-triaza-cyclohepta[e]inden-7-yl)-carbamic acid benzyl ester as a major product in 37% overall yield. $^1$H NMR (500 MHz, $CDCl_3$): in δ 7.96 (s, 1H), 7.35-7.24 (m, 5H), 6.7 (s, 1H), 6.43-6.41 (m, 1H), 5.25-5.05 (m, 3H), 4.18-4.10 (m, 2H), 3.07-3.05 (m, 2H), 3.00) s, 3H), 2.40 (s, 3H).

Intermediate 59

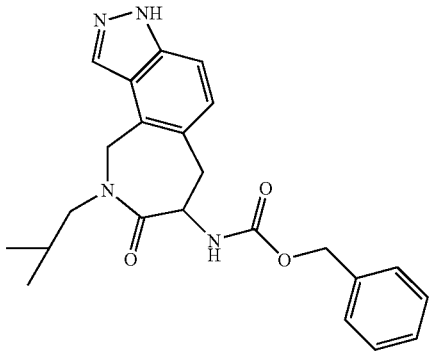

(9-Isobutyl-8-oxo-3,6,7,8,9,10-hexahydro-2,3,9-triaza-cyclohepta[e]inden-7-yl)-carbamic acid benzyl ester. In a manner similar to [9-(2,2-dimethyl-propyl)-8-oxo-3,6,7,8,9,10-hexahydro-2,3,9-triaza-(R)-cyclohepta[e]inden-7-yl]-carbamic acid benzyl ester, the title compound was prepared by treating 2-benzyloxycarbonylamino-3-(4-chloromethyl-1H-indazol-5-yl)-propionic acid methyl ester, hydrochloride with isobutylamine followed by treatment with acetic acid in refluxing toluene to give (9-Isobutyl-8-oxo-3,6,7,8,9,10-hexahydro-2,3,9-triaza-cyclohepta[e]inden-7-yl)-carbamic acid benzyl ester in 91% yield. MS (ESI) 407 (M+H); $R_f$=1.58.

Intermediate 60

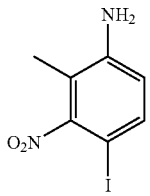

(8-Oxo-9-pyridin-4-ylmethyl-3,6,7,8,9,10-hexahydro-2,3,9-triaza-cyclohepta[e]inden-7-yl)-carbamic acid benzyl ester. In a manner similar to [9-(2,2-dimethyl-propyl)-8-oxo-3,6,7,8,9,10-hexahydro-2,3,9-triaza-(R)-cyclohepta[e]inden-7-yl]-carbamic acid benzyl ester, the title compound was prepared by treating 2-benzyloxycarbonylamino-3-(4-chloromethyl-1H-indazol-5-yl)-propionic acid methyl ester, hydrochloride with 4-(aminomethyl)pyridine followed by treatment with acetic acid in refluxing toluene to give (8-oxo-9-pyridin-4-ylmethyl-3,6,7,8,9,10-hexahydro-2,3,9-triaza-cyclohepta[e]inden-7-yl)-carbamic acid benzyl ester in 65% yield.

MS (ESI) 442 (M+H); $R_f$=1.10.

Intermediate 61

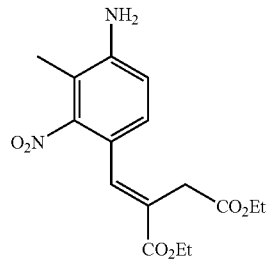

4-Iodo-2-methyl-3-nitrobenzenamine. To a well stirred solution of 2-methyl-3-nitroaniline (10 g, 66 mmol) in methanol (150 mL) was added sodium hydrogencarbonate (264 mmol) followed by 1.0 M solution of iodine monochloride (72 mmol) at room temperature. After stirring for 1 h, the solvent was removed, diluted with ether, washed with 10% aqueous sodium thiosulfate solution. The solvent was removed and the crude iodide was in the next step.

Intermediate 62

(E)-Diethyl 2-(4-amino-3-methyl-2-nitrobenzylidene)succinate. To a solution of 4-iodo-2-methyl-3-nitrobenzenamine (59 mmol) in dimethylformamide (100 mL) was added diethyl itaconate (13.2 g, 71 mmol), tetrabutylammonium chloride (16.4 g, 59 mmol), triethylamine (236 mmol) and palladium acetate (675 mg, 3 mmol) under nitrogen. The reaction mixture was heated to 80° C. for 2 h. The crude reaction mixture was then filtered, diluted with ether (250 mL), washed with water (2×300 mL). The crude product was purified by flash chromatography using 20% ethyl acetate in hexane to give 8.5 g of the title compound. $^1$H NMR (500 MHz, CDCl$_3$): in δ 7.58 (s, 1H), 7.10 (d, J=8.5 Hz, 1H), 6.73 (d, J=8.5 Hz, 1H), 4.24-4.15 (m, 4H), 3.40 (s, 2H), 2.06 (s, 3H), 1.30-1.23 (m, 6H).

Intermediate 63

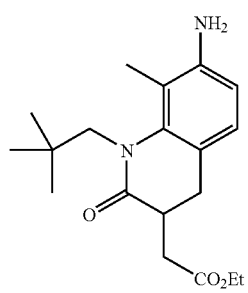

Ethyl 2-(7-amino-8-methyl-1-neopentyl-2-oxo-1,2,3,4-tetrahydroquinolin-3-yl)acetate. To a solution of (E)-diethyl 2-(4-amino-3-methyl-2-nitrobenzylidene)succinate (4.5 g, 13.4 mmol) in THF (100 mL) was added (Boc)$_2$O (16 mmol) followed by catalytic amount of dimethylaminopyridine (10 mg). The reaction mixture was heated in a sealed tube for 3 h at 100° C. The reaction mixture was cooled, removed solvent, diluted with ether and then washed with aqueous sodium hydrogencarbonate (50 mL). The crude product was found to contain both mono- and di-Boc protected compounds. The crude product was dissolved in methanol (200 mL) and was added water (150 ml) followed by ammonium chloride (14.3 g, 268 mmol) and iron powder (8.9 g, 160 mmol). The reaction mixture was heated at 50° C. for 1 h, cooled and then filtered over a pad of celite. The solvent was removed, extracted with ethyl acetate and then washed with brine and dried (Na$_2$SO$_4$). The crude product was purified by flash chromatography using 30% ethyl acetate in hexane as eluent to give the amine. The amine (4.1 g, 10 mmol) was dissolved in dichloroethane (100 mL) followed by addition of acetic acid (10 mL), trimethylacetaldehyde (11 mmol) and magnesium sulfate (5.0 g). The reaction mixture was stirred for 2 h and then filtered. To the filtered reaction mixture was added sodium triacetoxyborohydride (2.33 g, 11 mmol) and stirring continued for additional 2 h. The reaction mixture was diluted with hexane (150 mL), washed with water (2×100 mL), aqueous NaHCO$_3$ solution and dried (Na$_2$SO$_4$). The solvent was removed and the crude product was dissolved in methanol (100 mL) followed by addition of acetic acid (5 mL) and hydrogenated in a parr bottle at a pressure of 50 psi hydrogen. The catalyst was removed by filtration and the solvent was removed. The crude product was dissolved in toluene (100 mL) followed by addition of toxic acid (100 mg) and sodium cyanide (50 mg). The reaction mixture was refluxed for 12 h and the crude product was purified by flash chromatography using 50% ethyl acetate in hexane to give ethyl 2-(7-amino-8-methyl-1-neopentyl-2-oxo-1,2,3,4-tetrahydroquinolin-3-yl)acetate.

MS (ESI) 333 (M+H); R$_f$=1.29.

Intermediate 64

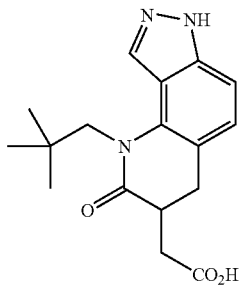

2-(1-Neopentyl-2-oxo-2,3,4,7-tetrahydro-1H-pyrazolo[3,4-h]quinolin-3-yl)acetic acid. To a solution of ethyl 2-(7-amino-8-methyl-1-neopentyl-2-oxo-1,2,3,4-tetrahydroquinolin-3-yl)acetate (170 mg, 0.51 mmol) in carbon tetrachloride (4.5 mL) was added acetic acid (0.5 mL) followed by isoamylnitrite (0.04 mL) and the reaction mixture was stirred for 2 h at room temperature. The reaction mixture was diluted with dichloromethane (40 mL), washed with aqueous NaHCO$_3$ and dried. The solvent was removed and the crude product was dissolved in THF (15 mL) followed by addition of lithium hydroxide (43 mg, 1 mmol) and water (5 mL). After stirring for 12 h, the solvent was removed, acidified with 6 M HCl and extracted with ethyl acetate to give 2-(1-neopentyl-2-oxo-2,3,4,7-tetrahydro-1H-pyrazolo[3,4-h]quinolin-3-yl)acetic acid.

MS (ESI) 316 (M+H); R$_f$=1.31.

Intermediate 65

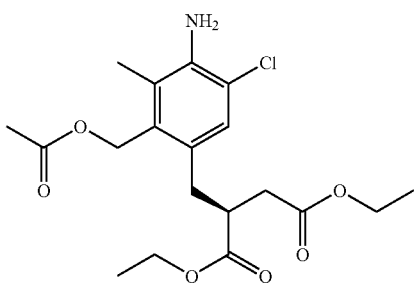

2-(S)-(2-Acetoxymethyl-4-amino-5-chloro-3-methyl-benzyl)-succinic acid diethyl ester. 2-(S)-(2-Acetoxymethyl-4-amino-3-methyl-benzyl)-succinic acid diethyl ester (3.0 g, 8.2 mmol) was dissolved in acetonitrile (40 mL). Mixture was warmed to 60° C. N-Chlorosuccinimide (1.29 g, 9.7 mmol) was added to the warm solution. Reaction mixture was heated at reflux for 10 minutes. Mixture was cooled to room temperature then diluted with ethyl acetate (20 mL). Mixture was washed successively with saturated aqueous sodium bicarbonate (40 mL), and brine (20 mL). Organic was dried (magnesium sulfate), filtered and concentrated in vacuo. Silica gel chromatography (ethyl acetate-hexanes) afforded the desired product in 59% yield as an amber oil. $^1$H NMR (300 MHz, CDCl$_3$): δ=6.98 (s, 1H), 5.15 (d, J=3.3, 2H), 4.09 (m, 4H), 2.99 (m, 2H), 2.69 (m, 2H), 2.39 (dd, J1=4.8, J2=16.5, 1H), 2.17 (s, 3H), 2.06 (s, 3H), 1.20 (m, 6H). MS m/e (M−C$_2$H$_4$O$_2$+H)$^+$=340.0.

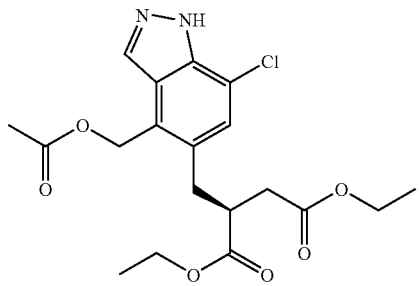

Intermediate 66

2-(S)-(4-Acetoxymethyl-7-chloro-1H-indazol-5-ylmethyl)-succinic acid diethyl ester. Isoamyl nitrite (700 μL, 5.2 mmol), was added dropwise to an ice cold solution of 2-(S)-(2-Acetoxymethyl-4-amino-5-chloro-3-methyl-benzyl)-succinic acid diethyl ester (1.91 g, 4.8 mmol) in 5% acetic acid in toluene (81.2 mL). Mixture stirred at 0° C. for 45 minutes. Potassium acetate (1.50 g, 15.3 mmol) was added to the mixture. Reaction was stirred at room temperature for 14 hours. Mixture was quenched with water. Mixture was extracted with ethyl acetate (30 mL). Mixture was washed 2× saturated aqueous sodium bicarbonate. Organic was dried (magnesium sulfate) filtered and concentrated. Silica gel chromatography (ethyl acetate-hexanes) afforded the desired product in 80% yield as an amber oil. $^1$H NMR (300 MHz, CDCl$_3$): δ=8.23 (s, 1H), 7.26 (s, 1H), 5.45 (s, 2H), 4.09 (q, J=7.0, 4H), 3.20 (dd, J1=7.32, J2=13.2, 1H), 3.10 (m, 1H), 2.97 (dd, J1=7.0, J2=13.3, 1H), 2.73 (dd, J1=8.4, J2=16.8, 1H), 2.44 (dd, J1=5.5, J2=16.8, 1H), 2.08 (s, 3H), 1.18 (m, 6H). MS m/e (M+H)$^+$=411.0.

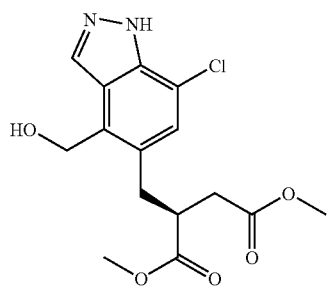

Intermediate 67

(S)-Dimethyl 2-((7-chloro-4-(hydroxymethyl)-1H-indazol-5-yl)methyl)succinate. 2-(S)-(2-Acetoxymethyl-4-amino-5-chloro-3-methyl-benzyl)-succinic acid diethyl ester (2.21 g, 5.4 mmol) was converted to the title compound in a manner analogous to the preparation of 2-(S)-(4-Hydroxymethyl-1H-indazol-5-ylmethyl)-succinic acid dimethyl ester. Material was obtained as amber solid in 99% yield. MS m/e (M+H)$^+$=241.2.

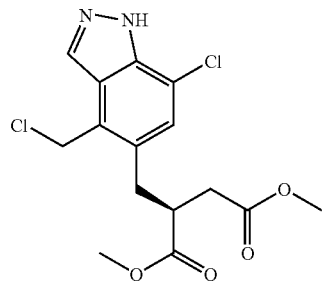

Intermediate 68

(S)-Dimethyl 2-((7-chloro-4-(chloromethyl)-1H-indazol-5-yl)methyl)succinate. (S)-Dimethyl 2-((7-chloro-4-(hydroxymethyl)-1H-indazol-5-yl)methyl)succinate (2.0 g, 5.9 mmol) was dissolved in dichloromethane (35 mL). Thionyl chloride (5.0 mL) was added to the mixture. Reaction stirred at room temperature for 1.5 hours. Mixture was concentrated. Residue was dissolved in ethyl acetate. Mixture was washed twice with aqueous sodium bicarbonate and once with brine. Organic was dried (magnesium sulfate), filtered and concentrated in vacuo. Title compound was obtained as amber solid in 89% yield. MS m/e (M+H)$^+$=359.1.

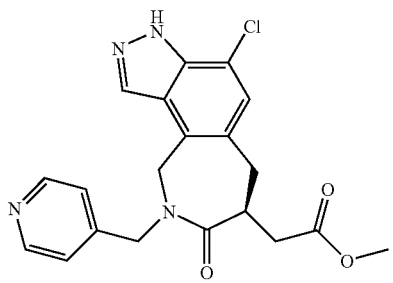

Intermediate 69

(S)-Methyl 2-(4-chloro-8-oxo-9-(pyridin-4-ylmethyl)-3,6,7,8,9,10-hexahydroazepino[3,4-e]indazol-7-yl)acetate. (S)-Dimethyl 2-((7-chloro-4-(chloromethyl)-1H-indazol-5-yl)methyl)succinate (120 mg, 0.33 mmol) was dissolved in DMF (1.0 mL). 4-Aminomethylpyridine (100 μL, 1.0 mmol) was added to the mixture. Reaction stirred at room temperature for 24 hours. Mixture was diluted with ethyl acetate. Mixture was washed twice with water and once with brine. Organic was dried (magnesium sulfate), filtered and concentrated in vacuo. Residue was dissolved in toluene (4 mL). Acetic acid (1 mL) was added to the mixture. Reaction was heated at reflux for 3.5 hours. Mixture was cooled to room temperature then diluted with ethyl acetate. Material was washed once with water and twice with aqueous sodium bicarbonate. Aqueous was made basic with sodium bicarbonate. Back extracted from the aqueous twice with ethyl acetate. Combined organics were dried (magnesium sulfate), filtered and concentrated in vacuo. Residue was purified with silica gel chromatography eluting dichloromethane and 2N ammonia in methanol. Title compound was obtained as yellow solid in 48% yield. MS m/e (M+H)$^+$=399.2.

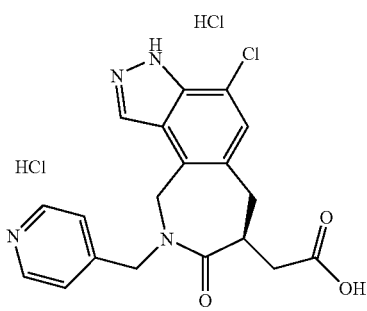

Intermediate 70

(S)-2-(4-Chloro-8-oxo-9-(pyridin-4-ylmethyl)-3,6,7,8,9,10-hexahydroazepino[3,4-e]indazol-7-yl)acetic acid dihydrochloride. (S)-Methyl 2-(4-chloro-8-oxo-9-(pyridin-4-ylmethyl)-3,6,7,8,9,10-hexahydroazepino[3,4-e]indazol-7-yl) acetate (21 mg, 0.05 mmol) was dissolved in 1N hydrochloric acid (1.0 mL). Reaction was heated at 50° C. for 5 hours. Another 1 mL of 1N hydrochloric acid was added to the mixture. Reaction was heated at 50° C. for 17 hours. Mixture was concentrated in vacuo. Residue was treated with acetonitrile and then the material was concentrated. Title compound was obtained as dark yellow solid in 83% yield. MS m/e (M+H)$^+$=385.2.

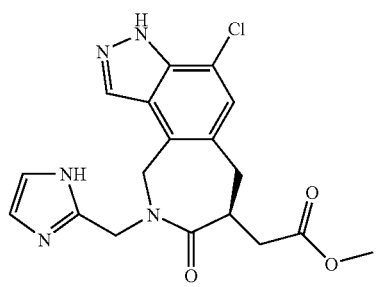

Intermediate 71

(S)-Methyl 2-(9-((1H-imidazol-2-yl)methyl)-4-chloro-8-oxo-3,6,7,8,9,10-hexahydroazepino[3,4-e]indazol-7-yl)acetate. (S)-Dimethyl 2-((7-chloro-4-(chloromethyl)-1H-indazol-5-yl)methyl)succinate (250 mg, 0.63 mmol) and (1H-imidazol-2-yl)methanamine dihydrochloride (170 mg, 1.0 mmol) were combined and suspended in acetonitrile (10 mL). Triethylamine (800 μL, 5.7 mmol) was added to the mixture. Reaction was warmed to reflux for 3 hours. Acetic acid (1.5 mL) was added to the mixture. Reaction was heated at reflux for 20 hours. Mixture was cooled to room temperature then diluted with dichloromethane. Mixture was extracted twice with water. Aqueous layer was concentrated in vacuo. Residue was purified by preparatory HPLC. Water was lyophilized off. Remaining residue was passed through a column of Dowex 1×4-200 ion exchange resin eluting methanol. Title compound was recovered as amber residue in 24% yield. MS m/e (M+H)$^+$=388.1.

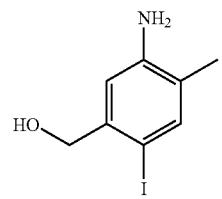

Intermediate 72

5-Amino-2-iodo-4-methybenzyl alcohol. To an ice cooled solution of 3-amino-4-methylbenzyl alcohol (10.0 g, 72.9 mmol) in methanol (200 mL) 1M iodinemonochloride in dichloromethane (80.0 mL, 80.0 mmoles) was added dropwise over 30 minutes. Ice bath was removed. Reaction was stirred at ambient temperature for 40 minutes. Mixture was concentrated in vacuo. Residue was treated with dichloromethane (250 mL). Solids were filtered off and washed with dichloromethane. Solids were partitioned between ethyl acetate and 1N aqueous sodium hydroxide. Layers were partitioned. Organic layer was washed with 1N aqueous sodium hydroxide. The combined aqueous layers were back extracted two times with ethyl acetate. Combined organic layers were washed with brine. Combined extracts were dried (magnesium sulfate), filtered and concentrated in vacuo. Desired product was obtained as tan solid in 81% yield. MS m/e (M+H)$^+$=264.

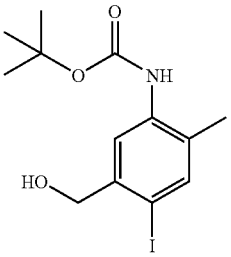

Intermediate 73 tert-Butyl 5-(hydroxymethyl)-4-iodo-2-methylphenylcarbamate. 5-Amino-2-iodo-4-methylbenzyl alcohol (4.60 g, 17.5 mmoles) was dissolved in tetrahydrofuran (80 mL). Di-tert-butyl dicarbonate (5.30 g, 24.3 mmoles) was added to the mixture. Reaction was heated at 60° C. for 20 hours. Mixture was concentrated. Residue was purified by silica gel chromatography eluting ethyl acetate-hexanes. Title compound was obtained as off-white solid. MS m/e (M-C$_4$H$_8$O+H)$^+$=290.

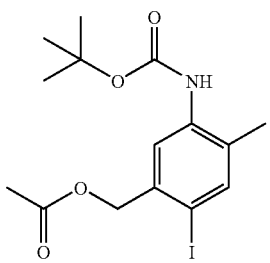

Intermediate 74

5-(tert-Butoxycarbonyl)-2-iodo-4-methylbenzyl acetate. tert-Butyl 5-(hydroxymethyl)-4-iodo-2-methylphenylcarbamate (4.32 g, 11.9 mmol) was dissolved in dichloromethane (60 mL). Acetic anhydride (2.6 mL, 27.6 mmol) was added to the mixture followed by potassium acetate (2.0 g, 20.4 mmol). Reaction was stirred at room temperature over 15 hours. Mixture was warmed to 50° C. and held for 1 hour. Mixture was cooled to room temperature then diluted with dichloromethane. Mixture was washed twice with water, and once with saturated aqueous sodium bicarbonate. Organic layer was dried (magnesium sulfate), filtered and concentrated in vacuo. Residue was treated with 10% ethyl acetate-hexanes (100 mL). Material was concentrated in vacuo. Desired compound was obtained as white solid in 98% yield. $^1$H NMR (300 MHz, CD$_3$OD): δ=7.64 (s, 1H), 7.54 (s, 1H), 4.51 (s, 2H), 2.19 (s, 3H), 1.51 (s, 9H).

Intermediate 75

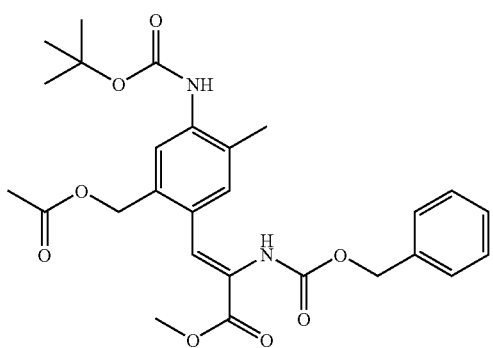

3-(2-Acetoxymethyl-4-tert-butoxycarbonylamino-5-methyl-phenyl)-2-benzyloxycarbonylamino-acrylic acid methyl ester. Title compound was prepared in a manner analogous to the preparation of 3-(2-Acetoxymethyl-4-tert-butoxycarbonylamino-3-methyl-phenyl)-2-benzyloxycarbonylamino-acrylic acid methyl ester. Material was obtained as a white solid in 65% yield. MS m/e (M+H)$^+$=513.

Intermediate 76

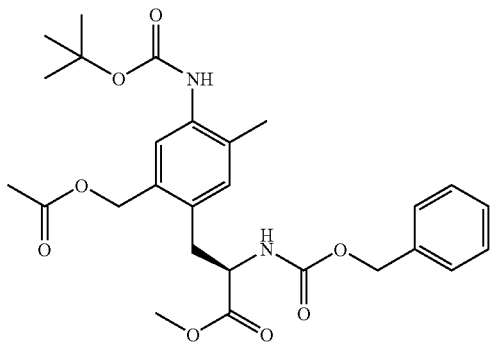

3-(2-Acetoxymethyl-4-tert-butoxycarbonylamino-5-methyl-phenyl)-2-(R)-benzyloxycarbonylamino-propionic acid methyl ester. Title compound was prepared in a manner analogous to the preparation of 2-(S)-(acetoxymethyl-4-tert-butoxycarbonylamino-3-methyl-benzyl)-succinic acid diethyl ester. Material was obtained as clear colorless oil in 99% yield. MS m/e (M−H)$^-$=513.

Intermediate 77

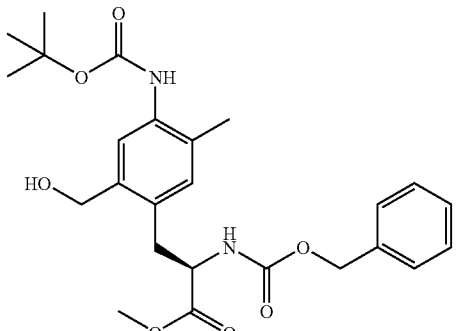

3-(2-Hydroxymethyl-4-tert-butoxycarbonylamino-5-methyl-phenyl)-2-(R)-benzyloxycarbonylamino-propionic acid methyl ester. Title compound was obtained in a manner analogous to the preparation of 2-(R)-Benzyloxycarbonylamino-3-(4-tert-butoxycarbonylamino-2-hydroxymethyl-3-methyl-phenyl)-propionic acid methyl ester. Material was obtained as white solid in 94% yield.

Intermediate 78

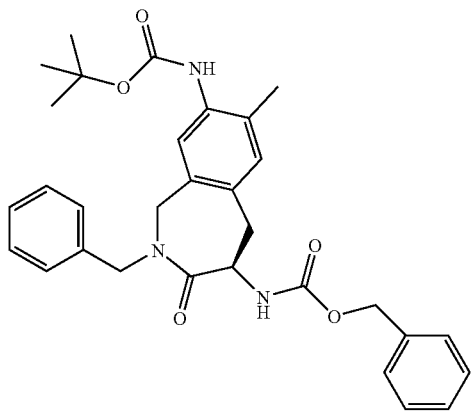

3-(2-Chloromethyl-4-tert-butoxycarbonylamino-5-methyl-phenyl)-2-(R)-benzyloxycarbonylamino-propionic acid methyl ester. 3-(2-Hydroxymethyl-4-tert-butoxycarbonylamino-5-methyl-phenyl)-2-(R)-benzyloxycarbonylamino-propionic acid methyl ester (510 mg, 1.1 mmol) was dissolved in dichloromethane (5 mL). Triethylamine (250 μL, 1.8 mmol) was added to the mixture followed by methanesulfonyl chloride (100 μL, 1.3 mmol). Mixture was stirred at room temperature for 1.5 hours. Mixture was diluted with dichloromethane then washed once with water, twice with 1N hydrochloric acid, and once with brine. Organics were dried (magnesium sulfate), filtered and concentrated in vacuo. Title compound was obtained as white solid in 91% yield. MS m/e (M+H)$^+$=491.

Intermediate 79

(R)-Benzyl 8-tert-butoxycarbonylamido-2-benzyl-7-methyl-3-oxo-2,3,4,5-tetrahydro-1H-benzo[c]azepin-4-ylcarbamate. 3-(2-Chloromethyl-4-tert-butoxycarbonylamino-5-methyl-phenyl)-2-(R)-benzyloxycarbonylamino-propionic acid methyl ester (335 mg, 0.72 mmol) was dissolved in acetonitrile (10 mL). Potassium carbonate (220 mg, 1.6 mmol) was added to the mixture followed by benzylamine (150 µL, 1.4 mmol). Reaction was heated to reflux for 4.5 hours. Mixture was cooled to room temperature. Mixture was filtered over celite. Filtrate was concentrated. Residue was dissolved in toluene (15 mL). Acetic acid (100 µL) was added to the mixture. Reaction was heated at reflux for 3 hours. Mixture was cooled to room temperature. Mixture was concentrated. Residue was purified by silica gel chromatography eluting ethyl acetate-hexanes. Title compound was obtained as clear colorless oil in 81% yield. MS m/e (M+H)$^+$=530.

tetrahydro-1H-benzo[c]azepin-8-ylcarbamate (155 mg, 0.39 mmol) was dissolved in dichloromethane (10 mL). Aqueous sodium bicarbonate (10 mL) was added to the mixture. A solution of 20% phosgene in toluene (230 µL, 0.43 mmol) was added to the mixture with vigorous stirring. Reaction stirred at room temperature for 20 minutes. 4-(2-oxo-1,4-dihydro-2H-quinazolin-3-yl)piperidine acetate (140 mg, 0.48 mmol) was added to the mixture. Reaction stirred at room temperature for 1 hour. Reaction layers were partitioned. Organic layer was washed successively with 1N hydrochloric acid and brine. Organic was dried (magnesium sulfate), filtered and concentrated in vacuo. Title compound was obtained as off-white solid in 94% yield. MS m/e (M+H)$^+$=653.

Intermediate 80

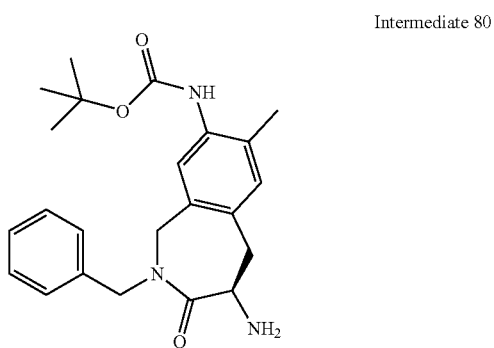

(R)-tert-Butyl-4-amino-2-benzyl-7-methyl-3-oxo-2,3,4,5-tetrahydro-1H-benzo[c]azepin-8-ylcarbamate. (R)-Benzyl 8-tert-butoxycarbonylamido-2-benzyl-7-methyl-3-oxo-2,3,4,5-tetrahydro-1H-benzo[c]azepin-4-ylcarbamate (305 mg, 0.58 mmol) was dissolved in methanol. A catalytic amount of 10% palladium on carbon was added to the mixture. Reaction was placed on a Parr apparatus under 50 psi of hydrogen gas. Reaction shook at room temperature for 1 hour. Reaction was removed from the apparatus. Catalyst was filtered off. Filtrate was concentrated in vacuo. Title compound was obtained as clear colorless oil in 97% yield. MS m/e (M+H)$^+$=396.

Intermediate 81

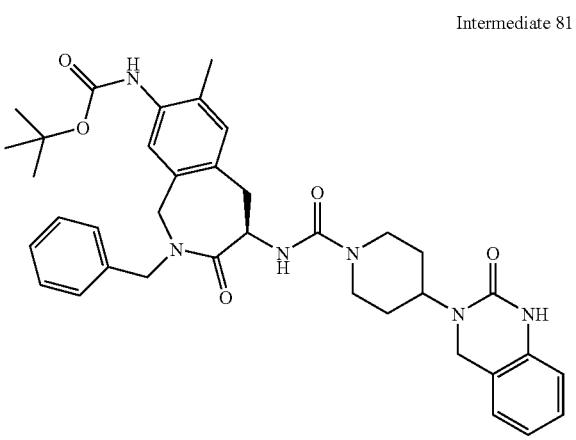

(R)-tert-Butyl 2-benzyl-7-methyl-3-oxo-4-(4-(2-oxo-1,2-dihydroquinazolin-3(4H)-yl)piperidine-1-carboxamido)-2,3,4,5-tetrahydro-1H-benzo[c]azepin-8-ylcarbamate. (R)-tert-Butyl-4-amino-2-benzyl-7-methyl-3-oxo-2,3,4,5-

Intermediate 82

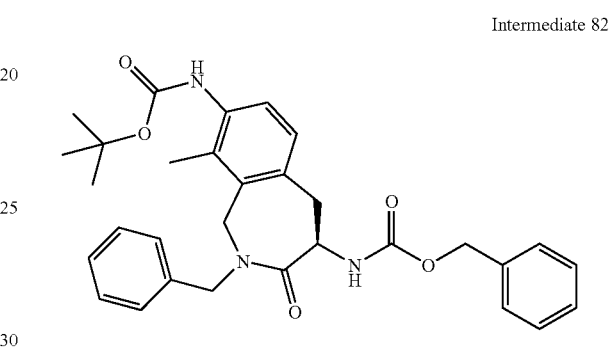

(R)-Benzyl 8-tert-butoxycarbonylamido-2-benzyl-9-methyl-3-oxo-2,3,4,5-tetrahydro-1H-benzo[c]azepin-4-ylcarbamate. 3-(2-Chloromethyl-4-tert-butoxycarbonylamino-3-methyl-phenyl)-2-(R)-benzyloxycarbonylamino-propionic acid methyl ester was reacted in a manner analogous to the preparation of (R)-benzyl 8-tert-butoxycarbonylamido-2-benzyl-7-methyl-3-oxo-2,3,4,5-tetrahydro-1H-benzo[c]azepin-4-ylcarbamate. Title compound was obtained as white solid in 78% yield. MS m/e (M+H)$^+$=530.

Intermediate 83

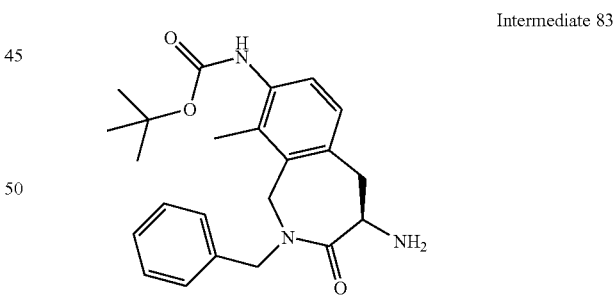

(R)-tert-Butyl-4-amino-2-benzyl-9-methyl-3-oxo-2,3,4,5-tetrahydro-1H-benzo[c]azepin-8-ylcarbamate. (R)-Benzyl 8-tert-butoxycarbonylamido-2-benzyl-9-methyl-3-oxo-2,3,4,5-tetrahydro-1H-benzo[c]azepin-4-ylcarbamate was reacted in a manner analogous to the preparation of (R)-tert-butyl-4-amino-2-benzyl-7-methyl-3-oxo-2,3,4,5-tetrahydro-1H-benzo[c]azepin-8-ylcarbamate. Title compound was obtained as clear colorless oil in 99% yield. MS m/e (M+H)$^+$= 340.

Intermediate 84

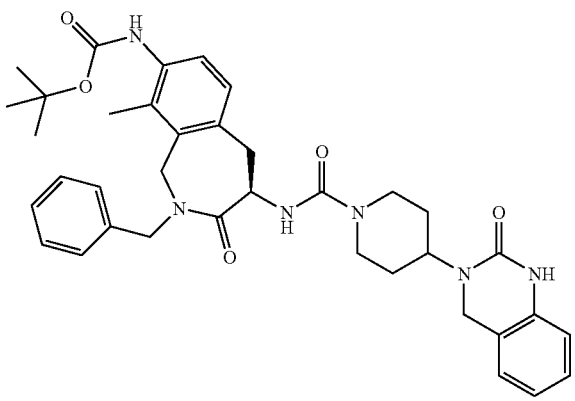

(R)-tert-Butyl 2-benzyl-9-methyl-3-oxo-4-(4-(2-oxo-1,2-dihydroquinazolin-3(4H)-yl)piperidine-1-carboxamido)-2,3,4,5-tetrahydro-1H-benzo[c]azepin-8-ylcarbamate. (R)-tert-Butyl-4-amino-2-benzyl-9-methyl-3-oxo-2,3,4,5-tetrahydro-1H-benzo[c]azepin-8-ylcarbamate was reacted in a manner analogous to the preparation of (R)-tert-butyl 2-benzyl-7-methyl-3-oxo-4-(4-(2-oxo-1,2-dihydroquinazolin-3(4H)-yl)piperidine-1-carboxamido)-2,3,4,5-tetrahydro-1H-benzo[c]azepin-8-ylcarbamate. Title compound was obtained as off-white solid in 94% yield.

Intermediate 85

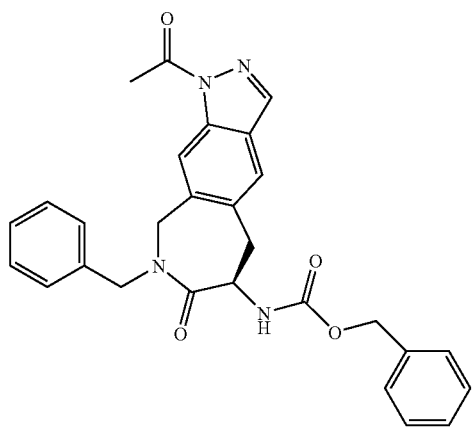

(R)-Benzyl-acetyl-8-benzyl-7-oxo-1,5,6,7,8,9-hexahydroazepino[4,3-f]indazol-6-ylcarbamate. 3-(2-Chloromethyl-4-tert-butoxycarbonylamino-5-methyl-phenyl)-2-(R)-benzyloxycarbonylamino-propionic acid methyl ester (160 mg, 0.33 mmol) was dissolved in dichloromethane (3 mL). Trifluoroacetic acid (1 mL) was added to the mixture. Reaction was stirred at room temperature for 45 minutes. Mixture was concentrated to a yellow oil. Residue was dissolved in chloroform (3 mL). Acetic acid (100 μL) was added to the mixture followed by isoamyl nitrite (50 μL, 0.37 mmol) then potassium acetate (65 mg, 0.66 mmol). Reaction was heated at reflux for 30 minutes. Mixture was cooled to room temperature then diluted with dichloromethane. Mixture was washed once with water, and twice with aqueous sodium bicarbonate. Organics were dried (magnesium sulfate), filtered and concentrated in vacuo. Reside was dissolved in acetonitrile (3 mL). Benzylamine (100 μL, 0.92 mmol) was added to the mixture followed by potassium carbonate (50 mg, 0.36 mmol). Reaction was heated at reflux for 1 hour. Mixture was cooled to room temperature. Solids were filtered. Filtrate was concentrated in vacuo. Residue was treated with toluene (3 mL) and acetic acid (100 μL). Reaction was heated at reflux for 1 hour. Mixture was cooled to room temperature. Acetic anhydride (1 mL) was added to the mixture. Reaction was stirred at room temperature for 1 hour. Mixture was concentrated. Residue was purified by silica gel chromatography eluting ethyl acetate-hexanes. Title compound was obtained as amber oil in 27% yield. MS m/e $(M+H)^+=483$.

Intermediate 86

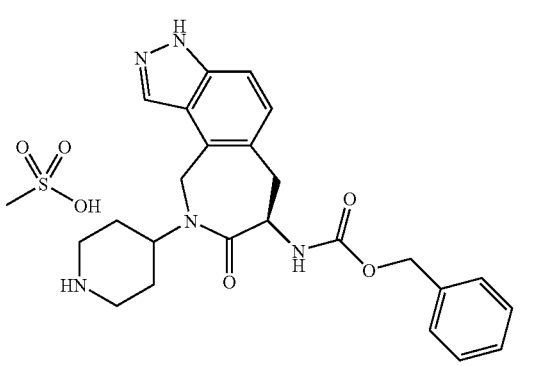

(R)-benzyl 8-oxo-9-(piperidin-4-yl)-3,6,7,8,9,10-hexahydroazepino[3,4-e]indazol-7-ylcarbamate methanesulfonate. 4-(7-(R)-Benzyloxycarbonylamino-8-oxo-6,7,8,10-tetrahydro-3H-2,3,9-triaza-cyclohepta[e]inden-9-yl)-piperidine-1-carboxylic acid tert-butyl ester (100 mg, 0.19 mmol) was dissolved in dichloromethane (2 mL). Anisole (100 μL, 0.92 mmol) was added to the mixture followed by methanesulfonic acid (200 μL). Reaction stirred at room temperature for 30 minutes. Mixture was diluted with diethyl ether, and the mixture stirred at room temperature for 30 minutes. Solvents were decanted off. Residue was dried in vacuo. Title compound was obtained as dark oil in quantitative yield. MS m/e $(M+H)^+=434$.

Intermediate 87

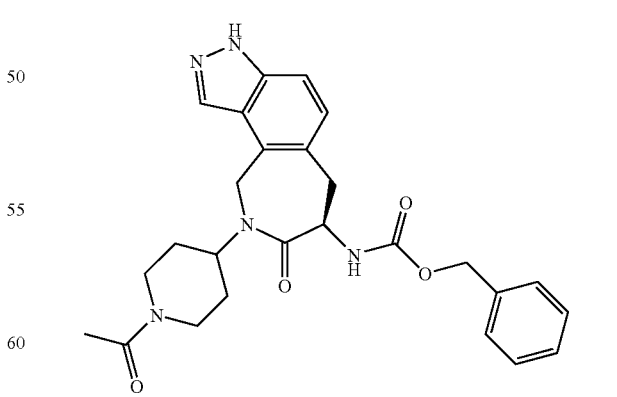

(R)-benzyl 9-(1-acetylpiperidin-4-yl)-8-oxo-3,6,7,8,9,10-hexahydroazepino[3,4-e]indazol-7-ylcarbamate. (R)-benzyl 8-oxo-9-(piperidin-4-yl)-3,6,7,8,9,10-hexahydroazepino[3,4-e]indazol-7-ylcarbamate methanesulfonate (100 mg, 0.19 mmol) was dissolved in a mixture of dichloromethane (4 mL) and triethylamine (500 μL, 3.6 mmol). Acetic anhydride (500 μL, 5.3 mmol) was added to the mixture. Reaction stirred at room temperature overnight. Reaction mixture was washed successively 1× water, 2×1N hydrochloric acid, 2×1N sodium hydroxide, and 1× brine. Organic was dried (magnesium sulfate), and filtered. Filtrate was concentrated in vacuo. Residue was treated with methanol (3 mL). Potassium carbonate (40 mg, 0.29 mmol) was added to the mixture. Reaction stirred at room temperature for 2 hours. Reaction was quenched with 1N hydrochloric acid (6 mL). Methanol was removed from the mixture in vacuo. Remaining aqueous mixture was made basic with sodium bicarbonate. Mixture was extracted with ethyl acetate. Organic layer was dried (magnesium sulfate), filtered and concentrated. Title compound was obtained as yellow solid in 43% yield. MS m/e $(M+H)^+=476$.

Intermediate 88

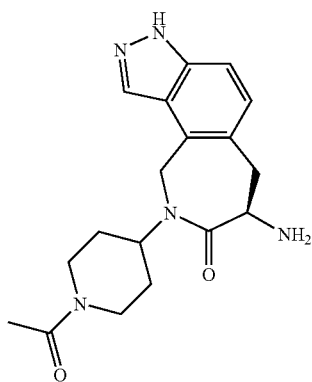

(R)-9-(1-acetylpiperidin-4-yl)-7-amino-6,7,9,10-tetrahydroazepino[3,4-e]indazol-8(3H)-one methanesulfonate. (R)-benzyl 9-(1-acetylpiperidin-4-yl)-8-oxo-3,6,7,8,9,10-hexahydroazepino[3,4-e]indazol-7-ylcarbamate (38 mg, 0.08 mmol) was dissolved in dichloromethane (1 mL). Anisole (30 μL, 0.27 mmol) was added to the mixture followed by methanesulfonic acid (250 μL). Reaction stirred at room temperature for 2 hours. Mixture was diluted with diethyl ether. Mixture sat at room temperature for 30 minutes. Solvents were decanted off. Remaining residue was dried in vacuo. Title compound was obtained as dark oil in quantitative yield. MS m/e $(M+H)^+=342$.

Intermediate 89

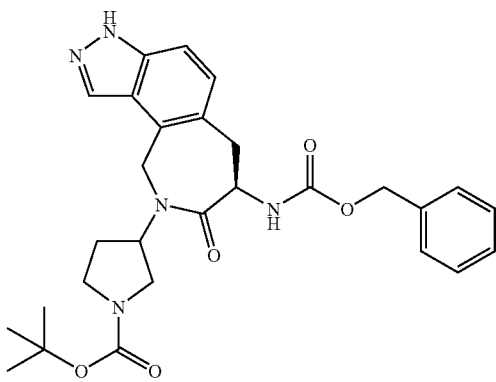

tert-butyl 3-((R)-7-(benzyloxycarbonyl)-8-oxo-7,8-dihydroazepino[3,4-e]indazol-9(3H,6H,10H)-yl)pyrrolidine-1-carboxylate. 2-(R)-Benzyloxycarbonylamino-3-(4-chloromethyl-1H-indazol-5-yl)-propionic acid methyl ester hydrochloride (150 mg, 0.31 mmol) and R,S-3-amino-1-N-Boc-pyrrolidine (90 μL, 0.48 mmol) were reacted in a manner analogous to the preparation of [9-(2,2-dimethyl-propyl)-8-oxo-3,6,7,8,9,10-hexahydro-2,3,9-triaza-(S)-cyclohepta[e]inden-7-yl]-acetic acid methyl ester. Title compound was obtained without purification as dark foam in 96% yield. MS m/e $(M+H)^+=342$.

Intermediate 90

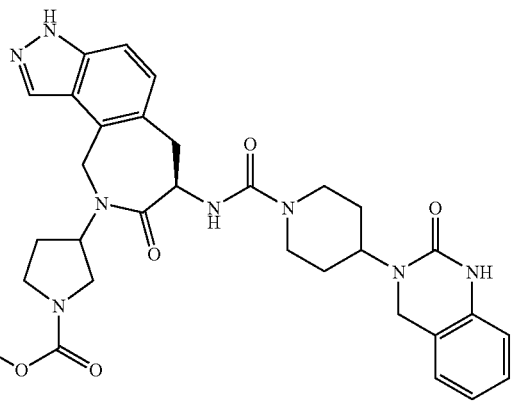

tert-butyl 3-((R)-8-oxo-7-(4-(2-oxo-1,2-dihydroquinazolin-3(4H)-yl)piperidine-1-carboxamido)-7,8-dihydroazepino[3,4-e]indazol-9(3H,6H,10H)-yl)pyrrolidine-1-carboxylate. tert-butyl 3-((R)-7-(benzyloxycarbonyl)-8-oxo-7,8-dihydroazepino[3,4-e]indazol-9(3H,6H,10H)-yl)pyrrolidine-1-carboxylate was dissolved in methanol (10 mL). Acetic acid (300 μL) was added to the mixture followed by 10% palladium on carbon. Reaction vessel was placed on a Parr apparatus and charged with 30 psi of hydrogen gas. Reaction shook at ambient temperature for 2 hours. Reaction mixture was filtered. Filtrate was concentrated in vacuo. Residue was dissolved in dichloromethane (2 mL). Triethylamine (500 μL, 3.6 mmol) was added to the mixture followed by N,N'-disuccinimidyl carbonate (90 mg, 0.35 mmol). Reaction stirred at room temperature for 30 minutes. 3-(piperidin-4-yl)-3,4-dihydroquinazolin-2(1H)-one acetate (80 mg, 0.27 mmol) was added to the mixture. Reaction stirred at room temperature for 1 hour. Mixture was diluted with dichloromethane. Mixture was washed with water. Organic layer was concentrated. C18 preparative HPLC purification afforded the title compound as yellow solid in 24% yield. MS m/e $(M-C_5H_8O_2+H)^+=543$.

Intermediate 91

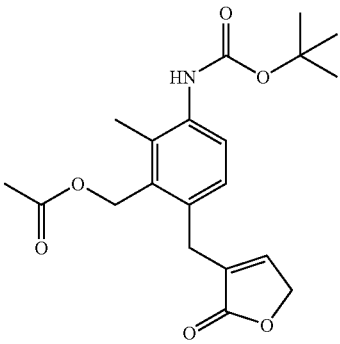

3-(tert-butoxycarbonyl)-2-methyl-6-((2-oxo-2,5-dihydrofuran-3-yl)methyl)benzyl acetate. Acetic acid 3-tert-butoxycarbonylamino-6-iodo-2-methyl-benzyl ester (575 mg, 1.4 mmol) was dissolved in N,N-dimethylformamide (2.5 mL). α-Methylene-γ-butyrolactone (190 μL, 2.2 mmol) was added to the mixture followed by potassium acetate (420 mg, 4.3 mmol), and then palladium(II) acetate (16 mg, 0.07 mmol). Reaction mixture was heated at 80° C. for 26 hours. Mixture was cooled to room temperature and partitioned between ethyl acetate and aqueous sodium bicarbonate. Layers were separated. Organic layer was dried (magnesium sulfate), filtered and concentrated in vacuo. Silica gel chromatography afforded the title compound as off-white solid in 54% yield. MS m/e (M−H)⁻=374.

Intermediate 92

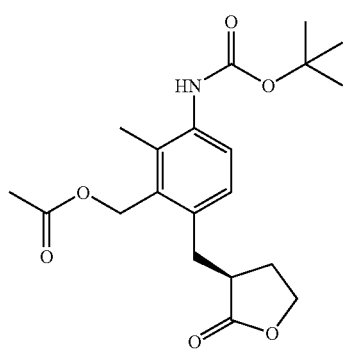

(S)-3-(tert-butoxycarbonyl)-2-methyl-6-((2-oxo-tetrahydrofuran-3-yl)methyl)benzyl acetate. 3-(tert-butoxycarbonyl)-2-methyl-6-((2-oxo-2,5-dihydrofuran-3-yl)methyl)benzyl acetate (280 mg, 0.75 mmol) was dissolved in a mixture of ethyl acetate (10 mL) and methanol (10 mL). A catalytic amount of (−)-1,2-bis((2R,5R)-diethylphospholano)benzene (cyclooctadiene)rhodium (I) tetrafluoroborate was added to the mixture. Reaction vessel was placed on a Parr apparatus and charged with 50 psi of hydrogen gas. Reaction shook at room temperature for 16 hours. A fresh portion of (−)-1,2-bis((2R,5R)-diethylphospholano)benzene(cyclooctadiene) rhodium (I) tetrafluoroborate was added to the mixture. Reaction vessel was charged with 50 psi of hydrogen gas. Reaction shook at room temperature for 24 hours. Reaction mixture was concentrated in vacuo. Residue was passed through a plug of silica gel eluting 80% ethyl acetate-hexanes. Filtrate was concentrated in vacuo. Title compound was obtained as clear colorless oil in 69% yield. MS m/e (M−H)⁻=376.

Intermediate 93

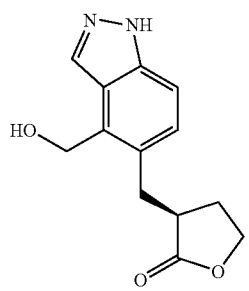

(S)-3-((4-(hydroxymethyl)-1H-indazol-5-yl)methyl)-dihydrofuran-2(3H)-one. (S)-3-(tert-butoxycarbonyl)-2-methyl-6-((2-oxo-tetrahydrofuran-3-yl)methyl)benzyl acetate (190 mg, 0.50 mmol) was dissolved in dichloromethane (4 mL). Trifluoroacetic acid (1 mL) was added to the mixture. Reaction stirred at room temperature for 30 minutes. Mixture was diluted with dichloromethane and then concentrated in vacuo. Residue was dissolved in chloroform (5 mL). Acetic acid (250 μL) was added to the mixture followed by isoamyl nitrite (80 μL, 0.60 mmol). Reaction stirred at room temperature for 20 minutes. Potassium acetate (400 mg, 4.1 mmol) was added to the mixture. Reaction stirred at room temperature for 1 hour. Mixture was diluted with dichloromethane. Mixture was washed successively 1× water, 2× aqueous sodium bicarbonate. Organic layer was dried (magnesium sulfate), filtered and concentrated in vacuo. Residue was dissolved in methanol (5 mL). Potassium carbonate (120 mg, 0.87 mmol) was added to the mixture. Reaction stirred at room temperature for 1 hour. Reaction was quenched with 1N hydrochloric acid. Methanol was removed from the mixture in vacuo. Remaining aqueous was extracted 2× diethyl ether, made basic with sodium bicarbonate, and then extracted again 2× diethyl ether. Combined extracts were dried (magnesium sulfate), filtered, and concentrated in vacuo. Title compound was obtained as amber oil in 73% yield. MS m/e (M+H)⁺=247.

Intermediate 94

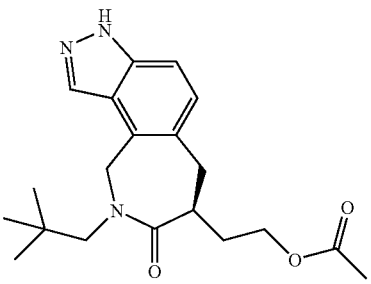

(S)-2-(9-neopentyl-8-oxo-3,6,7,8,9,10-hexahydroazepino[3,4-e]indazol-7-yl)ethyl acetate. (S)-3-((4-(hydroxymethyl)-1H-indazol-5-yl)methyl)-dihydrofuran-2(3H)-one (70 mg, 0.28 mmol), was dissolved in dichloromethane (1.5 mL). Thionyl chloride (500 μL) was added to the mixture. Reaction stirred at room temperature for 45 minutes. Mixture was concentrated. Residue was treated with dichloromethane and re-concentrated. Residue was dissolved in acetonitrile (3 mL). Potassium carbonate (150 mg, 1.1 mmol) was added to the mixture followed by neopentylamine (100 μL, 0.85 mmol). Mixture was heated at reflux for 45 minutes. Mixture was cooled to room temperature and filtered. Filtrate was concentrated in vacuo. Residue was dissolved in toluene (5 mL). Acetic acid (200 μL) was added to the mixture. Reaction was heated at reflux for 5.5 hours. Mixture was concentrated in vacuo. Preparatory HPLC purification gave the title compound as yellow solid in 19% yield. MS m/e (M−H)⁻=356.

Intermediate 95

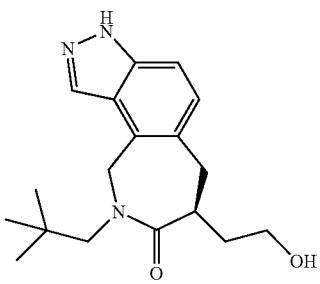

(S)-7-(2-hydroxyethyl)-9-neopentyl-6,7,9,10-tetrahydroazepino[3,4-e]indazol-8(3H)-one. (S)-2-(9-neopentyl-8-oxo-3,6,7,8,9,10-hexahydroazepino[3,4-e]indazol-7-yl)ethyl acetate (18 mg, 0.05 mmol) was dissolved in methanol (1 mL). Potassium carbonate (20 mg, 0.14 mmol) was added to the mixture. Reaction stirred at room temperature for 1 hour. Amberlite IRC-50 ion exchange resin was added to the mixture. Reaction stirred at room temperature for 15 minutes. Mixture was filtered. Filtrate was concentrated in vacuo. The title compound was obtained as yellow residue in 94% yield. MS m/e (M+H)$^+$=316.

Intermediate 96

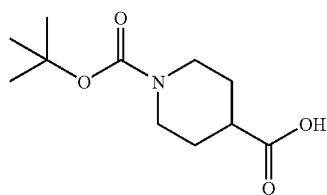

1-(tert-butoxycarbonyl)piperidine-4-carboxylic acid. Isonipecotic acid (1.05 g, 8.1 mmol) was suspended in a mixture of tetrahydrofuran (20 mL) and 1N sodium hydroxide (20 mL). Di-tert-butyl dicarbonate was added to the mixture. Reaction stirred at room temperature for 2.5 hours. Mixture was made acidic with 1N hydrochloric acid. Mixture was extracted 2× ethyl acetate. Combined organics were washed with brine and then dried (magnesium sulfate), filtered and concentrated in vacuo. Title compound was obtained as white solid in 94% yield. MS m/e (M−H)$^-$=228.0.

Intermediate 97

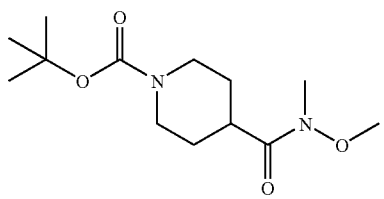

tert-Butyl 4-(methoxy(methyl)carbamoyl)piperidine-1-carboxylate. tert-Butyl 4-(methoxy(methyl)carbamoyl)piperidine-1-carboxylate (640 mg, 2.8 mmol) and o-benzotriazol-1-yl-N,N,N',N'-tetramethyluronium tetrafluoroborate (1.0 g, 3.1 mmol) were combined and dissolved in N,N-dimethylformamide (12 mL). N,N-Diisopropylethylamine was added to the mixture. Reaction stirred at room temperature for 45 minutes. N, O-Dimethylhydroxylamine hydrochloride (450 mg, 4.6 mmol) was added to the mixture. Reaction stirred at room temperature for 1.5 hours. Mixture was diluted with diethyl ether and then washed 3× water, 1×1N hydrochloric acid. Organic layer was dried (magnesium sulfate), filtered and concentrated in vacuo. Title compound was obtained as clear colorless oil in 70% yield. MS m/e (M−C$_4$H$_8$+H)$^+$=217.1.

Intermediate 98

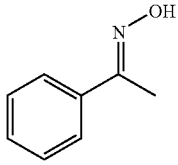

Acetophenone oxime. Acetophenone (5.0 mL, 43 mmol) was dissolved in methanol (50 mL). Hydroxylamine hydrochloride (6.1 g, 88 mmol) was added to the mixture followed by 10N sodium hydroxide (10 mL, 100 mmol). Reaction was stirred at room temperature for 20 minutes. 10N Sodium hydroxide (5 mL, 50 mmol) was added to the mixture. Reaction was heated at reflux for 1 hour. Mixture was cooled to room temperature and stirred for 4 hours. Reaction mixture was concentrated in vacuo. Residue was treated with water. Mixture was extracted 2× diethyl ether. Combined extracts were washed 1× water, 1× brine. Organic layer was dried (magnesium sulfate), filtered and concentrated. Title compound was obtained as white solid in 76% yield. MS m/e (M+H)$^+$=136.0.

Intermediate 99

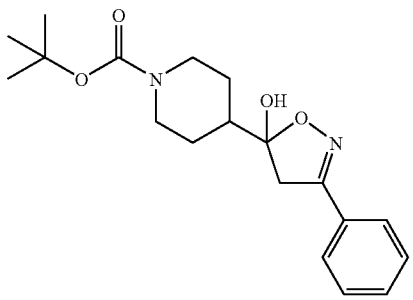

tert-Butyl 4-(5-hydroxy-3-phenyl-4,5-dihydroisoxazol-5-yl)piperidine-1-carboxylate. Acetophenone oxime (180 mg, 1.3 mmol) was dissolved in tetrahydrofuran (15 mL). Mixture was cooled to 0° C. 2.0M Butyllithium in pentanes (1.35 mL, 2.7 mmol) was added to the mixture drop-wise. Reaction stirred at 0° C. for 1 hour. A solution of tert-Butyl 4-(methoxy(methyl)carbamoyl)piperidine-1-carboxylate (360 mg, 1.3 mmol) in tetrahydrofuran (5 mL) was added to the reaction mixture drop-wise. Reaction stirred at 0° C. for 1 hour. Reaction was quenched with aqueous ammonium chloride. Mixture was extracted 2× ethyl acetate. Combined extracts were dried (magnesium sulfate), filtered and concentrated in vacuo. Silica gel chromatography afforded the title compound as clear colorless oil in 71% yield. MS m/e (M−H)$^-$=345.1.

Intermediate 100

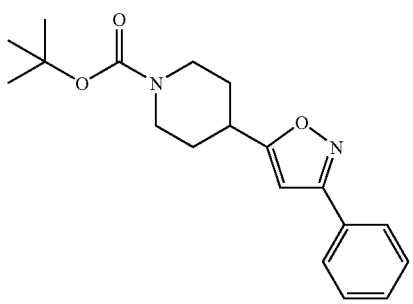

tert-Butyl 4-(3-phenylisoxazol-5-yl)piperidine-1-carboxylate. tert-Butyl 4-(5-hydroxy-3-phenyl-4,5-dihydroisoxazol-5-yl)piperidine-1-carboxylate (320 mg, 0.92 mmol) was dissolved in methanol (10 mL). A solution of sodium carbonate (200 mg, 1.9 mmol) in water (10 mL) was added to the mixture. Reaction was stirred at reflux for 2 hours. Methanol was removed from the reaction mixture in vacuo. Remaining aqueous was extracted 2× ethyl acetate. Combined extracts were washed with brine. Organic layer was dried (magnesium sulfate), filtered, and concentrated. Title compound was obtained as off-white solid in 86% yield. $(M-C_4H_8+H)^+=273.1$.

Intermediate 101

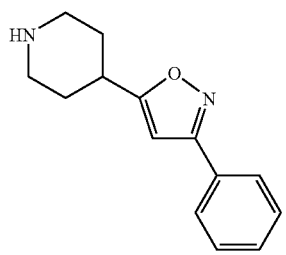

4-(3-Phenylisoxazol-5-yl)piperidine. tert-Butyl 4-(3-phenylisoxazol-5-yl)piperidine-1-carboxylate (225 mg, 0.78 mmol) was diluted in dichloromethane (3 mL). Trifluoroacetic acid (3 mL) was added to the mixture. Reaction stirred at room temperature for 1 hour. Mixture was diluted with dichloromethane and then concentrated in vacuo. Residue was treated with aqueous sodium bicarbonate. Mixture was extracted 2× ethyl acetate. Combined extracts were washed 1× water, 1× brine. Organic layer was dried (magnesium sulfate), filtered and concentrated in vacuo. Title compound was obtained as white solid in 76% yield. MS m/e $(M+H)^+=229.1$.

Intermediate 102

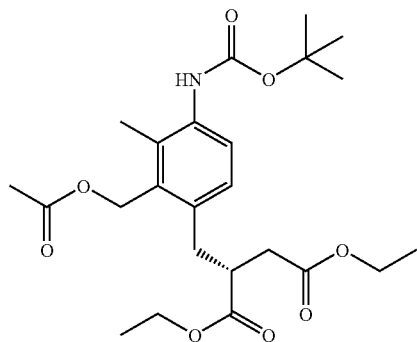

2-(R)-(Acetoxymethyl-4-tert-butoxycarbonylamino-3-methyl-benzyl)-succinic acid diethyl ester. 2-(S)-(Acetoxymethyl-4-tert-butoxycarbonylamino-3-methyl-benzylidene)-succinic acid diethyl ester (700 mg, 1.5 mmol) was hydrogenated in a manner analogous to the preparation of 2-(S)-(acetoxymethyl-4-tert-butoxycarbonylamino-3-methyl-benzyl)-succinic acid diethyl ester using (+)-1,2-bis((2S,5S)-diethylphospholano)benzene(cyclooctadiene)rhodium (I) trifluoromethane sulfonate as the catalyst. Silica gel chromatography afforded the title compound as lightly colored oil in 75% yield. MS m/e $(M-H)^-=464.0$.

Intermediate 103

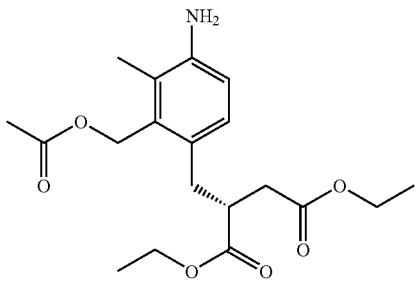

2-(R)-(2-Acetoxymethyl-4-amino-3-methyl-benzyl)-succinic acid diethyl ester. Trifluoroacetic acid (2.5 mL) was added to a solution of 2-(R)-(acetoxymethyl-4-tert-butoxycarbonylamino-3-methyl-benzyl)-succinic acid diethyl ester (525 mg, 1.1 mmol) in dichloromethane (10 mL). Reaction mixture was stirred at room temperature for 1 hour. Mixture was concentrated in vacuo. Residue was treated with aqueous sodium bicarbonate and extracted with ethyl acetate (2×20 mL). Combined organic layers were dried (magnesium sulfate), filtered and concentrated in vacuo. The title compound was obtained as amber oil in 99% yield. MS m/e $(M-C_2H_4O_2+H)^+=306.1$.

Intermediate 104

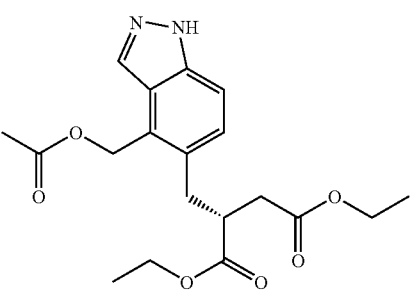

2-(R)-(4-Acetoxymethyl-1H-indazol-5-ylmethyl)-succinic acid diethyl ester. Isoamyl nitrite (170 µL, 1.3 mmol) was added dropwise to a cooled (water ice bath) solution of 2-(R)-(2-acetoxymethyl-4-amino-3-methyl-benzyl)-succinic acid diethyl ester in 5% acetic acid-chloroform (5 mL). Mixture was stirred at 0° C. for 1.5 hours. Mixture was diluted with dichloromethane (20 mL) and then washed with saturated aqueous sodium bicarbonate (2×20 mL). Organic was dried (magnesium sulfate), filtered and concentrated in vacuo. Title compound was obtained as amber oil in 99% yield. MS m/e $(M+H)^+=377.1$.

Intermediate 105

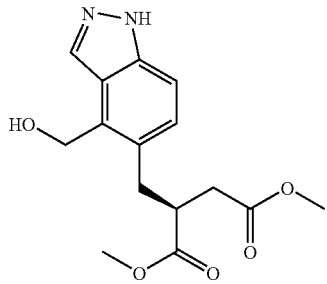

2-(R)-(4-Hydroxymethyl-1H-indazol-5-ylmethyl)-succinic acid dimethyl ester. Potassium carbonate (380 mg, 2.7 mmol) was added to a solution of 2-(R)-(4-acetoxymethyl-1H-indazol-5-ylmethyl)-succinic acid diethyl ester (420 mg, 1.1 mmol) in methanol (10 mL). Mixture was stirred at room temperature for 2 hours. Reaction was quenched with 1N hydrochloric acid. Methanol was removed from the mixture in vacuo. Remaining aqueous made basic with sodium bicarbonate. Mixture was extracted with ethyl acetate (2×20 mL). Combined organic layers were washed successively with water (20 mL) and brine (20 mL). Organic was dried (magnesium sulfate), filtered and concentrated in vacuo. Title compound was obtained as amber oil in 92% yield. MS m/e (M+H)$^+$=307.1.

Intermediate 106

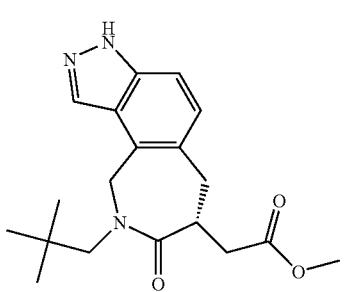

[9-(2,2-Dimethyl-propyl)-8-oxo-3,6,7,8,9,10-hexahydro-2,3,9-triaza-(R)-cyclohepta[e]inden-7-yl]-acetic acid methyl ester. Thionyl chloride (2 mL) was added to a solution of 2-(R)-(4-hydroxymethyl-1H-indazol-5-ylmethyl)-succinic acid dimethyl ester (280 mg, 0.91 mmol) in dichloromethane (4 mL). Reaction was stirred at room temperature for 1 hour. Mixture was diluted with dichloromethane and then concentrated in vacuo. Residue was suspended in acetonitrile (5 mL). Potassium carbonate (300 mg, 2.2 mmol) was added to the mixture followed by neopentylamine (250 μL, 2.1 mmol). Reaction was heated at reflux for 30 minutes. Neopentylamine (150 μL, 1.3 mmol) was added to the mixture. Reaction was heated at reflux for 20 minutes. Mixture was cooled to room temperature and filtered. Filtrate was concentrated in vacuo. Residue was dissolved in toluene (5 mL). Acetic acid (300 μL) was added to the mixture. Reaction was heated at reflux for 16 hours. Mixture was cooled to room temperature and diluted with ethyl acetate. Mixture was washed successively with aqueous sodium bicarbonate (2×), water, and brine. Organic layer was dried (magnesium sulfate), filtered and concentrated in vacuo. Silica gel chromatography afforded the title compound as amber oil in 29% yield. MS m/e (M−H)$^-$=342.1.

Intermediate 107

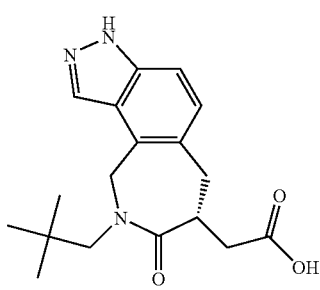

[9-(2,2-Dimethyl-propyl)-8-oxo-3,6,7,8,9,10-hexahydro-2,3,9-triaza-(R)-cyclohepta[e]inden-7-yl]-acetic acid. Lithium hydroxide monohydrate (31 mg, 0.74 mmol) was added to a solution of [9-(2,2-dimethyl-propyl)-8-oxo-3,6,7,8,9,10-hexahydro-2,3,9-triaza-(R)-cyclohepta[e]inden-7-yl]-acetic acid methyl ester (90 mg, 0.26 mmol) in methanol (2.5 mL), tetrahydrofuran (2 mL) and water (2.5 mL). Reaction mixture was heated at 50° C. for 1.5 hours. The organic solvents were removed from the mixture in vacuo. Remaining aqueous was neutralized with 1 N hydrochloric acid (730 μL). Mixture was extracted with ethyl acetate (2×20 mL). Combined organic layers were washed with brine (20 mL) and then dried (magnesium sulfate), filtered and concentrated in vacuo. Title compound was obtained as amber solid in 88% yield. MS m/e (M−H)$^-$=328.1.

Intermediate 108

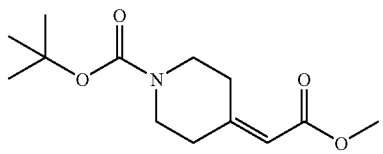

tert-Butyl 4-(2-methoxy-2-oxoethylidene)piperidine-1-carboxylate. 60% sodium hydride in mineral oil (7.92 g, 198.02 mmoles) was washed with hexanes then suspended in N,N-dimethylformamide (220.00 mL). The mixture was cooled to 0° C. Trimethyl phosphonoacetate (29.0 mL, 189.82 mmoles) was added drop-wise to the reaction. The mixture was held at 0° C. with stirring on and held for 20 min. A solution of N-tert-butoxycarbonyl-4-piperidone (30.41 g, 152.62 mmoles) in 80 mL N,N-dimethylformamide was added to the mixture drop-wise. Reaction was stirred at room temperature for 3 hours. Mixture was diluted with diethyl ether (650 mL). Mixture was washed once with water. Aqueous layer was back extracted once with diethyl ether. Organic layers were combined. The mixture was washed 4 times with water and the aqueous phase was discarded. The mixture was washed with brine and the aqueous phase was discarded. The material was dried over MgSO4, filtered, and concentrated to dryness. Title compound was obtained as white solid in 92% yield. $^1$H NMR (300 MHz, CDCl$_3$): δ=5.68 (s, 1H), 3.66 (s, 3H), 3.40-3.51 (m, 4H), 2.90 (t, J=5.49, 2H), 2.25 (t, J=5.49, 2H), 1.44 (s, 9H).

Intermediate 109

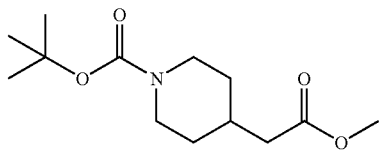

tert-Butyl 4-(2-methoxy-2-oxoethyl)piperidine-1-carboxylate. tert-Butyl 4-(2-methoxy-2-oxoethylidene)piperidine-1-carboxylate (35.71 g, 140 mmol) was dissolved in a mixture of ethyl acetate (110 mL) and methanol (110 mL). 50% wet 10% palladium on carbon (3.3 g) was added to the mixture. Reaction vessel was charged with 55 psi of hydrogen gas. Reaction shook on a Parr apparatus at room temperature for 16 hours. Reaction mixture was filtered to remove the catalyst. Filtrate was concentrated in vacuo. Title compound was obtained as clear colorless oil in 97% yield. $^1$H NMR (300 MHz, CDCl$_3$): δ=4.04 (d, J=10.25, 2H), 3.64 (s, 3H), 2.68 (t, J=12.44, 2H), 2.21 (d, J=6.95, 2H), 1.98-1.77 (m, 1H), 1.64 (d, J=13.54, 2H), 1.41 (s, 9H), 1.25-0.99 (m, 2H).

Intermediate 110

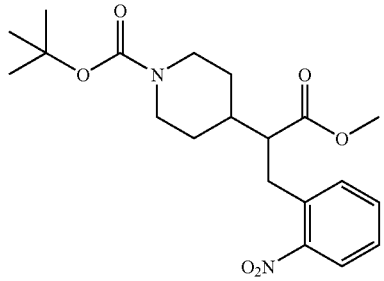

tert-butyl 4-(1-methoxy-3-(2-nitrophenyl)-1-oxopropan-2-yl)piperidine-1-carboxylate. tert-Butyl 4-(2-methoxy-2-oxoethyl)piperidine-1-carboxylate (240 mg, 0.93 mmol) was dissolved in tetrahydrofuran (7 mL). Mixture was cooled to −78° C. A 0.5 M solution of potassium bistrimethylsilyl) amide in toluene (2.2 mL, 1.1 mmol) was added to the mixture drop-wise. Reaction stirred at −78° C. for 20 minutes. A solution of 2-nitrobenzylbromide (240 mg, 1.1 mmol) in tetrahydrofuran (2 mL) was added to the reaction mixture drop-wise. Reaction stirred at −78° C. for 40 minutes. Dry ice bath was removed and the reaction mixture was allowed to warm to room temperature over 30 minutes. Reaction was quenched with aqueous ammonium chloride. Mixture was extracted with ethyl acetate (2×20 mL). Combined extracts were dried (magnesium sulfate), filtered and concentrated in vacuo. Silica gel chromatography afforded the title compound as yellow oil in 41% yield. MS m/e (M−C$_4$H$_8$+H)$^+$=337.3.

Intermediate 111

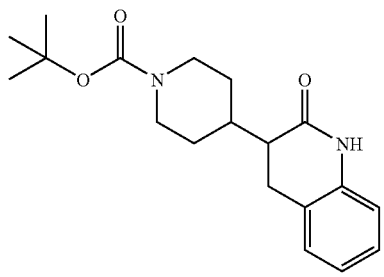

tert-Butyl 4-(2-oxo-1,2,3,4-tetrahydroquinolin-3-yl)piperidine-1-carboxylate. tert-butyl 4-(1-methoxy-3-(2-nitrophenyl)-1-oxopropan-2-yl)piperidine-1-carboxylate (660 mg, 1.7 mmol) was dissolved in a mixture of ethyl acetate (15 mL) and methanol (15 mL). Acetic acid (250 μL, 4.4 mmol) was added to the mixture. A catalytic amount of 50% wet 10% palladium on carbon was added to the mixture. Reaction vessel was charged with 15 psi of hydrogen gas. Reaction shook on a Parr apparatus at room temperature for 2 hours. Reaction mixture was filtered to removed the catalyst. Filtrated was concentrated in vacuo. Silica gel chromatography gave the title compound as orange foam in 47% yield. MS m/e (M−H)$^-$=329.1.

Intermediate 112

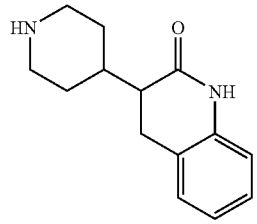

3-(piperidin-4-yl)-3,4-dihydroquinolin-2(1H)-one. Trifluoroacetic acid (3 mL) was added to a solution of tert-Butyl 4-(2-oxo-1,2,3,4-tetrahydroquinolin-3-yl)piperidine-1-carboxylate (260 mg, 0.79 mmol) in dichloromethane (3 mL). Reaction stirred at room temperature for 1 hour. Reaction mixture was concentrated in vacuo. Residue was dissolved in methanol. Dowex 1×4-200 ion exchange resin was added to the mixture to create a slurry. Mixture stirred at room temperature for 30 minutes. Resin was filtered off and washed with methanol. Filtrate was concentrated. Title compound was obtained as dark foam in quantitative yield. MS m/e (M+H)$^+$=231.1.

Intermediate 113

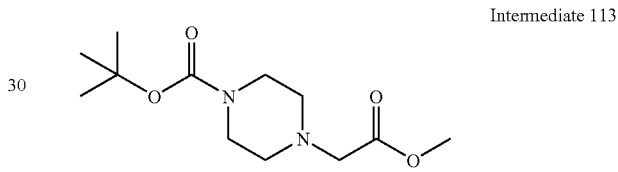

tert-Butyl 4-(2-methoxy-2-oxoethyl)piperazine-1-carboxylate. Potassium carbonate (3.4 g, 25 mmol) was added to a mixture of N-Boc-piperazine (3.0 g, 16 mmol) in acetonitrile (20 mL). Methyl bromoacetate (1.5 mL, 16 mmol) was added to the mixture. Reaction stirred at room temperature for 1.5 hours. Mixture was filtered over celite. Filtrate was concentrated in vacuo. Residue was treated with diethyl ether (10 mL), filtered and concentrated in vacuo. Bulb to bulb distillation (165° C. at 700 mtorr) gave the title compound as clear colorless oil in 60% yield. MS m/e (M+H)$^+$=259.4.

Intermediate 114

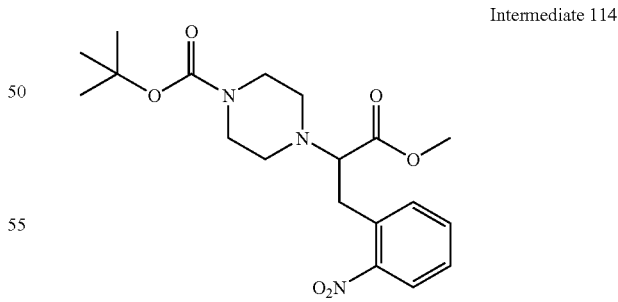

tert-Butyl 4-(1-methoxy-3-(2-nitrophenyl)-1-oxopropan-2-yl)piperazine-1-carboxylate. tert-Butyl 4-(2-methoxy-2-oxoethyl)piperazine-1-carboxylate (1.0 g, 3.9 mmol) and 2-nitrobenzylbromide (1.0 g, 4.6 mmol) were reacted in a manner analogous to the preparation of tert-butyl 4-(1-methoxy-3-(2-nitrophenyl)-1-oxopropan-2-yl)piperidine-1-carboxylate. Title compound was obtained as amber oil in 51% yield. MS m/e (M+H)$^+$=394.4.

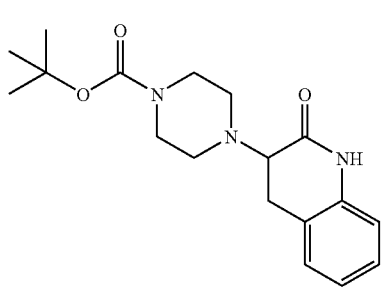

Intermediate 115 tert-Butyl 4-(2-oxo-1,2,3,4-tetrahydroquinolin-3-yl)piperazine-1-carboxylate. tert-Butyl 4-(1-methoxy-3-(2-nitrophenyl)-1-oxopropan-2-yl)piperazine-1-carboxylate (770 mg, 2.0 mmol) was reacted in a manner analogous to the preparation of tert-butyl 4-(2-oxo-1,2,3,4-tetrahydroquinolin-3-yl)piperidine-1-carboxylate. Title compound was obtained as amber oil in quantitative yield. MS m/e (M+H)$^+$=332.3.

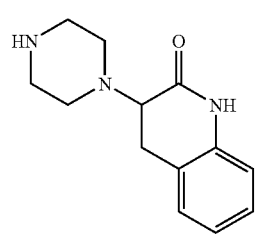

Intermediate 116

3-(Piperazin-1-yl)-3,4-dihydroquinolin-2(1H)-one. tert-Butyl 4-(2-oxo-1,2,3,4-tetrahydroquinolin-3-yl)piperazine-1-carboxylate (640 mg, 1.9 mmol) was reacted in a manner analogous to the preparation of 3-(piperidin-4-yl)-3,4-dihydroquinolin-2(1H)-one. Title compound was obtained as light brown solid in quantitative yield. MS m/e (M+H)$^+$=232.4.

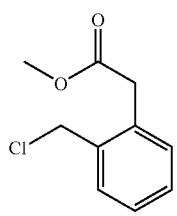

Intermediate 117

Methyl 2-(2-(chloromethyl)phenyl)acetate. Hydrogen chloride gas was bubbled though a solution of 3-isochromanone (1.2 g, 8.1 mmol) in methanol (30 mL) for 3 minutes. Reaction stirred at room temperature for 8 hours. Mixture was diluted with water (70 mL). Mixture was extracted with dichloromethane (2×40 mL). Combined organic layers were washed with brine (20 mL). Mixture was dried (magnesium sulfate), filtered and concentrated in vacuo. Title compound was obtained as clear colorless oil in 90% yield. $^1$H NMR (300 MHz, CDCl$_3$): δ=7.40-7.26 (m, 4H), 4.67 (s, 2H), 3.80 (s, 2H), 3.69 (s, 3H).

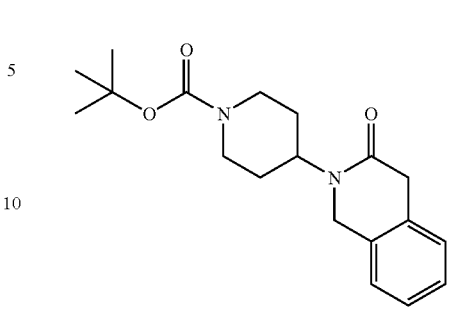

Intermediate 118 tert-Butyl 4-(3-oxo-3,4-dihydroisoquinolin-2(1H)-yl)piperidine-1-carboxylate. Potassium carbonate (1.4 g, 10 mmol) was added to a solution of methyl 2-(2-(chloromethyl)phenyl)acetate (940 mg, 4.7 mmol) in acetonitrile (20 mL). 4-Amino-N-Boc-piperidine (1.13 g, 5.6 mmol) was added to the mixture. Reaction was heated at reflux for 1 hour. Mixture was cooled to room temperature and then filtered over celite. Filtrate was concentrated in vacuo. Residue was treated with toluene (29 mL). Acetic acid (1.5 ml) was added to the mixture. Reaction was heated at reflux for 2 hours. Mixture was concentrated in vacuo. Residue was treated with ethyl acetate (50 mL). Mixture was washed successively with aqueous sodium bicarbonate (2×30 mL), 1N hydrochloric acid (30 mL), and brine (20 mL). Organic layer was dried (magnesium sulfate), filtered and concentrated in vacuo. Silica gel chromatography gave the title compound as lightly colored oil in 40% yield. MS m/e (M+H)$^+$=331.2.

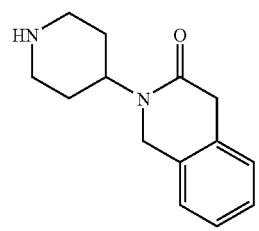

Intermediate 119

2-(Piperidin-4-yl)-1,2-dihydroisoquinolin-3(4H)-one. tert-Butyl 4-(3-oxo-3,4-dihydroisoquinolin-2(1H)-yl)piperidine-1-carboxylate (730 mg, 2.2 mmol) was reacted in a manner analogous to the preparation of 3-(piperidin-4-yl)-3,4-dihydroquinolin-2(1H)-one. Title compound was obtained as yellow solid in 96% yield. MS m/e (M+H)$^+$=231.4.

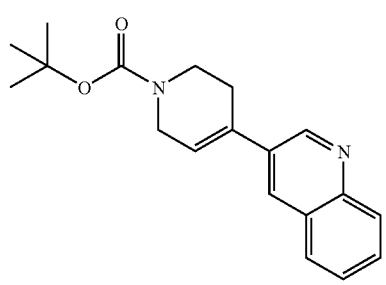

Intermediate 120 tert-Butyl 4-(quinolin-3-yl)-5,6-dihydropyridine-1(2H)-carboxylate. 3-Quinolineboronic acid (250 mg, 1.4 mmol)

and tert-butyl 4-(trifluoromethylsulfonyloxy)-5,6-dihydropyridine-1(2H)-carboxylate (580 mg, 1.8 mmol) were combined and dissolved in a mixture of toluene (10 mL) and ethanol (1 mL). 2M aqueous sodium bicarbonate solution (1.5 mL, 3.0 mmol) was added to the mixture followed by lithium chloride (180 mg, 4.2 mmol). Nitrogen gas was bubbled through the mixture for 10 minutes. Tetrakis(triphenylphosphine)palladium(0) (75 mg, 0.07 mmol) was added to the mixture. Reaction was heated at reflux for 3.5 hours. Mixture was cooled to room temperature and diluted with ethyl acetate (50 mL). Mixture was washed successively with water (2×30 mL) and brine (20 mL). Organic layer was dried (magnesium sulfate), filtered and concentrated in vacuo. Silica gel chromatography afforded the desired product as lightly colored oil in 76% yield. MS m/e (M−C$_4$H$_8$+H)$^+$= 255.1.

Intermediate 121

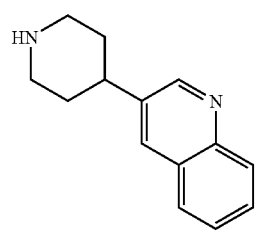

3-(Piperidin-4-yl)quinoline. A catalytic amount of 50% wet 10% palladium on carbon was added to a mixture of tert-butyl 4-(quinolin-3-yl)-5,6-dihydropyridine-1(2H)-carboxylate (260 mg, 0.84 mmol) in methanol (10 mL). Reaction vessel was placed on a Parr apparatus and charged with 10 psi of hydrogen gas. Reaction shook at room temperature for 4 hours. Mixture was filtered to removed catalyst. Filtrate was concentrated in vacuo. Residue was dissolved in dichloromethane (4 mL). Trifluoroacetic acid (1 mL) was added to the mixture. Reaction stirred at room temperature for 2 hours. Reaction mixture was concentrated in vacuo. Residue was dissolved in dichloromethane (20 mL). Mixture was washed with aqueous sodium bicarbonate (20 mL). Aqueous layer was back extracted with dichloromethane (30 mL). Organic layers were combined, dried (magnesium sulfate), filtered and concentrated in vacuo. Title compound was obtained as yellow oil in 45% yield. MS m/e (M+H)$^+$=213.2.

Intermediate 122

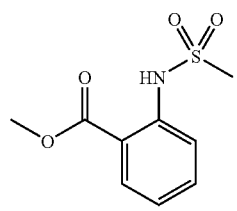

Methyl 2-(methylsulfonamido)benzoate. Methanesulfonyl chloride (3.4 mL, 44 mmol) was added to a solution of methyl anthranilate (5.0 mL, 39 mmol) in pyridine (10 mL, 124 mmol). Mixture stirred at room temperature for 16 hours. Reaction was quenched with 1N hydrochloric acid (150 mL). Mixture was extracted with ethyl acetate (2×200 mL). Organic layers were washed successively with 1N hydrochloric acid (2×100 mL) and brine (50 mL). Organic layer was dried (magnesium sulfate), filtered and concentrated in vacuo. Residue was crystallized from 50 mL isopropyl alcohol. Solids were filtered, washed with isopropyl alcohol and dried in vacuo. Title compound was obtained as pink crystals in 75% yield. MS m/e (M−H)$^−$=228.0.

Intermediate 123

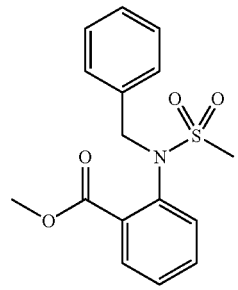

Methyl 2-(N-benzylmethan-2-ylsulfonamido)benzoate. 60% Sodium hydride in mineral oil (650 mg, 16.3 mmol) was washed with hexanes and then suspended in N,N-dimethylformamide (50 mL). Mixture was cooled to 0° C. A solution of methyl 2-(methylsulfonamido)benzoate (3.1 g, 13.5 mmol) in N,N-dimethylformamide (10 mL) was added to the mixture drop-wise with stirring. Reaction was held at 0° C. with stirring for 15 minutes. Benzylbromide (1.9 mL, 15.9 mmol) was added to the mixture drop-wise. Reaction was stirred at room temperature for 16 hours. Reaction was quenched with 1N hydrochloric acid (50 mL). Mixture was extracted with diethyl ether (2×50 mL). Organic layers were combined and washed successively with water (2×50 mL) and brine (30 mL). Organic layer was dried (magnesium sulfate), filtered and concentrated in vacuo. Silica gel chromatography afforded the title compound as clear colorless oil in 76% yield. MS m/e (M−CH$_4$O+H)$^+$=288.1.

Intermediate 124

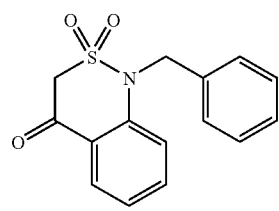

1-Benzyl-2,2-dioxo-2,3-dihydro-1H-2,1-benzothiazin-4-one. 60% Sodium hydride in mineral oil (500 mg, 12.5 mmol) was washed with hexanes and then suspended in N,N-dimethylformamide (15 mL). Mixture was cooled to 0° C. A solution of methyl 2-(N-benzylmethan-2-ylsulfonamido) benzoate (3.25 g, 10.2 mmol) in N,N-dimethylformamide (20 mL) was added to the mixture drop-wise. Mixture was warmed to room temperature. Reaction stirred at room temperature for 3 hours. Reaction was quenched with 1N hydrochloric acid (40 mL). Mixture was extracted with diethyl ether (2×40 mL). Combined organic layers were washed with water (2×40 mL). Organic layer was dried (magnesium sulfate), filtered and concentrated in vacuo. Title compound was obtained as light yellow solid in 85% yield. MS m/e (M−H)$^−$= 286.1.

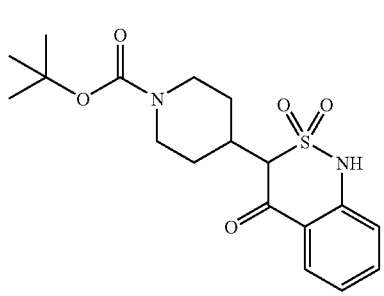

Intermediate 125

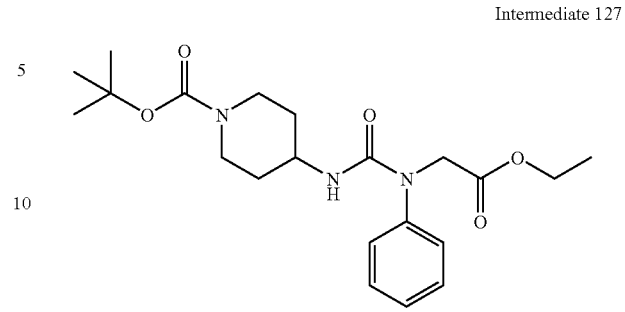

Intermediate 127

4-(2,2,4-Trioxo-1,2,3,4-tetrahydro-2,1-benzothiazin-3-yl)-piperidine-1-carboxylic acid tert-butyl ester. 1-Benzyl-2,2-dioxo-2,3-dihydro-1H-2,1-benzothiazin-4-one (1.51 g, 5.26 mmol) was dissolved in pyridine (50 mL). N-tert-Butoxycarbonyl-4-piperidinone (1.24 g, 6.33 mmol) was added to the mixture followed by piperidine (110 μL, 1.11 mmol). Molecular sieves were added to the mixture. Reaction stirred at room temperature for 40 hours. Reaction mixture was filtered over celite. Filtrate was concentrated in vacuo. Residue was purified by silica gel chromatography. The major component was isolated and the fractions concentrated in vacuo. Residue was dissolved in methanol (50 mL). A catalytic amount of 50% wet 10% palladium on carbon was added to the mixture. Reaction vessel was placed on a Parr apparatus and charged with 55 psi of hydrogen gas. Reaction shook at room temperature for 2 hours. Reaction mixture was filtered over celite. Fresh catalyst was added to the filtrate. Reaction vessel was placed on a Parr apparatus and charged with 55 psi of hydrogen gas. Reaction shook at room temperature for 1 hour. Mixture was filtered over celite. A third batch of fresh catalyst was added to the mixture. Reaction vessel was placed on a Parr apparatus and charged with 55 psi of hydrogen gas. Reaction shook at room temperature for 7.5 hours. Catalyst was filtered off. Filtrate was concentrated in vacuo. Silica gel chromatography afforded the title compound as pale yellow solid in 24% yield. MS m/e (M−H)$^-$=379.1.

tert-Butyl 4-(3-(2-ethoxy-2-oxoethyl)-3-phenylureido)piperidine-1-carboxylate. 4-Amino-1-N-Boc-piperidine (760 mg, 3.79 mmol) was dissolved in a mixture of dichloromethane (40 mL) and aqueous sodium bicarbonate (30 mL). A solution of 20% phosgene in toluene (10 mL, 18.9 mmol) was added to the mixture with vigorous stirring. Reaction stirred vigorously at room temperature for 40 minutes. Reaction layers were partitioned. Organic layer was dried (magnesium sulfate), filtered and concentrated in vacuo. Residue was dissolved in toluene (30 mL). N-Phenylglycine ethyl ester was added to the mixture. Reaction was heated at reflux for 15 hours. Mixture was cooled to room temperature and diluted with ethyl acetate (50 mL). Mixture was washed successively with 1N hydrochloric acid (3×50 mL) and brine (30 mL). Organic layer was dried (magnesium sulfate), filtered and concentrated in vacuo. Silica gel chromatography afforded the title compound as pale yellow solid in 63% yield. $^1$H NMR (300 MHz, CDCl$_3$): δ=7.47-7.26 (m, 5H), 4.30 (s, 1H), 4.16 (q, J=7.32, 2H), 3.88 (d, J=12.81, 2H), 3.81-3.69 (m, 1H), 2.89-2.70 (m, 2H), 1.83 (dd, J1=12.62, J2=3.11, 2H), 1.38 (s, 9H), 1.23 (t, J=7.14, 3H), 1.19-1.03 (m, 2H).

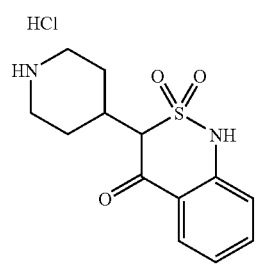

Intermediate 126

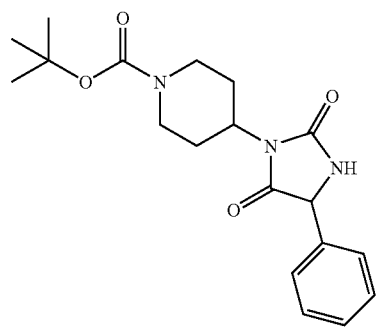

Intermediate 128

2,2-Dioxo-3-piperidin-4-yl-2,3-dihydro-1H-2,1-benzothiazin-4-one hydrochloride. 4-(2,2,4-Trioxo-1,2,3,4-tetrahydro-2,1-benzothiazin-3-yl)-piperidine-1-carboxylic acid tert-butyl ester (175 mg, 0.46 mmol) was dissolved in 4M hydrogen chloride in 1,4-dioxane (3.0 mL, 12.0 mmol). Reaction stirred at room temperature for 45 minutes. Reaction mixture was concentrated to dryness in vacuo. Title compound was obtained as pink solid in quantitative yield. MS m/e (M+H)$^+$=281.1.

tert-Butyl 4-(2,5-dioxo-4-phenylimidazolidin-1-yl)piperidine-1-carboxylate. Triethylamine (200 μL, 1.43 mmol) was added to a solution of tert-butyl 4-(3-(2-ethoxy-2-oxoethyl)-3-phenylureido)piperidine-1-carboxylate (90 mg, 0.22 mmol) in ethanol (1.8 mL). Reaction was held at 60° C. with stirring for 3 hours. Reaction mixture was concentrated in vacuo. Reside was treated with dichloromethane (20 mL) and then concentrated in vacuo. Title compound was obtained as white solid in 81% yield. MS m/e (M−C$_4$H$_8$+H)$^+$=304.2.

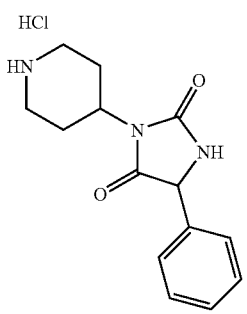

Intermediate 129

5-Phenyl-3-(piperidin-4-yl)imidazolidine-2,4-dione hydrochloride. tert-Butyl 4-(3-(2-ethoxy-2-oxoethyl)-3-phenylureido)piperidine-1-carboxylate (60 mg, 0.17 mmol) was dissolved in 4M hydrogen chloride solution in 1,4-dioxane (2.0 mL). Reaction stirred at room temperature for 30 minutes. Solids were filtered off and washed with diethyl ether and dried. Title compound was obtained as white solid in quantitative yield. MS m/e (M+H)$^+$=260.2.

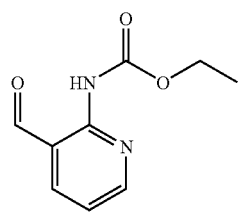

Intermediate 130

Ethyl 3-formylpyridin-2-ylcarbamate. Diethyl pyrocarbonate (570 µL, 3.9 mmol) was added to a solution of 2-aminopyridine-3-carboxaldehyde (400 mg, 3.3 mmol) in benzene (20 mL). Mixture was warmed to 60° C. and held for 4 hours. Diethyl pyrocarbonate (1 mL, 6.8 mmol) was added to the mixture. Reaction was warmed to 60° C. and held for 1 hour. Mixture was cooled to room temperature. Diethyl pyrocarbonate (1 mL, 6.8 mmol) was added to the mixture. Reaction stirred at room temperature for 16 hours. Mixture was concentrated in vacuo. Silica gel chromatography afforded to title compound as white solid in 58% yield. MS m/e (M+H)$^+$= 195.1.

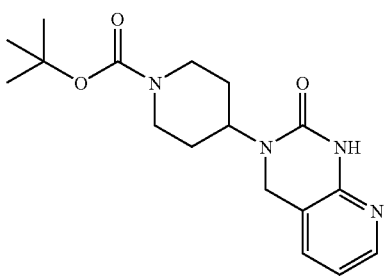

Intermediate 131 tert-Butyl 4-(2-oxo-1,2-dihydropyrido[2,3-d]pyrimidin-3 (4H)-yl)piperidine-1-carboxylate. 4-Amino-1-N-Boc-piperidine (290 mg, 1.4 mmol) was added to a solution of ethyl 3-formylpyridin-2-ylcarbamate (240 mg, 1.2 mmol) in methanol (10 mL). Mixture was warmed to 60° C. and held for 1.5 hours. Mixture was cooled to room temperature. Sodium borohydride (62 mg, 1.6 mmol) was added to the mixture. Reaction stirred at room temperature for 30 minutes. Toluene (20 mL) was added to the mixture followed by acetic acid (1.0 mL). Mixture was warmed to 110° C. Methanol was driven from the reaction mixture and collected in a Dean-Stark trap. Mixture was held at 110° C. for 5 hours. Mixture was cooled to room temperature and held for 16 hours. Reaction was quenched with aqueous sodium bicarbonate. Mixture was extracted with ethyl acetate (2×30 mL). Combined organics were washed successively with water (30 mL) and brine (20 mL). Organic layer was dried (magnesium sulfate), filtered and concentrated in vacuo. Silica gel chromatography afforded the title compound as white solid in 44% yield. MS m/e (M–H)$^-$=311.2.

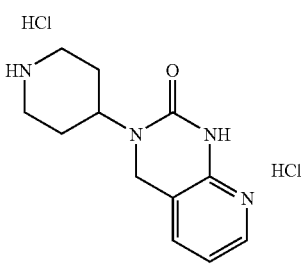

Intermediate 132

3-(Piperidin-4-yl)-3,4-dihydropyrido[2,3-d]pyrimidin-2 (1H)-one dihydrochloride. A suspension of tert-butyl 4-(2-oxo-1,2-dihydropyrido[2,3-d]pyrimidin-3(4H)-yl)piperidine-1-carboxylate (220 mg, 0.66 mmol) in 4N hydrogen chloride in 1,4-dioxane (5.0 mL) was stirred at room temperature for 45 minutes. Mixture was concentrated in vacuo. Crystallization from ethanol and ethyl acetate afforded the title compound as white solid in 62% yield. (M+H)$^+$=233.2.

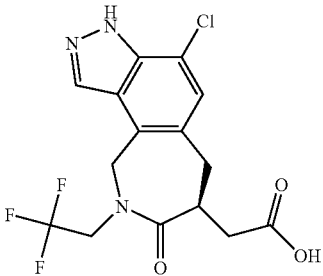

Intermediate 133

[4-Chloro-3,6,7,8,9,10-hexahydro-8-oxo-9-(2,2,2-trifluoroethyl)-2,3,9-triaza-(S)-cyclohepta[e]inden-7-yl]acetic acid. 2-(S)-(4-acetoxymethyl-7-chloro-1H-indazol-5-ylmethyl)-succinic acid diethyl ester (530 mg, 1.48 mmol) and 2,2,2-trifluoroethylamine (1 mL, 12.5 mmol) was reacted following reaction scheme and procedures analogous to the preparation of [4-Chloro-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 20% yield. MS m/e (M–H)$^-$=374.0.

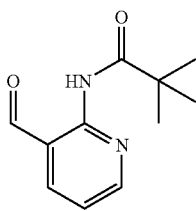

Intermediate 134

N-(3-Formylpyridin-2-yl)pivalamide. Triethylamine (7.6 mL, 54 mmol), was added to a solution of 2-aminopyridine-3-carboxaldehyde (4.45 g, 36 mmol) in dichloromethane (70 mL). Mixture was cooled to 0° C. A solution of pivaloyl chloride (5.3 mL, 43 mmol) in dichloromethane (30 mL) was added to the mixture. Reaction was warmed to room temperature. Mixture stirred at room temperature for 63 hours. Mixture was washed successively with water (2×50 mL) and brine (30 mL). Organic layer was dried (magnesium sulfate), filtered and concentrated in vacuo. Silica gel chromatography afforded the title compound as off-white solid in 90% yield. (M+H)$^+$=207.1.

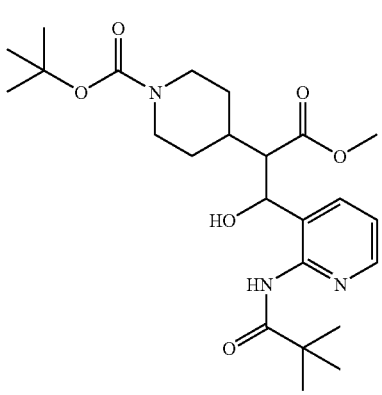

Intermediate 135 tert-Butyl 4-(1-hydroxy-3-methoxy-3-oxo-1-(2-pivalamidopyridin-3-yl)propan-2-yl)piperidine-1-carboxylate. A solution of diisopropylamine (6.0 mL, 43 mmol) in tetrahydrofuran (200 mL) was cooled to −78° C. A 2.5M solution of n-butyllithium in hexanes (17.0 mL, 43 mmol) was added to the mixture drop-wise. Mixture was held at −78° C. with stirring for 20 minutes. A solution of tert-butyl 4-(2-methoxy-2-oxoethyl)piperidine-1-carboxylate (9.3 g, 36 mmol) in tetrahydrofuran (35 mL) was added to the mixture drop-wise. Mixture was held at −78° C. for 1.5 hours. In a separate flask, 60% sodium hydride in mineral oil (1.57 g, 39 mmol) was washed in hexanes and then suspended in tetrahydrofuran (70 mL). Mixture was cooled to 0° C. A solution of N-(3-formylpyridin-2-yl)pivalamide (6.74 g, 33 mmol) in tetrahydrofuran (20 mL) was added to the mixture drop-wise. Reaction was held at 0° C. with stirring for 2 hours. Mixture was warmed to room temperature and then added to the butyllithium containing solution drop-wise. Reaction mixture was held at −78° C. with stirring for 2 hours. Mixture was allowed to slowly warm to room temperature. Mixture stirred at room temperature for 14 hours. Reaction was quenched with aqueous ammonium chloride. The mixture was extracted with ethyl acetate (2×100 mL). Organic extracts were combined, dried (magnesium sulfate), filtered and concentrated in vacuo. Silica gel chromatography afforded the title compound as white foam in 93% yield. (M+H)$^+$=464.2.

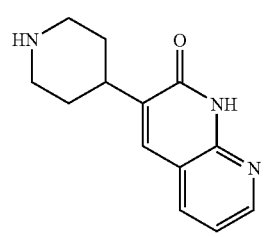

Intermediate 136

3-(Piperidin-4-yl)-1,8-naphthyridin-2(1H)-one dihydrochloride. Concentrated hydrochloric acid (25 mL, 305 mmol) was added with stirring to a mixture of tert-butyl 4-(1-hydroxy-3-methoxy-3-oxo-1-(2-pivalamidopyridin-3-yl)propan-2-yl)piperidine-1-carboxylate (14.0 g, 30.2 mmol) and water (75 mL). Reaction was heated to reflux and held for 25 hours. Mixture was concentrated in vacuo. Residue was crystallized from ethanol. Title compound was obtained as white solid in 33% yield. (M+H)$^+$=230.2.

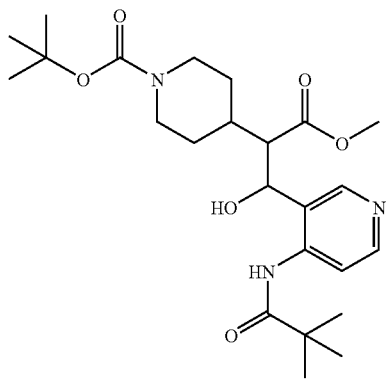

Intermediate 137 tert-Butyl 4-(1-hydroxy-3-methoxy-3-oxo-1-(4-pivalamidopyridin-3-yl)propan-2-yl)piperidine-1-carboxylate. tert-butyl 4-(2-methoxy-2-oxoethyl)piperidine-1-carboxylate (1.33 g, 5.2 mmol) and N-(3-formyl-4-pyridinyl-2,2-dimethylpropanamide (1.0 g, 4.7 mmol) were reacted in a manner analogous to the preparation of tert-butyl 4-(1-hydroxy-3-methoxy-3-oxo-1-(2-pivalamidopyridin-3-yl)propan-2-yl)piperidine-1-carboxylate. Title compound was obtained as white foam in 54% yield. (M+H)$^+$=464.2.

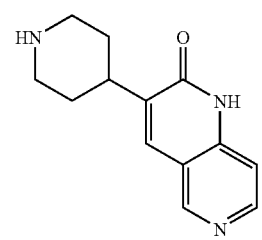

Intermediate 138

3-(piperidin-4-yl)-1,6-naphthyridin-2(1H)-one. Concentrated hydrochloric acid (8.0 mL, 97 mmol) was added with stirring to a mixture of tert-butyl 4-(1-hydroxy-3-methoxy- 3-oxo-1-(4-pivalamidopyridin-3-yl)propan-2-yl)piperidine-1-carboxylate (1.2 g, 2.6 mmol) and water (24 mL). Reaction was heated to reflux and held for 14 hours. Mixture was concentrated in vacuo. Residue was treated with acetonitrile (70 mL) and then concentrated in vacuo. Residue was crystallized from ethanol. Title compound was obtained as white solid in 77% yield. (M+H)$^+$=230.1.

Intermediate 139

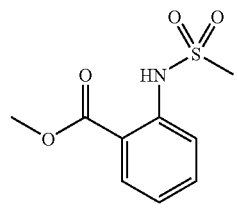

Methyl 2-(methylsulfonamido)benzoate. Methyl anthranilate (11.73 g, 77.6 mmol) was dissolved in pyridine (25 mL, 309 mmol). Mixture was cooled to 0° C. Methanesulfonyl chloride (6.60 mL, 85.3 mmol) was added to the mixture drop-wise. Reaction mixture was warmed to room temperature and held with stirring overnight. Mixture was diluted with ethyl acetate. Material was washed twice with water and three times with 1N hydrochloric acid. Organic layer was dried (magnesium sulfate), filtered and then concentrated. Residue was triturated with 50% diethyl ether in hexanes. Solids were filtered off, washed with 50% diethyl ether-hexanes, washed with hexanes and then dried under high vacuum. Title compound was obtained as an off-white solid in 88% yield. MS m/e (M−H)$^-$=227.9.

Intermediate 140

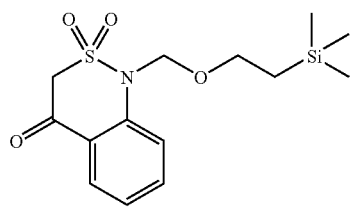

2,2-Dioxo-1-(2-trimethylsilanyl-ethoxymethyl)-2,3-dihydro-1H-2λ$^6$-2,1-benzothiazin-4-one. In a dry round bottom flask under a blanket of nitrogen 60% sodium hydride in mineral oil (1.05 g, 26 mmol) was washed with hexanes and then suspended in N,N-dimethylformamide (50 mL). Mixture was cooled to 0° C. A solution of methyl 2-(methylsulfonamido)benzoate (5.0 g, 22 mmol) in 10 mL N,N-dimethylformamide was added to the mixture drop-wise. Reaction was held at 0° C. with stirring for 25 minutes. 2-(Trimethylsilyl)ethoxymethyl chloride was added to the mixture drop-wise. Reaction stirred for 2 hours slowly warming to ambient temperature. Reaction was quenched with 1N hydrochloric acid. Material was extracted twice with ethyl acetate. Material was washed successively with water and brine. Organic phase was dried (magnesium sulfate), filtered and concentrated to dryness. Residue was dissolved in N,N-dimethylformamide (5 mL) and added drop-wise to a mixture of 60% sodium hydride in mineral oil (1.02 g, 26 mmol) that had been washed with hexanes, suspended in N,N-dimethylformamide (50 mL) and cooled to 0° C. Ice bath was removed and the mixture was allowed to warm to room temperature. Reaction was held at room temperature overnight with stirring. Reaction was quenched with 1N hydrochloric acid. Material was extracted twice with ethyl acetate. Organic phase was washed successively with water and brine. Organic phase was dried (magnesium sulfate), filtered and concentrated to dryness. Silica gel chromatography (ethyl acetate-hexanes) afforded the title compound as a white solid in 72% yield. MS m/e (M−H)$^-$=326.0.

Intermediate 141

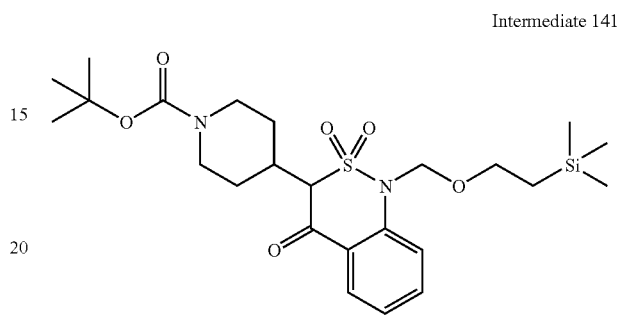

4-[2,2,4-Trioxo-1-(2-trimethylsilanyl-ethoxymethyl)-1,2,3,4-tetrahydro-2λ$^6$-2,1-benzothiazin-3-yl]-piperidine-1-carboxylic acid tert-butyl ester. N-tert-Botoxycarbonyl-4-piperidinone (2.44 g, 12 mmol) was dissolved in 1,2-dichloroethane (20 mL). Piperidine (1.2 mL, 12 mmol) was added to the mixture. Reaction was heated to 50° C. and held with stirring for 1.25 hours. Mixture was cooled to room temperature. A solution of 2,2-Dioxo-1-(2-trimethylsilanyl-ethoxymethyl)-2,3-dihydro-1H-2λ$^6$-2,1-benzothiazin-4-one (2.0 g, 6.1 mmol) in pyridine (5.0 mL, 62 mmol) was added to the mixture. Reaction was held overnight at room temperature with stirring. Material was concentrated by roto-vap. Residue was dissolved in ethyl acetate. Material was washed successively with three portions of 1N hydrochloric acid and one portion of water. Organic phase was dried (magnesium sulfate), filtered and concentrated to dryness. Residue was purified by silica gel chromatography (ethyl acetate-hexanes). Major peak was isolated and the fractions were concentrated to dryness. Residue was dissolved in methanol (40 mL). A catalytic amount of 10% palladium on carbon was added to the solution. Reaction vessel was placed on a Parr apparatus and charged with 60 psi of hydrogen gas. Reaction shook at room temperature overnight. Mixture was filtered over celite. Fresh catalyst was added to the filtrate. Reaction vessel was placed on a Parr apparatus and charged with 60 psi of hydrogen gas. Reaction shook at room temperature for 7 hours. Mixture was filtered over celite and the filtrate was concentrated to dryness. Material was purified by silica gel chromatography (ethyl acetate-hexanes). Major peak was isolated and the fractions were concentrated to dryness. Residue was dissolved in methanol (40 mL). Fresh catalyst was added to the mixture. Reaction vessel was placed on a Parr apparatus and charged with 60 psi of hydrogen gas. Reaction shook at room temperature overnight. Mixture was filtered over celite. Filtrate was concentrated to dryness. Silica gel chromatography (ethyl acetate-hexanes) afforded the title compound as yellow oil in 43% yield. MS m/e (M−H)$^-$=509.1.

Intermediate 142

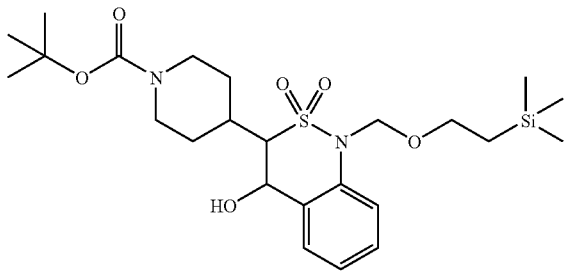

4-[4-Hydroxy-2,2-dioxo-1-(2-trimethylsilanyl-ethoxymethyl)-1,2,3,4-tetrahydro-2λ⁶-2,1-benzothiazin-3-yl]-piperidine-1-carboxylic acid tert-butyl ester Title compound was obtained as yellow oil in 85% yield. Material was carried forward without purification.

Intermediate 143

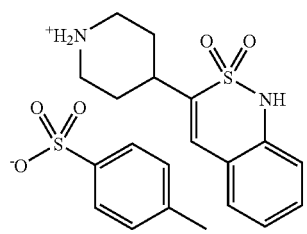

3-Piperidin-4-yl-1H-2,1-benzothiazine 2,2-dioxide para-toluenesulfonate. 4-[2,2,4-Trioxo-1-(2-trimethylsilanyl-ethoxymethyl)-1,2,3,4-tetrahydro-2λ⁶-2,1-benzothiazin-3-yl]-piperidine-1-carboxylic acid tert-butyl ester (865 mg, 1.7 mmol) was dissolved in methanol (25 mL). Mixture was cooled to 0° C. Sodium borohydride (100 mg, 2.6 mmol) was added to the mixture in three portions. Reaction stirred at 0° C. for 3 hours. Mixture was concentrated by roto-vap. Residue was treated with 1N hydrochloric acid. Material was extracted twice with ethyl acetate. Organic phase was dried (magnesium sulfate), filtered and concentrated to dryness. Residue was dissolved in benzene (20 mL). p-Toluenesulfonic acid monohydrate (475 mg, 2.5 mmol) was added to the mixture. Reaction was heated to reflux and held with stirring for 1 hour. Mixture was cooled to room temperature. Solids were filtered off. The sticky solid was treated with hot isopropyl alcohol (10 mL). Mixture was cooled to room temperature and allowed to stand overnight. Solids were filtered off, washed with isopropyl alcohol and then dried under high vacuum. Title compound was obtained as tan solid in 65% yield. MS m/e $(M+H)^+$=265.2.

Intermediate 144

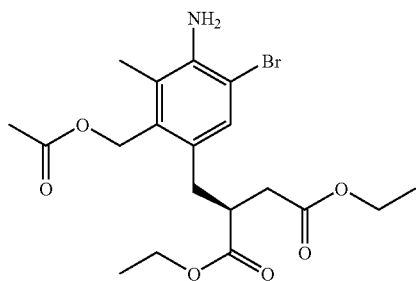

2-(S)-(2-Acetoxymethyl-4-amino-5-bromo-3-methyl-benzyl)-succinic acid diethyl ester. 2-(S)-(2-Acetoxymethyl-4-amino-3-methyl-benzyl)-succinic acid diethyl ester (7.6 g, 21 mmol) was dissolved in acetic acid (100 mL). Sodium acetate (4.2 g, 51 mmol) was added to the solution. Reaction vessel was placed in a cool water bath to control reaction exotherm. Bromine (1.1 mL, 22 mmol) was added to the mixture in one portion. Reaction stirred at ambient temperature for 10 minutes. Mixture was poured into 1N aqueous sodium thiosulfate solution (400 mL). Material was extracted twice with ethyl acetate. Organic phase was washed successively with water and brine. Organic was dried (magnesium sulfate), filtered and concentrated in vacuo. Silica gel chromatography (ethyl acetate-hexanes) afforded the desired product in 77% yield as an amber oil. MS m/e $(M-H)^-$=440.0, 442.0.

Intermediate 145

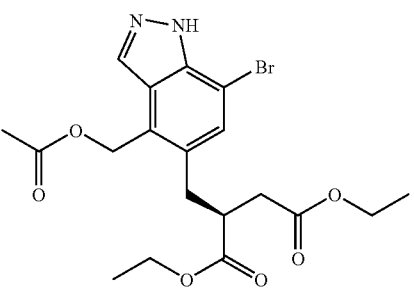

2-(S)-(4-Acetoxymethyl-7-bromo-1H-indazol-5-ylmethyl)-succinic acid diethyl ester. Isoamyl nitrite (2.3 mL, 17 mmol), was added drop-wise to an ice cold solution of 2-(S)-(2-Acetoxymethyl-4-amino-5-bromo-3-methyl-benzyl)-succinic acid diethyl ester (7.14 g, 16 mmol) in 5% acetic acid in toluene (280 mL). Mixture stirred at 0° C. for 40 minutes. Potassium acetate (4.00 g, 41 mmol) was added to the mixture. Mixture was slowly warmed to room temperature. Reaction was stirred at room temperature for 14 hours. Mixture was washed twice with water and once with brine. Organic was dried (magnesium sulfate) filtered and concentrated. Silica gel chromatography (ethyl acetate-hexanes) afforded the desired product in 77% yield as an amber oil. MS m/e $(M+H)^+$=455.0, 457.0.

Intermediate 146

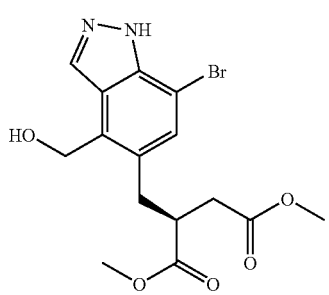

(S)-dimethyl 2-((7-bromo-4-(hydroxymethyl)-1H-indazol-5-yl)methyl)succinate. 2-(S)-(2-Acetoxymethyl-4-amino-5-bromo-3-methyl-benzyl)-succinic acid diethyl ester (2.78 g, 6.1 mmol) was converted to the title compound in a manner analogous to the preparation of 2-(S)-(4-Hydroxymethyl-1H-indazol-5-ylmethyl)-succinic acid dimethyl ester. Material was obtained as amber solid in 96% yield. MS m/e $(M-H)^-$=383.0, 385.0.

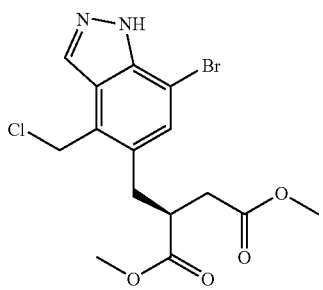

Intermediate 147

(S)-dimethyl 2-((7-bromo-4-(chloromethyl)-1H-indazol-5-yl)methyl)succinate. (S)-dimethyl 2-((7-bromo-4-(hydroxymethyl)-1H-indazol-5-yl)methyl)succinate (2.25 g, 5.8 mmol) was dissolved in 2M thionyl chloride in dichloromethane (42 mL, 84 mmol). Reaction stirred at room temperature for 2.0 hours. Mixture was concentrated. Residue was treated with toluene and then concentrated by roto-vap. Residue was dissolved in ethyl acetate. Mixture was washed twice with aqueous sodium bicarbonate. Organic was dried (magnesium sulfate), filtered and concentrated in vacuo. Title compound was obtained as amber solid in 99% yield. MS m/e (M+H)$^+$=404.9, 403.0, 406.9.

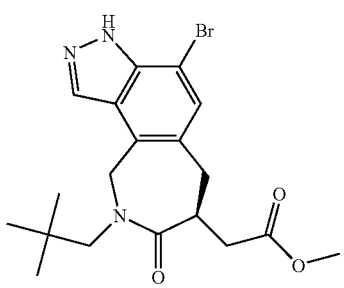

Intermediate 148

[4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester. (S)-dimethyl 2-((7-bromo-4-(chloromethyl)-1H-indazol-5-yl)methyl)succinate (860 mg, 2.1 mmol) was dissolved in acetonitrile (50 mL). Potassium carbonate (625 mg, 4.5 mmol) was added to the mixture followed by neopentylamine (800 μL, 6.78 mmol). Mixture was heated to reflux and held with stirring for 1.5 hours. Mixture was cooled to room temperature. Mixture was filtered over celite. Filtrate was concentrated by roto-vap. Residue was dissolved in a mixture of toluene (50 mL) and acetic acid (3 mL). Mixture was heated to reflux and held with stirring for 37 hours. Mixture concentrated by roto-vap. Silica gel chromatography (ethyl acetate-hexanes) afforded the title compound as tan solid in 75% yield. MS m/e (M−H)$^-$=420.0, 422.0.

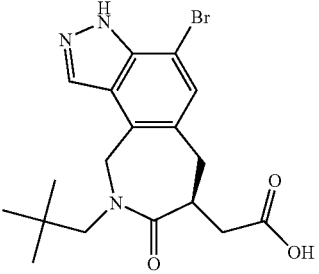

Intermediate 149

[4-Bromo-9-(2,2-dimethyl-propyl)-8-oxo-3,6,7,8,9,10-hexahydro-2,3,9-triaza-(S)-cyclohepta[e]inden-7-yl]-acetic acid. [4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester (160 mg, 0.38 mmol) was dissolved in a mixture of tetrahydrofuran (5.0 mL) and methanol (5.0 mL). Water (5.0 mL) was added to the mixture followed by lithium hydroxide monohydrate (41 mg, 0.98 mmol). Mixture was heated to 50° C. and held with stirring for 5 hours. Mixture was cooled to room temperature. Organic solvents were removed from the mixture in vacuo. Remaining aqueous was diluted with water and then made neutral with 1 mL of 1N hydrochloric acid. Material was extracted twice with ethyl acetate. Organic phase was dried (magnesium sulfate), filtered and concentrated to dryness. Title compound was obtained as tan solid in quantitative yield. $^1$H NMR (300 MHz, CDCl$_3$) δ=0.77 (s, 9H) 2.31-2.60 (m, 3H) 2.91 (dd, J=16.47, 8.42 Hz, 1H) 2.98-3.05 (m, 1H) 3.09 (d, J=13.54 Hz, 1H) 3.47 (d, J=13.91 Hz, 1H) 3.71-3.89 (m, 1H) 4.39 (d, J=17.20 Hz, 1H) 5.30 (d, J=17.20 Hz, 1H) 7.25 (s, 1H) 8.00 (s, 1H).

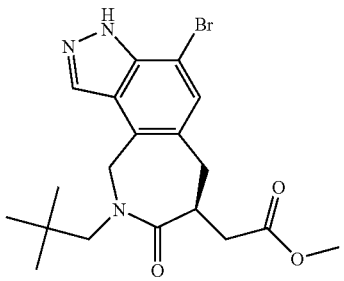

Intermediate 150

[4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester. (S)-dimethyl 2-((7-bromo-4-(chloromethyl)-1H-indazol-5-yl)methyl)succinate (860 mg, 2.1 mmol) was dissolved in acetonitrile (50 mL). Potassium carbonate (625 mg, 4.5 mmol) was added to the mixture followed by neopentylamine (800 μL, 6.78 mmol). Mixture was heated to reflux and held with stirring for 1.5 hours. Mixture was cooled to room temperature. Mixture was filtered over celite. Filtrate was concentrated by roto-vap. Residue was dissolved in a mixture of toluene (50 mL) and acetic acid (3 mL). Mixture was heated to reflux and held with stirring for 37 hours. Mixture concentrated by roto-vap. Silica gel chromatography (ethyl acetate-hexanes) afforded the title compound as tan solid in 75% yield. MS m/e (M−H)$^-$=420.0, 422.0.

Intermediate 151

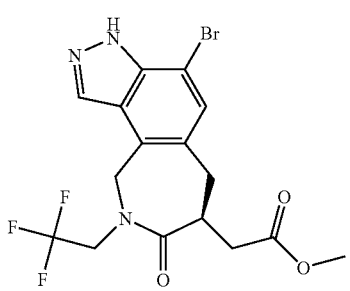

[4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester. 2-(S)-(4-chloromethyl-7-bromo-1H-indazol-5-ylmethyl)-succinic acid diethyl ester (325 mg, 0.81 mmol) was dissolved in acetonitrile (10 mL). Potassium carbonate (310 mg, 2.2 mmol) was added to the mixture with 2,2,2-trifluoroethylamine (1.2 mL, 15 mmol). Mixture was heated at 60° C. and held with stirring for 15 hours. Mixture was cooled to room temperature. Mixture was filtered over celite. Filtrate was concentrated by roto-vap. Residue was dissolved in a mixture of toluene (10 mL) and acetic acid (600 μL). Mixture was heated to reflux and held with stirring for 22 hours. Mixture was concentrated by roto-vap. Residue was dissolved in ethyl acetate. Material was washed successively with water and aqueous sodium bicarbonate. Organic phase was dried (magnesium sulfate), filtered and concentrated to dryness. Title compound was obtained as amber residue in 74% yield. MS m/e (M−H)⁻=431.9, 433.9.

Intermediate 152

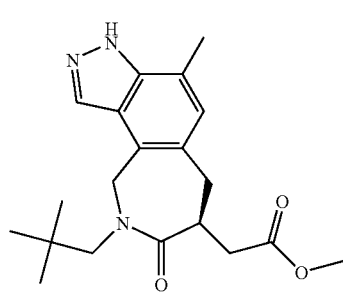

[4-Bromo-3,6,7,8,9,10-hexahydro-8-oxo-9-(2,2,2-trifluoroethyl)-2,3,9-triaza-(S)-cyclohepta[e]inden-7-yl]acetic acid. [4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester (250 mg, 0.58 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as light yellow solid in quantitative yield. MS m/e (M−H)⁻=417.9, 419.9.

Intermediate 153

[4-Methyl-9-(2,2-dimethyl-propyl)-8-oxo-3,6,7,8,9,10-hexahydro-2,3,9-triaza-(S)-cyclohepta[e]inden-7-yl]-acetic acid methyl ester. [4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester (110 mg, 0.26 mmol) was dissolved in N,N-dimethylformamide (1.0 mL). Nitrogen gas was bubbled through the mixture for 5 minutes. Tetrakis(triphenylphosphine)palladium(0) (6.0 mg, 0.01 mmol) was added to the mixture followed by tetramethyltin (100 μL, 0.72 mmol). Reaction vessel was flushed with nitrogen gas and then sealed. Reaction was subjected to microwave heating at 175° C. for 35 minutes. Mixture was diluted with ethyl acetate. Material was washed successively with water and brine. Silica gel chromatography (ethyl acetate-hexanes) afforded the title compound as white solid in 83% yield. MS m/e (M+H)⁺=358.2.

Intermediate 154

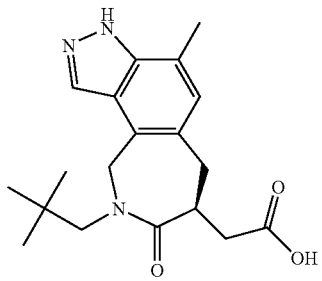

[4-Methyl-9-(2,2-dimethyl-propyl)-8-oxo-3,6,7,8,9,10-hexahydro-2,3,9-triaza-(S)-cyclohepta[e]inden-7-yl]-acetic acid. [4-Methyl-9-(2,2-dimethyl-propyl)-8-oxo-3,6,7,8,9,10-hexahydro-2,3,9-triaza-(S)-cyclohepta[e]inden-7-yl]-acetic acid methyl ester (70 mg, 196 μmol) was dissolved in tetrahydrofuran (2.0 mL). Methanol (2.0 mL) was added to the mixture followed by water (2.0 mL) and then lithium hydroxide hydrate (20 mg, 477 μmol). Reaction was warmed to 50° C. and held with stirring for 1.5 hours. Mixture was cooled to room temperature. Organic solvents were removed from the mixture by roto-vap. Remaining aqueous was diluted with water and then neutralized with 1N hydrochloric acid (500 μL). Mixture was extracted twice with ethyl acetate. Organics were dried MgSO4, filtered and then concentrated to dryness. Title compound was obtained as white solid in 95% yield. MS m/e (M−H)⁻=342.2.

Intermediate 155

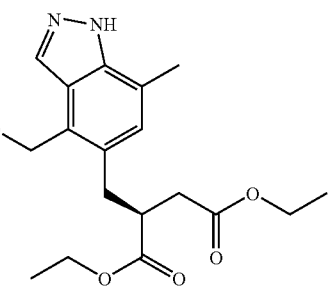

2-(S)-(4-Acetoxymethyl-7-methyl-1H-indazol-5-ylmethyl)-succinic acid diethyl ester. 2-(S)-(4-Acetoxymethyl-7-bromo-1H-indazol-5-ylmethyl)-succinic acid diethyl ester (350 mg, 0.77 mmol) and tetramethyltin (150 µL, 1.1 mmol) were reacted in a manner analogous to the preparation of [4-Methyl-9-(2,2-dimethyl-propyl)-8-oxo-3,6,7,8,9,10-hexahydro-2,3,9-triaza-(S)-cyclohepta[e]inden-7-yl]-acetic acid methyl ester. Title compound was obtained as pale yellow solid in 68% yield. MS m/e (M−H)⁻=389.1.

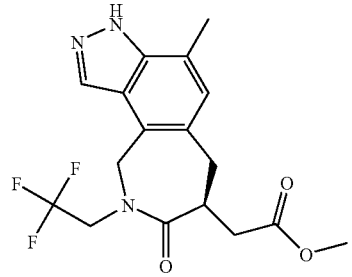

Intermediate 159

[4-Methyl-3,6,7,8,9,10-hexahydro-8-oxo-9-(2,2,2-trifluoroethyl)-2,3,9-triaza-(S)-cyclohepta[e]inden-7-yl]acetic acid methyl ester. 2-(S)-(4-chloromethyl-7-methyl-1H-indazol-5-ylmethyl)-succinic acid diethyl ester (190 mg, 0.56 mmol) and 2,2,2-trifluoroethylamine (45 µL, 0.56 mmol) were reacted in a manner analogous to the preparation of [4-bromo-3,6,7,8,9,10-hexahydro-8-oxo-9-(2,2,2-trifluoroethyl)-2,3,9-triaza-(S)-cyclohepta[e]inden-7-yl]acetic acid methyl ester. Title compound was obtained as amber residue in 76% yield. MS m/e (M+H)⁺=370.1.

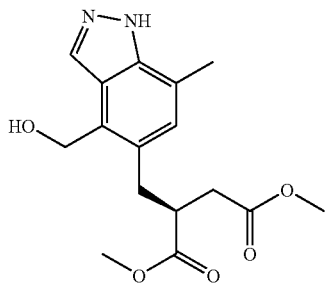

Intermediate 156

(S)-dimethyl 2-((7-methyl-4-(hydroxymethyl)-1H-indazol-5-yl)methyl)succinate. 2-(S)-(2-Acetoxymethyl-4-amino-5-methyl-3-methyl-benzyl)-succinic acid diethyl ester (230 mg, 0.59 mmol) was converted to the title compound in a manner analogous to the preparation of 2-(S)-(4-Hydroxymethyl-1H-indazol-5-ylmethyl)-succinic acid dimethyl ester. Material was obtained as off-white solid in 98% yield. MS m/e (M−H)⁻=319.2.

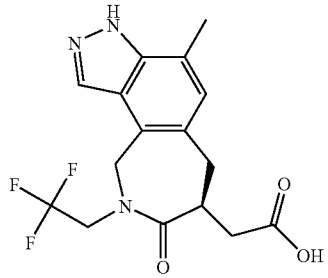

Intermediate 160

[4-Methyl-3,6,7,8,9,10-hexahydro-8-oxo-9-(2,2,2-trifluoroethyl)-2,3,9-triaza-(S)-cyclohepta[e]inden-7-yl]acetic acid. [4-Methyl-3,6,7,8,9,10-hexahydro-8-oxo-9-(2,2,2-trifluoroethyl)-2,3,9-triaza-(S)-cyclohepta[e]inden-7-yl]acetic acid methyl ester (250 mg, 0.58 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 97% yield. MS m/e (M−H)⁻=354.2.

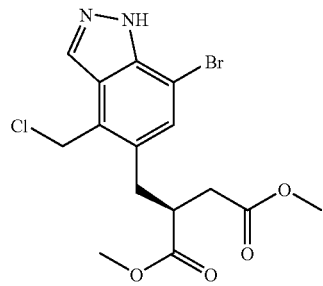

Intermediate 158

(S)-dimethyl 2-((7-methyl-4-(chloromethyl)-1H-indazol-5-yl)methyl)succinate. (S)-dimethyl 2-((7-methyl-4-(hydroxymethyl)-1H-indazol-5-yl)methyl)succinate (180 mg, 0.56 mmol) was dissolved in dichloromethane (4.0 mL). 2M Thionyl chloride in dichloromethane (4.0 mL, 8.0 mmol) was added to the mixture. Reaction stirred at room temperature for 2.5 hours. Mixture was concentrated. Residue was treated with toluene and then concentrated by roto-vap. Residue was dissolved in dichloromethane and then concentrated to dryness Title compound was obtained as amber solid in 99% yield. MS m/e (M+H)⁺=339.1.

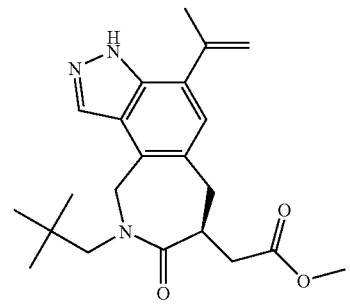

Intermediate 161

[(S)-9-(2,2-Dimethyl-propyl)-4-isopropenyl-8-oxo-3,6,7,8,9,10-hexahydro-2,3,9-triaza-cyclohept[e]inden-7-yl]-acetic acid methyl ester. [4-Bromo-9-(2,2-dimethyl-propyl)-8-oxo-3,6,7,8,9,10-hexahydro-2,3,9-triaza-(S)-cyclohepta[e]inden-7-yl]-acetic acid methyl ester (100 mg, 0.24 mmol) was dissolved in 2-propanol (1.0 mL). Nitrogen gas was bubbled through the mixture for 5 minutes. Triethylamine (60 μL, 0.43 mmol) was added to the mixture followed by [1,1'-bis(diphenylphosphino)ferrocene]palladium(II) chloride (19 mg, 0.02 mmol) and potassium 2-propenyltrifluoroborate (41 mg, 0.28 mmol). Reaction vessel was flushed with nitrogen gas and then sealed. Reaction was subjected to microwave heating at 150° C. for 30 minutes. Silica gel chromatography (ethyl acetate-hexanes) afforded the title compound as amber solid in 73% yield. MS m/e (M+H)$^+$=384.4.

Intermediate 162

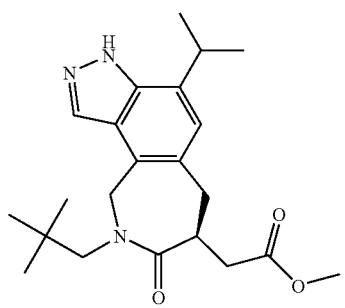

[(S)-9-(2,2-Dimethyl-propyl)-4-isopropyl-8-oxo-3,6,7,8,9,10-hexahydro-2,3,9-triaza-cyclohept[e]inden-7-yl]-acetic acid methyl ester. [(S)-9-(2,2-Dimethyl-propyl)-4-isopropenyl-8-oxo-3,6,7,8,9,10-hexahydro-2,3,9-triaza-cyclohept[e]inden-7-yl]-acetic acid methyl ester (100 mg, 0.26 mmol) was dissolved in a mixture of ethyl acetate (5.0 mL) and methanol (5.0 mL). A catalytic amount of 10% palladium on carbon was added to the mixture. Reaction vessel was placed on a Parr apparatus and charged with 50 psi of hydrogen gas. Reaction shook at room temperature for 1 hour. Mixture was filtered and the filtrate was concentrated to dryness. Title compound was obtained as brown residue in 90% yield. MS m/e (M+H)$^+$=386.3.

Intermediate 163

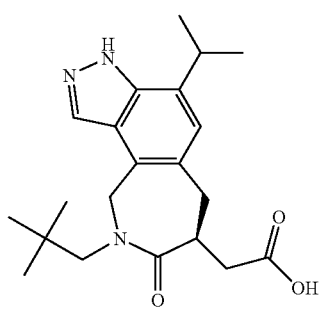

[(S)-9-(2,2-Dimethyl-propyl)-4-isopropyl-8-oxo-3,6,7,8,9,10-hexahydro-2,3,9-triaza-cyclohept[e]inden-7-yl]acetic acid. [(S)-9-(2,2-Dimethyl-propyl)-4-isopropyl-8-oxo-3,6,7,8,9,10-hexahydro-2,3,9-triaza-cyclohept[e]inden-7-yl]-acetic acid methyl ester (90 mg, 0.23 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 92% yield. MS m/e (M–H)$^-$=370.3.

Intermediate 164

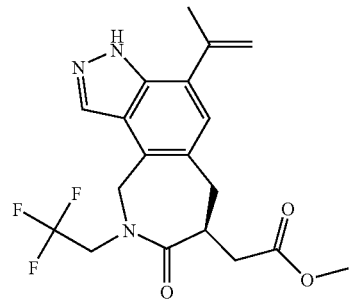

[4-Isopropenyl-3,6,7,8,9,10-hexahydro-8-oxo-9-(2,2,2-trifluoroethyl)-2,3,9-triaza-(S)-cyclohepta[e]inden-7-yl]acetic acid methyl ester. [4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester (400 mg, 0.92 mmol) and potassium 2-propenyltrifluoroborate (165 mg, 1.1 mmol) were reacted in a manner analogous to the preparation of [(S)-9-(2,2-Dimethyl-propyl)-4-isopropenyl-8-oxo-3,6,7,8,9,10-hexahydro-2,3,9-triaza-cyclohept[e]inden-7-yl]-acetic acid methyl ester. Title compound was obtained as amber oil in 71% yield. MS m/e (M–H)$^-$=394.1.

Intermediate 165

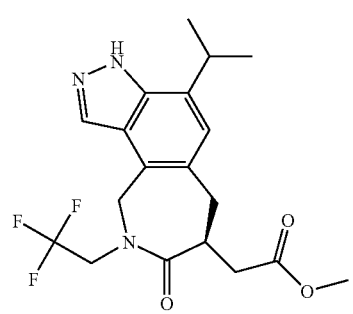

[4-Isopropyl-3,6,7,8,9,10-hexahydro-8-oxo-9-(2,2,2-trifluoroethyl)-2,3,9-triaza-(S)-cyclohepta[e]inden-7-yl]acetic acid methyl ester. [4-Isopropenyl-3,6,7,8,9,10-hexahydro-8-oxo-9-(2,2,2-trifluoroethyl)-2,3,9-triaza-(S)-cyclohepta[e]inden-7-yl]acetic acid methyl ester (150 mg, 0.38 mmol) was reacted in a manner analogous to the preparation of [(S)-9-(2,2-Dimethyl-propyl)-4-isopropyl-8-oxo-3,6,7,8,9,10-hexahydro-2,3,9-triaza-cyclohept[e]inden-7-yl]-acetic acid methyl ester. Title compound was obtained as white solid in 73% yield. MS m/e (M+H)$^+$=398.2.

Intermediate 166

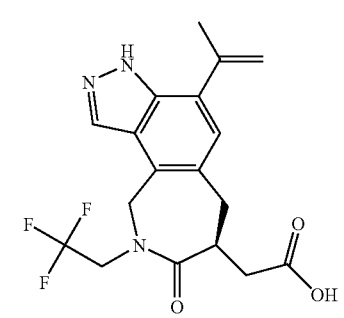

[4-Isopropenyl-3,6,7,8,9,10-hexahydro-8-oxo-9-(2,2,2-trifluoroethyl)-2,3,9-triaza-(S)-cyclohepta[e]inden-7-yl]acetic acid. [4-Isopropenyl-3,6,7,8,9,10-hexahydro-8-oxo-9-(2,2,2-trifluoroethyl)-2,3,9-triaza-(S)-cyclohepta[e]inden-7-yl]acetic acid methyl ester (100 mg, 0.25 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as off-white solid in 98% yield. MS m/e (M−H)⁻=380.2.

Intermediate 167

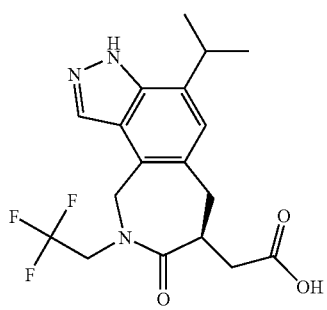

[4-Isopropyl-3,6,7,8,9,10-hexahydro-8-oxo-9-(2,2,2-trifluoroethyl)-2,3,9-triaza-(S)-cyclohepta[e]inden-7-yl]acetic acid. [4-Isopropyl-3,6,7,8,9,10-hexahydro-8-oxo-9-(2,2,2-trifluoroethyl)-2,3,9-triaza-(S)-cyclohepta[e]inden-7-yl]acetic acid methyl ester (105 mg, 0.26 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 99% yield. MS m/e (M−H)⁻=382.2.

Intermediate 168

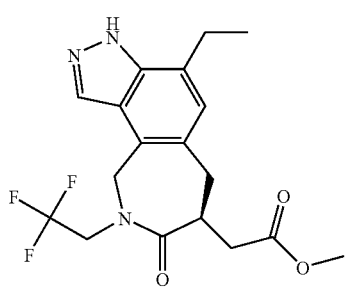

[4-Ethyl-3,6,7,8,9,10-hexahydro-8-oxo-9-(2,2,2-trifluoroethyl)-2,3,9-triaza-(S)-cyclohepta[e]inden-7-yl]acetic acid methyl ester. [4-Bromo-3,6,7,8,9,10-hexahydro-8-oxo-9-(2,2,2-trifluoroethyl)-2,3,9-triaza-(S)-cyclohepta[e]inden-7-yl]acetic acid methyl ester (150 mg, 0.35 mmol) and tetraethyltin (200 µL, 1.0 mmol) were reacted in a manner analogous to the preparation of [(S)-9-(2,2-Dimethyl-propyl)-4-methyl-8-oxo-3,6,7,8,9,10-hexahydro-2,3,9-triaza-cyclohept[e]inden-7-yl]-acetic acid methyl ester. Title compound was obtained as clear colorless oil in 28% yield. MS m/e (M+H)⁺=384.2.

Intermediate 169

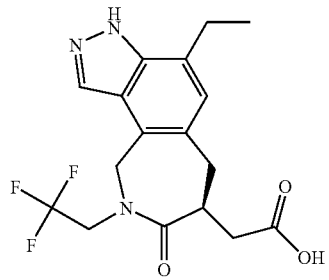

[4-Ethyl-3,6,7,8,9,10-hexahydro-8-oxo-9-(2,2,2-trifluoroethyl)-2,3,9-triaza-(S)-cyclohepta[e]inden-7-yl]acetic acid. [4-Ethyl-3,6,7,8,9,10-hexahydro-8-oxo-9-(2,2,2-trifluoroethyl)-2,3,9-triaza-(S)-cyclohepta[e]inden-7-yl]acetic acid methyl ester (105 mg, 0.26 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as white solid in 73% yield. MS m/e (M−H)⁻=368.3.

Intermediate 170

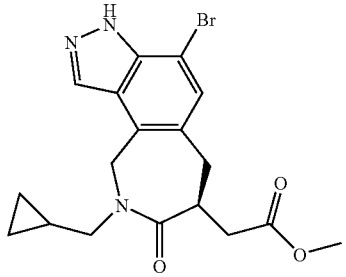

((S)-4-Bromo-9-cyclopropylmethyl-8-oxo-3,6,7,8,9,10-hexahydro-2,3,9-triaza-cyclohept[e]inden-7-yl)-acetic acid methyl ester. (S)-dimethyl 2-((7-bromo-4-(chloromethyl)-1H-indazol-5-yl)methyl)succinate (630 mg, 1.6 mmol) was dissolved in acetonitrile (5 mL). Potassium carbonate (560 mg, 4.1 mmol) was added to the mixture followed by (aminomethyl)cyclopropane (700 µL, 8.1 mmol). Mixture was heated to reflux and held with stirring for 1.5 hours. Mixture was cooled to room temperature. Mixture was filtered. Filtrate was concentrated by roto-vap. Residue was dissolved in a mixture of toluene (10 mL) and acetic acid (1 mL). Mixture was heated to reflux and held with stirring for 18 hours. Mixture was concentrated by roto-vap. Silica gel chromatography (ethyl acetate-hexanes) afforded the title compound as tan solid in 64% yield. MS m/e (M+H)⁺

Intermediate 171

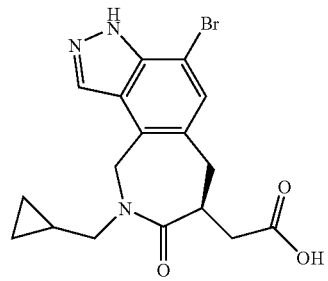

=406.0, 408.0.

((S)-4-Bromo-9-cyclopropylmethyl-8-oxo-3,6,7,8,9,10-hexahydro-2,3,9-triaza-cyclohept[e]inden-7-yl)-acetic acid. ((S)-4-Bromo-9-cyclopropylmethyl-8-oxo-3,6,7,8,9,10-hexahydro-2,3,9-triaza-cyclohept[e]inden-7-yl)-acetic acid methyl ester (290 mg, 0.71 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as yellow solid in 96% yield. MS m/e (M−H)⁻= 390.0, 392.0.

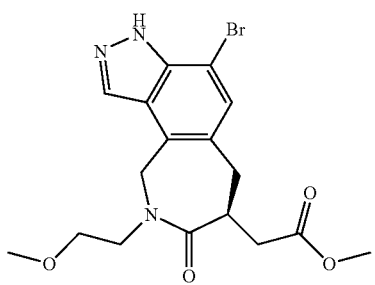

Intermediate 172

[(S)-4-Bromo-9-(2-methoxy-ethyl)-8-oxo-3,6,7,8,9,10-hexahydro-2,3,9-triaza-cyclohept[e]inden-7-yl]-acetic acid methyl ester. (S)-dimethyl 2-((7-bromo-4-(chloromethyl)-1H-indazol-5-yl)methyl)succinate (400 mg, 0.99 mmol) and 2-methoxyethylamine were reacted in a manner analogous to the preparation of ((S)-4-Bromo-9-cyclopropylmethyl-8-oxo-3,6,7,8,9,10-hexahydro-2,3,9-triaza-cyclohept[e]inden-7-yl)-acetic acid methyl ester. Title compound was obtained as tan solid in 66% yield. MS m/e (M−H)⁻=408.1, 410.0.

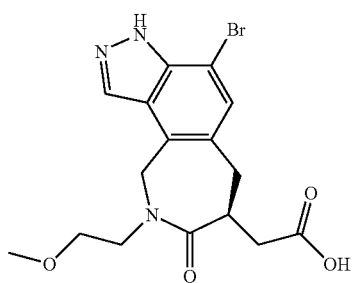

Intermediate 173

[(S)-4-Bromo-9-(2-methoxy-ethyl)-8-oxo-3,6,7,8,9,10-hexahydro-2,3,9-triaza-cyclohept[e]inden-7-yl]-acetic acid. [(S)-4-Bromo-9-(2-methoxy-ethyl)-8-oxo-3,6,7,8,9,10-hexahydro-2,3,9-triaza-cyclohept[e]inden-7-yl]-acetic acid methyl ester (265 mg, 0.65 mmol) was reacted in a manner analogous to the preparation of [4-Bromo-9-(2,2-dimethyl-propyl)-8-oxo-3,6,7,8,9,10-hexahydro-2,3,9-triaza-(S)-cyclohepta[e]inden-7-yl]-acetic acid. Title compound was obtained as tan solid in 89% yield. MS m/e (M−H)⁻=394.1, 396.0.

Intermediate 174

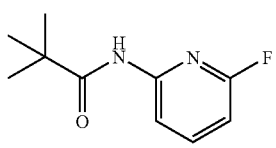

N-(6-Fluoropyridin-2-yl)pivalamide. 6-fluoropyridin-2-amine (13.1 g, 117 mmol) was dissolved in anhydrous pyridine (100 mL), and cooled to 0° C. followed by fast dropwise addition of trimethylacetyl chloride (15.9 mL, 129 mmol) over 2 min. 5 min later, the resulting slurry was stirred over night at room temperature. Partial of the solvent was removed on rotary vacuum. The residue was partitioned between saturated ammonium chloride (200 mL) and EtOAc (200 mL). After separation, the organic layer was washed with brine (50 mL), dried over MgSO₄, concentrated on rotary vacuum, and purified on flash chromatography eluting with 25~75% EtOAc/Hexanes (1400 mL) to afford the expected product as a white solid (21.4 g, 93% yield); ¹H NMR (400 MHz, CDCl₃) δ ppm 1.29 (s, 9H), 6.63 (dd, J=8.06, 2.01 Hz, 1H), 7.76 (q, J=8.14 Hz, 1H), 7.85 (s, 1H), 8.09 (dd, J=8.06, 1.76 Hz, 1H); Mass spec. 197.15 (MH⁺), Calc. for $C_{10}H_{13}FN_2O$ 196.1.

Intermediate 175

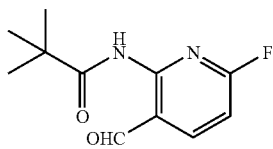

N-(6-Fluoro-3-formylpyridin-2-yl)pivalamide. N-(6-fluoropyridin-2-yl)pivalamide (1.67 g, 8.5 mmol) was dissolved in THF (15 mL) at room temperature, and the colorless solution was cooled to −78° C., followed by dropwise addition of t-BuLi (10.3 mL, 1.7M in heptane, 17.4 mmol) under nitrogen gas over 10 min. The resulting yellow solution was continued stirring at −78° C. for 3 hr, followed by dropwise addition of DMF (2.0 mL, 25.5 mmol) over 5 min. The light yellow solution was stirred for additional 30 min at −78° C. Thus the mixture was quenched with saturated NH₄Cl (30 mL), partitioned between H₂O/EtOAc (100 mL/100 mL). After separation, the organic phase was washed with brine (30 mL), dried over MgSO₄, concentrated on rotary vacuum, and purified on flash chromatography eluting with 25~50% EtOAc/hexanes (1400 mL) to afford an expected product, as a white solids (343 mg, 18% yield), plus the recovered starting material (622 mg); ¹H NMR (400 MHz, CDCl₃) δ ppm 1.23-1.30 (s, 9H), 8.12 (s, 1H), 8.18-8.27 (m, 2H), 10.13 (s, 1H); Mass spec. 225.13 (MH⁺), Calc. for $C_{11}H_{13}FN_2O_2$ 224.1.

Intermediate 176

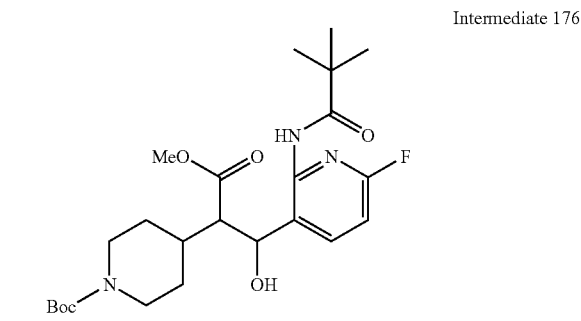

tert-butyl 4-(1-(6-Fluoro-2-pivalamidopyridin-3-yl)-1-hydroxy-3-methoxy-3-oxopropan-2-yl)piperidine-1-carboxylate. To diisopropylamine (0.47 mL, 3.35 mmol) in anhydrous THF (10 mL) was dropwise added n-BuLi (2.5 M in heptane, 1.4 mL, 3.48 mmol) at −78° C. under $N_2$ over 10 min. 15 min later, tert-butyl 4-(2-methoxy-2-oxoethyl)piperidine-1-carboxylate (861 mg, 3.35 mmol) in THF (10 mL) was dropwise added at −78° C. over 10 min. The resulting mixture was stirred for 45 min. At the same time, N-(6-fluoro-3-formylpyridin-2-yl)pivalamide (500 mg, 2.23 mmol), was dissolved in anhydrous THF (10 mL) in another oven dried round bottom flask, and dropwise added to NaH (60% in mineral oil, 93.7 mg, 2.34 mmol) in THF (10 mL) at ° C. The resulting yellow suspension was stirred at 0° C. under $N_2$ for 1 hr, which then was transferred to the above anion solution at −78° C. through a syringe over 10 min. The resulting suspension was continued stirring at −78° C. for 1 hr. Quenched with saturated $NH_4Cl$ (50 mL), extracted with EtOAc (2×100 mL). The combined organic layers were washed with brine (30 mL), dried on $MgSO_4$, concentrated on rotary vacuum and purified on flash chromatography column eluting with 20~75% EtOAc/hexanes (1000 mL), 75~100% EtOAc/hexanes (600 mL) to afford the expected inseparable stereo isomer mixture, as a white product (536 mg, 50% yield), plus recovered starting material, N-(6-fluoro-3-formylpyridin-2-yl)pivalamide (140 mg); Mass spec. 482.23 ($MH^+$), Calc. for $C_{24}H_{36}FN_3O_6$ 481.26

Intermediate 177

7-Fluoro-3-(piperidin-4-yl)-1,8-naphthyridin-2(1H)-one hydrochloride. The mixture of tert-butyl 4-(1-(6-fluoro-2-pivalamidopyridin-3-yl)-1-hydroxy-3-methoxy-3-oxopropan-2-yl)piperidine-1-carboxylate (238 mg, 0.494 mmol), and concentrated HCl (1 mL) in MeOH (1 mL) and $H_2O$ (1 mL) was refluxed under $N_2$ over night. The solvents were removed on rotary vacuum, the residue, as a yellow solid, was triturated with cold EtOH (2×3 mL), filtrated and dried under vacuum to afford an expected product, a yellow solid (139 mg, 99% yield); $^1H$ NMR (400 MHz, MeOD) δ ppm 1.27 (s, 1H), 1.83-1.95 (m, 2H), 2.13 (d, J=14.10 Hz, 2H), 3.06-3.18 (m, 3H), 3.49 (d, J=12.84 Hz, 2H), 6.47 (d, J=8.81 Hz, 1H), 7.69 (s, 1H), 7.85 (d, J=9.06 Hz, 1H); Mass spec. 248.13 ($MH^+$), Calc. for $C_{13}H_{14}FN_3O$ 247.11.

Intermediate 178

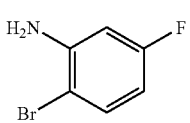

2-Bromo-5-fluorobenzenamine. To a solution of 1-bromo-4-fluoro-2-nitrobenzene (5.0 g, 22.7 mmol) in HOAc/EtOH (20 mL/20 mL) was added iron powder in one portion at room temperature. The mixture was bubbled with $N_2$ for 5 min, and then refluxed for 2 hrs. Partial of the solvents were removed on rotary vacuum, then the residue was partitioned between aqueous NaOH (10N, 200 mL) and $Et_2O$ (200 mL). After separation, the organic phase was washed with $H_2O$ (50 mL), brine (50 mL), dried on $MgSO_4$, and concentrated on rotary vacuum to afford the expected product, as an light tan oil (quantitative yield), which was pure enough to be used in next step without further purification; $^1H$ NMR (400 MHz, $CDCl_3$) δ ppm 4.15 (s, 1H), 6.34 (td, J=8.44, 2.77 Hz, 1H), 6.46 (dd, J=10.20, 2.90 Hz, 1H), 7.31 (dd, J=8.81, 5.79 Hz, 1H); Mass spec. 189.94 ($MH^+$), Calc. for $C_6H_5BrFN$ 188.96.

Intermediate 179

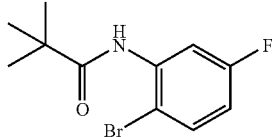

N-(2-Bromo-5-fluorophenyl)pivalamide. Trimethylacetyl chloride (4.2 mL, 34.1 mL) was fast dropwise added to a solution of 2-bromo-5-fluorobenzenamine (4.31 g, 22.7 mmol) in $CH_2Cl_2$ (50 mL) at room temperature, followed by the addition of DIEA (7.9 mL, 45.4 mmol). The resulting mixture was stirred at room temperature for 2 hrs, and then partitioned between HCl (1N, 200 mL) and EtOAc (250 mL). After separation, the organic phase was washed with brine (50 mL), dried on $MgSO_4$, concentrated on rotary vacuum, and purified on flash chromatography eluting with 20~40% EtOAc/hexanes (1200 mL) to afford the expected product, as a colorless oil (6.07 g, 98% yield); $^1H$ NMR (400 MHz, $CDCl_3$) δ ppm 1.33 (s, 9H), 6.69 (ddd, J=8.81, 7.55, 3.02 Hz, 1H), 7.45 (dd, J=8.81, 5.79 Hz, 1H), 8.04 (s, 1H), 8.28 (dd, J=11.08, 3.02 Hz, 1H); Mass spec. 274.04 ($MH^+$), Calc. for $C_{11}H_{13}BrFNO$ 273.02.

Intermediate 180

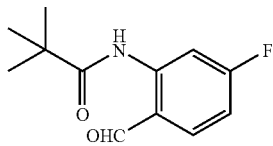

N-(5-Fluoro-2-formylphenyl)pivalamide. N-(2-bromo-5-fluorophenyl)pivalamide (2.4 g, 8.75 mmol)) was dissolved in THF (30 mL) at room temperature, and the colorless solution was cooled to −78° C., followed by fast dropwise addition of t-BuLi (10.3 mL, 1.7M in heptane, 17.4 mmol) under $N_2$ over 10 min. The resulting yellow solution was continued stirring at −78° C. for 1 hr, followed by dropwise addition of DMF (2.7 mL, 35.0 mmol) over 5 min. The light yellow solution was stirred for additional 30 min at −78° C. Thus the mixture was quenched with saturated $NH_4Cl$ (30 mL), extracted with $Et_2O$ (2×150 mL). The combined organic phase was washed with brine (30 mL), dried over $MgSO_4$, concentrated on rotary vacuum, and purified on flash chromatography eluting with 25~50% EtOAc/hexanes (1400 mL) to afford an expected product, as a white solids (1.03 g, 53% yield); $^1H$ NMR (400 MHz, $CDCl_3$) δ ppm 1.30 (s, 9H), 6.80-6.86 (m, 1H), 7.63 (dd, J=8.56, 6.04 Hz, 1H), 8.53 (dd, J=12.21, 2.39 Hz, 1H), 9.83 (s, 1H), 11.54 (s, 1H); Mass spec. 224.16 ($MH^+$), Calc. for $C_{12}H_{14}FNO_2$ 223.1.

Intermediate 181

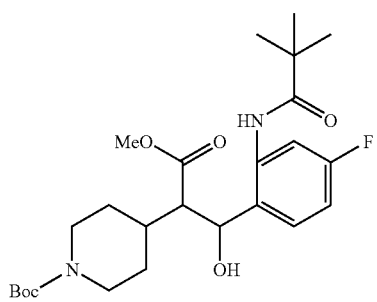

tert-butyl 4-(1-(4-Fluoro-2-pivalamidophenyl)-1-hydroxy-3-methoxy-3-oxopropan-2-yl)piperidine-1-carboxylate. The procedure was the same as the synthesis of t-butyl 4-(1-(6-fluoro-2-pivalamidopyridin-3-yl)-1-hydroxy-3-methoxy-3-oxopropan-2-yl)piperidine-1-carboxylate. The reaction gave an inseparable stereo isomer mixture, tert-butyl 4-(1-(4-fluoro-2-pivalamidophenyl)-1-hydroxy-3-methoxy-3-oxopropan-2-yl)piperidine-1-carboxylate. The crude compound was used directly in the next step without further purification. Mass spec. 481.25 (MH$^+$), Calc. for $C_{25}H_{37}FN_2O_6$ 480.26.

Intermediate 182

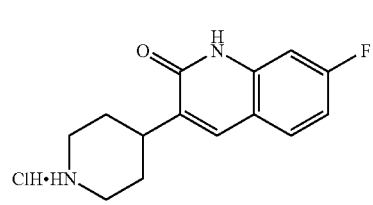

7-Fluoro-3-(piperidin-4-yl)quinolin-2(1H)-one hydrochloride. The procedure was the same as the synthesis of 7-fluoro-3-(piperidin-4-yl)-1,8-naphthyridin-2(1H)-one, and gave the expected product, 7-fluoro-3-(piperidin-4-yl)quinolin-2(1H)-one hydrochloride, as a white solid at the 41% yield after two steps; $^1$H NMR (400 MHz, MeOD) δ ppm 1.84-1.96 (m, 2H), 2.15 (d, J=14.10 Hz, 2H), 3.07-3.16 (m, 3H), 3.50 (d, J=12.84 Hz, 2H), 6.98-7.05 (m, 2H), 7.69 (dd, J=8.56, 5.79 Hz, 1H), 7.78 (s, 1H); Mass spec. 247.12 (MH$^+$), Calc. for $C_{14}H_{15}FN_2O$ 246.12.

Intermediate 183

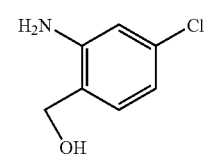

(2-Amino-4-chlorophenyl)methanol. Methyl 2-amino-4-chlorobenzoate (1.5 g, 8.08 mmol) in THF (15 mL) was dropwise added to the suspension of LAH (429 mg, 11.3 mmol) in THF (10 mL) under $N_2$ at 0° C. over 10 min. The resulting mixture was stirred at room temperature for 2 hrs, then the reaction was quenched at 0° C. with saturated $Na_2SO_4$ (50 mL), extracted with $Et_2O$ (2×70 mL). The combined organic solutions were washed with brine (30 mL), dried on MgSO$_4$, and concentrated on rotary vacuum to afford the expected product as a white solid (874 mg, 69% yield); $^1$H NMR (400 MHz, MeOD) δ ppm 4.50 (s, 2H), 6.58 (dd, J=8.06, 2.01 Hz, 1H), 6.70 (d, J=2.01 Hz, 1H), 7.01 (d, J=8.06 Hz, 1H); Mass spec. 157.06 (MH$^+$), Calc. for $C_7H_8ClNO$ 157.03.

Intermediate 184

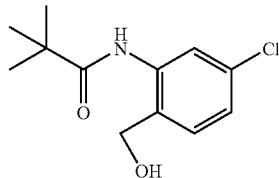

N-(5-Chloro-2-(hydroxymethyl)phenyl)pivalamide. Trimethylacetyl chloride (0.72 mL, 5.82 mmol) was fast dropwise added to (2-amino-4-chlorophenyl)methanol (874 mg, 5.55 mmol) in $CH_2Cl_2$ (20 mL) and THF (6 mL) at 0° C., and followed by the addition of DIEA (2.41 mL, 13.9 mmol). The resulting mixture was stirred for 30 min. Then the mixture was partitioned between saturated NaHCO$_3$ (50 mL) and $CH_2Cl_2$ (100 mL). After separation, the organic phase was washed with brine (30 mL), dried on MgSO$_4$, and concentrated on rotary vacuum to afford the expected crude product (1.34, 100% yield), which was pure enough to be used in next step. Mass spec. 242.08 (MH$^+$), Calc. for $C_{12}H_{16}ClNO_2$ 241.09.

Intermediate 185

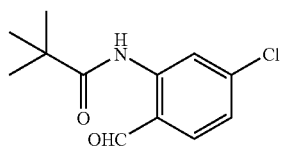

N-(5-Chloro-2-formylphenyl)pivalamide. Pyridiniumchlorochromate (1.67 g, 7.77 mmol) was added to N-(5-chloro-2-(hydroxymethyl)phenyl)pivalamide (1.34 g, 5.55 mmol) in $CH_2Cl_2$ (100 mL) at 0° C. 5 min later, the reaction mixture was stirred at room temperature for 3 hrs. Then it was passed through a thin silica gel pad with $CH_2Cl_2$ (100 mL), concentrated on rotary vacuum and purified on flash chromatography eluting with 20~40% EtOAc/hexanes (800 mL) to afford the expected product as a white solid (937 mg, 70% yield). $^1$H NMR (400 MHz, CHLOROFORM-D) δ ppm 1.28-1.34 (s, 9H), 7.15 (dd, J=8.31, 2.01 Hz, 1H), 7.53-7.59 (m, 1H), 8.87 (d, J=2.01 Hz, 1H), 9.84-9.88 (m, 1H), 11.42 (s, 1H); Mass spec. 240.07 (MH$^+$), Calc. for $C_{12}H_{14}ClNO_2$ 239.07.

Intermediate 186

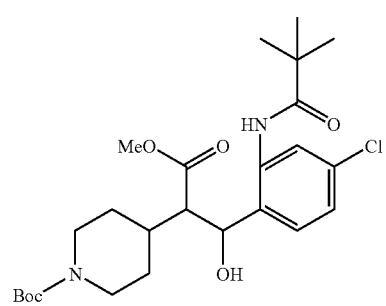

tert-butyl 4-(1-(4-Chloro-2-pivalamidophenyl)-1-hydroxy-3-methoxy-3-oxopropan-2-yl)piperidine-1-carboxylate. The reaction procedure was the same as the synthesis of tert-butyl 4-(1-(6-fluoro-2-pivalamidopyridin-3-yl)-1-hydroxy-3-methoxy-3-oxopropan-2-yl)piperidine-1-carboxylate. The reaction afforded tert-butyl 4-(1-(4-chloro-2-pivalamidophenyl)-1-hydroxy-3-methoxy-3-oxopropan-2-yl)piperidine-1-carboxylate stereoisomer mixture as a white solid (73% total yield) after purification on flash chromatography, which was directly used in next step. Mass spec. 497.19 (MH$^+$), Calc. for $C_{25}H_{37}ClN_2O_6$ 496.23.

Intermediate 187

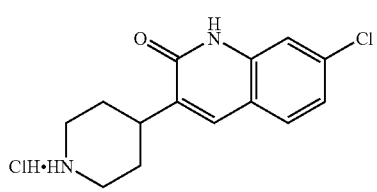

7-Chloro-3-(piperidin-4-yl)quinolin-2(1H)-one hydrochloride. The procedure was the same as the synthesis of 7-fluoro-3-(piperidin-4-yl)-1,8-naphthyridin-2(1H)-one. After reaction, partial of the solvent was removed on rotary vacuum, the expected product came out from the solution, filtration and washing with EtOH to gave a white solid (71% yield). $^1$H NMR (400 MHz, MeOD) δ ppm 1.83-1.94 (m, 2H), 2.14 (d, J=12.84 Hz, 2H), 3.07-3.19 (m, 3H), 3.48 (s, 1H), 3.51 (d, J=3.02 Hz, 1H), 7.18-7.23 (m, J=6.30, 4.34, 2.20, 2.01 Hz, 1H), 7.30-7.35 (m, 1H), 7.59-7.65 (m, 1H), 7.74-7.78 (m, 1H); Mass spec. 263.07 (MH$^+$), Calc. for $C_{14}H_{15}ClN_2O$ 262.09.

Intermediate 188

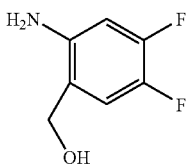

(2-Amino-4,5-difluorophenyl)methanol. 2-Amino-4,5-difluorobenzoic acid (5.37 g, 31.0 mmol) in THF (50 mL) was dropwise added to the suspension on LAH (1.65 g, 43.5 mmol) in THF (15 mL) at room temperature under N$_2$ over 10 min. The resulting suspension was stirred at room temperature for 1 hr. Then the mixture was cooled down to 0° C., quenched with saturated Na$_2$SO$_4$ (100 mL), and extracted with Et$_2$O (2×100 mL), the combined organic layers were washed with brine (60 mL), dried over MgSO$_4$, and concentrated on rotary vacuum to afford the expected crude product as a brown solid, which was pure enough to be used in next step without further purification. $^1$H NMR (400 MHz, CDCl$_3$) δ ppm 4.07 (s, 1H), 4.56 (s, 2H), 6.46 (dd, J=11.71, 6.92 Hz, 1H), 6.87 (dd, J=10.58, 8.56 Hz, 1H); Mass spec. 160.04 (MH$^+$), Calc. for $C_7H_7F_2NO$ 159.05.

Intermediate 189

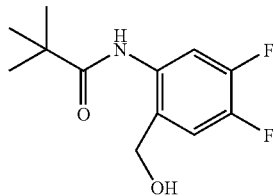

N-(4,5-Difluoro-2-(hydroxymethyl)phenyl)pivalamide. Trimethylacetyl chloride (4.01 mL, 32.55 mmol) was added to the solution of the crude (2-amino-4,5-difluorophenyl)methanol in CH$_2$Cl$_2$/THF (50 mL/10 mL) at 0° C., followed by the addition of DIEA (10.8 mL, 62 mmol). The resulting mixture was stirred for 30 min, and then partitioned between saturated NaHCO$_3$ (100 mL) and CH$_2$Cl$_2$ (150 mL). After separation, the organic phase was washed with brine (40 mL), dried over MgSO$_4$, and concentrated on rotary vacuum to afford the expected product, which was pure enough to be used in next step without further purification; $^1$H NMR (400 MHz, CDCl$_3$) δ ppm 1.28 (s, 9H), 4.62 (s, 2H), 6.94 (dd, J=10.20, 8.44 Hz, 1H), 8.08 (dd, J=12.72, 7.68 Hz, 1H), 9.04 (s, 1H); Mass spec. 244.11 (MH$^+$), Calc. for $C_{12}H_{15}F_2NO_2$ 243.11.

Intermediate 190

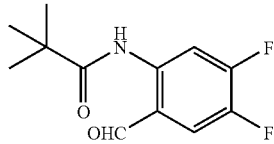

N-(4,5-Difluoro-2-formylphenyl)pivalamide. Pyridiniumchlorochromate (9.36 g, 43.4 mmol) was added to the solution of the crude N-(4,5-difluoro-2-(hydroxymethyl)phenyl)pivalamide in CH$_2$Cl$_2$ (150 mL) at rt. The yellow solution turned into dark brown in 10 min, and the mixture was continued stirring for 3 hr, and then passed through a thin silica gel pad with CH$_2$Cl$_2$ (2×50 mL). The combined organic solution was concentrated on rotary vacuum, and purified on flash chromatography eluting with 20~60% EtOAc/hexanes (1300 mL) to afford the expected product as a brown solid (1.91 g, 26% yield after three step); $^1$H NMR (400 MHz, CDCl$_3$) δ ppm 1.29 (s, 9H), 7.42-7.48 (m, 1H), 8.75 (dd, J=13.35, 7.30 Hz, 1H), 9.77-9.80 (m, 1H), 11.40 (s, 1H); Mass spec. 242.08 (MH$^+$), Calc. for $C_{12}H_{13}F_2NO_2$ 241.09.

Intermediate 200

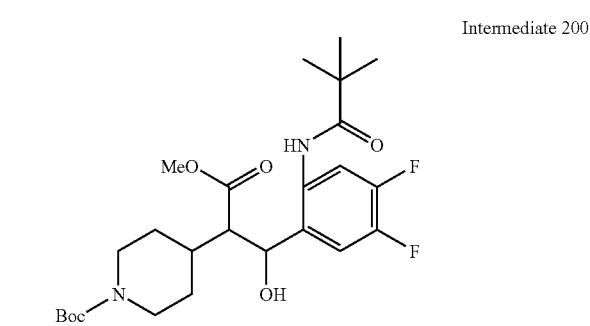

tert-butyl 4-(1-(4,5-Difluoro-2-pivalamidophenyl)-1-hydroxy-3-methoxy-3-oxopropan-2-yl)piperidine-1-carboxylate. The reaction procedure was the same as the synthesis of tert-butyl 4-(1-(6-fluoro-2-pivalamidopyridin-3-yl)-1-hydroxy-3-methoxy-3-oxopropan-2-yl)piperidine-1-carboxylate. The reaction afforded an inseparable tert-butyl 4-(1-(4,5-difluoro-2-pivalamidophenyl)-1-hydroxy-3-methoxy-3-oxopropan-2-yl)piperidine-1-carboxylate stereo isomer mixture, as a white solid (70% total yield) after purification on flash chromatography, which was used in next step. Mass spec. 499.19 (MH$^+$), Calc. for $C_{25}H_{36}F_2N_2O_6$ 498.25

Intermediate 201

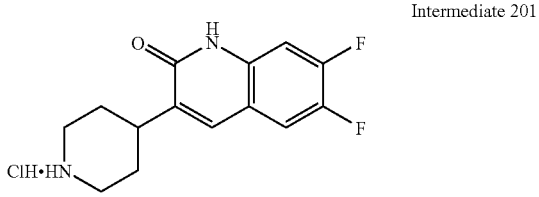

6,7-Difluoro-3-(piperidin-4-yl)quinolin-2(1H)-one hydrochloride. The procedure was the same as the synthesis of 7-fluoro-3-(piperidin-4-yl)-1,8-naphthyridin-2(1H)-one.
After reaction, partial of the solvent was removed on rotary vacuum, the expected product came out from the solution, filtration and washing with ethanol to gave a white solid (77% yield); $^1$H NMR (400 MHz, MeOD) δ ppm 1.81-1.93 (m, 2H), 2.13 (d, J=2.01 Hz, 2H), 3.07-3.19 (m, 4H), 3.50 (d, J=14.35 Hz, 2H), 7.16-7.23 (m, 1H), 7.55-7.62 (m, 1H), 7.71-7.77 (m, 1H); Mass spec. 265.07 (MH$^+$), Calc. for $C_{14}H_{14}F_2N_2O$ 264.11.

Intermediate 202

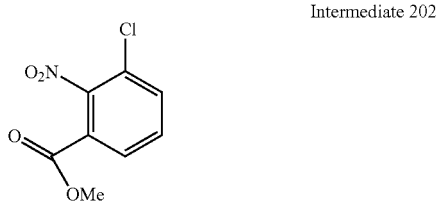

Methyl 3-chloro-2-nitrobenzoate. To 3-chloro-2-nitrobenzoic acid (3.15 g, 15.6 mmol) in methanol/acetonitrile (20 mL/20 mL) was dropwise added TMSCHN$_2$ (2N in hexanes, 11.7 mL, and 23.4 mmol) at 0° C. under N$_2$ over 10 min until the yellow color persist. The mixture was continued stirring for 20 min, followed by dropwise addition of HOAc until the yellow color disappeared to kill excessive TMSCHN$_2$. Partial of the solvent was removed on rotary vacuum, the product came out solution as a light yellow solid, which was filtered and washed with Et$_2$O (2×2 mL) to afford the expected product as a white solid (2.5 g, 74% yield); $^1$H NMR (400 MHz, CDCl$_3$) δ ppm 3.91 (s, 3H), 7.51 (t, J=8.06 Hz, 1H), 7.70 (dd, J=8.06, 1.26 Hz, 1H), 7.97 (dd, J=7.81, 1.26 Hz, 1H); Mass spec. 216.02 (MH$^+$), Calc. for $C_8H_6ClNO_4$ 215.00.

Intermediate 203

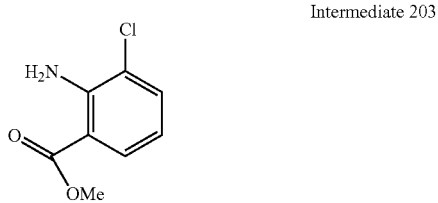

Methyl 2-amino-3-chlorobenzoate. Iron powder (1.94 g, 34.8 mmol) was added to the solution of methyl 3-chloro-2-nitrobenzoate (2.5 g, 11.6 mmol) in EtOH/HOAc (100 mL/100 mL) at room temperature, and then the suspension was refluxed under N$_2$ for 2 hrs. After cooling down to room temperature, partial of the solvents was removed on rotary vacuum, the resulting residue was partitioned between H$_2$O/EtOAc (200 mL/300 mL). The separated organic phase was washed with aqueous NaOH (1N, 50 mL), brine (50 mL), dried over MgSO$_4$, and concentrated on rotary vacuum to afford the expected product as a tan oil (1.7 g, 79% yield) which became wax type solid standing on bench. The crude product was pure enough to be used in next step without further purification; $^1$H NMR (400 MHz, CDCl$_3$) δ ppm 3.86 (s, 3H), 6.25 (s, 2H), 6.57 (t, J=7.93 Hz, 1H), 7.39 (dd, J=7.81, 1.51 Hz, 1H), 7.79 (dd, J=8.06, 1.51 Hz, 1H); Mass spec. 185.95 (MH$^+$), Calc. for $C_8H_8ClNO_2$ 185.02.

Intermediate 204

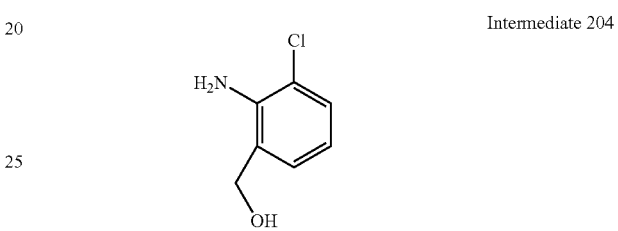

(2-Amino-3-chlorophenyl)methanol. A solution of methyl 2-amino-3-chlorobenzoate (1.7 g, 9.16 mmol) in THF (40 mL) was dropwise added to a suspension of the LAH (521 mg, 13.7 mmol) in THF (15 mL) at room temperature over 10 min under N$_2$, and stirred for 2 hrs. The reaction was carefully quenched with saturated Na$_2$SO$_4$ (10 mL) at 0° C., extracted with Et$_2$O (2×50 mL). The combined organic layers were washes with brine (30 mL), dried on MgSO$_4$, and concentrated on rotary vacuum to afford the expected product as a yellow solid (1.08 g, 75%), which was pure enough to be used in the next step without further purification; $^1$H NMR (400 MHz, CDCl$_3$) δ ppm 1.65 (s, 1H), 4.59-4.70 (m, 4H), 6.60-6.65 (m, 1H), 6.96 (dd, J=7.55, 1.26 Hz, 1H), 7.19-7.25 (m, 1H); Mass spec. 158.02 (MH$^+$), Calc. for $C_7H_8ClNO_2$ 157.03.

Intermediate 205

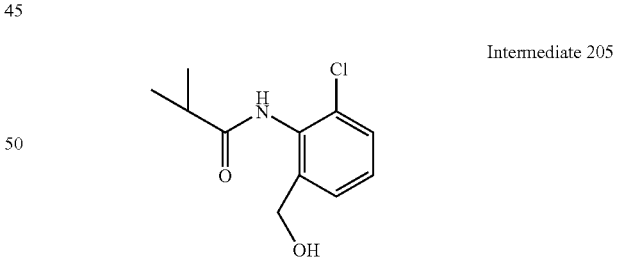

N-(2-Chloro-6-(hydroxymethyl)phenyl)pivalamide. To the crude (2-amino-3-chlorophenyl)methanol (1.08 g, 6.88 mmol) in CH$_2$Cl$_2$ (15 mL) was fast dropwise added trimethylacetyl chloride (0.89 mL, 7.23 mmol), followed by DIEA (2.4 mL, 13.8 mmol) at 0° C. 5 min later, the reaction mixture was stirred at room temperature for 1 hr. Normal aqueous work-up to afford the expected product as a white solid (1.58 g, 95% yield), which was pure enough to be used in next step; $^1$H NMR (400 MHz, CDCl$_3$) δ ppm 1.30 (s, 9H), 3.35 (s, 2H), 4.36 (d, J=6.29 Hz, 1H), 7.06-7.22 (m, J=7.81, 7.81 Hz, 1H), 7.29-7.33 (m, 2H), 7.58 (s, 1H); Mass spec. 242.08 (MH$^+$), Calc. for $C_{12}H_{16}ClNO_2$ 241.09.

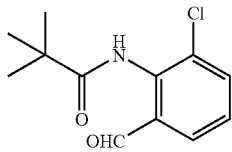

Intermediate 206

N-(5-Chloro-2-formylphenyl)pivalamide. Pyridinium chlorochromate (1.19 g, 5.5 mmol) was added to a solution of N-(2-chloro-6-(hydroxymethyl)phenyl) pivalamide (884 mg, 3.67 mmol) in $CH_2Cl_2$ (100 mL) at 0° C. 5 min later the mixture was allowed stirring at room temperature for 3 hrs. The reaction mixture was passed through a thin pad layer of silica gel with $CH_2Cl_2$ (2×100 mL), concentrated on rotary vacuo, and purified on a flash chromatography column eluting with 20~50% EtOAc/hexanes (1000 mL) to afford the expected product as a white solid (414 mg, 47% yield); $^1H$ NMR (400 MHz, $CDCl_3$) δ ppm 1.37 (s, 9H), 7.30 (t, J=7.81 Hz, 1H), 7.64 (dd, J=7.93, 1.39 Hz, 1H), 7.77 (dd, J=7.55, 1.51 Hz, 1H), 8.25 (s, 1H), 9.84 (s, 1H); Mass spec. 240.08 (MH$^+$), Calc. for $C_{12}H_{14}ClNO_2$ 239.07.

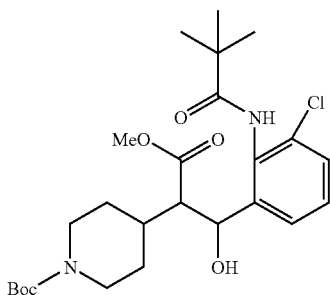

Intermediate 207 tert-butyl 4-(1-(3-Chloro-2-pivalamidophenyl)-1-hydroxy-3-methoxy-3-oxopropan-2-yl)piperidine-1-carboxylate. The reaction procedure was the same as the synthesis of tert-butyl 4-(1-(6-fluoro-2-pivalamidopyridin-3-yl)-1-hydroxy-3-methoxy-3-oxopropan-2-yl)piperidine-1-carboxylate. The reaction afforded an inseparable stereo isomer mixture of tert-butyl 4-(1-(3-chloro-2-pivalamidophenyl)-1-hydroxy-3-methoxy-3-oxopropan-2-yl)piperidine-1-carboxylate, as a white solid (56% yield) after purification on flash chromatography. Mass spec. 497.22 (MH$^+$), Calc. for $C_{25}H_{37}ClN_2O_6$ 496.23.

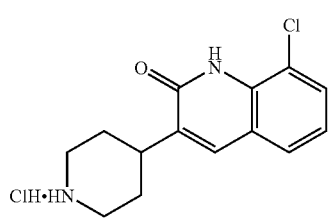

Intermediate 208

8-Chloro-3-(piperidin-4-yl)quinolin-2(1H)-one hydrochloride. The procedure was the same as the synthesis of 7-fluoro-3-(piperidin-4-yl)-1,8-naphthyridin-2(1H)-one. After reaction, partial of the solvent was removed on rotary vacuum, the expected product came out as a solid from the solution, filtration and washing with ethanol to gave the expected product, 8-chloro-3-(piperidin-4-yl)quinolin-2 (1H)-one hydrochloride, a white solid (71% yield); $^1H$ NMR (400 MHz, MeOD) δ ppm 1.85-1.96 (m, 2H), 2.17 (d, J=13.85 Hz, 2H), 3.10-3.20 (m, 4H), 3.46-3.54 (m, 2H), 7.23 (t, J=7.81 Hz, 1H), 7.59-7.64 (m, 2H), 7.81 (s, 1H); Mass spec. 263.08 (MH$^+$), Calc. for $C_{14}H_{15}ClN_2O$ 262.09.

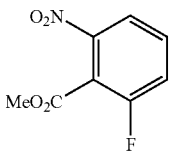

Intermediate 209

Methyl 2-fluoro-6-nitrobenzoate. To 2-fluoro-6-nitrobenzoic acid (712 mg, 3.85 mmol) in methanol/acetonitrile (10 mL/10 mL) was dropwise added $TMSCHN_2$ at 0° C. under $N_2$ until yellow color persistent, and stirred additional 30 min. Then the reaction was quenched with HOAc at 0° C. until the yellow color disappears. Partial of the solvent was removed o rotary vacuum, the residue was dissolved in small amount of EtOAc, purified on flash chromatography eluting with 30~50% EtOAc/hexanes (600 mL) to afford the expected product, methyl 2-fluoro-6-nitrobenzoate, (716 mg, 94% yield) which was used in step-2; $^1H$ NMR (400 MHz, $CDCl_3$) δ ppm 3.96 (s, 3H), 7.40-7.48 (m, 1H), 7.58 (td, J=8.31, 5.54 Hz, 1H), 7.94 (d, J=8.31 Hz, 1H); Mass spec. 200.05 (MH$^+$), Calc. for $C_8H_6FNO_4$ 199.03.

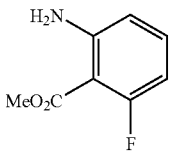

Intermediate 210

Methyl 2-amino-6-fluorobenzoate. Methyl 2-fluoro-6-nitrobenzoate (715 mg, 3.59 mmol) was dissolved in EtOH/HOAc/(10 mL/10 mL), followed by addition of iron powder (602 mg, 10.8 mmol) at room temperature. The resulting mixture was refluxed under $N_2$ for 2 hrs. After cooling down to room temperature, the brown suspension was partitioned between $H_2O$ (30 mL) and $Et_2O$ (100 mL). After separation, the aqueous solution was extracted with $Et_2O$ (50 mL). The combined organic layers were washed with 1N NaOH (3×50 mL), brine (50 mL), dried on $MgSO_4$, and concentrated on rotary vacuum to afford the expected product, methyl 2-amino-6-fluorobenzoate, an colorless oil which became wax-type solid on standing. The crude compound was pure enough to be used in next step without further purification; $^1H$ NMR (400 MHz, $CDCl_3$) δ ppm 3.89 (s, 3H), 5.67 (s, 2H), 6.34 (ddd, J=11.58, 8.06, 1.01 Hz, 1H), 6.41 (d, J=8.31 Hz, 1H), 7.13 (td, J=8.18, 5.79 Hz, 1H); Mass spec. 170.06 (MH$^+$), Calc. for $C_8H_8FNO_2$ 169.05.

Intermediate 211

(2-Amino-6-fluorophenyl)methanol. Methyl 2-amino-6-fluorobenzoate, a crude compound obtained in the last step, dissolved in THF (15 mL) was dropwise added to the suspension of LAH (204 mg, 5.39 mmol) at room temperature over 5 minutes. The mixture was stirred for 1 hr, then cooled down to 0° C., quenched with saturated $Na_2SO_4$ and extracted with $Et_2O$ (2×50 mL). The combined organic layers were washed with brine (30 mL). dried on $MgSO_4$, concentrated on rotary vacuum to give an expected crude product, (2-amino-6-fluorophenyl)methanol, as a brown solid (268.1 mg), which was pure enough to be used in the next step without further purification; $^1H$ NMR (400 MHz, $CDCl_3$) δ ppm 1.64 (s, 1H), 4.30 (s, 2H), 4.75 (s, 2H), 6.39-6.47 (m, 2H), 7.02 (td, J=8.18, 6.30 Hz, 1H); Mass spec. 142.08 ($MH^+$), Calc. for $C_7H_8FNO$ 141.06.

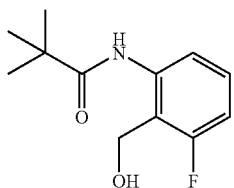

Intermediate 212

N-(3-Fluoro-2-(hydroxymethyl)phenyl)pivalamide. Trimethylacetyl chloride (0.25 mL, 1.99 mmol) was added to a solution of (2-amino-6-fluorophenyl)methanol (268 mg, 1.90 mmol) in $CH_2Cl_2$ (10 mL) at 0° C., followed by the addition of DIEA (1.0 mL, 5.7 mmol). The mixture was stirred for 1 hr, followed by normal aqueous work-up to afford the expected crude product, N-(3-fluoro-2-(hydroxymethyl)phenyl)pivalamide, as a colorless oil (415 mg, 97% yield), which was used directly in the next step; $^1H$ NMR (400 MHz, $CDCl_3$) δ ppm 1.29 (s, 9H), 2.64 (s, 1H), 4.78 (d, J=4.78 Hz, 2H), 6.75-6.84 (m, 1H), 7.23 (td, J=8.62, 5.92 Hz, 1H), 7.86 (d, J=8.31 Hz, 1H), 8.97 (s, 1H); Mass spec. 226.11 ($MH^+$), Calc. for $C_{12}H_{16}FNO_2$ 225.12.

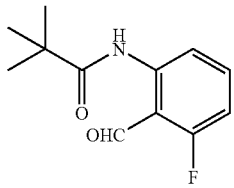

Intermediate 213

N-(3-Fluoro-2-formylphenyl)pivalamide. Pyridinium chlorochromate (596 mg, 2.76 mmol) was added to a solution of N-(3-fluoro-2-(hydroxymethyl)phenyl) pivalamide (415 mg, 1.84 mmol) in $CH_2Cl_2$ (50 mL) at 0° C. 5 min later the mixture was allowed stirring at room temperature for 3 hrs. The reaction mixture was passed through a thin pad layer of silica gel with $CH_2Cl_2$ (2×50 mL), concentrated on rotary vacuum, and purified on a flash chromatography column eluting with 20~50% EtOAc/hexanes (600 mL) to afford the expected product, N-(3-fluoro-2-formylphenyl)pivalamide, as a white solid (396 mg, 46% yield after five steps); $^1H$ NMR (400 MHz, $CDCl_3$) δ ppm 1.33 (s, 9H), 6.76-6.83 (m, 1H), 7.54 (td, J=8.44, 6.55 Hz, 1H), 8.56 (d, J=8.56 Hz, 1H), 10.38 (s, 1H), 11.57 (s, 1H); Mass spec. 224.11 ($MH^+$), Calc. for $C_{12}H_{14}FNO_2$ 223.1.

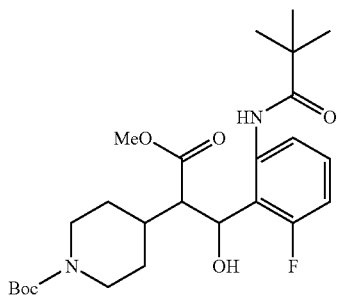

Intermediate 214 tert-butyl 4-(1-(2-Fluoro-6-pivalamidophenyl)-1-hydroxy-3-methoxy-3-oxopropan-2-yl)piperidine-1-carboxylate. The reaction procedure was the same as the synthesis of tert-butyl 4-(1-(6-fluoro-2-pivalamidopyridin-3-yl)-1-hydroxy-3-methoxy-3-oxopropan-2-yl)piperidine-1-carboxylate. The reaction afforded a stereo isomer mixture of the expected crude product, tert-butyl 4-(1-(2-fluoro-6-pivalamidophenyl)-1-hydroxy-3-methoxy-3-oxopropan-2-yl)piperidine-1-carboxylate, as a colorless oil which was used directly in the next step without further purification. Mass spec. 481.24 ($MH^+$), Calc. for $C_{25}H_{37}FN_2O_6$ 480.26.

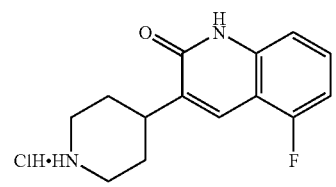

Intermediate 215

5-Fluoro-3-(piperidin-4-yl)quinolin-2(1H)-one hydrochloride. The procedure was the same as the synthesis of 7-fluoro-3-(piperidin-4-yl)-1,8-naphthyridin-2(1H)-one.

After reaction, partial of the solvent was removed on rotary vacuum, the expected product came out as a solid from the solution, filtration and washing with ethyl ethanol to gave the expected product, 5-fluoro-3-(piperidin-4-yl)quinolin-2 (1H)-one hydrochloride, a white solid (43% yield after two steps); $^1H$ NMR (400 MHz, MeOD) δ ppm 1.85-1.96 (m, 2H), 2.16 (d, J=14.10 Hz, 2H), 3.16 (td, J=13.03, 2.90 Hz, 3H), 3.51 (dd, J=10.58, 2.01 Hz, 2H), 4.55 (s, 1H), 6.94-6.99 (m, 1H), 7.13 (d, J=8.31 Hz, 1H), 7.48 (td, J=8.31, 5.79 Hz, 1H), 7.90 (s, 1H); Mass spec. 247.11 ($MH^+$), Calc. for $C_{14}H_{15}FN_2O$ 246.12.

EXAMPLE 1

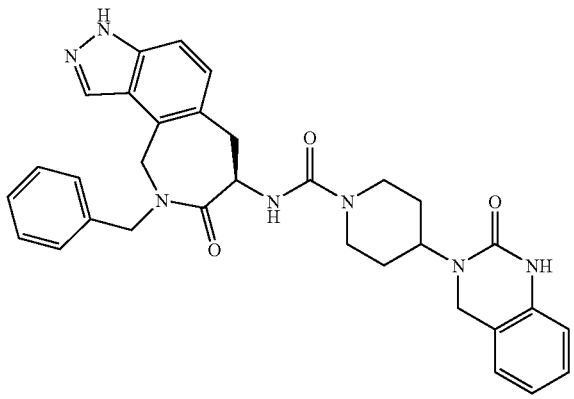

4-(2-Oxo-1,4-dihydro-2H-quinazolin-3-yl)-piperidine-1-carboxylic acid (9-benzyl-8-oxo-3,6,7,8,9,10-hexahydro-2,3,9-triaza-(R)-cyclohepta[e]inden-7-yl)-amide. Potassium carbonate (25 mg, 0.18 mmol) was added to a solution of 4-(2-Oxo-1,4-dihydro-2H-quinazolin-3-yl)-piperidine-1-carboxylic acid (3-acetyl-9-benzyl-8-oxo-3,6,7,8,9,10-hexahydro-2,3,9-triaza-(R)-cyclohepta[e]inden-7-yl)-amide (19 mg, 0.03 mmol). Reaction was stirred at room temperature for 1.25 hours. Reaction was quenched with 1N hydrochloric acid (5 mL). Methanol was removed from the mixture in vacuo. Remaining aqueous was made basic with sodium bicarbonate. Mixture was extracted with dichloromethane (3×10 mL). Combined extracts were dried (magnesium sulfate), filtered and concentrated in vacuo. Title compound was obtained as an off-white solid in 90% yield. $^1$H NMR (300 MHz, CDCl$_3$): δ=7.64 (s, 1H), 7.18 (m, 6H), 7.06 (m, 1H), 6.96 (t, J=7.1, 1H), 6.84 (m, 2H), 6.67 (m, 1H), 6.24 (d, J=5.9, 1H), 5.40 (m, 1H), 4.96 (d, J=14.6, 1H), 4.76 (d, J=17.2, 1H), 4.58 (m, 2H), 4.15 (m, 5H), 3.83 (d, J=13.2, 1H), 3.46 (dd, J1=3.1, J2=16.7, 1H), 2.98 (m, 3H), 1.78 (m, 4H). MS m/e (M+H)$^+$=564.3.

EXAMPLE 2

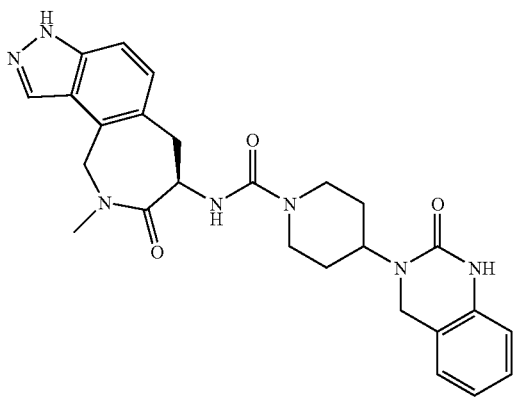

4-(2-Oxo-1,4-dihydro-2H-quinazolin-3-yl)-piperidine-1-carboxylic acid (9-methyl-8-oxo-3,6,7,8,9,10-hexahydro-2,3,9-triaza-(R)-cyclohepta[e]inden-7-yl)-amide. A catalytic amount of 10% palladium on carbon was added to a mixture of (3-acetyl-9-methyl-8-oxo-3,6,7,8,9,10-hexahydro-2,3,9-triaza-(R)-cyclohepta[e]inden-7-yl)-carbamic acid benzyl ester (30 mg, 0.07 mmol), and acetic acid (20 μL, 0.35 mmol) in methanol (6 mL) and ethyl acetate (3 mL). Reaction vessel was placed on a Parr hydrogenation apparatus and charged with 50 psi of hydrogen gas. Reaction mixture was allowed to shake at room temperature for 1.5 hours. Mixture was filtered. Filtrate was concentrated. Residue was treated with dichloromethane (3 mL) and saturated aqueous sodium bicarbonate (1 mL). 20% phosgene in toluene (48 μL, 0.09 mmol) was added to the mixture. Reaction was stirred at room temperature for 5 minutes. 4-(2-Oxo-1,4-dihydro-2H-quinazolin-3-yl)piperidinium acetate (25 mg, 0.09 mmol) was added to the mixture. Reaction mixture was allowed to stir at room temperature for 1 hour. Another 20 μL of phosgene solution was added to the mixture followed after 15 minutes by another 20 mg of 4-(2-Oxo-1,4-dihydro-2H-quinazolin-3-yl)piperidinium acetate. Reaction mixture was stirred at room temperature for 30 minutes. Reaction layers were partitioned. Organic was washed successively with 1N hydrochloric acid (2×5 mL), and brine (5 mL). Organic was dried (magnesium sulfate), filtered and concentrated in vacuo. Residue was dissolved in methanol (3 mL). Potassium carbonate (25 mg, 0.18 mmol) was added to the mixture. Reaction mixture was stirred at room temperature for 1 hour. Reaction was quenched with a couple of drops of trifluoroacetic acid. C18 preparatory HPLC (acetonitrile-water-trifluoroacetic acid) yielded the title compound as a white solid in 16% yield. $^1$H NMR (300 MHz, CDCl$_3$): δ=7.94 (s, 1H), 7.17 (m, 2H), 7.06 (t, J=7.1, 2H), 6.93 (m, 2H), 6.82 (d, J=9.2, 1H), 6.66 (d, J=7.3, 1H), 6.19 (d, J=5.9, 1H), 5.37 (m, 1H), 5.16 (m, 1H), 5.03 (d J=17.2, 1H), 4.59 (m, 1H), 4.34 (s, 3H), 4.19 (m, 2H), 3.42 (m, 1H), 2.94 (m, 4H), 1.80 (m, 4H). MS m/e (M+H)$^+$= 488.4.

EXAMPLE 3

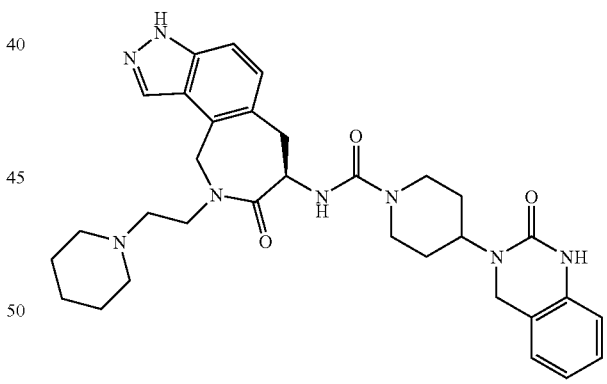

4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. N,N'-Disuccinimidyl carbonate (55 mg, 0.21 mmol) was added to a mixture of 7-(R)-amino-9-(2-piperidin-1-yl-ethyl)-6,7,9,10-tetrahydro-3H-2,3,9-triaza-cyclohepta[e]inden-8-one (60 mg, 0.18 mmol) and triethylamine (150 μL, 1.1 mmol) in dichloromethane (3 mL). Reaction was stirred at room temperature for 30 minutes. 4-(2-Oxo-1,4-dihydro-2H-quinazolin-3-yl)piperidinium acetate (65 mg, 0.22 mmol) was added to the reaction mixture. Reaction was stirred until judged complete by HPLC (1.75 hours). Mixture was washed successively with water (2×5 mL) and brine (1×5 mL).

Organic was concentrated in vacuo. C18 preparatory HPLC (acetonitrile-water-trifluoroacetic acid) afforded the desired product as a tan solid in 34% yield. $^1$H NMR (300 MHz, DMSO-D$_6$): δ=9.23 (s, 1H), 8.34 (s, 1H), 7.43 (d, J=8.8, 1H), 7.13 (m, 2H), 6.86 (t, J=7.0, 1H), 6.77 (d, J=7.7, 1H), 6.68 (d, J=7.7, 1H), 5.26 (m, 2H), 4.71 (d, J=17.2, 1H), 4.36 (m, 1H), 4.13 (m, 4H), 3.48 (m, 2H), 3.26 (m, 2H), 3.08 (m, 1H), 2.92 (m, 2H), 2.80 (m, 2H), 1.80 (m, 2H), 1.62 (m, 4H). MS m/e (M+H)$^+$=585.4.

EXAMPLE 4

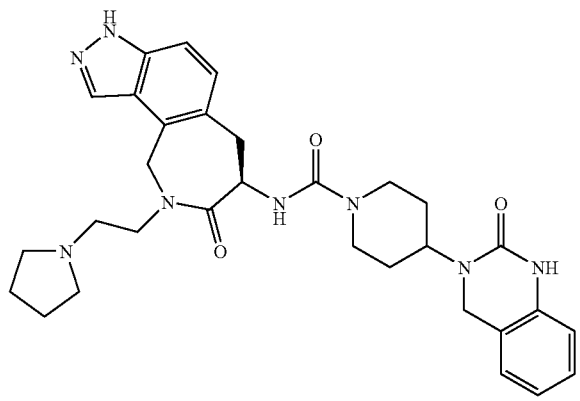

4-(2-Oxo-1,4-dihydro-2H-quinazolin-3-yl)-piperidine-1-carboxylic acid [8-oxo-9-(2-pyrrolidin-1-yl-ethyl)-3,6,7,8,9,10-hexahydro-2,3,9-triaza-(R)-cyclohepta[e]inden-7-yl]-amide. 7-(R)-Amino-9-(2-pyrrolidin-1-yl-ethyl)-6,7,9,10-tetrahydro-3H-2,3,9-triaza-cyclohepta[e]inden-8-one (27 mg, 0.09 mmol) was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. Title compound was obtained as a white solid in 20% yield. $^1$H NMR (300 MHz, DMSO-D$_6$): δ=9.23 (s, 1H), 8.34 (s, 1H), 7.43 (d, J=8.4, 1H), 7.13 (m, 2H), 6.86 (t, J=7.3, 1H), 6.76 (d, J=7.7, 1H), 6.67 (d, J=7.0, 1H), 5.26 (m, 2H), 4.70 (d, J=17.2, 1H), 4.37 (m, 2H), 4.12 (m, 6H), 3.62 (m, 2H), 3.36 (m, 4H), 3.04 (m, 3H), 2.80 (m, 2H), 2.00 (m, 2H), 1.86 (m, 2H), 1.70 (m, 2H), 1.57 (m, 2H). MS m/e (M+H)$^+$=571.4.

EXAMPLE 5

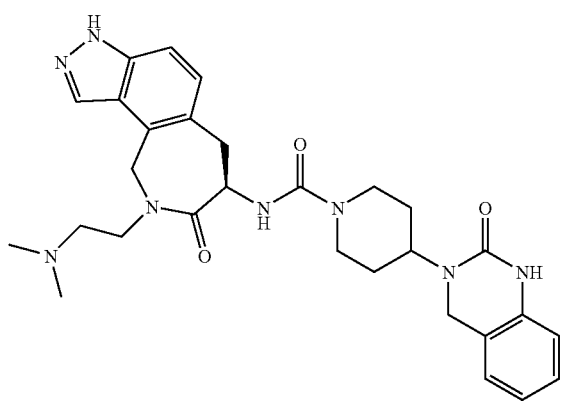

4-(2-Oxo-1,4-dihydro-2H-quinazolin-3-yl)-piperidine-1-carboxylic acid [9-(2-dimethylamino-ethyl)-8-oxo-3,6,7,8,9,10-hexahydro-2,3,9-triaza-(R)-cyclohepta[e]inden-7-yl]-amide. 7-(R)-Amino-9-(2-dimethylamino-ethyl)-6,7,9,10-tetrahydro-3H-2,3,9-triaza-cyclohepta[e]inden-8-one (11 mg, 0.04 mmol) was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. Desired compound was obtained as a white solid in 34% yield. $^1$H NMR (300 MHz, DMSO-D$_6$): δ=9.23 (s, 1H), 8.34 (s, 1H), 7.42 (d, J=8.4, 1H), 7.12 (m, 2H), 6.87 (t, J=7.5, 1H), 6.77 (d, J=8.1, 1H), 6.64 (d, J=7.3, 1H), 5.26 (m, 2H), 4.69 (d, J=17.2, 1H), 4.36 (m, 1H), 4.13 (m, 6H), 3.37 (m, 2H), 3.21 (m, 2H), 3.05 (m, 2H), 2.82 (m, 8H), 1.71 (m, 2H), 1.57 (m, 2H). MS m/e (M+H)$^+$=545.4.

EXAMPLE 6

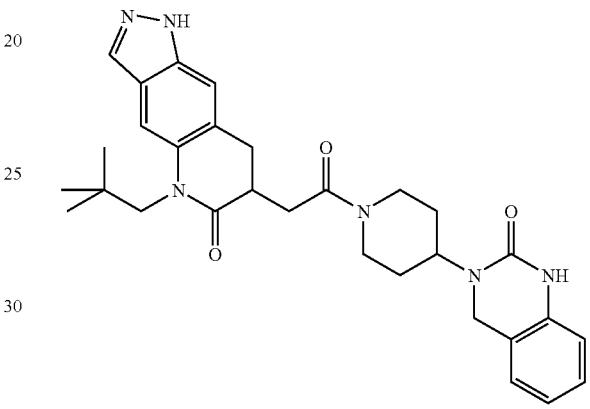

5-Neopentyl-7-(2-oxo-2-(4-(2-oxo-1,2-dihydroquinazolin-3(4H)-yl)piperidin-1-yl)ethyl)-7,8-dihydro-1H-pyrazolo[3,4-g]quinolin-6(5H)-one. O-(7-Azabenzotriazol-1-yl)-N,N,N',N'-tetramethyluronium hexafluorophosphate (116 mg, 0.3 mmol) was added to a solution of 2-(1-neopentyl-2-oxo-2,3,4,7-tetrahydro-1H-pyrazolo[3,4-h]quinolin-3-yl)acetic acid (95 mg, 0.3 mmol) and N,N-diisopropylethylamine (158 µL, 0.9 mmol) in dichloromethane (5.0 mL). Mixture was stirred at room temperature for 45 minutes. 4-(2-Oxo-1,4-dihydro-2H-quinazolin-3-yl)piperidine (70 mg, 0.3 mmol) was then added to the mixture. After 3 h stirring at room temperature, the crude reaction mixture was purified by prep HPLC starting from 30% methanol in water to 90% methanol in water over a period of 8 min and at a flow rate of 40 ml/min. Removal of solvent furnished the desired. MS (ESI) 529 (M+H); R$_f$=1.57.

EXAMPLE 7

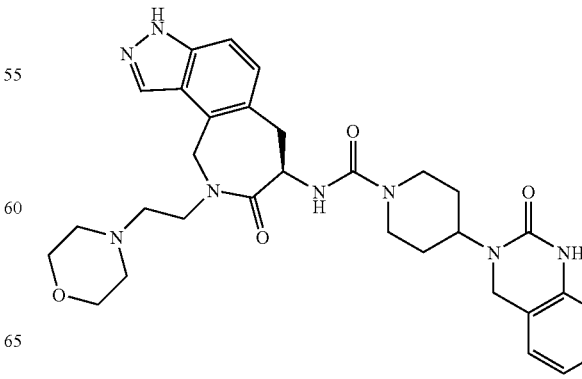

4-(2-Oxo-1,4-dihydro-2H-quinazolin-3-yl)-piperidine-1-carboxylic acid [9-(2-morpholin-4-yl-ethyl)-8-oxo-3,6,7,8,9,10-hexahydro-2,3,9-triaza-(R)-cyclohepta[e]inden-7-yl]-amide. 7-(R)-Amino-9-(2-morpholin-4-yl-ethyl)-6,7,9,10-tetrahydro-3H-2,3,9-triaza-cyclohepta[e]inden-8-one (18 mg, 0.05 mmol) was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. The title compound was obtained as a light yellow solid in 43% yield. $^1$H NMR (300 MHz, DMSO-D$_6$): δ=9.23 (s, 1H), 8.33 (s, 1H), 7.44 (d, J=8.4, 1H), 7.13 (t, J=8.4, 2H), 6.86 (t, J=7.5, 1H), 6.77 (d, J=8.4, 1H), 6.66 (d, J=7.0, 1H), 5.27 (m, 2H), 4.71 (d, J=17.2, 1H), 4.38 (m, 1H), 4.16 (m, 4H), 3.98 (m, 2H), 3.61 (m, 4H), 3.42 (m, 4H), 3.29 (m, 2H), 3.10 (m, 4H), 2.79 (m, 2H), 1.72 (m, 2H), 1.56 (m, 2H), 1.56 (m, 2H). MS m/e (M+H)$^+$=587.4.

EXAMPLE 8

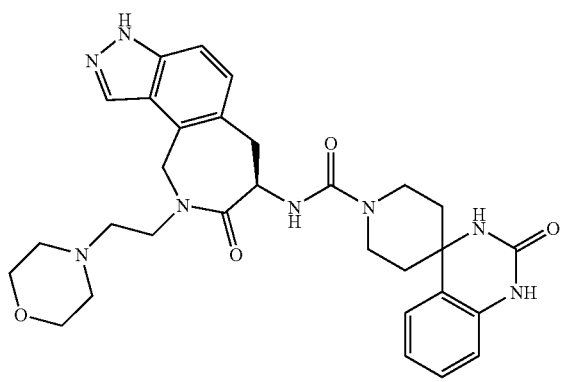

'H-Spiro[piperidine-4,4'-quinazolin]-2'(3'H)-one-1-carboxylic acid [9-(2-morpholin-4-yl-ethyl)-8-oxo-3,6,7,8,9,10-hexahydro-2,3,9-triaza-(R)-cyclohepta[e]inden-7-yl]-amide. N,N'-Disuccinimidyl carbonate (21 mg, 0.08 mmol) was added to a mixture of 7-(R)-Amino-9-(2-morpholin-4-yl-ethyl)-6,7,9,10-tetrahydro-3H-2,3,9-triaza-cyclohepta[e]inden-8-one (22 mg, 0.07 mmol) and triethylamine (40 μL, 0.29 mmol) in dichloromethane (1 mL). Reaction was stirred at room temperature for 30 minutes. 4-(2-Oxo-1,4-dihydro-2H-quinazolin-3-yl)piperidinium acetate (65 mg, 0.22 mmol) was added to the reaction mixture. Reaction was stirred until judged complete by HPLC (1.5 hours). Mixture was concentrated in vacuo. C18 preparatory HPLC (acetonitrile-water-trifluoroacetic acid) afforded the desired product as a white solid in 34% yield. $^1$H NMR (300 MHz, DMSO-D$_6$): δ=9.26 (s, 1H), 8.34 (s, 1H), 7.43 (d, J=8.8, 1H), 7.18 (m, 3H), 6.91 (t J=7.0, 1H), 6.83 (d, J=8.1, 1H), 6.66 (d, J=7.0, 1H), 5.28 (m, 2H), 4.70 (d, J=17.6, 1H), 3.62 (m, 6H), 3.62 (m, 4H), 3.41 (m, 4H), 3.27 (m, 4H), 3.09 (m, 2H), 1.86 (m, 2H), 1.72 (m, 2H). MS m/e (M+H)$^+$=573.4.

EXAMPLE 9

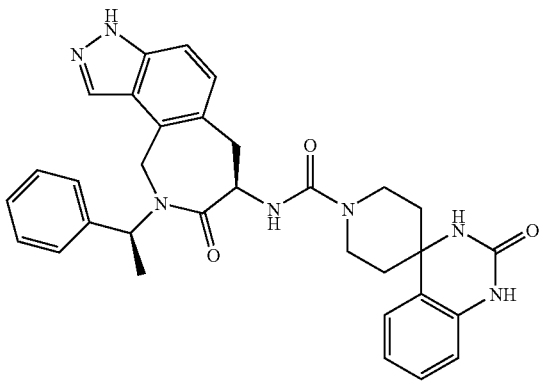

'H-Spiro[piperidine-4,4'-quinazolin]-2'(3'H)-one-1-carboxylic acid [8-oxo-9-(1-(S)-phenyl-ethyl)-3,6,7,8,9,10-hexahydro-2,3,9-triaza-(R)-cyclohepta[e]inden-7-yl]-amide. 7-Amino-9-(1-(S)-phenyl-ethyl)-6,7,9,10-tetrahydro-3H-2,3,9-triaza-(R)-cyclohepta[e]inden-8-one (27 mg, 0.08 mmol) was reacted in a manner analogous to the preparation of 'H-spiro[piperidine-4,4'-quinazolin]-2'(3'H)-one-1-carboxylic acid [9-(2-morpholin-4-yl-ethyl)-8-oxo-3,6,7,8,9,10-hexahydro-2,3,9-triaza-(R)-cyclohepta[e]inden-7-yl]-amide. The title compound was obtained as a white solid in 14% yield. $^1$H NMR (300 MHz, CD$_3$OD): δ=7.92 (s, 1H), 7.46 (m, 5H), 7.37 (m, 1H), 7.30 (m, 1H), 7.19 (m, 2H), 7.00 (t J=7.7, 1H), 6.85 (d, J=7.7, 1H), 5.98 (q, J=6.8, 1H), 5.46 (dd, J1=4.6, J2=13.0, 1H), 4.98 (d, J=17.2, 1H), 4.90 (m, 1H), 4.37 (d, J=17.6, 1H), 4.11 (m, 2H), 3.40 (m, 4H), 3.22 (m, 2H), 2.12 (m, 2H), 1.92 (d, J=13.5, 2H), 1.24 (d, J=7.3, 3H). MS m/e (M+H)$^+$=564.1.

EXAMPLE 10

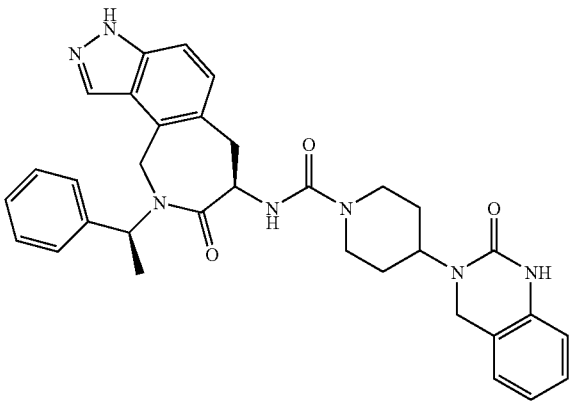

4-(2-Oxo-1,4-dihydro-2H-quinazolin-3-yl)-piperidine-1-carboxylic acid [8-oxo-9-(1-(S)-phenyl-ethyl)-3,6,7,8,9,10-hexahydro-2,3,9-triaza-(R)-cyclohepta[e]inden-7-yl]-amide. 7-Amino-9-(1-(S)-phenyl-ethyl)-6,7,9,10-tetrahydro-3H-2,3,9-triaza-(R)-cyclohepta[e]inden-8-one (27 mg, 0.08 mmol) was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. Title compound was obtained as a white solid in 20% yield. $^1$H NMR (300 MHz, CD$_3$OD): δ=7.92 (s, 1H), 7.47 (m, 5H), 7.43 (d, J=8.8, 1H), 7.21 (d, J=8.8, 1H), 7.12 (m, 2H), 6.95 (t, J=7.0, 1H), 6.78 (d, J=7.7, 1H), 5.98 (d, J=7.0, 1H), 5.44 (dd, J1=4.4, J2=13.7, 1H), 4.98 (d, J=17.2, 1H), 4.49 (m, 1H), 4.41 (m, 3H), 4.31 (m, 4H), 3.36 (m, 1H), 3.24 (m, 1H), 2.99 (m, 2H), 1.93 (m, 2H), 1.73 (m, 2H), 1.24 (d, J=7.0, 3H). MS m/e (M+H)$^+$=578.2.

EXAMPLE 11

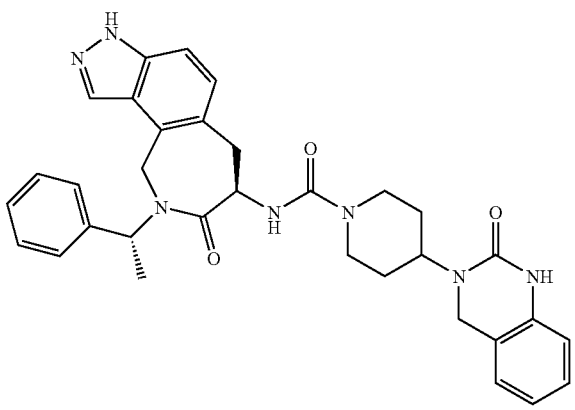

4-(2-Oxo-1,4-dihydro-2H-quinazolin-3-yl)-piperidine-1-carboxylic acid [8-oxo-9-(1-(R)-phenyl-ethyl)-3,6,7,8,9,10-hexahydro-2,3,9-triaza-(R)-cyclohepta[e]inden-7-yl]-amide. 7-Amino-9-(1-(R)-phenyl-ethyl)-6,7,9,10-tetrahydro-3H-2,3,9-triaza-(R)-cyclohepta[e]inden-8-one (48 mg. 0.15 mmol) was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. Title compound was obtained as an off-white solid in 10% yield. $^1$H NMR (300 MHz, CD$_3$OD): δ=7.50 (s, 21H), 7.25 (d, J=8.4, 1H), 7.14 (m, 2H), 7.07 (m, 4H), 6.93 (t, J=7.5, 1H), 6.83 (m, 2H), 6.78 (d, J=7.7, 1H), 5.97 (q, J=6.7, 1H), 5.40 (dd, J1=4.6, J2=13.0, 1H), 5.05 (d, J=17.6, 1H), 4.49 (m, 3H), 4.42 (s, 2H), 4.30 (m, 3H), 3.37 (m, 1H), 3.24 (m, 1H), 2.99 (m, 2H), 1.93 (m, 2H), 1.76 (m, 2H), 1.70 (d, J=7.3, 3H). MS m/e (M+H)$^+$=578.1.

EXAMPLE 12

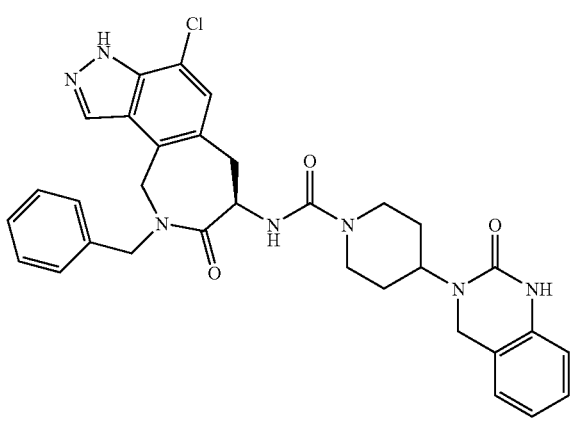

4-(2-Oxo-1,4-dihydro-2H-quinazolin-3-yl)-piperidine-1-carboxylic acid (9-benzyl-4-chloro-8-oxo-3,6,7,8,9,10-hexahydro-2,3,9-triaza-(R)-cyclohepta[e]inden-7-yl)-amide. N,N'-Disuccinimidyl carbonate (63 mg, 0.25 mmol) was added to a mixture of 7-(R)-Amino-9-(2-morpholin-4-yl-ethyl)-6,7,9,10-tetrahydro-3H-2,3,9-triaza-cyclohepta[e]inden-8-one (120 mg, 0.24 mmol) and triethylamine (500 μL, 3.6 mmol) in dichloromethane (5 mL). Reaction was stirred at room temperature for 30 minutes. 4-(2-Oxo-1,4-dihydro-2H-quinazolin-3-yl)piperidine (54 mg, 0.23 mmol) was added to the reaction mixture. Reaction was stirred until judged complete by HPLC (0.5 hours). Mixture was washed successively with water (2×5 mL) and brine (5 mL). Organic layer was concentrated in vacuo. Residue was purified by C18 preparatory HPLC (acetonitrile-water-trifluoroacetic acid). Acetonitrile was removed from the product containing fractions in vacuo. Remaining aqueous was made basic with sodium bicarbonate. Mixture was extracted with ethyl acetate (2×20 mL). Combined extracts were washed with brine (10 mL). Organic was dried (magnesium sulfate), filtered and concentrated. Desired product was obtained as a white solid in 24% yield. $^1$H NMR (500 MHz, CD$_3$OD): δ=7.91 (s, 1H), 7.16 (m, 4H), 7.10 (d, J=7.3, 1H), 7.04 (m, 3H), 6.92 (t, J=7.5, 1H), 6.79 (d, J=7.9, 1H), 5.45 (dd, J1=4.4, J2=13.3, 1H), 5.29 (d, J=16.8, 1H), 4.99 (d, J=14.7, 1H), 4.60 (m, 2H), 4.49 (m, 3H), 4.39 (s, 2H), 4.28 (t, J=12.7, 2H), 3.36 (m, 1H), 3.19 (dd, J1=14.0, J2=16.2, 1H), 2.98 (m, 2H), 1.91 (m, 2H), 1.71 (m, 2H). MS m/e (M+H)$^+$=598.1.

EXAMPLE 13

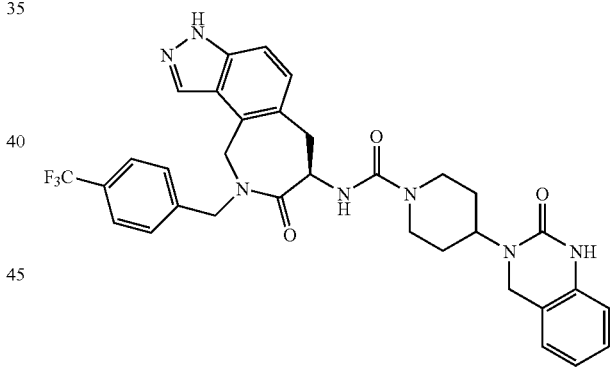

4-(2-Oxo-1,4-dihydro-2H-quinazolin-3-yl)-piperidine-1-carboxylic acid [8-oxo-9-(4-trifluoromethyl-benzyl)-3,6,7,8,9,10-hexahydro-2,3,9-triaza-(R)-cyclohepta[e]inden-7-yl]-amide. 7-Amino-9-(4-trifluoromethyl-benzyl)-6,7,9,10-tetrahydro-3H-2,3,9-triaza-(R)-cyclohepta[e]inden-8-one bismethanesulfonate was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. Title compound was obtained as a white solid in 19% yield. $^1$H NMR (500 MHz, DMSO-D$_6$): δ=9.19 (s, 1H), 8.09 (s, 1H), 7.48 (d, J=7.9, 1H), 7.38 (d, J=8.4, 1H), 7.34 (d, J=8.5, 1H), 7.10 (m, 3H), 6.85 (t, J=7.0, 1H), 6.77 (d, J=7.9, 1H), 6.66 (d, J=6.4, 1H), 5.35 (m, 2H), 4.71 (m, 3H), 4.36 (m, 2H), 4.29 (s, 2H), 4.18 (d, J=12.8, 2H), 3.29 (m, 1H), 3.13 (dd, J1=13.6, J2=16.6, 1H), 2.81 (m, 2H), 1.72 (m, 2H), 1.56 (d, J=111.3, 2H). MS m/e (M+H)$^+$=632.1.

EXAMPLE 14

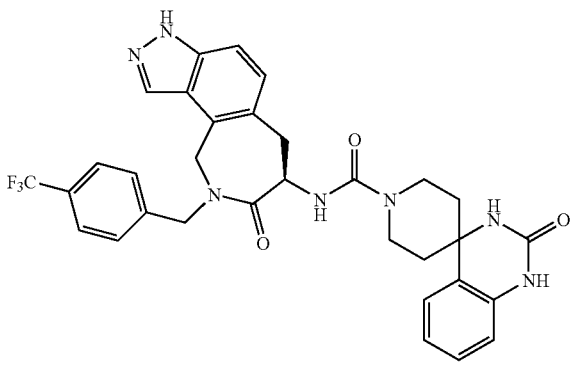

'H-spiro[piperidine-4,4'-quinazolin]-2'(3'H)-one-1-carboxylic acid [8-oxo-9-(4-trifluoromethyl-benzyl)-3,6,7,8,9,10-hexahydro-2,3,9-triaza-(R)-cyclohepta[e]inden-7-yl]-amide. 7-Amino-9-(4-trifluoromethyl-benzyl)-6,7,9,10-tetrahydro-3H-2,3,9-triaza-(R)-cyclohepta[e]inden-8-one bismethanesulfonate was reacted in a manner analogous to the preparation of 'H-spiro[piperidine-4,4'-quinazolin]-2'(3'H)-one-1-carboxylic acid [9-(2-morpholin-4-yl-ethyl)-8-oxo-3,6,7,8,9,10-hexahydro-2,3,9-triaza-(R)-cyclohepta[e]inden-7-yl]-amide. The title compound was obtained as a white solid in 6% yield. $^1$H NMR (500 MHz, CD$_3$OD): δ=7.91 (s, 1H), 7.46 (d, J=8.2, 1H), 7.35 (d, J=8.6, 1H), 7.30 (m, 5H), 7.17 (m, 2H), 7.01 (t, J=7.6, 1H), 6.84 (d, J=8.2, 1H), 5.51 (dd, J1=4.6, J2=13.1, 1H), 5.40 (d, J=17.1, 1H), 5.07 (d, J=15.3, 1H), 4.64 (d, J=4.9, 1H), 4.61 (s, 1H), 4.43 (s, 1H), 4.09 (m, 2H), 3.42 (m, 3H), 3.35 (m, 1H), 3.22 (m, 1H), 2.16 (m, 1H), 2.07 (m, 1H), 1.92 (d, J=13.4, 2H). MS m/e (M+H)$^+$= 618.1.

EXAMPLE 15

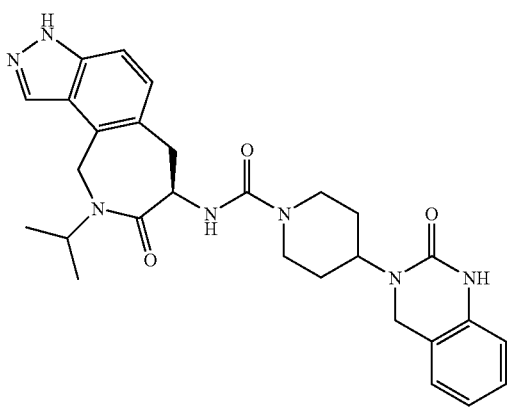

4-(2-Oxo-1,4-dihydro-2H-quinazolin-3-yl)-piperidine-1-carboxylic acid (9-isopropyl-8-oxo-3,6,7,8,9,10-hexahydro-2,3,9-triaza-(R)-cyclohepta[e]inden-7-yl)-amide. 7-(R)-Amino-9-isopropyl-6,7,9,10-tetrahydro-3H-2,3,9-triaza-cyclohepta[e]inden-8-one bismethanesulfonate was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. The desired product was obtained as light yellow solid in 28% yield. $^1$H NMR (400 MHz, DMSO-D$_6$): δ=9.21 (s, 1H), 8.45 (s, 1H), 7.37 (d, J=8.6, 1H), 7.10 (m, 3H), 6.86 (m, 1H), 6.77 (d, J=7.6, 1H), 6.56 (m, 1H), 5.26 (m, 1H), 5.00 (d, J=17.1, 1H), 4.74 (m, 2H), 4.65 (d, J=17.4, 1H), 4.36 (m, 1H), 4.29 (s, 2H), 4.15 (m, 2H), 3.25 (dd, J1=3.7, J2=16.9, 1H), 3.04 (dd, J1=13.6, J2=16.5, 1H), 2.80 (m, 2H), 1.71 (m, 2H), 1.57 (d, J=11.7, 2H), 1.23 (d, J=6.9, 3H), 0.80 (d, J=6.9, 3H). MS m/e (M+H)$^+$=516.4.

EXAMPLE 16

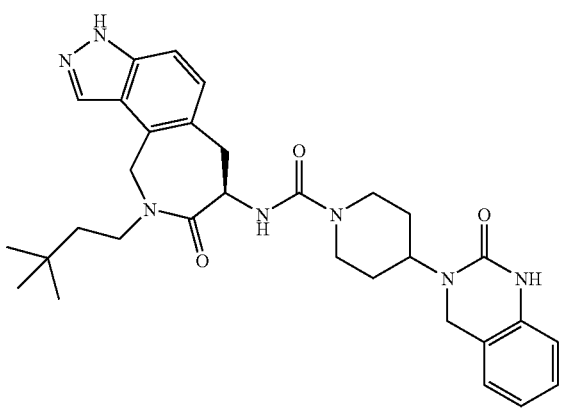

4-(2-Oxo-1,4-dihydro-2H-quinazolin-3-yl)-piperidine-1-carboxylic acid [9-(3,3-dimethyl-butyl)-8-oxo-3,6,7,8,9,10-hexahydro-2,3,9-triaza-(R)-cyclohepta[e]inden-7-yl]-amide. 7-(R)-Amino-9-(3,3-dimethyl-butyl)-6,7,9,10-tetrahydro-3H-2,3,9-triaza-cyclohepta[e]inden-8-one bismethanesulfonate was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. The desired product was obtained as an off-white solid in 29% yield. $^1$H NMR (500 MHz, DMSO-D$_6$): δ=9.19 (s, 1H), 8.32 (s, 1H), 7.38 (d, J=8.6, 1H), 7.10 (t, J=9.2, 3H), 6.86 (t, J=7.5, 1H), 6.77 (d, J=7.6, 1H), 6.53 (s, 1H), 5.24 (d, J=16.5, 2H), 4.62 (d, J=17.9, 1H), 4.35 (m, 1H), 4.29 (s, 2H), 4.14 (m, 2H), 3.57 (m, 1H), 3.36 (m, 1H), 3.26 (dd, J1=2.8, J2=17.1, 1H), 3.01 (m, 1H), 2.80 (t, J=12.4, 2H), 1.72 (m, 2H), 1.56 (d, J=11.3, 2H), 1.27 (m, 1H), 1.15 (m, 1H), 0.79 (s, 9H). MS m/e (M+H)$^+$=558.2.

EXAMPLE 17

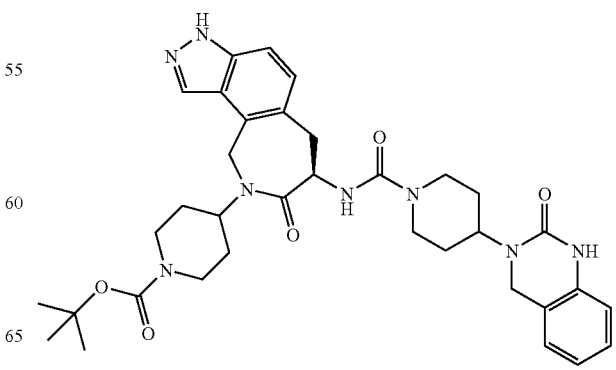

4-(8-Oxo-7-{[4-(2-oxo-1,4-dihydro-2H-quinazolin-3-yl)-piperidine-1-carbonyl]-amino}-6,7,8,9,10-tetrahydro-3H-2,3,9-triaza-(R)-cyclohepta[e]inden-9-yl)-piperidine-1-carboxylic acid tert-butyl ester. 4-(7-(R)-Amino-8-oxo-6,7,8,10-tetrahydro-3H-2,3,9-triaza-cyclohepta[e]inden-9-yl)-piperidine-1-carboxylic acid tert-butyl ester acetate was reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC gave the desired product as an off-white solid in 26% yield. $^1$H NMR (500 MHz, DMSO-D$_6$): δ=9.22 (s, 1H), 8.38 (s, 1H), 7.38 (d, J=8.6, 1H), 7.10 (m, 3H), 6.85 (m, 1H), 6.75 (d, J=7.6, 1H), 6.57 (s, 1H), 5.28 (m, 1H), 5.02 (d, J=17.1, 1H), 4.66 (d, J=17.1, 1H), 4.46 (m, 1H), 4.34 (m, 1H), 4.30 (s, 2H), 4.08 (m, 4H), 3.76 (m, 1H), 3.25 (d, J=17.4, 1H), 3.04 (m, 1H), 2.79 (m, 4H), 1.91 (m, 1H), 1.68 (m, 2H), 1.54 (m, 4H), 1.39 (s, 9H). MS m/e (M+H)$^+$=679.3.

EXAMPLE 18

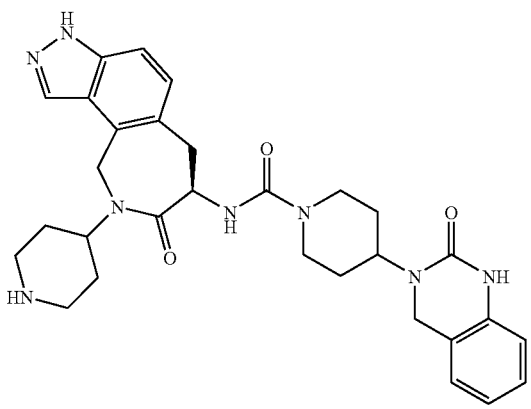

4-(2-Oxo-1,4-dihydro-2H-quinazolin-3-yl)-piperidine-1-carboxylic acid (8-oxo-9-piperidin-4-yl-3,6,7,8,9,10-hexahydro-2,3,9-triaza-(R)-cyclohepta[e]inden-7-yl)-amide. Trifluoroacetic acid (250 μL) was added to a chilled (water ice bath) solution of 4-(8-oxo-7-{[4-(2-oxo-1,4-dihydro-2H-quinazolin-3-yl)-piperidine-1-carbonyl]-amino}-6,7,8,10-tetrahydro-3H-2,3,9-triaza-(R)-cyclohepta[e]inden-9-yl)-piperidine-1-carboxylic acid tert-butyl ester (60 mg, 0.08 mmol) in dichloromethane (1 mL). Reaction was stirred at 0° C. for 1 hour. Mixture was concentrated in vacuo. The desired product was obtained as alight yellow solid in 65% yield. $^1$H NMR (500 MHz, DMSO-D$_6$): δ=9.23 (s, 1H), 8.32 (s, 1H), 7.41 (d, J=8.6, 1H), 7.11 (m, 3H), 6.86 (t, J=7.5, 1H), 6.76, d, J=7.9, 1H), 6.62 (d, J=6.7, 1H), 5.29 (m, 1H), 5.11 (d, J=16.8, 1H), 4.66 (t, J=1H), 4.53 (d, J=17.4, 1H), 4.35 (m, 1H), 4.29 (s, 2H), 4.16 (d, J=12.5, 4H), 3.42 (d, J=11.9, 1H), 3.26 (dd, J1=3.8, J2=16.3, 1H), 3.16 (d, J=10.7, 1H), 3.05 (m, 2H), 2.83 (m, 3H), 2.15 (m, 1H), 1.70 (m, 4H), 1.57 (d, J=10.7, 2H). MS m/e (M+H)$^+$=557.2.

EXAMPLE 19

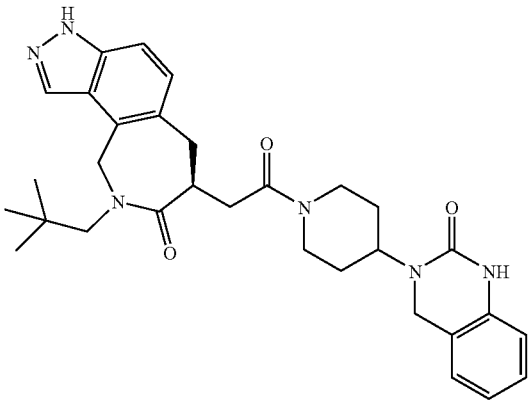

9-(2,2-Dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. O-(7-Azabenzotriazol-1-yl)-N,N,N',N'-tetramethyluronium hexafluorophosphate (62 mg, 0.16 mmol) was added to a solution of [9-(2,2-dimethyl-propyl)-8-oxo-3,6,7,8,9,10-hexahydro-2,3,9-triaza-(S)-cyclohepta[e]inden-7-yl]-acetic acid (45 mg, 0.14 mmol) and N,N-diisopropylethylamine (100 μL, 0.57 mmol) in DMF (1.5 mL). Mixture was stirred at room temperature for 45 minutes. 4-(2-Oxo-1,4-dihydro-2H-quinazolin-3-yl)piperidine (40 mg, 0.17 mmol) was then added to the mixture. Reaction was stirred at room temperature until it was judged complete by HPLC (45 minutes). C18 Preparatory HPLC (acetonitrile-water-trifluoroacetic acid) was performed on the crude mixture. Acetonitrile was removed from the fractions containing the desired product in vacuo. Remaining aqueous was made basic with sodium bicarbonate. Mixture was extracted with ethyl acetate (2×15 mL). Combined extracts were washed with saturated aqueous sodium bicarbonate (10 mL). Organic was dried (magnesium sulfate), filtered and concentrated in vacuo. Title compound was obtained as a white solid in 50% yield. $^1$H NMR (500 MHz, DMSO-D$_6$): δ=9.23 (s, 1H), 8.23 (s, 1H), 7.37 (d, J=8.5, 1H), 7.10 (m, 3H), 6.86 (t, J=7.3, 1H), 6.77 (d, J=7.9, 1H), 5.38 (d, J=16.2, 1H), 4.63 (d, J=17.4, 1H), 4.50 (m, 1H), 4.40 (m, 1H), 4.28 (s, 2H), 4.09 (m, 1H), 3.87 (m, 1H), 3.55 (t, J=13.0, 1H), 3.10 (m, 2H), 3.01 (m, 3H), 2.88 (m, 1H), 2.59 (m, 1H), 2.34 (m 1H), 1.84 (m, 1H), 1.59 (m, 3H), 0.74 (d, J=19.2, 9H). MS m/e (M+H)$^+$=543.2.

EXAMPLE 20

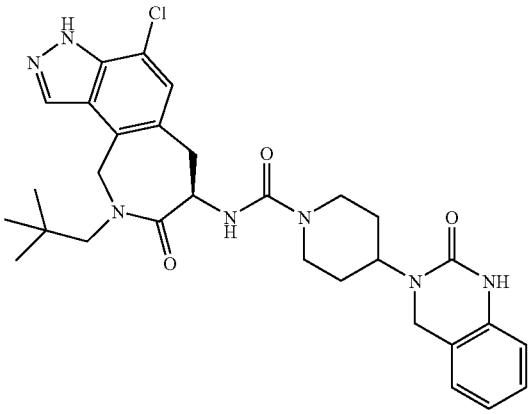

4-(2-Oxo-1,4-dihydro-2H-quinazolin-3-yl)-piperidine-1-carboxylic acid [4-chloro-9-(2,2-dimethyl-propyl)-8-oxo-3,6,7,8,9,10-hexahydro-2,3,9-triaza-(R)-cyclohepta[e]inden-7-yl]-amide. Methanesulfonic acid (250 µL) was added to a solution of [4-chloro-9-(2,2-dimethyl-propyl)-8-oxo-3,6,7,8,9,10-hexahydro-2,3,9-triaza-(R)-cyclohepta[e]inden-7-yl]-carbamic acid benzyl ester (90 mg, 0.20 mmol) and anisole (70 µL, 0.64 mmol) in dichloromethane (2 mL). Reaction stirred at room temperature for 2 hours. Mixture was diluted with diethyl ether (40 mL). Mixture was allowed to stand at room temperature for 30 minutes. Solvents were decanted off. Residue was washed with diethyl ether (30 mL) then dried in vacuo. Residue was dissolved in a mixture of triethylamine (250 µL, 1.8 mmol) in dichloromethane (5 mL). N,N'-Disuccinimidyl carbonate (61 mg, 0.24 mmol) was added to the mixture. Reaction was stirred at ambient temperature for 30 minutes. 4-(2-Oxo-1,4-dihydro-2H-quinazolin-3-yl)piperidine (55 mg, 0.24 mmol) was then added to the mixture. Reaction was stirred at ambient temperature for 30 minutes. Mixture was washed successively with water (2×5 mL) and brine (5 mL). Organic was dried (magnesium sulfate), filtered and concentrated. C18 Preparatory HPLC (acetonitrile-water-trifluoroacetic acid) was preformed on the residue. Acetonitrile was removed from the product containing fractions in vacuo. Remaining aqueous was made basic with sodium bicarbonate. Mixture was extracted with ethyl acetate (2×15 mL). Combined extracts were dried (magnesium sulfate), filtered and concentrated in vacuo. Title compound was obtained as a white solid in 37% yield. $^1$H NMR (500 MHz, CD$_3$OD): δ=8.26 (s, 1H), 7.26 (s, 1H), 7.13 (m, 3H), 6.93 (t, J=7.5, 1H), 6.78 (d, J=7.9, 1H), 5.44 (d, J=17.1, 1H), 5.34 (dd, J1=3.5, J2=13.0, 1H), 4.70 (d, J=17.4, 1H), 4.47 (m, 1H), 4.40 (s, 2H), 4.26 (m, 2H), 3.82 (d, J=13.4, 1H), 3.19 (m, 1H), 3.08 (d, J=13.7, 1H), 2.94 (m, 2H), 1.90 (m, 2H), 1.71 (d, J=12.2, 2H), 0.81 (s, 9H). MS m/e (M+H)$^+$=578.3.

EXAMPLE 21

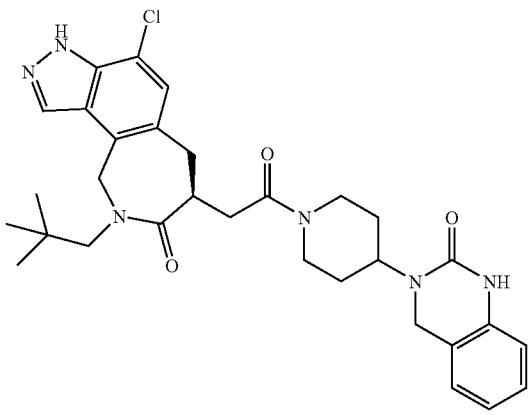

4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. O-(1H-Benzotriazol-1-yl)-N,N,N',N'-tetramethyluronium tetrafluoroborate (90 mg, 0.28 mmol) was added to a solution of [4-chloro-9-(2,2-dimethyl-propyl)-8-oxo-3,6,7,8,9,10-hexahydro-2,3,9-triaza-(S)-cyclohepta[e]inden-7-yl]-acetic acid (85 mg, 0.23 mmol) and N,N-diisopropylethyl amine (100 µL, 0.57 mmol) in DMF (3 mL). Mixture was stirred at ambient temperature for 15 minutes. 4-(2-Oxo-1,4-dihydro-2H-quinazolin-3-yl)piperidine (65 mg, 0.28 mmol) was then added to the mixture. Reaction was stirred at ambient temperature for 1 hour. Mixture was diluted with ethyl acetate (20 mL). Mixture was washed successively with water (2×15 mL), and brine (10 mL). Organic was dried (magnesium sulfate), filtered and concentrated in vacuo. Residue was purified by C18 preparatory HPLC (acetonitrile-water-trifluoroacetic acid). Acetonitrile was removed from the product containing fractions in vacuo. Remaining aqueous was made basic with sodium bicarbonate. Mixture was extracted with ethyl acetate (2×20 mL). Combined extracts were washed with brine (10 mL). Organic was dried (magnesium sulfate), filtered and concentrated in vacuo. Title compound was obtained as a white solid in 37% yield. $^1$H NMR (500 MHz, DMSO-D$_6$): δ=13.55 (s, 1H), 9.21 (s, 1H), 8.36 (s, 1H), 7.25 (s, 1H), 7.09 (m, 2H), 6.86 (t J=7.3, 1H), 6.77 (d, J=7.9, 1H), 5.36 (d, J=15.6, 1H), 4.63 (d, J=17.1, 1H), 4.51 (m, 1H), 4.40 (m, 1H), 4.29 (s, 2H), 4.10 (d, J=13.2, 1H), 3.87 (m, 1H), 3.57 (m, 1H), 3.11 (m, 2H), 3.00 (m, 2H), 2.88 (m, 1H), 2.59 (m, 1H), 2.32 (m, 1H), 1.85 (m, 1H), 1.59 (m, 3H), 0.74 (d, J=18.3, 9H). MS m/e (M+H)$^+$=577.0.

EXAMPLE 22

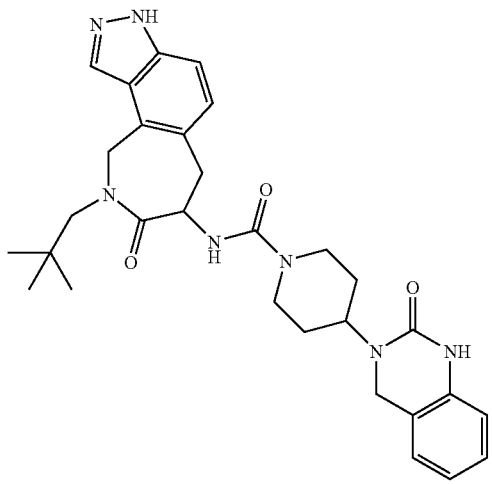

4-(2-Oxo-1,4-dihydro-2H-quinazolin-3-yl)-piperidine-1-carboxylic acid [9-(2,2-dimethyl-propyl)-8-oxo-3,6,7,8,9,10-hexahydro-2,3,9-triaza-cyclohepta[e]inden-7-yl]-amide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-(2,2-dimethyl-propyl)-6,7,9,10-tetrahydro-3H-2,3,9-triaza-cyclohepta[e]inden-8-one, dihydrochloride with 3-piperidin-4-yl-3,4-dihydro-1H-quinazolin-2-one, hydrochloride to give the title compound (80% yield). MS (ESI) 544 (M+H); R$_f$=1.51.

EXAMPLE 23

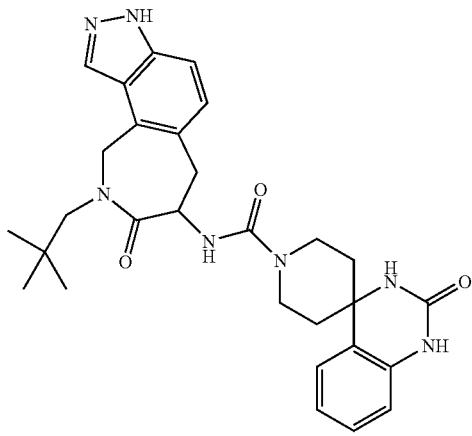

N-[9-(2,2-dimethylpropyl)-8-oxo-3,6,7,8,9,10-hexahydroazepino[3,4-e]indazol-7-yl]-2'-oxo-2,3'-dihydro-1H,1'H-spiro[piperidine-4,4'-quinazoline]-1-carboxamide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-Amino-9-(2,2-dimethyl-propyl)-6,7,9,10-tetrahydro-3H-2,3,9-triaza-cyclohepta[e]inden-8-one, dihydrochloride with 1'H-spiro[piperidine-4,4'-quinazolin]-2'(3'H)-one, hydrochloride to give the title compound (80% yield). MS (ESI) 530 (M+H); $R_f$=1.44.

EXAMPLE 24

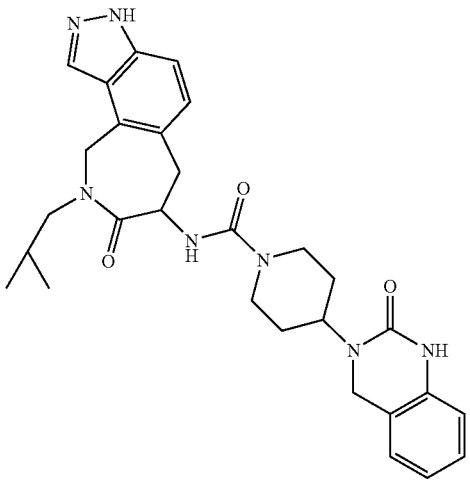

4-(2-Oxo-1,4-dihydro-2H-quinazolin-3-yl)-piperidine-1-carboxylic acid (9-isobutyl-8-oxo-3,6,7,8,9,10-hexahydro-2,3,9-triaza-cyclohepta[e]inden-7-yl)-amide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-isobutyl-6,7,9,10-tetrahydro-3H-2,3,9-triaza-cyclohepta[e]inden-8-one, dihydrochloride with 3-piperidin-4-yl-3,4-dihydro-1H-quinazolin-2-one, hydrochloride to give the title compound (80% yield). MS (ESI) 530 (M+H); $R_f$=1.41.

EXAMPLE 25

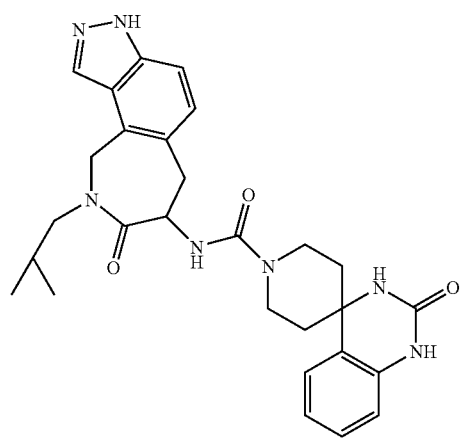

N-[9-(2-methylpropyl)-8-oxo-3,6,7,8,9,10-hexahydroazepino[3,4-e]indazol-7-yl]-2'-oxo-2,3'-dihydro-1H,1'H-spiro/piperidine-4,4'-quinazoline-1-carboxamide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-isobutyl-6,7,9,10-tetrahydro-3H-2,3,9-triaza-cyclohepta[e]inden-8-one, dihydrochloride with 1'H-spiro[piperidine-4,4'-quinazolin]-2'(3'H)-one, hydrochloride to give the title compound (80% yield). MS (ESI) 516 (M+H); $R_f$=1.35.

EXAMPLE 26

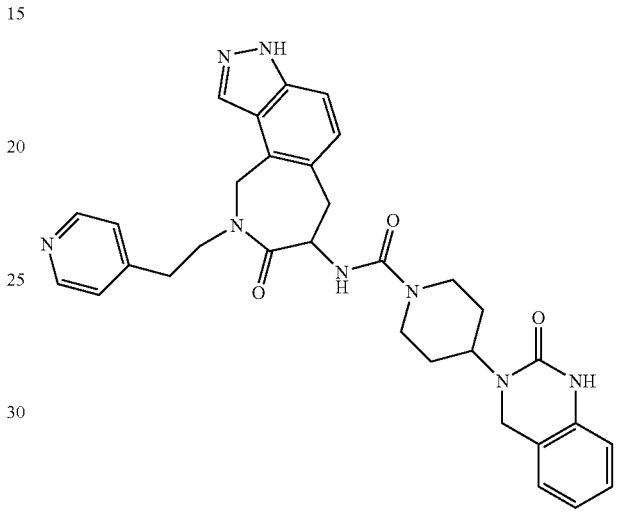

4-(2-Oxo-1,4-dihydro-2H-quinazolin-3-yl)-piperidine-1-carboxylic acid [8-oxo-9-(2-pyridin-4-yl-ethyl)-3,6,7,8,9,10-hexahydro-2,3,9-triaza-cyclohepta[e]inden-7-yl]-amide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-(2-pyridin-4-yl-ethyl)-6,7,9,10-tetrahydro-3H-2,3,9-triaza-cyclohepta[e]inden-8-one, dihydrochloride with 3-piperidin-4-yl-3,4-dihydro-1H-quinazolin-2-one, hydrochloride to give the title compound (80% yield). MS (ESI) 530 (M+H); $R_f$=1.41.

EXAMPLE 27

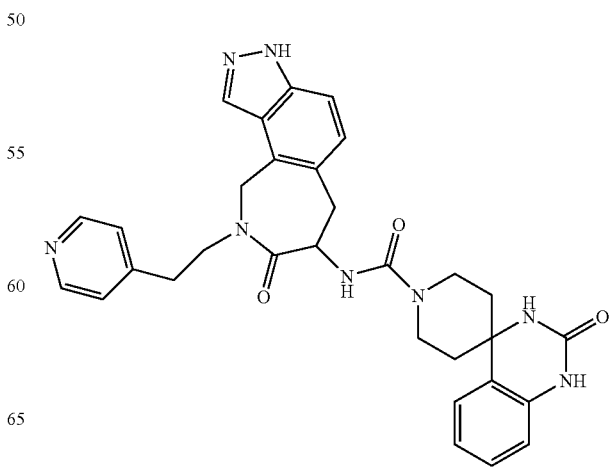

N-[9-(2-pyridin-4-yl-ethyl)-8-oxo-3,6,7,8,9,10-hexahydroazepino[3,4-e]indazol-7-yl]-2'-oxo-2,3'-dihydro-1H,1'H-spiro[piperidine-4,4'-quinazoline]-1-carboxamide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-(2-pyridin-4-yl-ethyl)-6,7,9,10-tetrahydro-3H-2,3,9-triaza-cyclohepta[e]inden-8-one, dihydrochloride with 1'H-spiro[piperidine-4,4'-quinazolin]-2'(3'H)-one, hydrochloride to give the title compound (80% yield). MS (ESI) 516 (M+H); $R_f$=1.35.

EXAMPLE 28

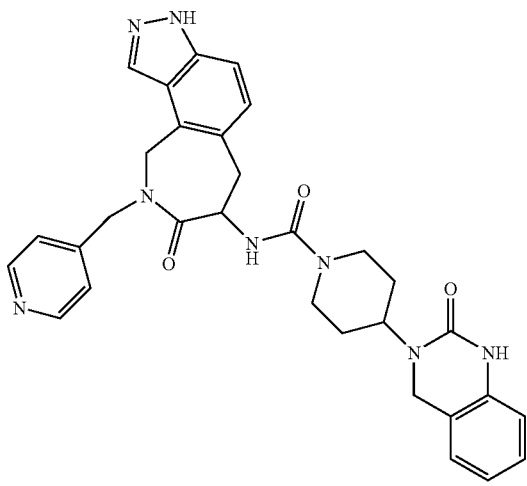

4-(2-Oxo-1,4-dihydro-2H-quinazolin-3-yl)-piperidine-1-carboxylic acid (8-oxo-9-pyridin-4-ylmethyl-3,6,7,8,9,10-hexahydro-2,3,9-triaza-cyclohepta[e]inden-7-yl)-amide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-pyridin-4-ylmethyl-6,7,9,10-tetrahydro-3H-2,3,9-triaza-cyclohepta[e]inden-8-one, dihydrochloride with 3-piperidin-4-yl-3,4-dihydro-1H-quinazolin-2-one, hydrochloride to give the title compound (80% yield). MS (ESI) 565 (M+H); $R_f$=1.09.

EXAMPLE 29

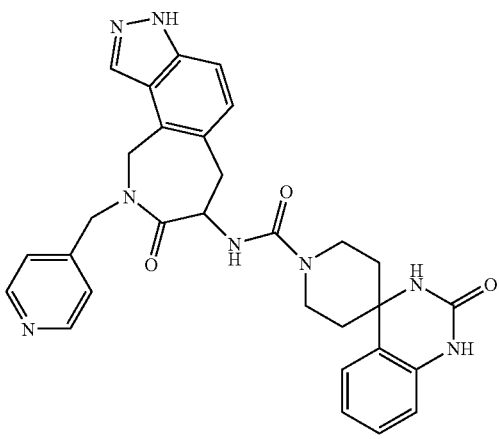

N-[9-pyridin-4-ylmethyl-8-oxo-3,6,7,8,9,10-hexahydroazepino[3,4-e]indazol-7-yl]-2'-oxo-2,3'-dihydro-1H,1'H-spiro[piperidine-4,4'-quinazoline]-1-carboxamide. In a manner similar to 4-(2-Oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide, the title compound was prepared by reacting (7R)-7-amino-9-pyridin-4-ylmethyl-6,7,9,10-tetrahydro-3H-2,3,9-triaza-cyclohepta[e]inden-8-one, dihydrochloride with 1'H-spiro[piperidine-4,4'-quinazolin]-2'(3'H)-one, hydrochloride to give the title compound (80% yield). MS (ESI) 551 (M+H); $R_f$=1.07.

EXAMPLE 30

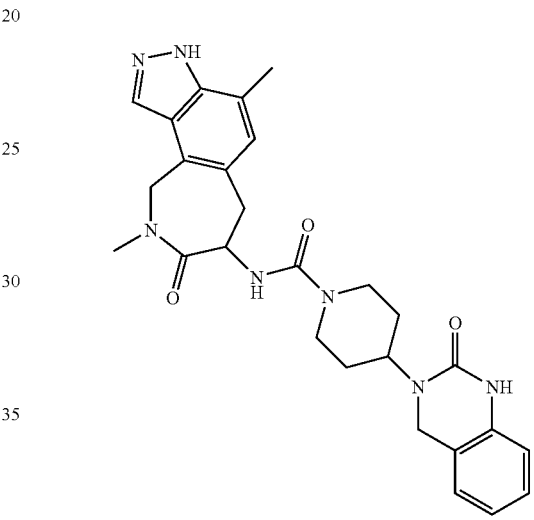

4-(2-Oxo-1,4-dihydro-2H-quinazolin-3-yl)-piperidine-1-carboxylic acid (4,9-dimethyl-8-oxo-3,6,7,8,9,10-hexahydro-2,3,9-triaza-cyclohepta[e]inden-7-yl)-amide. To a solution of (4,9-dimethyl-8-oxo-3,6,7,8,9,10-hexahydro-2,3,9-triaza-cyclohepta[e]inden-7-yl)-carbamic acid benzyl ester (50 mg, 0.132 mmol) in methanol and chloroform (0.5 mL) was added 10% palladium on carbon (20 mg) under nitrogen atmosphere. The reaction mixture was brought to hydrogen atmosphere (1 atm) and stirred for 3 h. The catalyst was filtered and the solvent was evaporated to give 7-amino-4,9-dimethyl-6,7,9,10-tetrahydro-3H-2,3,9-triaza-cyclohepta[e]inden-8-one, hydrochloride in almost quantitative yield. To the amine salt in dichloromethane was added disuccinimidyl carbonate (37 mg, 0.145 mmol) and triethylamine (0.11 mL, 0.8 mmol) at room temperature. After 120 min, 3-piperidin-4-yl-3,4-dihydro-1H-quinazolin-2-one, hydrochloride (39 mg, 0.145 mmol) was added and stirring continued for 12 h. The solvent was evaporated and the crude product was purified by Prep HPLC to give 4-(2-Oxo-1,4-dihydro-2H-quinazolin-3-yl)-piperidine-1-carboxylic acid (4,9-dimethyl-8-oxo-3,6,7,8,9,10-hexahydro-2,3,9-triaza-cyclohepta[e]inden-7-yl)-amide in 59% overall yield. MS (ESI) 502 (M+H); $R_f$=1.31.

EXAMPLE 31

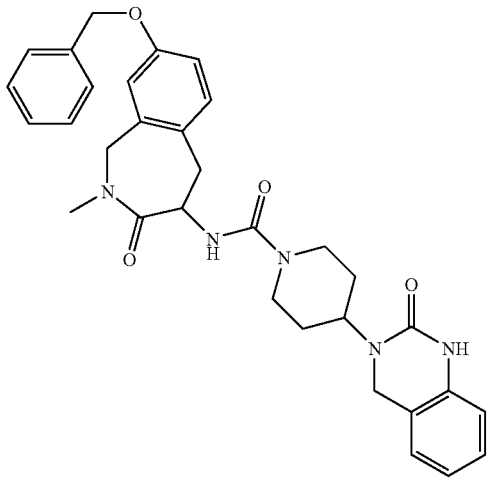

4-(2-Oxo-1,4-dihydro-2H-quinazolin-3-yl)-piperidine-1-carboxylic acid (8-benzyloxy-2-methyl-3-oxo-2,3,4,5-tetrahydro-1H-benzo[c]azepin-4-yl)-amide. To a stirred solution of (8-benzyloxy-2-methyl-3-oxo-2,3,4,5-tetrahydro-1H-benzo[c]azepin-4-yl)-carbamic acid tert-butyl ester (300 mg, 0.76 mmol) in dichloromethane (2 mL) was added a 4.0 M solution of hydrogen chloride in dioxane (15 mL). The reaction mixture was stirred and removed the solvent to give the amine salt in quantitative yield. The amine salt was dissolved in dichloromethane (20 mL) followed by addition of N,N'-disuccinimidyl carbonate (214 mg, 0.83 mmol) and triethylamine (0.64 mL, 4.6 mmol). After 15 min, 3-piperidin-4-yl-3,4-dihydro-1H-quinazolin-2-one, hydrochloride (225 mg, 0.84 mmol) was added and stirring continued for 12 h. The reaction mixture was then washed with aqueous sodium hydrogencarbonate, 1.0 M hydrochloric acid and dried (Na$_2$SO$_4$). The crude product was purified by flash chromatography using 5% methanol in dichloromethane to give 4-(2-Oxo-1,4-dihydro-2H-quinazolin-3-yl)-piperidine-1-carboxylic acid (8-benzyloxy-2-methyl-3-oxo-2,3,4,5-tetrahydro-1H-benzo[c]azepin-4-yl)-amide in 66% yield. MS (ESI) 554 (M+H); R$_f$=1.67.

EXAMPLE 32

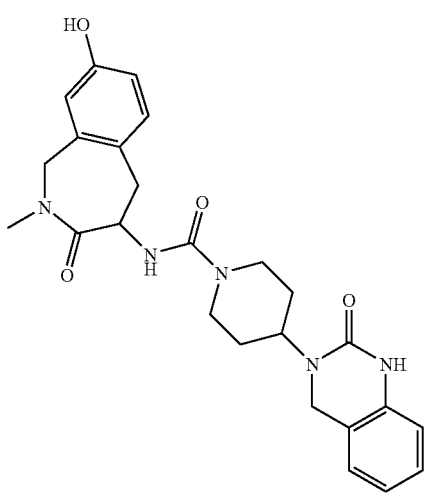

4-(2-Oxo-1,4-dihydro-2H-quinazolin-3-yl)-piperidine-1-carboxylic acid (8-hydroxy-2-methyl-3-oxo-2,3,4,5-tetrahydro-1H-benzo[c]azepin-4-yl)-amide. To a stirred solution of 4-(2-oxo-1,4-dihydro-2H-quinazolin-3-yl)-piperidine-1-carboxylic acid (8-benzyloxy-2-methyl-3-oxo-2,3,4,5-tetrahydro-1H-benzo[c]azepin-4-yl)-amide (187 mg, 0.34 mmol) in methanol (30 mL) followed by 10% palladium on carbon (30 mg) under nitrogen. The reaction mixture was brought to 1 atmosphere of hydrogen and stirred for 12 h. The catalyst was filtered and the solvent was evaporated to give 4-(2-Oxo-1,4-dihydro-2H-quinazolin-3-yl)-piperidine-1-carboxylic acid (8-hydroxy-2-methyl-3-oxo-2,3,4,5-tetrahydro-1H-benzo[c]azepin-4-yl)-amide in quantitative yield. MS (ESI) 464 (M+H); R$_f$=1.34.

EXAMPLE 33

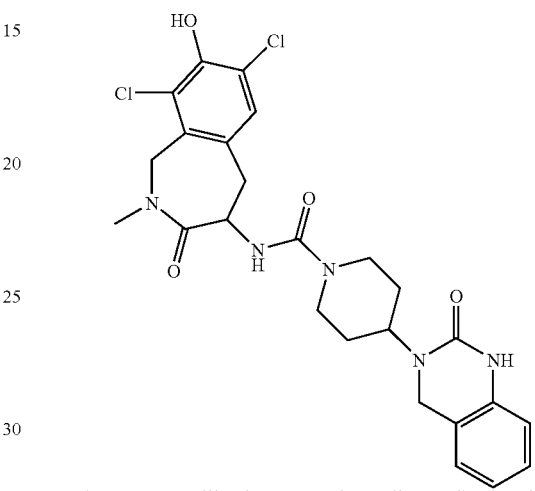

4-(2-Oxo-1,4-dihydro-2H-quinazolin-3-yl)-piperidine-1-carboxylic acid (7,9-dichloro-8-hydroxy-2-methyl-3-oxo-2,3,4,5-tetrahydro-1H-benzo[c]azepin-4-yl)-amide. To a stirred solution of 4-(2-oxo-1,4-dihydro-2H-quinazolin-3-yl)-piperidine-1-carboxylic acid (8-hydroxy-2-methyl-3-oxo-2,3,4,5-tetrahydro-1H-benzo[c]azepin-4-yl)-amide (27 mg, 0.058 mmol) in dichloromethane (10 mL) was added methanol (2 mL), ether (3 mL) followed by sulfuryl chloride (70 µL) at room temperature. The reaction mixture was stirred for additional 12 h and then concentrated. The crude product was purified by Prep HPLC to give 4-(2-Oxo-1,4-dihydro-2H-quinazolin-3-yl)-piperidine-1-carboxylic acid (7,9-dichloro-8-hydroxy-2-methyl-3-oxo-2,3,4,5-tetrahydro-1H-benzo[c]azepin-4-yl)-amide in 58% yield. MS (ESI) 532 (M+H); R$_f$=1.40.

EXAMPLE 34

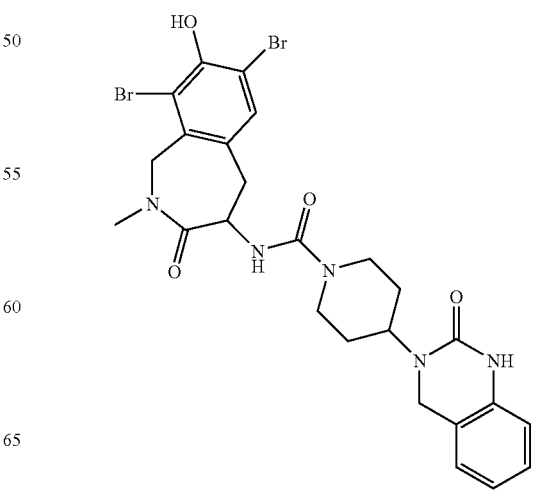

4-(2-Oxo-1,4-dihydro-2H-quinazolin-3-yl)-piperidine-1-carboxylic acid (7,9-dibromo-8-hydroxy-2-methyl-3-oxo-2,3,4,5-tetrahydro-1H-benzo[c]azepin-4-yl)-amide. To a stirred solution of 4-(2-oxo-1,4-dihydro-2H-quinazolin-3-yl)-piperidine-1-carboxylic acid (8-hydroxy-2-methyl-3-oxo-2,3,4,5-tetrahydro-1H-benzo[c]azepin-4-yl)-amide (39 mg, 0.084 mmol) in dichloromethane (10 mL) was added diisopropylamine (0.06 mL, 0.42 mmol) followed by N-bromosuccinimide (33 mg, 0.185 mmol) at room temperature. The reaction mixture was stirred for additional 1 h and then the solvent was removed. The crude product was purified by Prep HPLC to give 4-(2-Oxo-1,4-dihydro-2H-quinazolin-3-yl)-piperidine-1-carboxylic acid (7,9-dibromo-8-hydroxy-2-methyl-3-oxo-2,3,4,5-tetrahydro-1H-benzo[c]azepin-4-yl)-amide in 74% yield. MS (ESI) 620 (M+H); $R_f$=1.45.

EXAMPLE 35

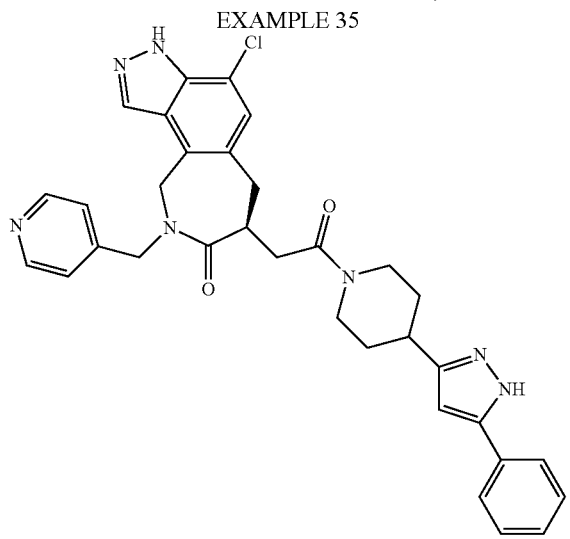

(S)-4-Chloro-7-(2-oxo-2-(4-(5-phenyl-1H-pyrazol-3-yl)piperidin-1-yl)ethyl)-9-(pyridin-4-ylmethyl)-6,7,9,10-tetrahydroazepino[3,4-e]indazol-8(3H)-one. (S)-2-(4-chloro-8-oxo-9-(pyridin-4-ylmethyl)-3,6,7,8,9,10-hexahydroazepino[3,4-e]indazol-7-yl)acetic acid dihydrochloride (66 mg, 0.23 mmol) and 4-(5-phenyl-1H-pyrazol-3-yl)piperidine hydrochloride (40 mg, 0.15 mmol) were reacted following a procedure analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound (34 mg) was obtained as white solid. MS (ESI) 594 (M+H); $R_f$=1.99.

EXAMPLE 36

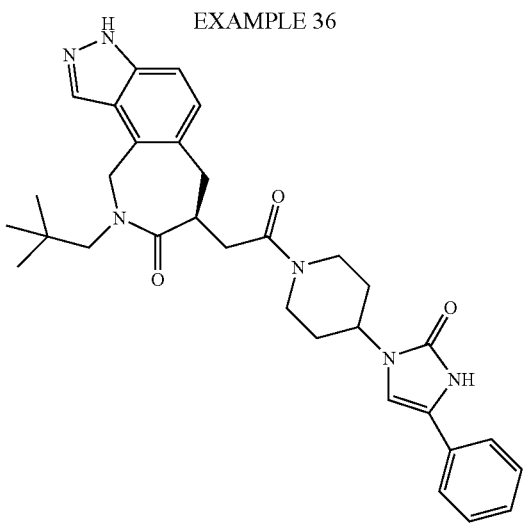

(S)-9-Neopentyl-7-(2-oxo-2-(4-(2-oxo-4-phenyl-2,3-dihydroimidazol-1-yl)piperidin-1-yl)ethyl)-6,7,9,10-tetrahydroazepino[3,4-e]indazol-8(3H)-one. O-(7-Azabenzotriazol-1-yl)-N,N,N',N'-tetramethyluronium hexafluorophosphate (62 mg, 0.16 mmol) was added to a solution of [9-(2,2-dimethyl-propyl)-8-oxo-3,6,7,8,9,10-hexahydro-2,3,9-triaza-(S)-cyclohepta[e]inden-7-yl]-acetic acid (50 mg, 0.16 mmol) and N,N-diisopropylethylamine (85 μL, 0.48 mmol) in DMF (2.0 mL). Mixture was stirred at room temperature for 45 minutes. 4-phenyl-1-(piperidin-4-yl)-1H-imidazol-2(3H)-one hydrochloride (53 mg, 0.19 mmol) was then added to the mixture. The desired compound was purified by prep HPLC. The title compound (49 mg) was obtained as a white foam. MS (ESI) 555 (M+H); $R_f$=1.54.

EXAMPLE 37

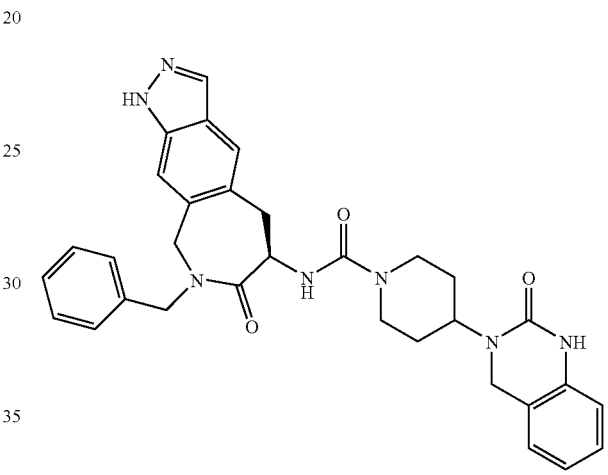

(R)—N-(8-Benzyl-7-oxo-1,5,6,7,8,9-hexahydroazepino[4,3-f]indazol-6-yl)-4-(2-oxo-1,2-dihydroquinazolin-3(4H)-yl)piperidine-1-carboxamide. (R)-Benzyl 1-acetyl-8-benzyl-7-oxo-1,5,6,7,8,9-hexahydroazepino[4,3-f]indazol-6-ylcarbamate (52 mg, 0.11 mmol) was dissolved in a mixture of methanol (7 mL) and acetic acid (100 μL). A catalytic amount of 10% palladium on carbon was added to the mixture. Reaction was placed on a Parr apparatus under 60 psi of hydrogen gas. Reaction shook at room temperature for 2 hours. Mixture was filtered. Filtrate was concentrated. Residue was dissolved in dichloromethane (5 mL). Aqueous sodium bicarbonate (5 mL) was added to the mixture. 20% Phosgene in toluene (62 μL, 0.12 mmol) was added to the mixture with vigorous stirring. Reaction was stirred vigorously at room temperature for 20 minutes. 4-(2-oxo-1,4-dihydro-2H-quinazolin-3-yl)piperidinium acetate was added to the mixture. Reaction stirred at room temperature for 1 hour. Layers were partitioned. Organics were washed twice with 1N hydrochloric acid and once with brine. Organic layer was dried (magnesium sulfate), filtered and concentrated in vacuo. Residue was dissolved in methanol (5 mL). Potassium carbonate (20 mg, 0.14 mmol) was added to the mixture. Reaction stirred at room temperature for 1 hour. Reaction was quenched with trifluoroacetic acid. Mixture was purified by prep HPLC. Title compound was obtained as a white solid in 11% yield. MS m/e (M+H)$^+$=564.3. $R_f$=1.89 min.

EXAMPLE 38

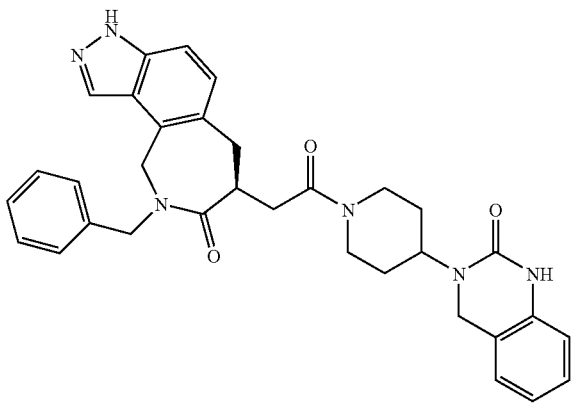

(S)-9-Benzyl-7-(2-oxo-2-(4-(2-oxo-1,2-dihydroquinazolin-3(4H)-yl)piperidin-1-yl)ethyl)-6,7,9,10-tetrahydroazepino[3,4-e]indazol-8(3H)-one. Title compound was prepared in a manner analogous to the preparation of 4-chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 18% yield. MS m/e (M+H)$^+$=563.1. $^1$H NMR (500 MHz, DMSO-D$_6$): δ=12.93 (s, 1H), 9.23 (d, J=6.71, 1H), 8.05 (d, J=10.38, 1H), 7.33 (d, J=8.55, 1H), 7.13 (m, 7H), 6.99 (d, J=7.63, 1H), 6.84 (m, 1H), 6.76 (m, 1H), 5.34 (d, J=17.4, 1H), 4.62 (m, 4H), 4.41 (m, 1H), 4.27 (d, J=22.89, 2H), 4.11 (d, J=12.82, 1H), 3.99 (m, 1H), 3.14 (d, J=15.87, 2H), 3.07 (m, 1H), 2.61 (m, 1H), 2.42 (m, 1H), 1.84 (m, 1H), 1.62 (m, 3H).

EXAMPLE 39

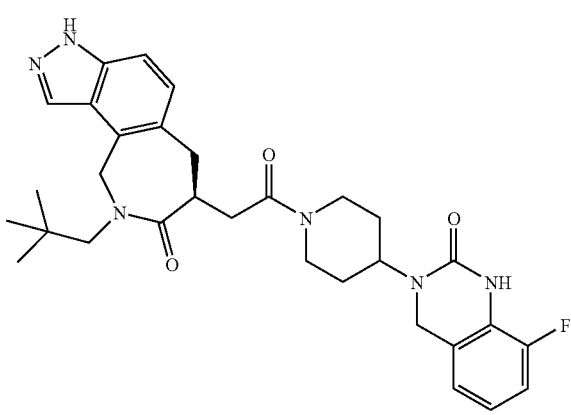

(S)-7-(2-(4-(8-Fluoro-2-oxo-1,2-dihydroquinazolin-3(4H)-yl)piperidin-1-yl)-2-oxoethyl)-9-neopentyl-6,7,9,10-tetrahydroazepino[3,4-e]indazol-8(3H)-one. Title compound was prepared in a manner analogous to the preparation of 9-(2,2-Dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 35% yield. MS m/e (M+H)$^+$=561.3. $^1$H NMR (500 MHz, DMSO-D$_6$): δ=13.00 (s, 1H), 9.24 (s, 1H), 8.22 (s, 1H), 7.37 (d, J=8.54, 1H), 7.11 (d, J=7.63, 7H), 7.05 (m, 1H), 6.94 (m, 1H), 6.88 (m, 1H), 5.38 (d, J=17.09, 1H), 4.62 (d, J=17.09, 1H), 4.51 (m, 1H), 4.40 (m, 1H), 4.35 (s, 2H), 4.10 (d, J=13.43, 2H), 3.88 (m, 1H), 3.55 (t, J=12.67, 1H), 3.11 (m, 2H), 3.01 (m, 2H), 2.87 (m, 1H), 2.60 (m, 1H) 2.34 (m, 1H), 1.84 (m, 1H), 1.61 (m, 3H), 0.74 (d, J=17.70, 9H).

EXAMPLE 40

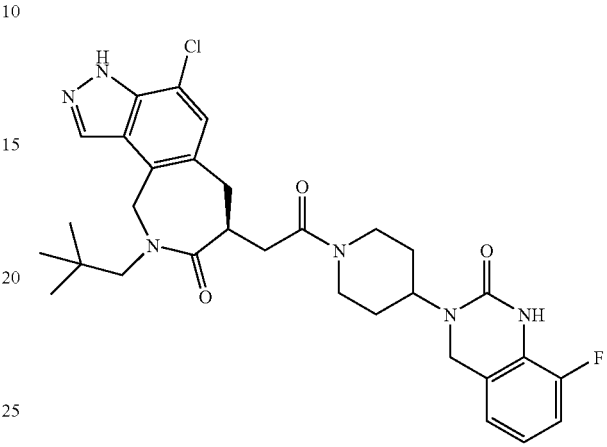

(S)-4-Chloro-7-(2-(4-(8-fluoro-2-oxo-1,2-dihydroquinazolin-3(4H)-yl)piperidin-1-yl)-2-oxoethyl)-9-neopentyl-6,7,9,10-tetrahydroazepino[3,4-e]indazol-8(3H)-one. Title compound was prepared in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 49% yield. MS m/e (M+H)$^+$=595.2. $^1$H NMR (500 MHz, DMSO-D$_6$): δ=13.55 (s, 1H), 9.24 (s, 1H), 8.37 (s, 1H), 7.37 (d, J=8.54, 1H), 7.24 (s, 1H), 7.05 (m, 1H), 6.96 (m, 1H), 6.88 (dd, J1=12.21, J2=7.32, 1H), 5.36 (d, J=18.01, 1H), 4.63 (d, J=17.09, 1H), 4.50 (m, 1H), 4.42 (m, 1H), 4.35 (s, 2H), 4.10 (d, J=12.51, 1H), 3.88 (m, 1H), 3.57 (m, 1H), 3.09 (d, J=15.56, 2H), 3.00 (m, 2H), 2.88 (t, J=13.12, 1H), 2.60 (m, 1H) 2.33 (d, J=15.26, 1H), 1.85 (m, 1H), 1.60 (m, 3H), 0.73 (d, J=17.09, 9H).

EXAMPLE 41

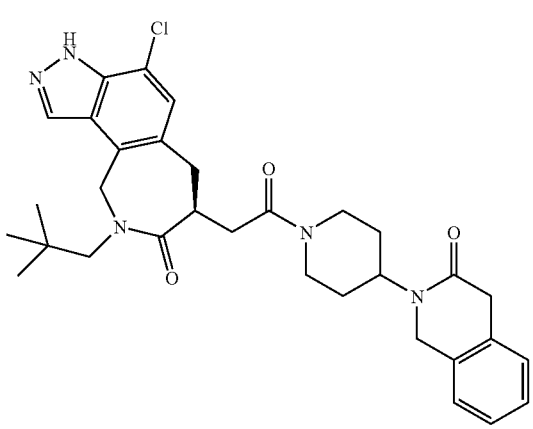

(S)-4-Chloro-9-neopentyl-7-(2-oxo-2-(4-(3-oxo-3,4-dihydroisoquinolin-2(1H)-yl)piperidin-1-yl)ethyl)-6,7,9,10-tetrahydroazepino[3,4-e]indazol-8(3H)-one. Title compound was prepared from 2-(piperidin-4-yl)-1,2-dihydroisoquinolin-3(4H)-one hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as yellow solid in 35% yield. MS m/e (M+H)$^+$=576.2. $^1$H NMR (500 MHz, DMSO-D$_6$): δ=13.55 (s, 1H), 8.37 (s, 1H), 7.29 (s, 1H), 7.23 (dd, J1=7.63, J2=6.10, 4H), 5.37 (dd, J1=16.48, J2=7.63, 1H), 4.64 (d, J=17.70, 2H), 4.48 (s, 1H), 4.38 (s, 2H), 4.09 (m, 1H), 3.57 (m, 1H), 3.54 (s, 2H), 3.11 (m, 3H), 3.00 (m, 2H), 2.89 (m, 1H), 2.61 (m, 1H), 2.36 (m, 1H), 1.54 (m, 2H), 0.74 (d, J=28.08, 9H).

EXAMPLE 42

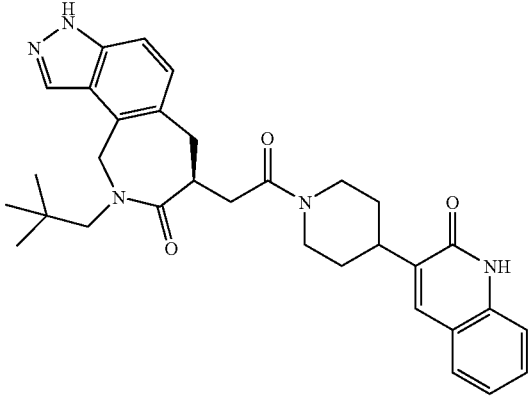

(S)-9-Neopentyl-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. Title compound was prepared from 3-(piperidin-4-yl)quinolin-2(1H)-one hydrochloride in a manner analogous to the preparation of 9-(2,2-Dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 31% yield. MS m/e (M+H)$^+$=540.2. $^1$H NMR (500 MHz, DMSO-D$_6$): δ=11.76 (s, 1H), 8.22 (s, 1H), 7.70 (d, J=8.85, 1H), 7.62 (s, 1H), 7.43 (t, J=7.48, 1H), 7.37 (d, J=8.55, 1H), 7.28 (d, J=8.24, 1H), 7.15 (t, J=7.32, 1H) 7.11 (d, J=8.55, 1H), 5.38 (d, J=17.09, 1H), 4.62 (d, J=16.79, 1H), 4.55 (d, J=11.29, 1H), 4.13 (s, 1H), 3.88 (s, 1H), 3.58 (s, 2H), 3.16 (m, 2H), 3.07 (m, 3H), 2.88 (t, J=14.34, 1H), 2.64 (m, 1H), 2.36 (m, 1H), 1.92 (d, J=10.38, 1H), 1.84 (d, J=11.29, 1H), 1.57 (m, 1H), 1.40 (m, 1H), 0.73 (s, 9H).

EXAMPLE 43

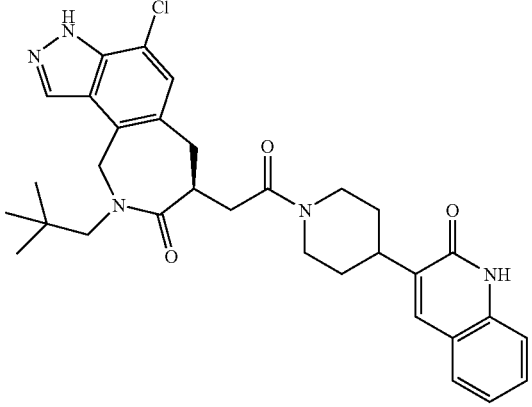

(S)-4-Chloro-9-neopentyl-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. Title compound was prepared from 3-(piperidin-4-yl)quinolin-2(1H)-one hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as off-white solid in 46% yield. MS m/e (M+H)$^+$=574.2. $^1$H NMR (500 MHz, DMSO-D$_6$): δ=13.54 (s, 1H), 11.76 (s, 1H), 8.36 (s, 1H), 7.70 (d, J=5.80, 1H), 7.61 (d, J=7.63, 1H), 7.43 (t, J=7.63, 1H), 7.28 (d, J=7.93, 1H), 7.24 (s, 1H), 7.15 (t, J=7.32, 1H), 5.37 (d, J=17.09, 1H), 4.63 (d, J=16.79, 1H), 4.55 (d, J=12.21, 1H), 4.13 (m, 1H), 3.87 (m, 1H), 3.58 (d, J=13.12, 1H), 3.15 (m, 2H), 3.03 (m, 3H), 2.88 (m, 1H), 2.63 (m, 1H), 2.34 (d, J=16.17 1H), 1.91 (d, J=1.22, 1H), 1.84 (d, J=11.29, 1H), 1.57 (m, 1H), 1.40 (m, 1H), 0.72 (s, 9H).

EXAMPLE 44

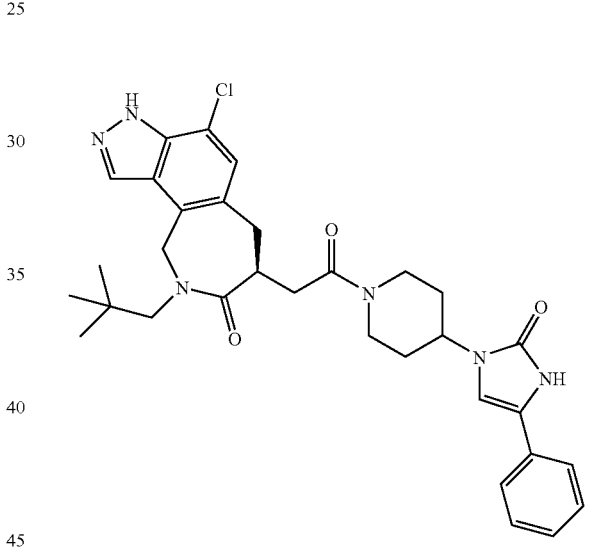

(S)-4-Chloro-9-neopentyl-7-(2-oxo-2-(4-(2-oxo-4-phenyl-2,3-dihydroimidazol-1-yl)piperidin-1-yl)ethyl)-6,7,9,10-tetrahydroazepino[3,4-e]indazol-8(3H)-one. Title compound was prepared from 4-phenyl-1-(piperidin-4-yl)-1H-imidazol-2(3H)-one in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 46% yield. MS m/e (M+H)$^+$=589.2. $^1$H NMR (500 MHz, DMSO-D$_6$): δ=13.55 (s, 1H), 10.68 (s, 1H), 8.37 (s, 1H), 7.50 (d, J=7.63, 2H), 7.32 (t, J=7.02, 2H), 7.24 (s, 1H), 7.16 (m, 2H), 5.37 (d, J=14.34, 1H), 4.63 (d, J=16.79, 1H), 4.51 (t, J=10.83, 1H), 4.13 (m, 2H), 3.89 (m, 1H), 3.57 (m, 1H), 3.18 (m, 1H), 3.03 (m, 3H), 2.89 (t, J=15.11, 1H), 2.66 (m, 1H), 2.34 (d, J=16.17 1H), 1.84 (m, 3H), 1.60 (m, 1H), 0.73 (d, J=13.73, 9H).

EXAMPLE 45

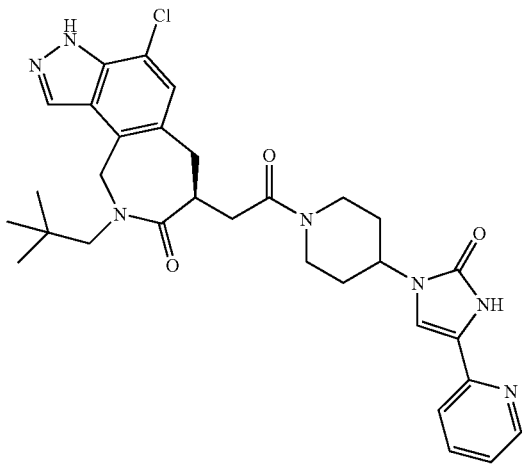

(S)-4-Chloro-9-neopentyl-7-(2-oxo-2-(4-(2-oxo-4-(pyridin-2-yl)-2,3-dihydroimidazol-1-yl)piperidin-1-yl)ethyl)-6,7,9,10-tetrahydroazepino[3,4-e]indazol-8(3H)-one. Title compound was prepared from 1-(piperidin-4-yl)-4-(pyridine-2-yl)-1H-imidazol-2(3H)-one in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 37% yield. MS m/e (M+H)$^+$=590.2. $^1$H NMR (500 MHz, DMSO-D$_6$): δ=13.54 (s, 1H), 10.69 (d, 1H), 8.45 (s, 1H), 8.37 (s, 1H), 7.74 (s, 1H), 7.54 (d, J=8.24, 1H), 7.33 (d, J=4.88, 1H), 7.25 (s, 1H), 7.15 (dd, J1=6.71, J2=5.19, 1H), 5.37 (d, J=17.09, 1H), 4.63 (d, J=15.87, 1H), 4.50 (s, 1H), 4.12 (m, 2H), 3.87 (m, 1H), 3.56 (dd, J1=28.69, J2=13.43, 1H), 3.18 (t, J=13.73, 1H), 3.10 (d, J=14.65, 1H), 3.01 (m, 2H), 2.88 (t, J=15.26, 1H), 2.66 (m, 1H), 2.35 (d, J=14.95, 1H), 1.84 (m, 3H), 1.57 (m, 1H), 0.73 (d, J=16.17, 9H).

EXAMPLE 46

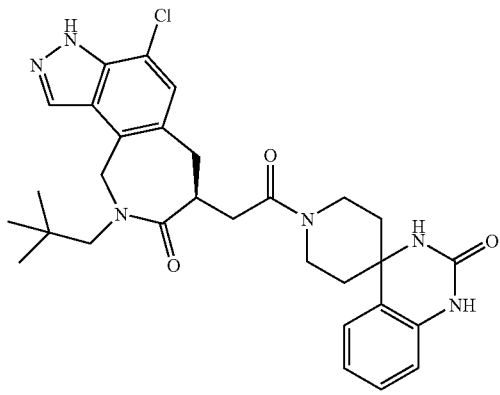

(S)-4-Chloro-9-neopentyl-7-(2-oxo-2-(4-(2-oxo-1'H-spiro(piperidine-4,4'-quinazoline)ethyl)-6,7,9,10-tetrahydroazepino[3,4-e]indazol-8(3H)-one. Title compound was prepared from 1'H-spiro(piperidine-4,4')quinazolin)-2'(3'H)-one in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one.

Material was obtained as white solid in 37% yield. MS m/e (M+H)$^+$=563.2. $^1$H NMR (500 MHz, DMSO-D$_6$): δ=13.54 (s, 1H), 9.22 (d, J=10.68, 1H), 8.36 (s, 1H), 7.30 (m, 2H), 7.24 (s, 1H), 7.12 (m, 1H), 6.85 (m, 2H), 5.36 (d, J=16.78, 1H), 4.62 (dd, J1=16.94, J2=9.31, 1H), 4.26 (t, J=14.34, 1H), 3.89 (m, 2H), 3.63 (m, 1H), 3.52 (m, 1H), 3.09 (m, 3H), 2.98 (m, 1H), 2.88 (m, 1H), 2.33 (dd, J1=51.12, J2=15.72, 1H), 1.96 (m, 1H), 1.74 (m, 3H), 0.74 (d, J=16.48, 9H).

EXAMPLE 47

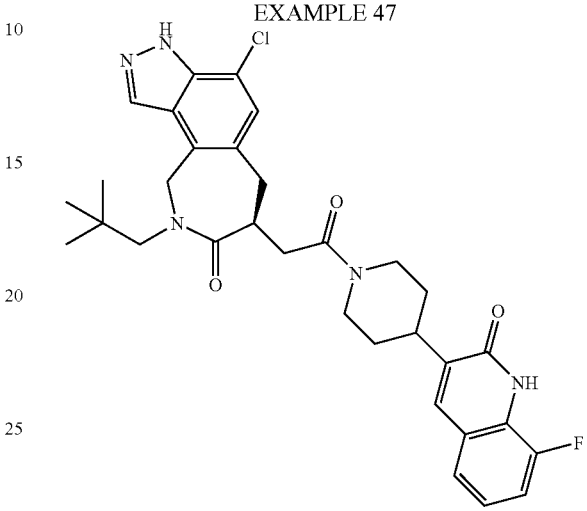

(S)-4-Chloro-7-(2-(4-(8-fluoro-2-oxo-1,2-dihydroquinolin-3-yl)piperidin-1-yl)-2-oxoethyl)-9-neopentyl-6,7,9,10-tetrahydroazepino[3,4-e]indazol-8(3H)-one. Title compound was prepared from 8-fluoro-3-(piperidin-4-yl)quinolin-2(1H)-one hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 36% yield. MS m/e (M+H)$^+$=592.2. $^1$H NMR (500 MHz, DMSO-D$_6$): δ=13.54 (s, 1H), 11.78 (s, 1H), 8.36 (s, 1H), 7.76 (d, J=5.19, 1H), 7.46 (d, J=7.93, 1H), 7.34 (dd, J1=10.53, J2=8.70, 1H), 7.24 (s, 1H), 7.14 (m, 1H), 5.36 (d, J=16.48, 1H), 4.63 (d, J=17.40, 1H), 4.55 (d, J=11.29, 1H), 4.12 (m, 1H), 3.87 (m, 1H), 3.58 (d, J=13.12, 1H), 3.17 (m, 1H), 3.05 (m, 4H), 2.88 (m, 1H), 2.65 (m, 1H), 2.34 (d, J=15.87 1H), 1.92 (d, J=12.51, 1H), 1.84 (d, J=11.29, 1H), 1.57 (m, 1H), 1.40 (m, 1H), 0.72 (s, 9H).

EXAMPLE 48

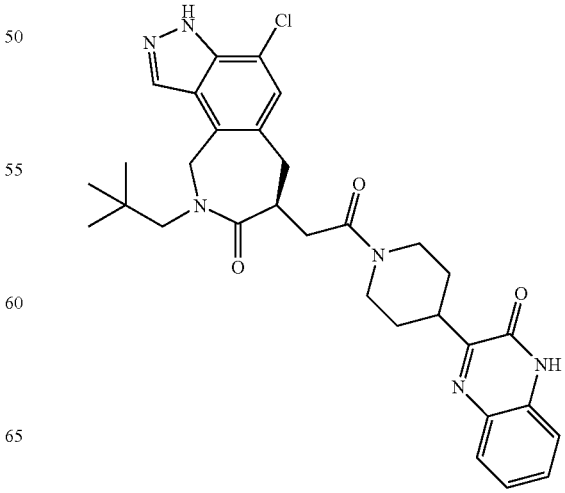

(S)-4-Chloro-9-neopentyl-7-(2-oxo-2-(4-(3-oxo-3,4-dihydroquinoxalin-2-yl)piperidin-1-yl)ethyl)-6,7,9,10-tetrahydroazepino[3,4-e]indazol-8(3H)-one. Title compound was prepared from 3-(piperidin-4-yl)quinoxalin-2(1H)-one hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 49% yield. MS m/e (M−H)⁻=573.2. ¹H NMR (500 MHz, DMSO-D₆): δ=13.53 (s, 1H), 12.35 (s, 1H), 8.36 (s, 1H), 7.72 (t, J=8.70, 1H), 7.48 (t, J=7.78, 1H), 7.28 (m, 2H), 7.24 (s, 1H), 5.37 (d, J=17.09, 1H), 4.63 (d, J=17.09, 1H), 4.49 (m, 1H), 4.12 (m, 1H), 3.86 (m, 1H), 3.59 (t, J=12.36, 1H), 3.45 (m, 1H), 3.22 (m, 1H), 3.10 (m, 1H), 2.99 (m, 1H), 2.87 (dd, J1=15.56, J2=14.34, 1H), 2.72 (m, 1H), 2.36 (m, 1H), 1.96 (d, J=12.82, 1H), 1.89 (d, J=13.12, 1H), 1.70 (m, 1H), 1.52 (m, 1H), 0.72 (s, 9H).

EXAMPLE 49

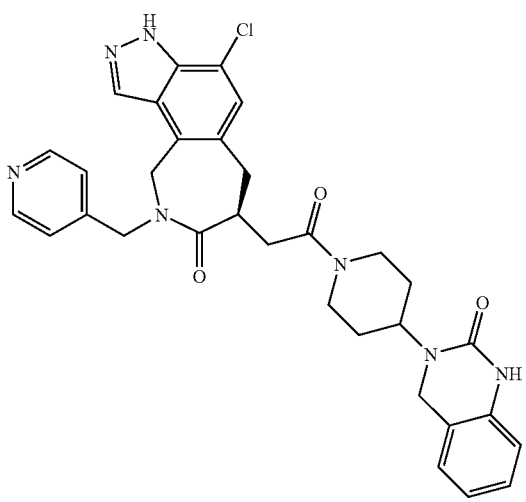

(S)-4-Chloro-7-(2-oxo-2-(4-(2-oxo-1,2-dihydroquinazolin-3(4H)-yl)piperidin-1-yl)ethyl)-9-(pyridin-4-ylmethyl)-6,7,9,10-tetrahydroazepino[3,4-e]indazol-8(3H)-one. (S)-2-(4-Chloro-8-oxo-9-(pyridin-4-ylmethyl)-3,6,7,8,9,10-hexahydroazepino[3,4-e]indazol-7-yl)acetic acid dihydrochloride (90 mg, 0.23 mmol) and 4-(2-oxo-1,4-dihydro-2H-quinazolin-3-yl)piperidine hydrochloride (75 mg, 0.28 mmol) were reacted following a procedure analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 27% yield. MS m/e (M+H)⁺=598.2. ¹H NMR (500 MHz, DMSO-D₆): δ=13.47 (s, 1H), 9.19 (s, 1H), 8.31 (s, 2H), 8.23 (s, 1H), 7.22 (s, 1H), 7.12 (s, 3H), 6.99 (m, 1H), 6.84 (m, 2H), 6.77 (s, 1H), 5.40 (d, J=15.26, 1H), 4.65 (m, 3H), 4.54 (d, J=10.38, 1H), 4.40 (m, 1H), 4.30 (s, 1H), 4.22 (s, 1H), 4.09 (m, 1H), 3.99 (m, 1H), 3.14 (m, 2H), 3.03 (m, 1H), 2.93 (m, 1H), 2.60 (m, 1H), 1.78 (m, 1H), 1.58 (m, 3H).

EXAMPLE 50

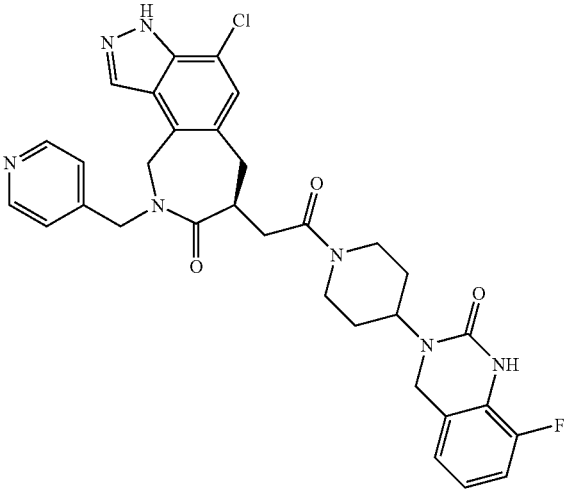

(S)-4-Chloro-7-(2-(4-(8-fluoro-2-oxo-1,2-dihydroquinazolin-3(4H)-yl)piperidin-1-yl)-2-oxoethyl)-9-(pyridin-4-ylmethyl)-6,7,9,10-tetrahydroazepino[3,4-e]indazol-8(3H)-one. (S)-2-(4-Chloro-8-oxo-9-(pyridin-4-ylmethyl)-3,6,7,8,9,10-hexahydroazepino[3,4-e]indazol-7-yl)acetic acid dihydrochloride (100 mg, 0.2 mmol) and 8-fluoro-3-(piperidin-4-yl)-3,4-dihydroquinazolin-2(1H)-one hydrochloride (61 mg, 0.2 mmol) were reacted in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 16% yield. MS m/e (M+H)⁺=616.2. ¹H NMR (500 MHz, DMSO-D₆): δ=13.46 (s, 1H), 9.23 (d, J=6.41, 1H), 8.31 (m, 2H), 8.24 (d, J=6.10, 1H), 7.22 (s, 1H), 7.13 (dd, J1=9.46, J2=4.88, 2H), 7.05 (m, 1H), 6.91 (m, 1H), 6.85 (s, 1H), 5.40 (d, J=17.09, 1H), 4.66 (m, 3H), 4.54 (d, J=11.90, 1H), 4.41 (m, 1H), 4.36 (s, 1H), 4.28 (d, J=4.58, 1H), 4.10 (d, J=12.51, 1H), 4.00 (m, 1H), 3.17 (m, 2H), 3.04 (m, 1H), 2.94 (m, 1H), 2.62 (d, J=11.29, 1H), 2.43 (m, 1H), 1.83 (m, 1H), 1.62 (m, 3H).

EXAMPLE 51

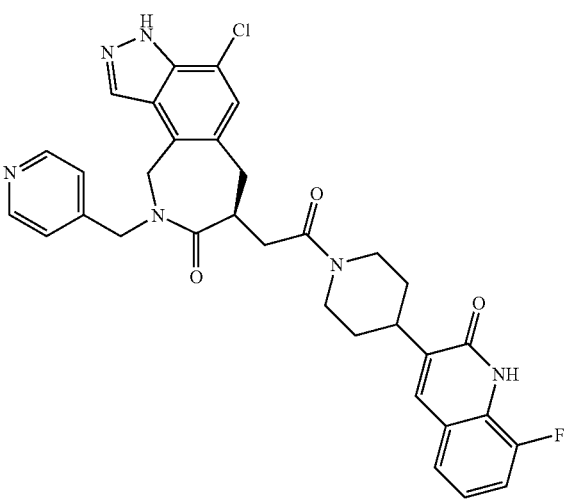

(S)-4-Chloro-7-(2-(4-(8-fluoro-2-oxo-1,2-dihydroquinolin-3-yl)piperidin-1-yl)-2-oxoethyl)-9-(pyridin-4-ylmethyl)-6,7,9,10-tetrahydroazepino[3,4-e]indazol-8(3H)-one. (S)-2-(4-Chloro-8-oxo-9-(pyridin-4-ylmethyl)-3,6,7,8,9,10-hexahydroazepino[3,4-e]indazol-7-yl)acetic acid dihydrochloride (100 mg, 0.22 mmol) and 8-fluoro-3-(piperidin-4-yl)quinolin-2(1H)-one acetate (90 mg, 0.29 mmol) were reacted following a procedure analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as tan solid in 13% yield. MS m/e (M+H)$^+$=613.3. $^1$H NMR (500 MHz, DMSO-D$_6$): δ=13.46 (s, 1H), 11.78 (s, 1H), 8.30 (s, 2H), 8.23 (s, 1H), 7.75 (d, J=19.53, 1H), 7.45 (m, 1H), 7.34 (m, 1H), 7.21 (s, 1H), 7.12 (m, 3H), 5.40 (d, J=16.48, 1H), 4.64 (m, 4H), 4.13 (d, J=12.82, 1H), 4.00 (m, 1H), 3.17 (m, 2H), 3.04 (m, 2H), 2.94 (m, 1H), 2.67 (m, 1H), 2.44 (m, 1H), 1.94 (m, 1H), 1.86 (m, 1H), 1.57 (m, 1H), 1.42 (m, 1H).

EXAMPLE 52

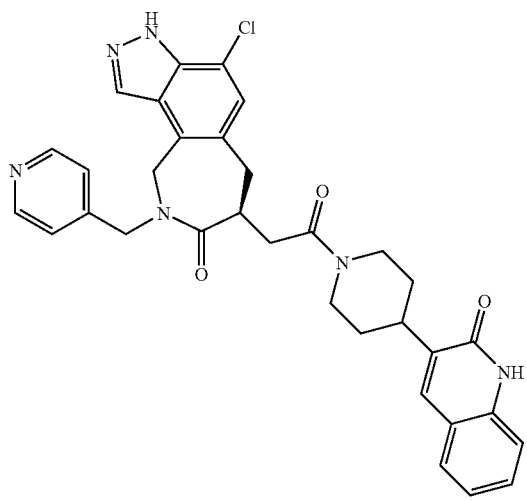

(S)-4-Chloro-7-(2-oxo-2-(4-(2-oxo-1,2-dihydroquinolin-3-yl)piperidin-1-yl)ethyl)-9-(pyridin-4-ylmethyl)-6,7,9,10-tetrahydroazepino[3,4-e]indazol-8(3H)-one. (S)-2-(4-Chloro-8-oxo-9-(pyridin-4-ylmethyl)-3,6,7,8,9,10-hexahydroazepino[3,4-e]indazol-7-yl)acetic acid dihydrochloride (100 mg, 0.23 mmol) and 3-(piperidin-4-yl)quinolin-2(1H)-one (55 mg, 0.24 mmol) were reacted following a procedure analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 41% yield. MS m/e (M+H)$^+$=595.2. $^1$H NMR (500 MHz, DMSO-D$_6$): δ=13.46 (s, 1H), 11.76 (s, 1H), 8.30 (d, J=5.19, 2H), 8.23 (s, 1H), 7.69 (d, J=19.84, 1H), 7.62 (m, 1H), 7.44 (m, 1H), 7.28 (d, J=7.93, 1H), 7.21 (s, 1H), 7.14 (m, 3H), 5.40 (d, J=17.09, 1H), 4.65 (m, 3H), 4.13 (d, J=13.43, 1H), 4.01 (m, 1H), 3.17 (d, J=14.95, 2H), 3.04 (m, 2H), 2.94 (m, 1H), 2.66 (m, 1H), 2.45 (m, 2H), 1.93 (d, J=11.60, 1H), 1.85 (d, J=12.82, 1H), 1.56 (m, 1H), 1.41 (m, 1H).

EXAMPLE 53

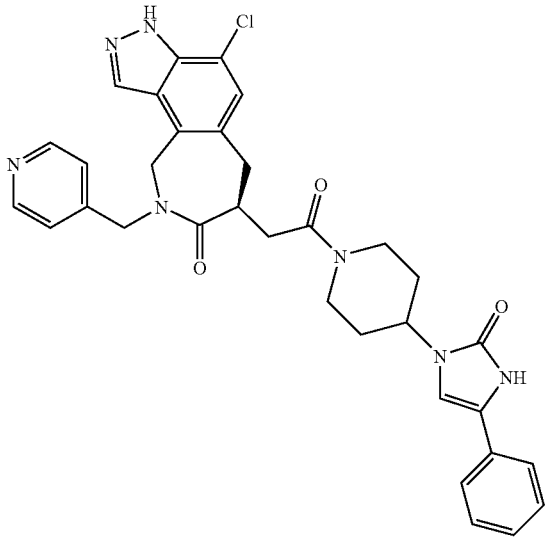

(S)-4-Chloro-7-(2-oxo-2-(4-(2-oxo-4-phenyl-2,3-dihydroimidazol-1-yl)piperidin-1-yl)ethyl)-9-(pyridin-4-ylmethyl)-6,7,9,10-tetrahydroazepino[3,4-e]indazol-8(3H)-one. (S)-2-(4-Chloro-8-oxo-9-(pyridin-4-ylmethyl)-3,6,7,8,9,10-hexahydroazepino[3,4-e]indazol-7-yl)acetic acid dihydrochloride (100 mg, 0.23 mmol) and 4-phenyl-1-(piperidin-4-yl)-1H-imidazol-2(3H)-one (60 mg, 0.28 mmol) were reacted following a procedure analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 30% yield. MS m/e (M+H)$^+$=610.3. $^1$H NMR (500 MHz, DMSO-D$_6$): δ=13.46 (s, 1H), 10.68 (d, J=4.27, 1H), 8.30 (d, J=3.97, 2H), 8.23 (s, 1H), 7.50 (d, J=7.93, 1H), 7.45 (d, J=7.63, 1H), 7.31 (m, 2H), 7.22 (s, 1H), 7.14 (m, 4H), 5.41 (d, J=16.78, 1H), 4.66 (m, 3H), 4.55 (m, 1H), 4.13 (m, 2H), 3.99 (m, 1H), 3.33 (m, 1H), 3.18 (m, 1H), 3.05 (dd, J1=16.02, J2=8.70, 1H), 2.94 (m, 1H), 2.68 (m, 1H), 2.44 (m, 1H), 1.81 (m, 3H), 1.62 (m, 1H).

EXAMPLE 54

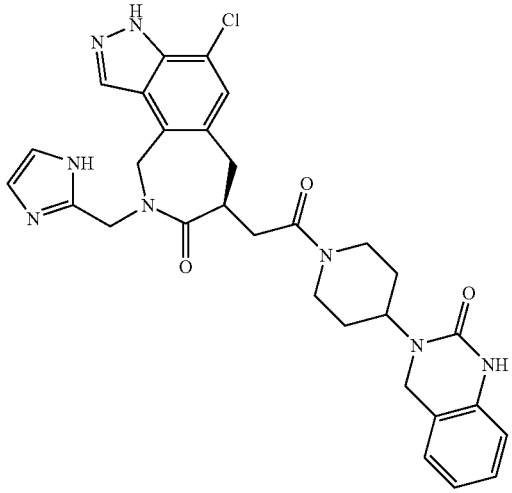

(S)-9-((1H-Imidazol-2-yl)methyl)-4-chloro-7-(2-oxo-2-(4-(2-oxo-1,2-dihydroquinazolin-3(4H)-yl)piperidin-1-yl)ethyl)-6,7,9,10-tetrahydroazepino[3,4-e]indazol-8(3H)-one. (S)-Methyl 2-(9-((1H-imidazol-2-yl)methyl)-4-chloro-8-oxo-3,6,7,8,9,10-hexahydroazepino[3,4-e]indazol-7-yl)acetate (58 mg, 0.15 mmol) was dissolved in a mixture containing methanol (2 mL), tetrahydrofuran (2 mL), and water (2 mL). Lithium hydroxide monohydrate (20 mg, 0.48 mmol) was added to the mixture. Reaction stirred at room temperature for 15 hours. Reaction was quenched with 1N hydrochloric acid (0.5 mL). Mixture was concentrated in vacuo. Residue was dissolved in DMF (2 mL). N,N-Diisopropylethylamine was added to the mixture followed by o-Benzotriazol-1-yl-N,N,N',N'-tetramethyluronium Tetrafluoroborate (60 mg, 0.19 mmol). Mixture stirred at room temperature for 30 minutes. 4-(2-Oxo-1,4-dihydro-2H-quinazolin-3-yl)piperidine hydrochloride (50 mg, 0.19 mmol) was added to the mixture. Reaction stirred at room temperature for 3 hours. Reaction mixture was purified by preparatory HPLC. Desired fractions were identified. Acetonitrile was removed from the fractions in vacuo. Remaining aqueous was made basic with sodium bicarbonate. Mixture was extracted twice with ethyl acetate. Combined extracts were dried (magnesium sulfate), filtered and concentrated in vacuo. Title compound was obtained as white solid in 28% yield. MS m/e (M+H)$^+$=587.2. $^1$H NMR (500 MHz, DMSO-D$_6$): δ=13.46 (s, 1H), 11.75 (s, 1H), 9.20 (s, 1H), 8.14 (s, 1H), 7.19 (s, 1H), 7.12 (m, 2H), 6.84 (m, 2H), 6.77 (d, J=7.93, 1H), 5.23 (d, J=15.16, 1H), 4.76 (m, 1H), 4.69 (dd, J1=15.26, J2=5.19, 1H), 4.53 (d, J=13.43, 1H), 4.47 (d, J=15.26, 1H), 4.40 (m, 1H), 4.29 (d, J=3.97, 2H), 4.08 (m, 1H), 3.89 (d, J=9.77, 1H), 3.15 (m, 2H), 3.00 (m, 1H), 2.91 (m, 3H), 2.60 (m, 1H) 2.44 (m, 2H), 1.80 (m, 1H), 1.60 (m, 3H).

EXAMPLE 55

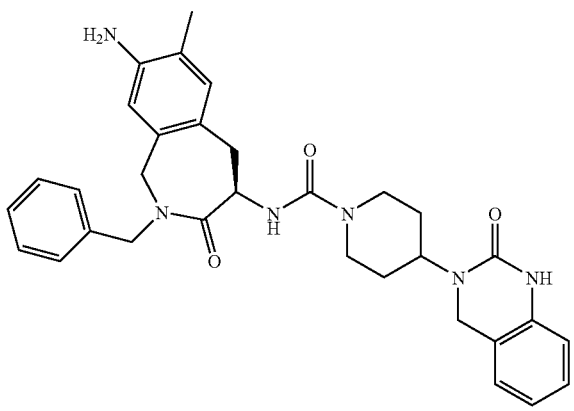

(R)—N-(8-Amino-2-benzyl-7-methyl-3-oxo-2,3,4,5-tetrahydro-1H-benzo[c]azepin-4-yl)-4-(2-oxo-1,2-dihydroquinazolin-3(4H)-yl)piperidine-1-carboxamide trifluoroacetate. (R)—N-(8-Amino-2-benzyl-7-methyl-3-oxo-2,3,4,5-tetrahydro-1H-benzo[c]azepin-4-yl)-4-(2-oxo-1,2-dihydroquinazolin-3(4H)-yl)piperidine-1-carboxamide (95 mg, 0.15 mmol) was dissolved in dichloromethane (2 mL). Trifluoroacetic acid (1 mL) was added to the mixture. Reaction stirred at room temperature for 1 hour. Mixture was concentrated in vacuo. Residue was purified by preparatory HPLC. Solvent was lyophilized from the proper fractions. Title compound was obtained as white solid in 64% yield. MS m/e (M+H)$^+$=553.

EXAMPLE 56

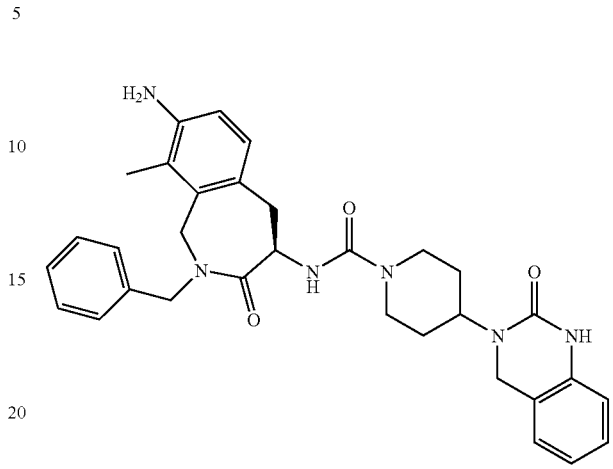

(R)—N-(8-Amino-2-benzyl-7-methyl-3-oxo-2,3,4,5-tetrahydro-1H-benzo[c]azepin-4-yl)-4-(2-oxo-1,2-dihydroquinazolin-3(4H)-yl)piperidine-1-carboxamide trifluoroacetate. (R)-tert-Butyl 2-benzyl-9-methyl-3-oxo-4-(4-(2-oxo-1,2-dihydroquinazolin-3(4H)-yl)piperidine-1-carboxamido)-2,3,4,5-tetrahydro-1H-benzo[c]azepin-8-ylcarbamate was reacted in a manner analogous with the preparation of (R)—N-(8-amino-2-benzyl-7-methyl-3-oxo-2,3,4,5-tetrahydro-1H-benzo[c]azepin-4-yl)-4-(2-oxo-1,2-dihydroquinazolin-3(4H)-yl)piperidine-1-carboxamide trifluoroacetate. Title compound was obtained as off-white solid in 31% yield. MS m/e (M+H)$^+$=553.

EXAMPLE 57

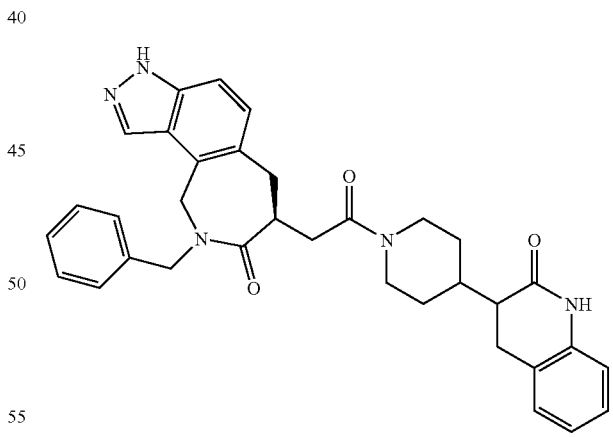

N—((R)-9-Benzyl-8-oxo-3,6,7,8,9,10-hexahydroazepino[3,4-e]indazol-7-yl)-4-(2-oxo-1,2,3,4-tetrahydroquinolin-3-yl)piperidine-1-carboxamide. (S)-2-(9-Benzyl-8-oxo-3,6,7,8,9,10-hexahydroazepino[3,4-e]indazol-7-yl)acetic acid (80 mg, 0.24 mmol) and 3-(piperidin-4-yl)-3,4-dihydroquinolin-2(1H)-one (75 mg, 0.33 mmol) were reacted in a manner analogous to the preparation of 4-Chloro-9-(2,2-dimethylpropyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid in 33% yield. MS m/e (M+H)$^+$=542.3. $^1$H NMR (500 MHz, DMSO-D$_6$): δ=13.01 (s, 1H), 10.11 (s, 1H), 8.21 (s, 1H), 7.36 (d, J=7.93, 1H), 7.17 (m, 1H), 7.11 (m, 2H), 6.91 (m, 1H), 6.83 (d, J=7.63, 1H), 5.35 (d, J=17.09, 1H), 4.61 (d, J=17.40, 1H), 4.38 (m, 1H), 4.02 (m, 1H), 3.83 (s, 1H), 3.55 (t, J=12.36, 1H), 2.95(m, 6H), 2.79(m, 1H), 2.42(m, 1H), 2.31(m, 2H), 1.90(m, 1H), 1.63(m, 2H), 1.17(m, 1H), 0.72(d, J=9.77, 9H).

EXAMPLE 58

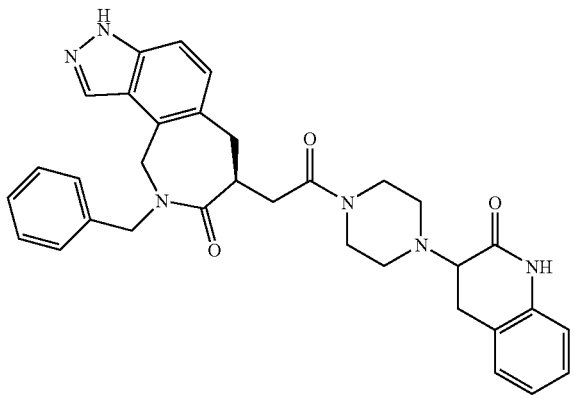

(7S)-9-Benzyl-7-(2-oxo-2-(4-(2-oxo-1,2,3,4-tetrahydroquinolin-3-yl)piperazin-1-yl)ethyl)-6,7,9,10-tetrahydroazepino[3,4-e]indazol-8(3H)-one. (S)-2-(9-Benzyl-8-oxo-3,6,7,8,9,10-hexahydroazepino[3,4-e]indazol-7-yl)acetic acid (80 mg, 0.24 mmol) and 3-(piperazin-1-yl)-3,4-dihydroquinolin-2(1H)-one (75 mg, 0.32 mmol) were reacted in a manner analogous to the preparation of 4-chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cycloheptafelinden-8-one. Material was obtained as white solid in 21% yield. MS m/e (M+H)$^+$=543.3. $^1$H NMR (500 MHz, DMSO-D$_6$): δ=13.01(s, 1H), 10.13(s, 1H), 8.21(s, 1H), 7.36(d, J=8.54, 1H), 7.19(d, J=7.02, 1H), 7.11(m, 2H), 6.90(t, J=7.32, 1H), 6.82(d, J=7.93, 1H), 5.36(d, J=17.40, 1H), 4.61(d, J=17.09, 1H), 3.84(m, 1H), 3.57(d, J=13.12, 1H), 3.47(m, 2H), 3.38(m, 1H), 3.32(M, 1H), 3.09(m, 1H), 3.02(d, J=14.04, 1H), 2.985(m, 2H), 2.85(m, 1H), 2.75(m, 1H), 2.65(m, 3H), 2.50(m, 2H), 2.31(d, J=16.48, 1H), 0.71(s, 9H).

EXAMPLE 59

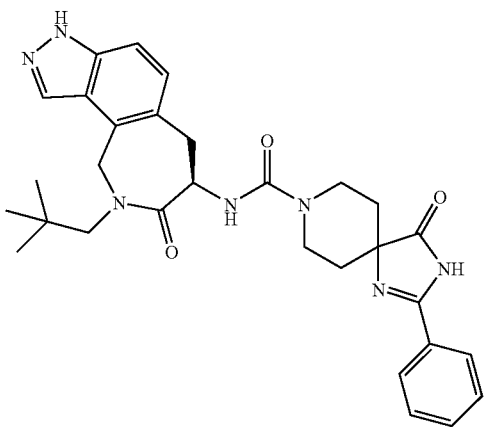

4-Oxo-2-phenyl-1,3,8-triaza-spiro[4.5]dec-1-ene-8-carboxylic acid [(R)-9-(2,2-dimethyl-propyl)-8-oxo-3,6,7,8,9,10-hexahydro-2,3,9-triaza-cyclohepta[e]inden-7-yl]-amide. 2-Phenyl-1,3,8-triaza-spiro[4.5]dec-1-en-4-one trifluoroacetate (55 mg, 0.16 mmol) and (R)-7-amino-9-neopentyl-6,7,9,10-tetrahydroazepino[3,4-e]indazol-8(3H)-one (40 mg, 0.14 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as white solid in 25% yield. High resolution MS m/e (M+H)$^+$=542.2888.

EXAMPLE 60

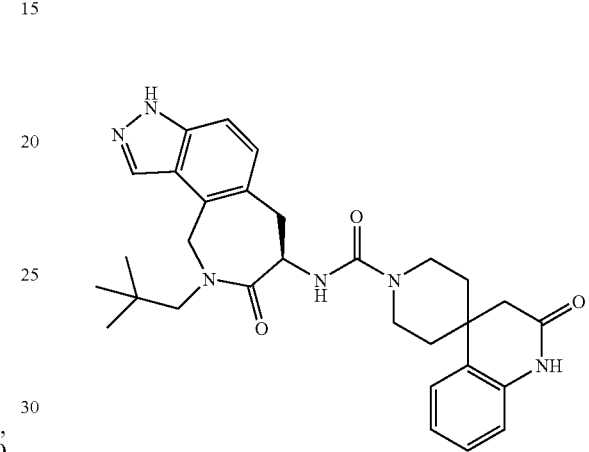

Spiro[2,3-dihydro-1H-quinoline-2-one-4(1H),4'piperidine]-1'-carboxylic acid [(R)-9-(2,2-dimethyl-propyl)-8-oxo-3,6,7,8,9,10-hexahydro-2,3,9-triaza-cyclohepta[e]inden-7-yl]-amide. Spiro[2,3-dihydro-1H-quinoline-2-one-4(1H),4'piperidine] (32 mg, 0.15 mmol) and (R)-7-amino-9-neopentyl-6,7,9,10-tetrahydroazepino[3,4-e]indazol-8(3H)-one (35 mg, 0.12 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as white solid in 46% yield. High resolution MS m/e (M+H)$^+$=529.2924.

EXAMPLE 61

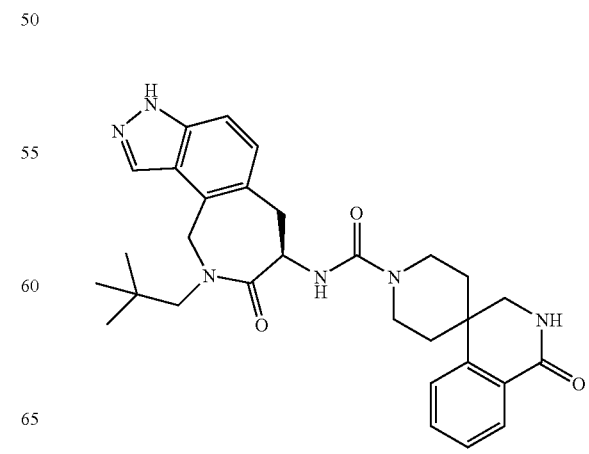

Spiro[2,3-dihydro-1H-isoquinoline-1-one-4(1H),4'piperidine]-1'-carboxylic acid [(R)-9-(2,2-dimethyl-propyl)-8-oxo-3,6,7,8,9,10-hexahydro-2,3,9-triaza-cyclohepta[e]inden-7-yl]-amide. Spiro[2,3-dihydro-1H-isoquinoline-1-one-4(1H),4'piperidine] (32 mg, 0.15 mmol) and (R)-7-amino-9-neopentyl-6,7,9,10-tetrahydroazepino[3,4-e]indazol-8(3H)-one (35 mg, 0.12 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as white solid in 41% yield. High resolution MS m/e (M+H)⁺=529.2927.

EXAMPLE 62

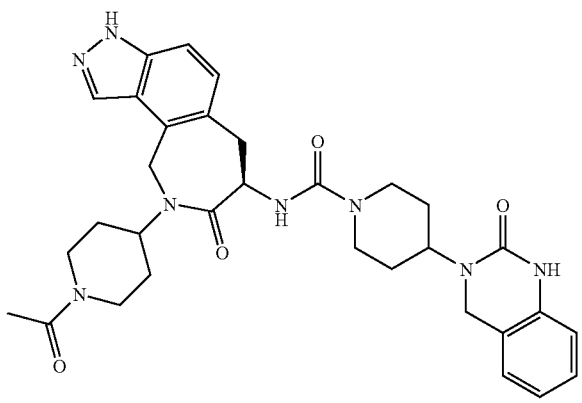

(R)—N-(9-(1-acetylpiperidin-4-yl)-8-oxo-3,6,7,8,9,10-hexahydroazepino[3,4-e]indazol-7-yl)-4-(2-oxo-1,2-dihydroquinazolin-3(4H)-yl)piperidine-1-carboxamide. (R)-9-(1-acetylpiperidin-4-yl)-7-amino-6,7,9,10-tetrahydroazepino[3,4-e]indazol-8(3H)-one methanesulfonate (42 mg, 0.08 mmol) and 3-(piperidin-4-yl)-3,4-dihydroquinazolin-2(1H)-one acetate (30 mg, 0.10 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as white solid in 28% yield. High resolution MS m/e (M+H)⁺=599.3085.

EXAMPLE 63

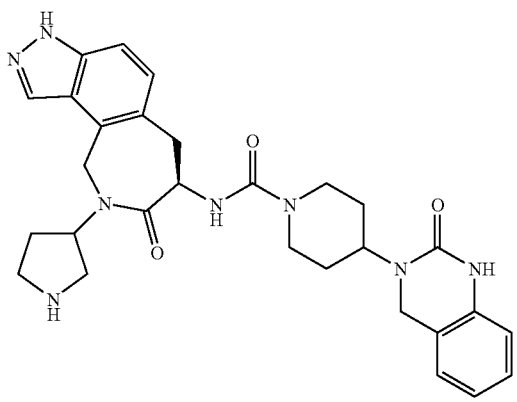

4-(2-oxo-1,2-dihydroquinazolin-3(4H)-yl)-N—((R)-8-oxo-9-(pyrrolidin-3-yl)-3,6,7,8,9,10-hexahydroazepino[3,4-e]indazol-7-yl)piperidine-1-carboxamide. (R)-tert-butyl 4-(8-oxo-7-(4-(2-oxo-1,2-dihydroquinazolin-3(4H)-yl)piperidine-1-carboxamido)-7,8-dihydroazepino[3,4-e]indazol-9(3H,6H,10H)-yl)piperidine-1-carboxylate (45 mg, 0.06 mmol) was dissolved in dichloromethane (1 mL). Trifluoroacetic acid (0.25 mL) was added to the mixture. Reaction stirred at room temperature for 1.5 hour. Reaction mixture was concentrated in vacuo. C18 preparatory HPLC purification afforded the title compound as yellow solid in 52% yield. High resolution MS m/e (M+H)⁺=543.2830.

EXAMPLE 64

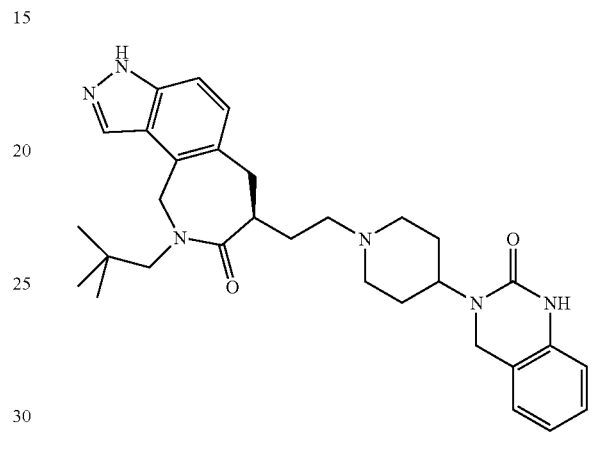

(S)-9-neopentyl-7-(2-(4-(2-oxo-1,2-dihydroquinazolin-3(4H)-yl)piperidin-1-yl)ethyl)-6,7,9,10-tetrahydroazepino[3,4-e]indazol-8(3H)-one. (S)-7-(2-hydroxyethyl)-9-neopentyl-6,7,9,10-tetrahydroazepino[3,4-e]indazol-8(3H)-one (15 mg, 0.04 mmol) was dissolved in dichloromethane (1 mL). Thionyl chloride (100 μL) was added to the mixture. Reaction stirred at room temperature for 2 hours. Thionyl chloride (500 μL) was added to the mixture. Reaction stirred at room temperature for 2 hours and then was warmed to reflux for 2 hours. Reaction mixture was concentrated in vacuo. Residue was dissolved in acetonitrile (1 mL). Potassium carbonate (25 mg, 0.18 mmol) was added to the mixture followed by 3-(piperidin-4-yl)-3,4-dihydroquinazolin-2(1H)-one (16 mg, 0.07 mmol). Reaction was heated at reflux for 2 hours. Preparatory HPLC purification afforded the title compound as white solid in 25% yield. High resolution MS m/e (M+H)⁺=529.3282.

EXAMPLE 65

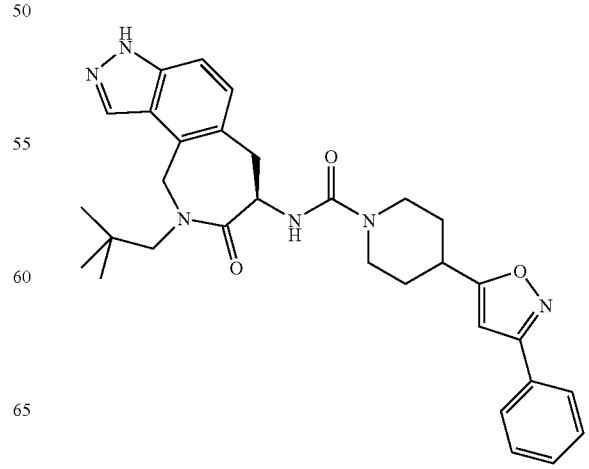

(R)—N-(9-neopentyl-8-oxo-3,6,7,8,9,10-hexahydroazepino[3,4-e]indazol-7-yl)-4-(3-phenylisoxazol-5-yl)piperidine-1-carboxamide. 4-(3-Phenylisoxazol-5-yl)piperidine (46 mg, 0.20 mmol) and (R)-7-amino-9-neopentyl-6,7,9,10-tetrahydroazepino[3,4-e]indazol-8(3H)-one (110 mg, 0.22 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as tan solid in 33% yield. High resolution MS m/e (M+H)$^+$=541.2916.

EXAMPLE 66

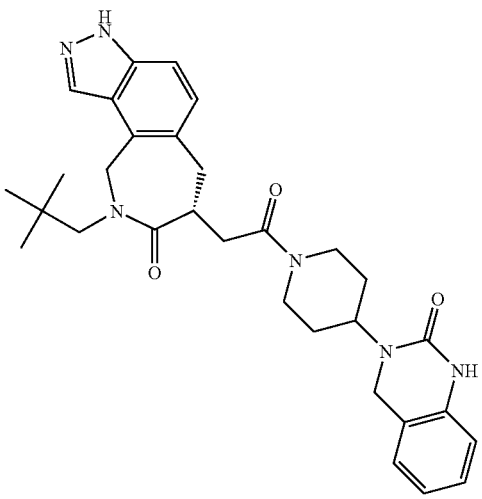

9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. [9-(2,2-dimethyl-propyl)-8-oxo-3,6,7,8,9,10-hexahydro-2,3,9-triaza-(R)-cyclohepta[e]inden-7-yl]-acetic acid (75 mg, 0.23 mmol) and 4-(2-Oxo-1,4-dihydro-2H-quinazolin-3-yl) piperidine (65 mg, 0.28 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as a white solid in 32% yield. High resolution MS m/e (M+H)$^+$=543.3084.

EXAMPLE 67

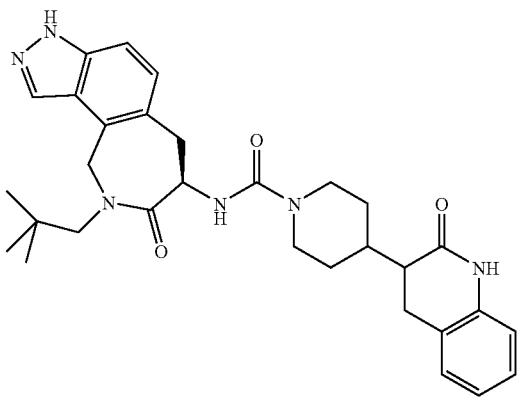

N—((R)-9-neopentyl-8-oxo-3,6,7,8,9,10-hexahydroazepino[3,4-e]indazol-7-yl)-4-(2-oxo-1,2,3,4-tetrahydroquinolin-3-yl)piperidine-1-carboxamide. 3-(piperidin-4-yl)-3,4-dihydroquinolin-2(1H)-one (50 mg, 0.22 mmol) and (R)-7-amino-9-neopentyl-6,7,9,10-tetrahydroazepino[3,4-e]indazol-8(3H)-one (110 mg, 0.22 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as off-white solid in 25% yield. High resolution MS m/e (M+H)$^+$=543.3084.

EXAMPLE 68

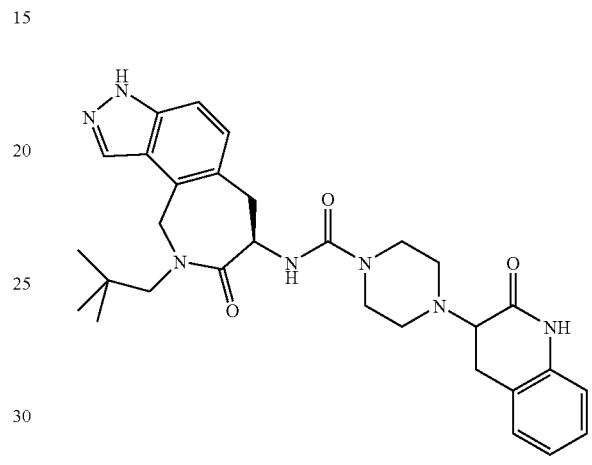

N—((R)-9-Neopentyl-8-oxo-3,6,7,8,9,10-hexahydroazepino[3,4-e]indazol-7-yl)-4-(2-oxo-1,2,3,4-tetrahydroquinolin-3-yl)piperazine-1-carboxamide. 3-(piperazin-1-yl)-3,4-dihydroquinolin-2(1H)-one (45 mg, 0.19 mmol) and (R)-7-amino-9-neopentyl-6,7,9,10-tetrahydroazepino[3,4-e]indazol-8(3H)-one (75 mg, 0.15 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]inden-7-yl]-amide. C18 preparatory HPLC afforded the title compound as white solid in 17% yield. High resolution MS m/e (M+H)$^+$=544.3022.

EXAMPLE 69

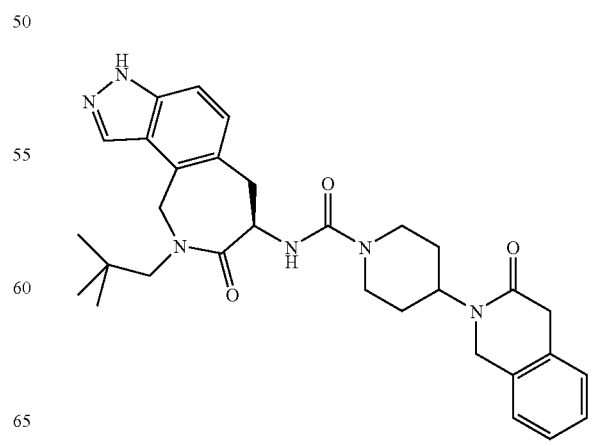

(R)—N-(9-Neopentyl-8-oxo-3,6,7,8,9,10-hexahydroazepino[3,4-e]indazol-7-yl)-4-(3-oxo-3,4-dihydroisoquinolin-2(1H)-yl)piperidine-1-carboxamide. 2-(Piperidin-4-yl)-1,2-dihydroisoquinolin-3(4H)-one (60 mg, 0.26 mmol) and (R)-7-amino-9-neopentyl-6,7,9,10-tetrahydroazepino[3,4-e]indazol-8(3H)-one (100 mg, 0.20 mmol) were reacted in a manner analogous to the preparation of 4-(2-oxo-1,4-dihydro-2H-quinazolin-3-yl)-piperidine-1-carboxylic acid [8-oxo-9-(2-piperidin-1-yl-ethyl)-3,6,7,8,9,10-hexahydro-2,3,9-triaza-(R)-cyclohepta[e]indazol-7-yl]-amide. C18 preparatory HPLC afforded the title compound as yellow solid in 29% yield. High resolution MS m/e (M+H)⁺=543.3074.

EXAMPLE 70

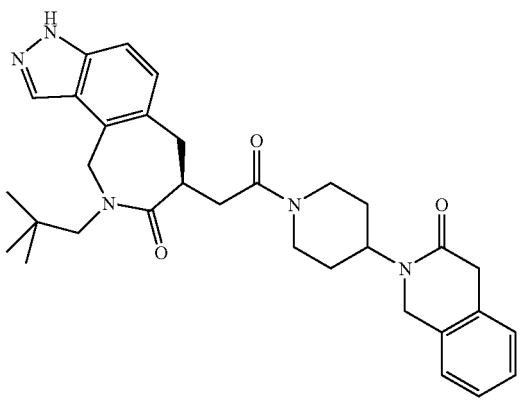

(S)-9-Neopentyl-7-(2-oxo-2-(4-(3-oxo-3,4-dihydroisoquinolin-2(1H)-yl)piperidin-1-yl)ethyl)-6,7,9,10-tetrahydroazepino[3,4-e]indazol-8(3H)-one. 2-(Piperidin-4-yl)-1,2-dihydroisoquinolin-3(4H)-one (105 mg, 0.46 mmol) and [9-(2,2-dimethyl-propyl)-8-oxo-3,6,7,8,9,10-hexahydro-2,3,9-triaza-(S)-cyclohepta[e]inden-7-yl]acetic acid (110 mg, 0.33 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as a white solid in 40% yield. High resolution MS m/e (M+H)⁺=541.3111.

EXAMPLE 71

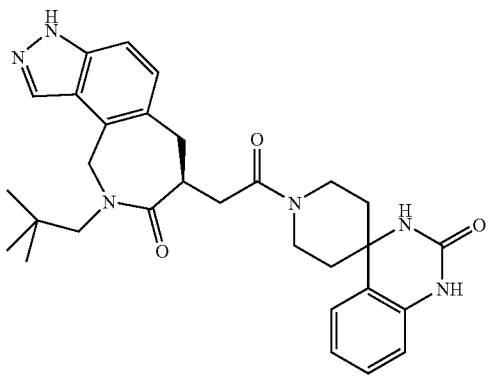

1-[[7-(S)-9-(2,2-Dim ethylpropyl)-3,6,7,8,9,10-hexahydro-8-oxoazepino[3,4-e]indazol-7-yl]acetyl-spiro/piperidine-4,4'(1'H)-quinazolin]-2'(3'H)-one. Spiro[piperidine-4,4'(1'H)-quinazolin]-2'(3'H)-one hydrochloride (50 mg, 0.20 mmol) and [9-(2,2-dimethyl-propyl)-8-oxo-3,6,7,8,9,10-hexahydro-2,3,9-triaza-(S)-cyclohepta[e]inden-7-yl]acetic acid (55 mg, 0.17 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 35% yield. High resolution MS m/e (M+H)⁺=529.2921.

EXAMPLE 72

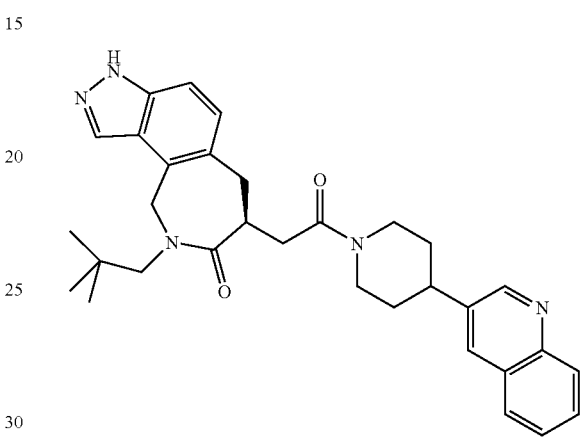

1-[[7-(S)-9-(2,2-Dim ethylpropyl)-3,6,7,8,9,10-hexahydro-8-oxoazepino[3,4-e]indazol-7-yl]acetyl]-4-(3-quinolinyl)piperidine. 3-(piperidin-4-yl)quinoline (75 mg, 0.35 mmol) and [9-(2,2-dimethyl-propyl)-8-oxo-3,6,7,8,9,10-hexahydro-2,3,9-triaza-(S)-cyclohepta[e]inden-7-yl]acetic acid (95 mg, 0.29 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as off-white solid in 50% yield. High resolution MS m/e (M+H)⁺=522.2878.

EXAMPLE 73

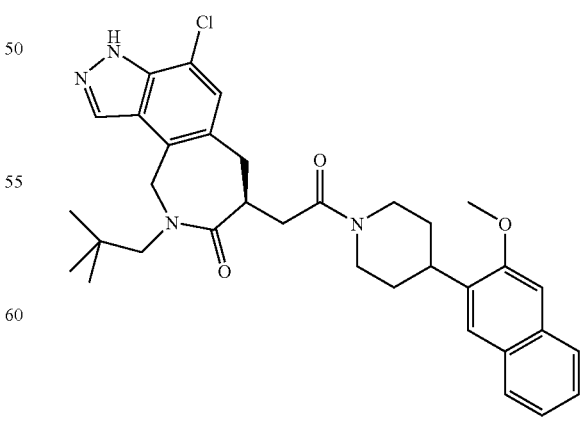

1-[[7-(S)-4-chloro-9-(2,2-Dimethylpropyl)-3,6,7,8,9,10-hexahydro-8-oxoazepino[3,4-e]indazol-7-yl]acetyl]-4-(3- methoxy-2-naphthalenyl)piperidine. 4-(3-Methoxynaphthalen-2-yl)piperidine hydrochloride (78 mg, 0.28 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (88 mg, 0.24 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as tan solid in 88% yield. An analytical sample was prepared by C18 preparatory HPLC giving white solid with 30% recovery. High resolution MS m/e (M+H)$^+$=587.2791.

EXAMPLE 74

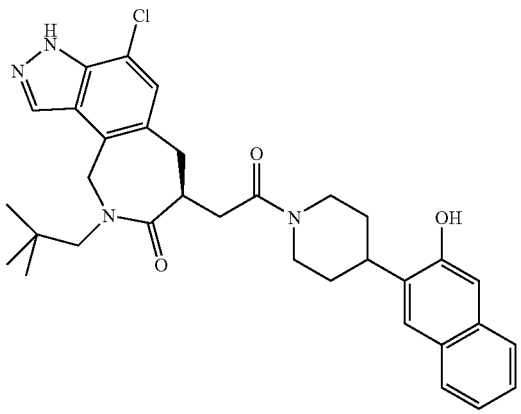

1-[[7-(S)-4-chloro-9-(2,2-Dimethylpropyl)-3,6,7,8,9,10-hexahydro-8-oxoazepino[3,4-e]indazol-7-yl]acetyl]-4-(3-hydroxy-2-naphthalenyl)piperidine. A 1M solution of boron tribromide in dichloromethane (580 µL, 0.58 mmol) was added to a solution of 1-[[7-(S)-4-chloro-9-(2,2-Dimethylpropyl)-3,6,7,8,9,10-hexahydro-8-oxoazepino[3,4-e]indazol-7-yl]acetyl]-4-(3-methoxy-2-naphthalenyl)piperidine (78 mg, 0.13 mmol) in dichloromethane (3 mL). Reaction stirred at room temperature for 4 hours. 1M Boron tribromide in dichloromethane (500 µL, 0.5 mmol) was added to the mixture. Reaction stirred at room temperature for 30 minutes. Reaction mixture was concentrated in vacuo. Residue was purified by C18 preparatory HPLC. Major peak was isolated. Methanol was removed from the combined fractions in vacuo. Remaining aqueous was extracted with ethyl acetate (30 mL). Organic layer was washed with aqueous sodium bicarbonate (2×15 mL). Organic was dried (magnesium sulfate), filtered and concentrated in vacuo. Title compound was obtained as tan solid in 37% yield. High resolution MS m/e (M+H)$^+$=573.2636.

EXAMPLE 75

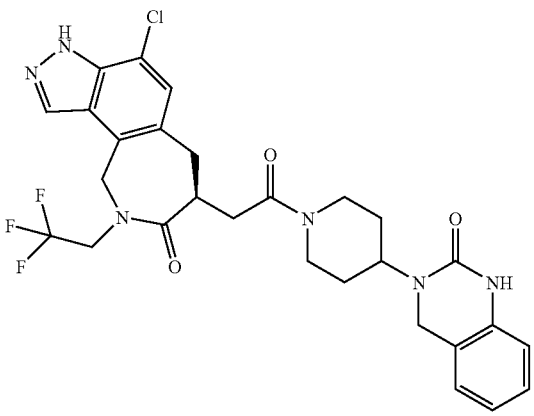

1-[[(7S)-4-Chloro-3,6,7,8,9,10-hexahydro-8-oxo-9-(2,2,2-trifluoroethly)azepino[3,4-e]indazol-7-yl]acetyl]-4-(1,4-dihydro-2-oxo-3(2H)-quinazolinyl)-piperidine. [4-Chloro-3,6,7,8,9,10-hexahydro-8-oxo-9-(2,2,2-trifluoroethyl)-2,3,9-triaza-(S)-cyclohepta[e]inden-7-yl]acetic acid (105 mg, 0.28 mmol) and 4-(2-Oxo-1,4-dihydro-2H-quinazolin-3-yl)piperidine hydrochloride (85 mg, 0.32 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as pale yellow solid in 58% yield. High resolution MS m/e (M+H)$^+$=589.1932.

EXAMPLE 76

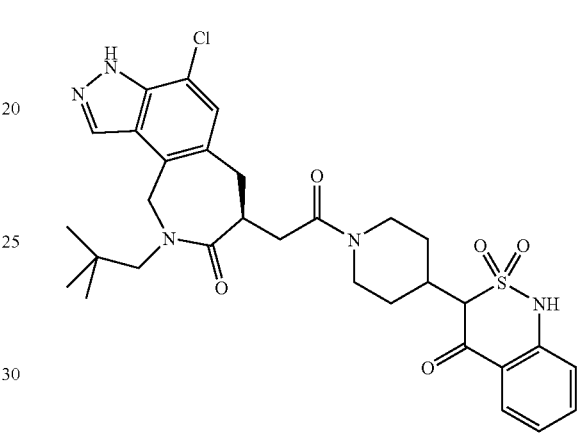

1-[[7-(S)-4-chloro-9-(2,2-Dimethylpropyl)-3,6,7,8,9,10-hexahydro-8-oxoazepino[3,4-e]indazol-7-yl]acetyl]-4-(3,4-dihydro-2,2-dioxido-4-oxo-1H-2,1-benzothiazin-3-yl)piperidine. 2,2-Dioxo-3-piperidin-4-yl-2,3-dihydro-1H-2,1-benzothiazin-4-one (86 mg, 0.27 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (85 mg, 0.23 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as tan solid in 37% yield. High resolution MS m/e (M+H)$^+$=626.2217.

EXAMPLE 77

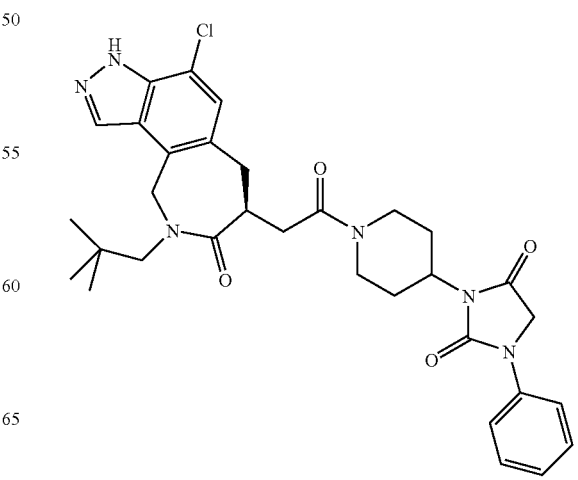

1-[[7-(S)-4-chloro-9-(2,2-Dimethylpropyl)-3,6,7,8,9,10-hexahydro-8-oxoazepino[3,4-e]indazol-7-yl]acetyl]-4-(2,5-dioxo-3-phenyl-1-imidazolidinyl)piperidine. 5-Phenyl-3-(piperidin-4-yl)imidazolidine-2,4-dione hydrochloride (46 mg, 0.16 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (46 mg, 0.13 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as yellow solid in 67% yield. High resolution MS m/e (M+H)$^+$=605.2645.

EXAMPLE 78

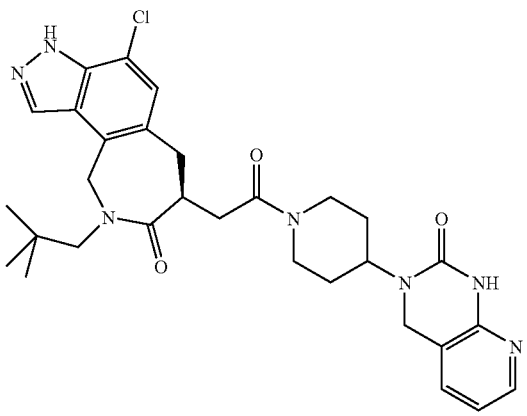

1-[[7-(S)-4-chloro-9-(2,2-Dimethylpropyl)-3,6,7,8,9,10-hexahydro-8-oxoazepino[3,4-e]indazol-7-yl]acetyl]-4-(1,4-dihydro-2-oxopyrido[2,3-d]pyrimidin-3(2H)-yl)-piperidine. 3-(Piperidin-4-yl)-3,4-dihydropyrido[2,3-d]pyrimidin-2(1H)-one dihydrochloride (64 mg, 0.21 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (63 mg, 0.17 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 41% yield. High resolution MS m/e (M+H)$^+$=578.2630.

EXAMPLE 79

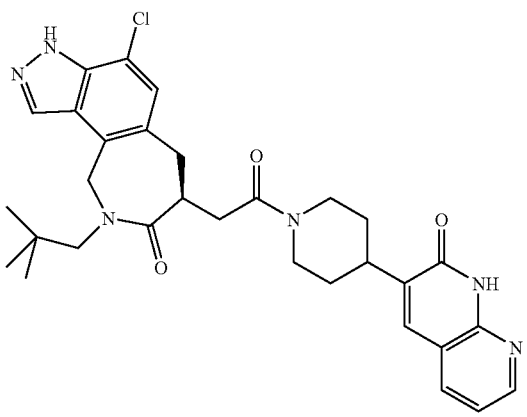

1-[[(7S)-4-chloro-9-(2,2-dimethylpropyl)-3,6,7,8,9,10-hexahydro-8-oxoazepino[3,4-e]indazol-7-yl]acetyl]-4-(1,2-dihydro-2-oxo-1,8-naphthyridin-3-yl)-piperidine. 3-(piperidin-4-yl)-1,8-naphthyridin-2(1H)-one (57 mg, 0.19 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (60 mg, 0.16 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 64% yield. High resolution MS m/e (M+H)$^+$=575.2538.

EXAMPLE 80

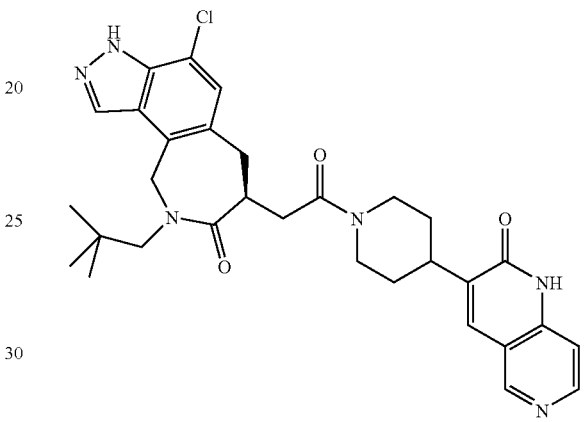

1-[[(7S)-4-chloro-9-(2,2-dimethylpropyl)-3,6,7,8,9,10-hexahydro-8-oxoazepino[3,4-e]indazol-7-yl]acetyl]-4-(1,2-dihydro-2-oxo-1,6-naphthyridin-3-yl)-piperidine. 3-(piperidin-4-yl)-1,6-naphthyridin-2(1H)-one (89 mg, 0.29 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (95 mg, 0.26 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 27% yield. High resolution MS m/e (M+H)$^+$=575.2538.

EXAMPLE 81

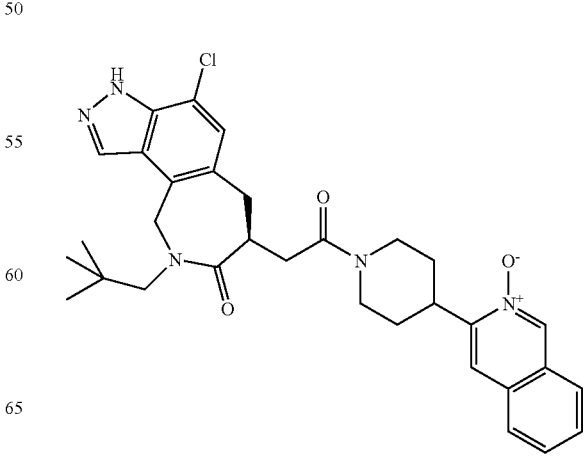

(S)-1-[[(7S)-4-chloro-9-(2,2-dimethylpropyl)-3,6,7,8,9,10-hexahydro-8-oxoazepino[3,4-e]indazol-7-yl]acetyl]-4-(2-oxido-3-isoquinolinyl)-piperidine. Title compound was prepared from 3-piperidin-4-ylisoquinoline hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as light brown solid. MS (ESI) 574(M+H); $R_f$=2.39(3 min gradient run).

EXAMPLE 82

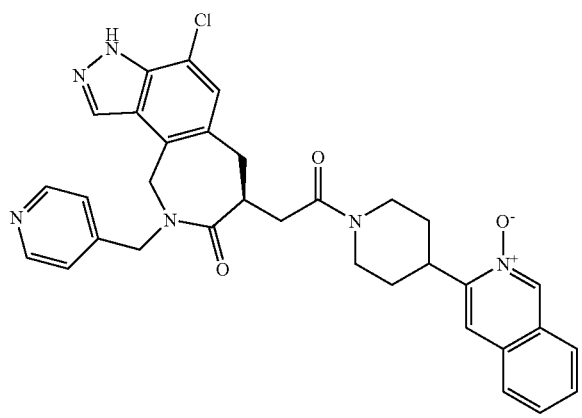

(S)-1-[[(7S)-4-chloro-3,6,7,8,9,10-hexahydro-8-oxo-9-(4-pyridinylmethyl)azepino[3,4-e]indazol-7-yl]acetyl]-4-(2-oxido-3-isoquinolinyl)-piperidine. Title compound was prepared from 3-piperidin-4-ylisoquinoline hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid. MS (ESI) 595(M+H); $R_f$=1.73(3 min gradient run).

EXAMPLE 83

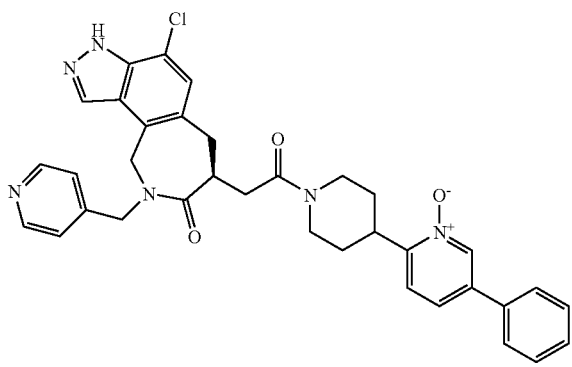

(S)-1-[[(7S)-4-chloro-3,6,7,8,9,10-hexahydro-8-oxo-9-(4-pyridinylmethyl)azepino[3,4-e]indazol-7-yl]acetyl]-4-(1-oxido-5-phenyl-2-pyridinyl)-piperidine. Title compound was prepared from 5-phenyl-2-piperidin-4-ylpyridine 1-oxide hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid. MS (ESI) 621(M+H); $R_f$=1.87(3 min gradient run).

EXAMPLE 84

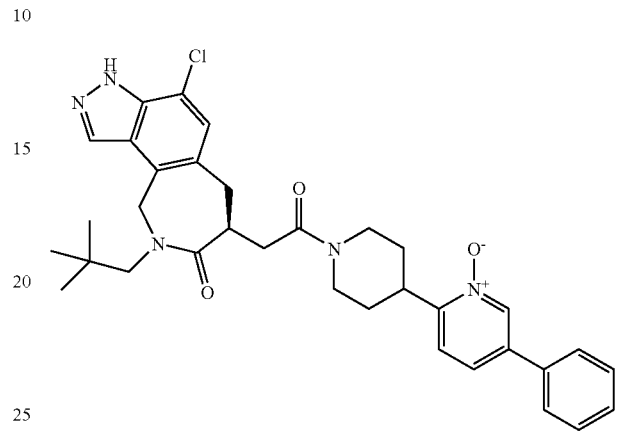

(S)-1-[[(7S)-4-chloro-9-(2,2-dimethylpropyl)-3,6,7,8,9,10-hexahydro-8-oxoazepino[3,4-e]indazol-7-yl]acetyl]-4-(1-oxido-5-phenyl-2-pyridinyl)-piperidine. Title compound was prepared from 2-(piperidin-4-yl)-1,2-dihydroisoquinolin-3(4H)-one hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as white solid. MS (ESI) 600(M+H); $R_f$=2.51(3 min gradient run).

EXAMPLE 85

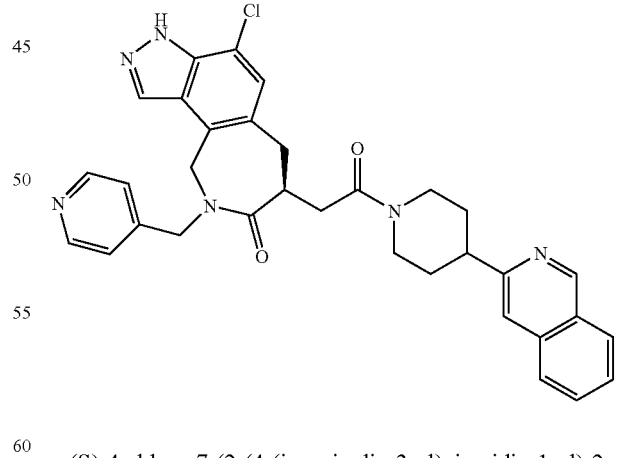

(S)-4-chloro-7-(2-(4-(isoquinolin-3-yl)piperidin-1-yl)-2-oxoethyl)-9-(pyridin-4-ylmethyl)-6,7,9,10-tetrahydroazepino[3,4-e]indazol-8(3H)-one. Title compound was prepared from 3-(piperidin-4-yl)isoquinoline hydrochloride in a manner analogous to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro- 3H-2,3,9-triaza-cyclohepta[e]inden-8-one. Material was obtained as white solid. MS (ESI) 579(M+H); $R_f$=1.43(3 min gradient run).

EXAMPLE 86

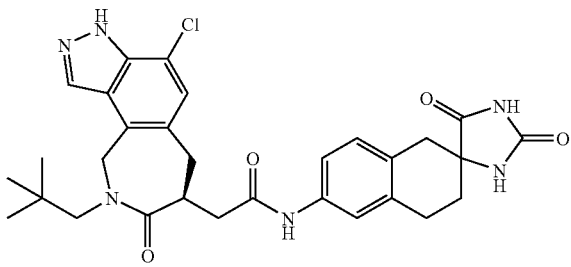

(+/−)-1-[[(7S)-4-chloro-9-(2,2-dimethylpropyl)-3,6,7,8,9,10-hexahydro-8-oxoazepino[3,4-e]indazol-7-yl]acetyl]-Amino-3',4'-dihydro-1'H-spiro[imidazolidine-4,2'-naphthalene]-2,5-dione. Title compound was prepared from (+/−)-6'-Amino-3',4'-dihydro-1'H-spiro[imidazolidine-4,2'-naphthalene]-2,5-dione in a manner analogues to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as a white solid. $^1$H-NMR (CD$_3$OD, 400 MHz) δ 0.78(s, 9H), 1.80-1.89(m, 1H), 2.07-2.15(m, 1H), 2.53(dd, J=15.61, 5.04 Hz, 1H), 2.76 (d, J=16.87 Hz, 1H), 2.92-3.18(m, 8H), 3.62-3.70(m, 1H), 3.90-4.07(m, 1H), 4.64(d, J=17.37 Hz, 1H), 5.47(d, J=17.37 Hz, 1H), 7.02(d, J=8.31 Hz, 1H), 7.21(s, 1H), 7.22-7.30(m, 1H), 7.35-7.45(m 1H), 8.22(d, J=2.52 Hz, 1H); Mass spec. 577.25(MH$^+$), Calc. for C$_{30}$H$_{33}$ClN$_6$O$_4$ 576.23; $R_f$=2.15 (4 min gradient run).

EXAMPLE 87

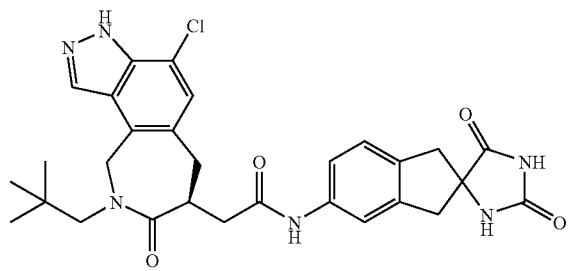

(+/−)-1-[[(7S)-4-chloro-9-(2,2-dimethylpropyl)-3,6,7,8,9,10-hexahydro-8-oxoazepino[3,4-e]indazol-7-yl]acetyl]-Amino-spiro[imidazolidine-4,2'-indane]-2,5-dione. Title compound was prepared from (+/−)-5'-Amino-spiro[imidazolidine-4,2'-indane]-2,5-dione in a manner analogues to the preparation of 4-Chloro-9-(2,2-dimethyl-propyl)-7-(S)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Material was obtained as a white solid. $^1$H-NMR (CD$_3$OD, 400 MHz) δ 0.79(s, 9H), 2.53(dd, J=15.61, 5.04 Hz, 1H), 2.92-3.3(m, 6H), 3.46(dd, J=16.49, 9.44 Hz, 2H), 3.66(d, J=13.60 Hz, 1H), 3.98-4.08(m, 1H), 4.63(d, J=17.37 Hz, 1H), 5.47(d, J=16.87 Hz, 1H), 7.15(d, J=8.06 Hz, 1H), 7.21(s, 1H), 7.25-7.35(m, 1H), 7.50(d, J=16.12 Hz, 1H), 8.23(s, 1H); Mass spec. 563.24(MH$^+$), Calc. for C$_{29}$H$_{31}$ClN$_6$O$_4$ 562.21; $R_f$=2.15(4 min gradient run).

EXAMPLE 88

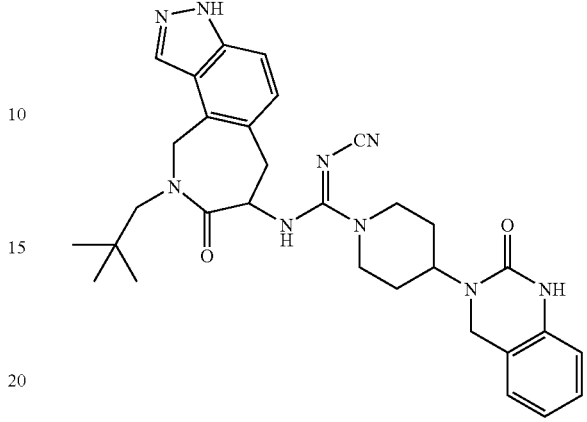

(E,Z)-N'-cyano-N-(9-neopentyl-8-oxo-3,6,7,8,9,10-hexahydroazepino[3,4-e]indazol-7-yl)-4-(2-oxo-1,2-dihydroquinazolin-3(4H)-yl)piperidine-1-carboxamidine. To a solution of 7-amino-9-neopentyl-6,7,9,10-tetrahydroazepino[3,4-e]indazol-8(3H)-one, methanesulfonate (300 mg, 0.78 mmol) in CH$_2$Cl$_2$(20 mL) was added diphenyl N-cyanocarbonimidate (221 mg, 0.93 mmol) followed by triethylamine (1 mL). The reaction mixture was stirred at room temperature for 12 h. The reaction mixture was then washed with aqueous sodium hydrogencarbonate to give (E,Z)-1-cyano-3-(9-neopentyl-8-oxo-3,6,7,8,9,10-hexahydroazepino[3,4-e]indazol-7-yl)-2-phenylisourea in 95% yield. MS (ESI) 431 (M+H); $R_f$=2.22(3 min gradient run).

To a solution of (E,Z)-1-cyano-3-(9-neopentyl-8-oxo-3,6,7,8,9,10-hexahydroazepino[3,4-e]indazol-7-yl)-2-phenylisourea (301 mg, 0.7 mmol) in isopropanol (25 mL) was added 3-(piperidin-4-yl)-3,4-dihydroquinazolin-2(1H)-one (323 mg, 1.4 mmol) and the reaction mixture was refluxed for 72 h. The solvent was evaporated and the crude product was purified by flash chromatography to give (E, Z)-N'-cyano-N-(9-neopentyl-8-oxo-3,6,7,8,9,10-hexahydroazepino[3,4-e]indazol-7-yl)-4-(2-oxo-1,2-dihydroquinazolin-3(4H)-yl)piperidine-1-carboxamidine (130 mg) in 33% yield. MS (ESI) 568(M+H); $R_f$=2.19(3 min gradient run).

EXAMPLE 89

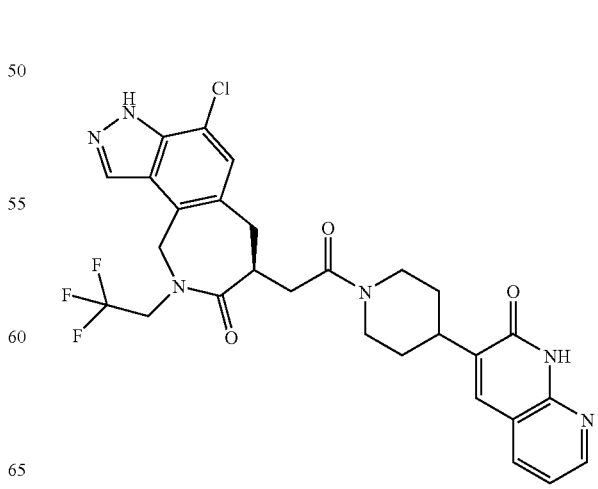

(S)-4-chloro-7-(2-oxo-2-(4-(2-oxo-1,2-dihydro-1,8-naphthyridin-3-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (120 mg, 0.32 mmol) and 3-(piperidin-4-yl)-3,4-dihydropyrido[2,3-d]pyrimidin-2(1H)-one dihydrochloride (120 mg, 0.40 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as pale yellow solid in 43% yield. High resolution MS m/e (M+H)$^+$=587.1785.

EXAMPLE 90

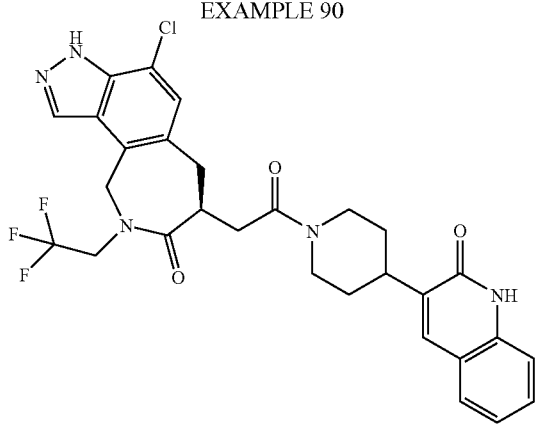

(S)-4-chloro-7-(2-oxo-2-(4-(2-oxo-1,2-dihydroquinolin-3-yl)piperidin-1-yl)ethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (115 mg, 0.31 mmol) and 3-(piperidin-4-yl)quinolin-2(1H)-one hydrochloride (96 mg, 0.36 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 65% yield. High resolution MS m/e (M+H)$^+$=586.1811.

EXAMPLE 91

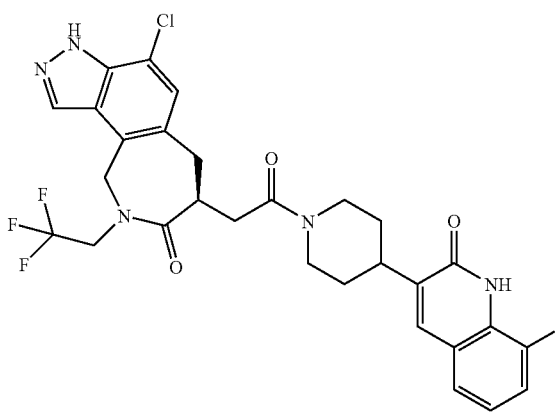

(S)-4-chloro-7-(2-(4-(8-fluoro-2-oxo-1,2-dihydroquinolin-3-yl)piperidin-1-yl)-2-oxoethyl)-9-(2,2,2-trifluoroethyl)-6,7,9,10-tetrahydroazepino[3,4-e]indazol-8(3H)-one. [4-Chloro-3,6,7,8,9,10-hexahydro-8-oxo-9-(2,2,2-trifluoroethyl)-2,3,9-triaza-(S)-cyclohepta[e]inden-7-yl]acetic acid (115 mg, 0.31 mmol) and 8-fluoro-3-(piperidin-4-yl)quinolin-2(1H)-one hydrochloride (96 mg, 0.36 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 55% yield. High resolution MS m/e (M+H)$^+$=604.1760.

EXAMPLE 92

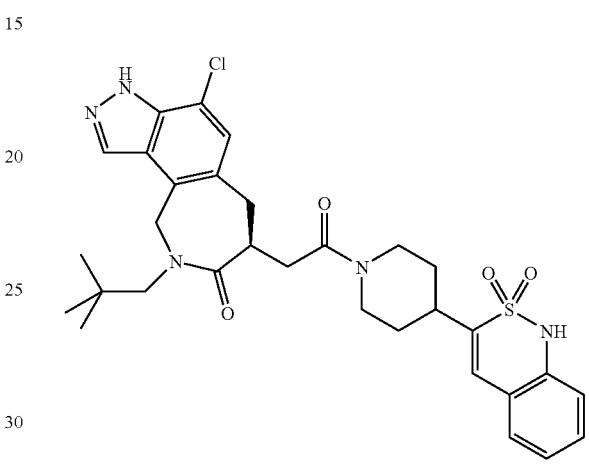

3-Piperidin-4-yl-1H-2,1-benzothiazine 2,2-dioxide p-toluenesulfonate (55 mg, 0.13 mmol) and [4-chloro-9-(2,2-dimethyl-propyl)-8-oxo-3,6,7,8,9,10-hexahydro-2,3,9-triaza-(S)-cyclohepta[e]inden-7-yl]acetic acid (40 mg, 0.11 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as tan solid in 57% yield. High resolution MS m/e (M+H)$^+$=610.2268.

EXAMPLE 93

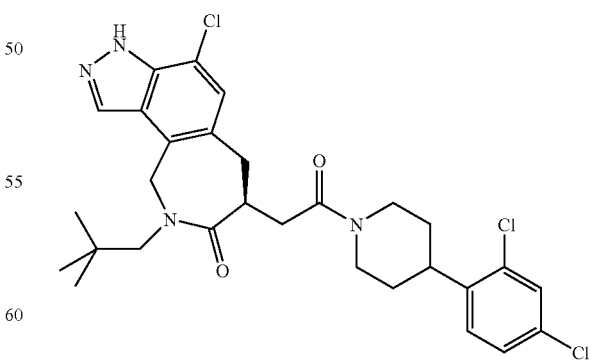

(S)-4-chloro-7-(2-(4-(2,4-dichlorophenyl)piperidin-1-yl)-2-oxoethyl)-9-neopentyl-6,7,9,10-tetrahydroazepino[3,4-e]indazol-8(3H)-one. 4-(2,4-Dichlorophenyl)-piperidine (32 mg, 0.0.8 mmol) and [4-chloro-9-(2,2-dimethyl-propyl)-8- oxo-3,6,7,8,9,10-hexahydro-2,3,9-triaza-(S)-cyclohepta[e]inden-7-yl]acetic acid (25 mg, 0.07 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as off-white solid in 40% yield. High resolution MS m/e (M+H)⁺=575.1747.

EXAMPLE 94

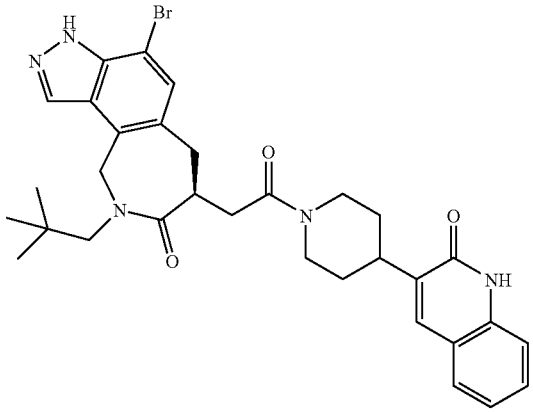

(S)-4-bromo-9-neopentyl-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. [4-Bromo-9-(2,2-dimethyl-propyl)-8-oxo-3,6,7,8,9,10-hexahydro-2,3,9-triaza-(S)-cyclohepta[e]inden-7-yl]-acetic acid (56 mg, 0.14 mmol) and 3-(piperidin-4-yl)quinolin-2(1H)-one hydrochloride (35 mg, 0.15 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 61% yield. High resolution MS m/e (M+H)⁺= 618.2064.

EXAMPLE 95

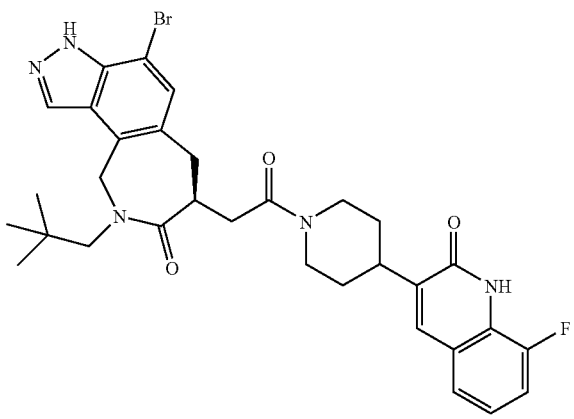

(S)-4-bromo-7-(2-(4-(8-fluoro-2-oxo-1,2-dihydroquinolin-3-yl)piperidin-1-yl)-2-oxoethyl)-9-neopentyl-6,7,9,10-tetrahydroazepino[3,4-e]indazol-8(3H)-one. [4-Bromo-9-(2,2-dimethyl-propyl)-8-oxo-3,6,7,8,9,10-hexahydro-2,3,9-triaza-(S)-cyclohepta[e]inden-7-yl]-acetic acid (65 mg, 0.16 mmol) and 8-fluoro-3-(piperidin-4-yl)quinolin-2(1H)-one hydrochloride (45 mg, 0.16 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 57% yield. High resolution MS m/e (M+H)⁺=636.1973.

EXAMPLE 96

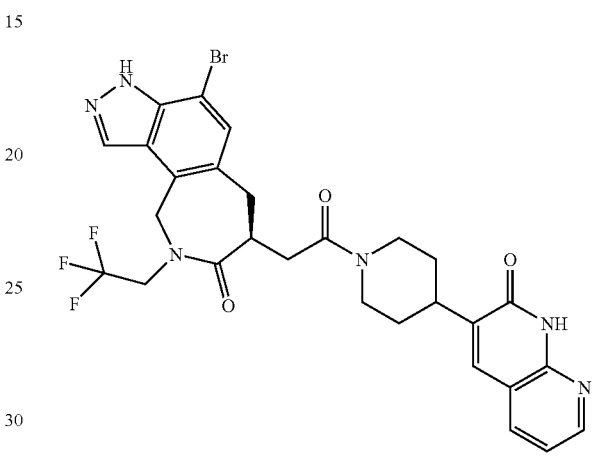

(S)-4-bromo-7-(2-oxo-2-(4-(2-oxo-1,2-dihydro-1,8-naphthyridin-3-yl)piperidin-1-yl)ethyl)-9-(2,2,2-trifluoroethyl)-6,7,9,10-tetrahydroazepino[3,4-e]indazol-8(3H)-one. [4-Bromo-3,6,7,8,9,10-hexahydro-8-oxo-9-(2,2,2-trifluoro-ethyl)-2,3,9-triaza-(S)-cyclohepta[e]inden-7-yl]acetic acid (69 mg, 0.16 mmol) and 3-(piperidin-4-yl)-3,4-dihydropyrido[2,3-d]pyrimidin-2(1H)-one dihydrochloride (120 mg, 0.40 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 55% yield. High resolution MS m/e (M+H)⁺= 631.1279.

EXAMPLE 97

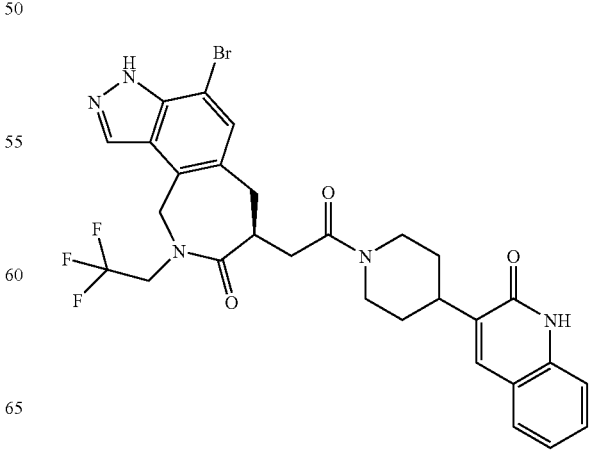

(S)-4-bromo-7-(2-oxo-2-(4-(2-oxo-1,2-dihydroquinolin-3-yl)piperidin-1-yl)ethyl)-9-(2,2,2-trifluoroethyl)-6,7,9,10-tetrahydroazepino[3,4-e]indazol-8(3H)-one. [4-Bromo-3,6,7,8,9,10-hexahydro-8-oxo-9-(2,2,2-trifluoroethyl)-2,3,9-triaza-(S)-cyclohepta[e]inden-7-yl]acetic acid (73 mg, 0.17 mmol) and 3-(piperidin-4-yl)quinolin-2(1H)-one hydrochloride (50 mg, 0.19 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as yellow solid in 62% yield. High resolution MS m/e (M+H)$^+$=630.1315.

EXAMPLE 98

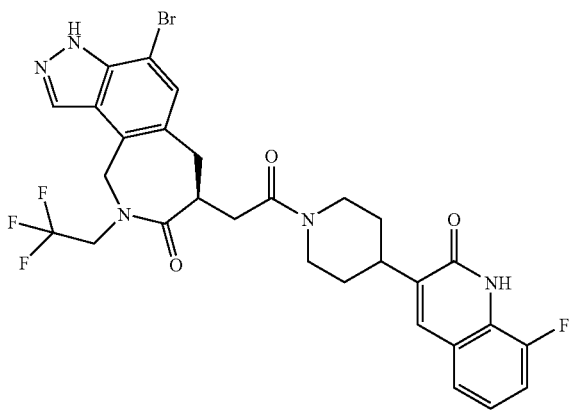

(S)-4-bromo-7-(2-(4-(8-fluoro-2-oxo-1,2-dihydroquinolin-3-yl)piperidin-1-yl)-2-oxoethyl)-9-(2,2,2-trifluoroethyl)-6,7,9,10-tetrahydroazepino[3,4-e]indazol-8(3H)-one. [4-Bromo-3,6,7,8,9,10-hexahydro-8-oxo-9-(2,2,2-trifluoroethyl)-2,3,9-triaza-(S)-cyclohepta[e]inden-7-yl]acetic acid (80 mg, 0.19 mmol) and 8-fluoro-3-(piperidin-4-yl)quinolin-2(1H)-one hydrochloride (61 mg, 0.22 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as off-white solid in 64% yield. High resolution MS m/e (M+H)$^+$=648.1217.

EXAMPLE 99

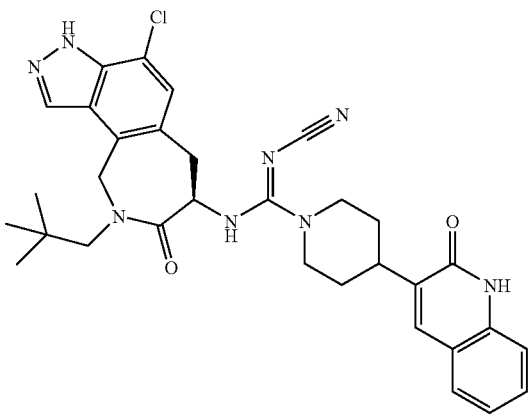

(R)-7-Amino-4-chloro-9-(2,2-dimethyl-propyl)-6,7,9,10-tetrahydro-3H-2,3,9-triaza-cyclohept[e]inden-8-one (108 mg, 0.34 mmol) was dissolved in N,N-dimethylformamide (1.8 mL). N,N-Diisopropylethylamine (200 µL, 1.1 mmol) was added to the mixture followed by diphenyl cyanocarbonimidate (86 mg, 0.36 mmol). Mixture was held at room temperature with stirring for 1.25 hours. 3-(Piperidin-4-yl)quinolin-2(1H)-one hydrochloride (100 mg, 0.38 mmol) was added to the mixture with N,N-dimethylformamide (2.0 mL). Reaction was warmed to 110° C. and held with stirring for 5.5 hours. Mixture was cooled to 80° C. and held with stirring for 20 hours. Reaction was quenched with 1:1 acetonitrile:water. Material was purified by preparatory HPLC (C18, acetonitrile-water-ammonium acetate). Major peak was isolated. Acetonitrile was removed from the proper fractions in vacuo. Material was extracted from the remaining aqueous twice with ethyl acetate. Organic phase was dried (magnesium sulfate), filtered and concentrated to dryness. Title compound was obtained as pale yellow solid in 40% yield. High resolution MS m/e (M+H)$^+$=599.2622.

EXAMPLE 100

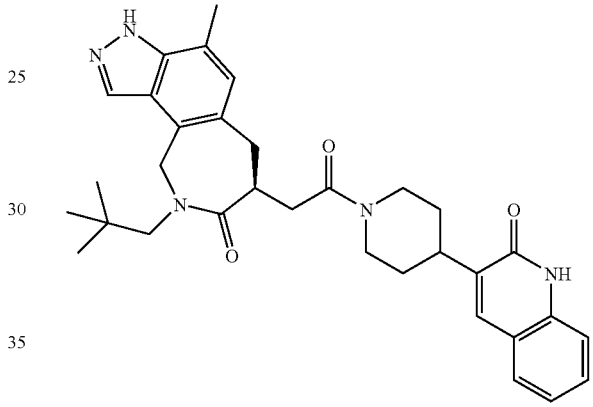

(S)-4-methyl-9-neopentyl-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. [4-Methyl-9-(2,2-dimethyl-propyl)-8-oxo-3,6,7,8,9,10-hexahydro-2,3,9-triaza-(S)-cyclohepta[e]inden-7-yl]-acetic acid (37 mg, 0.11 mmol) and 3-(piperidin-4-yl)quinolin-2(1H)-one hydrochloride (32 mg, 0.12 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 55% yield. High resolution MS m/e (M+H)$^+$= 554.3121.

EXAMPLE 101

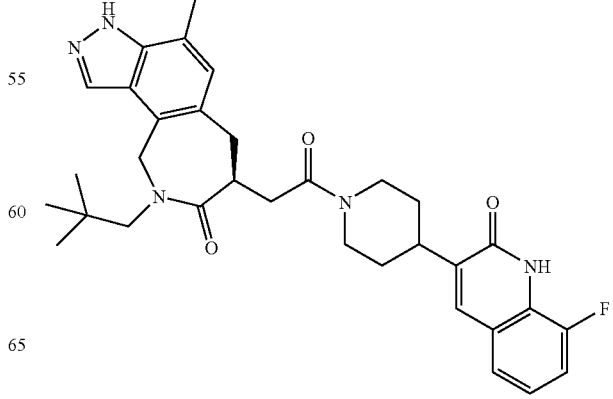

(S)-7-(2-(4-(8-fluoro-2-oxo-1,2-dihydroquinolin-3-yl)piperidin-1-yl)-2-oxoethyl)-4-methyl-9-neopentyl-6,7,9,10-tetrahydroazepino[3,4-e]indazol-8(3H)-one. [4-Methyl-9-(2,2-dimethyl-propyl)-8-oxo-3,6,7,8,9,10-hexahydro-2,3,9-triaza-(S)-cyclohepta[e]inden-7-yl]-acetic acid (60 mg, 0.18 mmol) and 8-fluoro-3-(piperidin-4-yl)quinolin-2(1H)-one hydrochloride (60 mg, 0.21 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 48% yield. High resolution MS m/e (M+H)$^+$=572.3021.

EXAMPLE 102

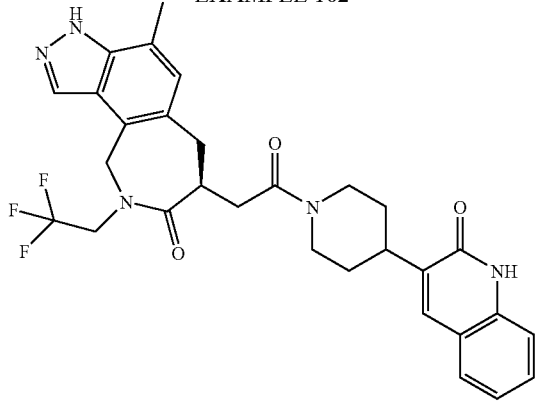

(S)-4-methyl-7-(2-oxo-2-(4-(2-oxo-1,2-dihydroquinolin-3-yl)piperidin-1-yl)ethyl)-9-(2,2,2-trifluoroethyl)-6,7,9,10-tetrahydroazepino[3,4-e]indazol-8(3H)-one. [4-Methyl-3,6,7,8,9,10-hexahydro-8-oxo-9-(2,2,2-trifluoroethyl)-2,3,9-triaza-(S)-cyclohepta[e]inden-7-yl]acetic acid (65 mg, 0.18 mmol) and 3-(piperidin-4-yl)quinolin-2(1H)-one hydrochloride (55 mg, 0.21 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 58% yield. High resolution MS m/e (M+H)$^+$=566.2364

EXAMPLE 103

(S)-7-(2-(4-(8-fluoro-2-oxo-1,2-dihydroquinolin-3-yl)piperidin-1-yl)-2-oxoethyl)-4-methyl-9-(2,2,2-trifluoroethyl)-6,7,9,10-tetrahydroazepino[3,4-e]indazol-8(3H)-one.

[4-Methyl-3,6,7,8,9,10-hexahydro-8-oxo-9-(2,2,2-trifluoroethyl)-2,3,9-triaza-(S)-cyclohepta[e]inden-7-yl]acetic acid (65 mg, 0.18 mmol) and 8-fluoro-3-(piperidin-4-yl)quinolin-2(1H)-one hydrochloride (62 mg, 0.22 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 53% yield. High resolution MS m/e (M+H)$^+$=584.2302.

EXAMPLE 104

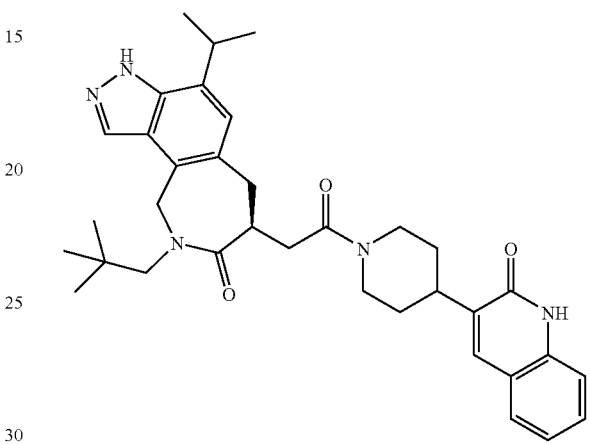

(S)-4-isopropyl-9-neopentyl-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. [4-Isopropyl-9-(2,2-dimethyl-propyl)-8-oxo-3,6,7,8,9,10-hexahydro-2,3,9-triaza-(S)-cyclohepta[e]inden-7-yl]-acetic acid (42 mg, 0.11 mmol) and 3-(piperidin-4-yl)quinolin-2(1H)-one hydrochloride (36 mg, 0.14 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 33% yield. High resolution MS m/e (M+H)$^+$=582.3466.

EXAMPLE 105

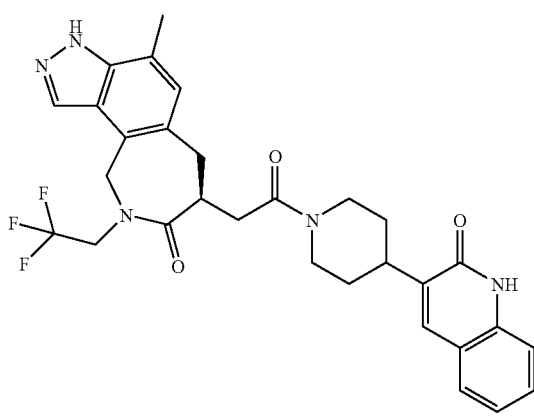

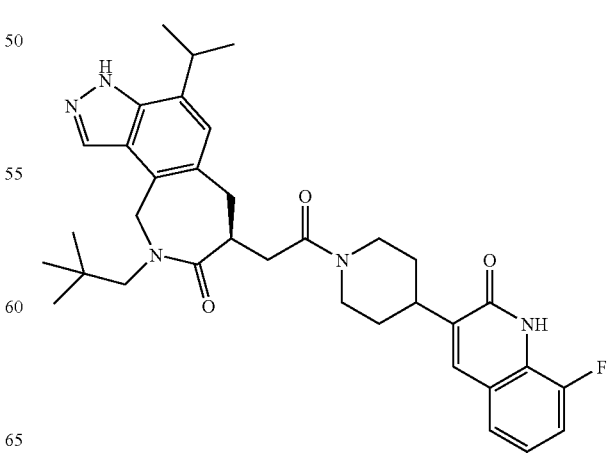

(S)-7-(2-(4-(8-fluoro-2-oxo-1,2-dihydroquinolin-3-yl)piperidin-1-yl)-2-oxoethyl)-4-isopropyl-9-neopentyl-6,7,9,10-tetrahydroazepino[3,4-e]indazol-8(3H)-one. [4-Isopropyl-9-(2,2-dimethyl-propyl)-8-oxo-3,6,7,8,9,10-hexahydro-2,3,9-triaza-(S)-cyclohepta[e]inden-7-yl]-acetic acid (80 mg, 0.22 mmol) and 8-fluoro-3-(piperidin-4-yl)quinolin-2(1H)-one hydrochloride (70 mg, 0.25 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 60% yield. High resolution MS m/e (M+H)$^+$=600.3372.

EXAMPLE 106

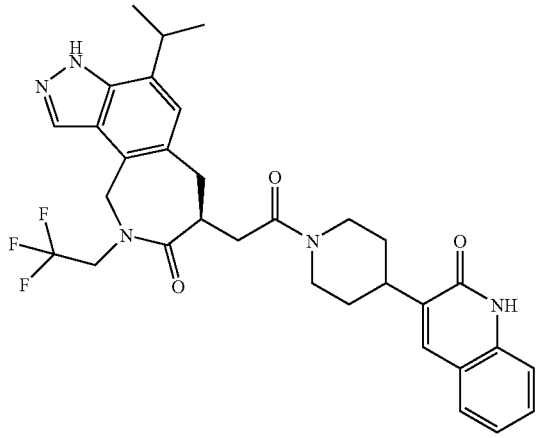

(S)-4-isopropyl-7-(2-oxo-2-(4-(2-oxo-1,2-dihydroquinolin-3-yl)piperidin-1-yl)ethyl)-9-(2,2,2-trifluoroethyl)-6,7,9,10-tetrahydroazepino[3,4-e]indazol-8(3H)-one. [4-Isopropyl-3,6,7,8,9,10-hexahydro-8-oxo-9-(2,2,2-trifluoroethyl)-2,3,9-triaza-(S)-cyclohepta[e]inden-7-yl]acetic acid (50 mg, 0.13 mmol) and 3-(piperidin-4-yl)quinolin-2(1H)-one hydrochloride (41 mg, 0.15 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 62% yield. High resolution MS m/e (M+H)$^+$=594.2682.

EXAMPLE 107

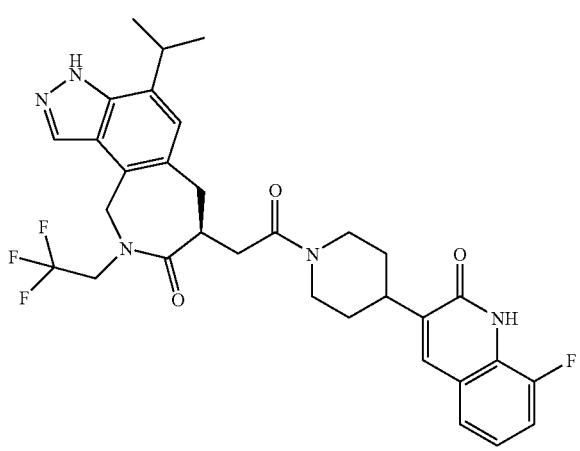

(S)-7-(2-(4-(8-fluoro-2-oxo-1,2-dihydroquinolin-3-yl)piperidin-1-yl)-2-oxoethyl)-4-isopropyl-9-(2,2,2-trifluoroethyl)-6,7,9,10-tetrahydroazepino[3,4-e]indazol-8(3H)-one. [4-Isopropyl-3,6,7,8,9,10-hexahydro-8-oxo-9-(2,2,2-trifluoroethyl)-2,3,9-triaza-(S)-cyclohepta[e]inden-7-yl]acetic acid (50 mg, 0.13 mmol) and 8-fluoro-3-(piperidin-4-yl)quinolin-2(1H)-one hydrochloride (43 mg, 0.15 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 66% yield. High resolution MS m/e (M+H)$^+$=612.2578.

EXAMPLE 108

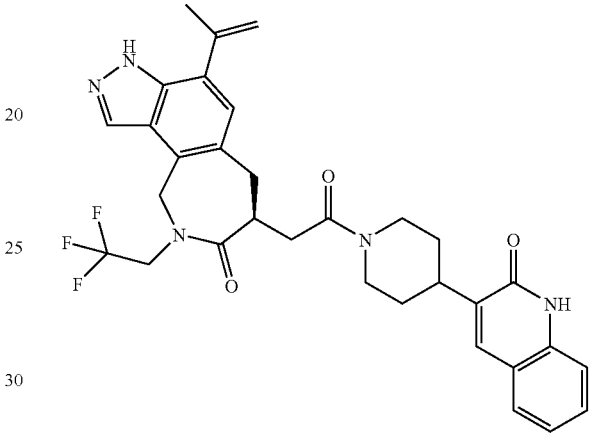

(S)-7-(2-oxo-2-(4-(2-oxo-1,2-dihydroquinolin-3-yl)piperidin-1-yl)ethyl)-4-(prop-1-en-2-yl)-9-(2,2,2-trifluoroethyl)-6,7,9,10-tetrahydroazepino[3,4-e]indazol-8(3H)-one. [4-Isopropenyl-3,6,7,8,9,10-hexahydro-8-oxo-9-(2,2,2-trifluoroethyl)-2,3,9-triaza-(S)-cyclohepta[e]inden-7-yl]acetic acid (47 mg, 0.12 mmol) and 3-(piperidin-4-yl)quinolin-2(1H)-one hydrochloride (42 mg, 0.16 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 55% yield. High resolution MS m/e (M+H)$^+$=592.2544.

EXAMPLE 109

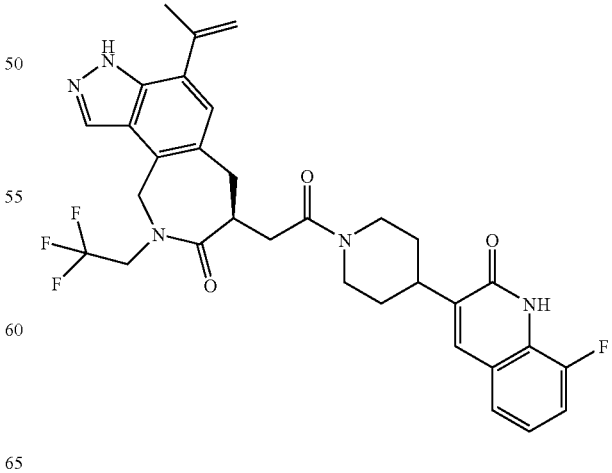

(S)-7-(2-(4-(8-fluoro-2-oxo-1,2-dihydroquinolin-3-yl)piperidin-1-yl)-2-oxoethyl)-4-(prop-1-en-2-yl)-9-(2,2,2-trifluoroethyl)-6,7,9,10-tetrahydroazepino[3,4-e]indazol-8 (3H)-one. [4-Isopropenyl-3,6,7,8,9,10-hexahydro-8-oxo-9-(2,2,2-trifluoroethyl)-2,3,9-triaza-(S)-cyclohepta[e]inden-7-yl]acetic acid (47 mg, 0.12 mmol) and 8-fluoro-3-(piperidin-4-yl)quinolin-2(1H)-one hydrochloride (44 mg, 0.16 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 60% yield. High resolution MS m/e (M+H)⁺=610.2457.

EXAMPLE 110

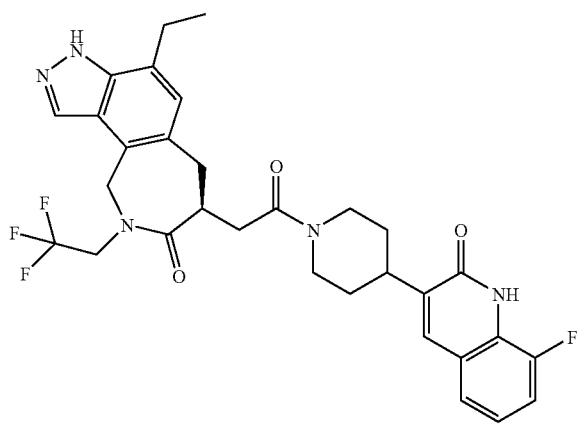

(S)-4-ethyl-7-(2-(4-(8-fluoro-2-oxo-1,2-dihydroquinolin-3-yl)piperidin-1-yl)-2-oxoethyl)-9-(2,2,2-trifluoroethyl)-6,7,9,10-tetrahydroazepino[3,4-e]indazol-8(3H)-one. [4-Ethyl-3,6,7,8,9,10-hexahydro-8-oxo-9-(2,2,2-trifluoroethyl)-2,3,9-triaza-(S)-cyclohepta[e]inden-7-yl]acetic acid (25 mg, 0.07 mmol) and 8-fluoro-3-(piperidin-4-yl)quinolin-2(1H)-one hydrochloride (24 mg, 0.09 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 49% yield. High resolution MS m/e (M+H)⁺=598.2465.

EXAMPLE 111

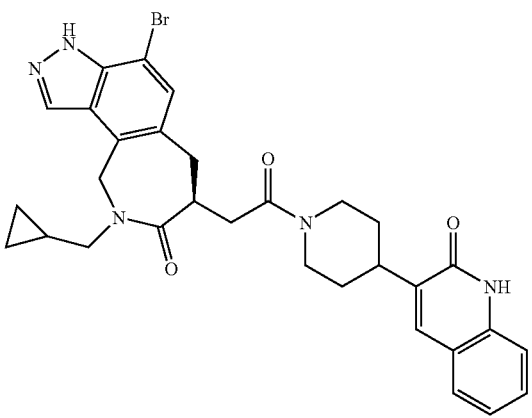

(S)-4-bromo-9-(cyclopropylmethyl)-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. ((S)-4-Bromo-9-cyclopropylmethyl-8-oxo-3,6,7,8,9,10-hexahydro-2,3,9-triaza-cyclohept[e]inden-7-yl)-acetic acid (90 mg, 0.23 mmol) and 3-(piperidin-4-yl)quinolin-2(1H)-one hydrochloride (80 mg, 0.30 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 32% yield. High resolution MS m/e (M+H)⁺=602.1776.

EXAMPLE 112

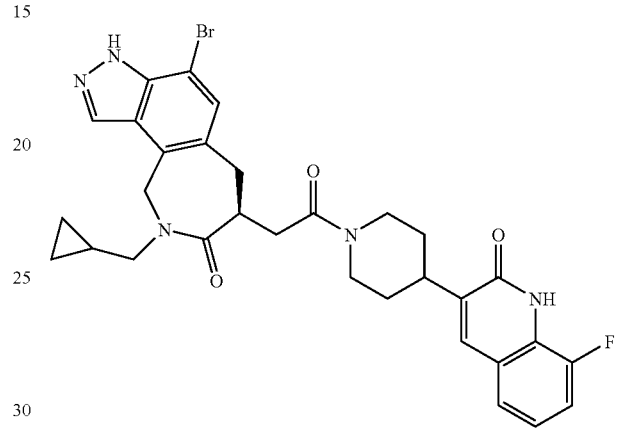

(S)-4-bromo-9-(cyclopropylmethyl)-7-(2-(4-(8-fluoro-2-oxo-1,2-dihydroquinolin-3-yl)piperidin-1-yl)-2-oxoethyl)-6,7,9,10-tetrahydroazepino[3,4-e]indazol-8(3H)-one. ((S)-4-Bromo-9-cyclopropylmethyl-8-oxo-3,6,7,8,9,10-hexahydro-2,3,9-triaza-cyclohept[e]inden-7-yl)-acetic acid (90 mg, 0.23 mmol) and 8-fluoro-3-(piperidin-4-yl)quinolin-2(1H)-one hydrochloride (80 mg, 0.28 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 56% yield. High resolution MS m/e (M+H)⁺=620.1665.

EXAMPLE 113

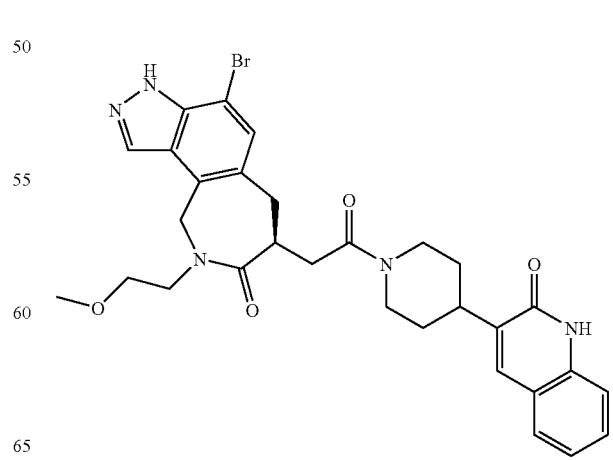

(S)-4-bromo-9-(2-methoxyethyl)-7-(2-oxo-2-(4-(2-oxo-1,2-dihydroquinolin-3-yl)piperidin-1-yl)ethyl)-6,7,9,10-tetrahydroazepino[3,4-e]indazol-8(3H)-one. [(S)-4-Bromo-9-(2-methoxy-ethyl)-8-oxo-3,6,7,8,9,10-hexahydro-2,3,9-triaza-cyclohept[e]inden-7-yl]-acetic acid (100 mg, 0.25 mmol) and 3-(piperidin-4-yl)quinolin-2(1H)-one hydrochloride (80 mg, 0.30 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 35% yield. High resolution MS m/e (M+H)$^+$=606.1730.

EXAMPLE 114

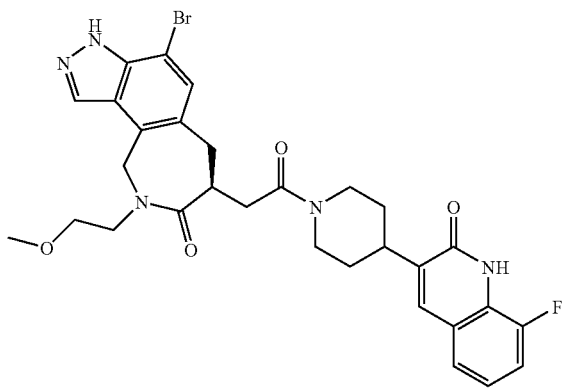

(S)-4-bromo-7-(2-(4-(8-fluoro-2-oxo-1,2-dihydroquinolin-3-yl)piperidin-1-yl)-2-oxoethyl)-9-(2-methoxyethyl)-6,7,9,10-tetrahydroazepino[3,4-e]indazol-8(3H)-one. [(S)-4-Bromo-9-(2-methoxy-ethyl)-8-oxo-3,6,7,8,9,10-hexahydro-2,3,9-triaza-cyclohept[e]inden-7-yl]-acetic acid (100 mg, 0.25 mmol) and 8-fluoro-3-(piperidin-4-yl)quinolin-2(1H)-one hydrochloride (85 mg, 0.30 mmol) were combined in a manner analogous to the preparation of 4-Chloro-9-(2,2-dimethyl-propyl)-7-(R)-{2-oxo-2-[4-(2-oxo-1,4-dihydro-2H-quinazolin-3-yl)-piperidin-1-yl]-ethyl}-6,7,9,10-tetrahydro-3H-2,3,9-triaza-cyclohepta[e]inden-8-one. Title compound was obtained as white solid in 56% yield. High resolution MS m/e (M+H)$^+$=624.1631.

EXAMPLE 115

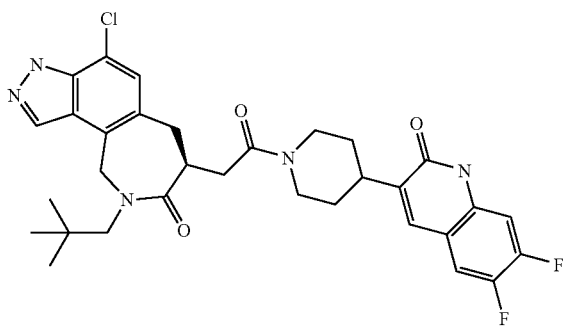

$^1$H NMR (400 MHz, MeOD) δ ppm 0.79(s, 9H), 1.45-1.52 (m, 2H), 1.83-2.02(m, 2H), 2.37-2.42(m, 1H), 2.68-2.76(m, 1H), 3.04-3.17(m, 4H), 3.64-3.68(m, 2H), 3.92-4.06(m, 1H), 4.18-4.25(m, 1H), 4.63-4.74(m, 3H), 5.46-5.54(m, 1H), 7.23 (s, 1H), 7.12-7.23(m, 1H), 7.53-7.59(m, 1H), 7.75(s, 1H), 8.23(s, 1H); Mass spec. 610.25(MH$^+$), Calc. for $C_{32}H_{34}ClF_2N_5O_3$ 609.23.

EXAMPLE 116

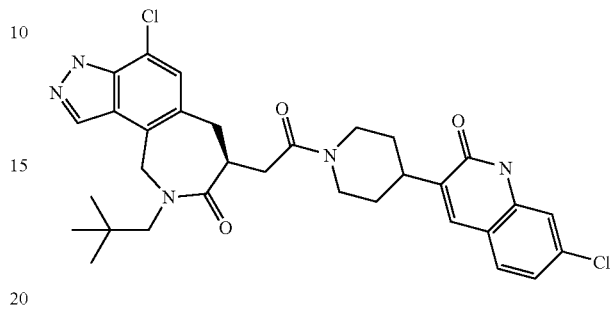

$^1$H NMR (400 MHz, MeOD) δ ppm 0.80(s, 9H), 1.47-1.60 (m, 2H), 1.75-1.80(m, 1H), 1.88-2.03(m, 2H), 2.32-2.48(m, 1H), 2.68-2.78(m, 1H), 3.07-3.18 (m, 4H), 3.66-3.68(m, 1H), 3.96-4.05(m, 1H), 4.13-4.24(m, 1H), 4.53(s, 2H), 4.62-4.72 (m, 2H), 5.45-5.60(m, 1H), 7.17-7.24(m, 1H), 7.33(s, 1H), 7.61(d, J=8.31 Hz, 1H), 7.75(d, J=14.86 Hz, 1H), 8.23(s, 1H); Mass spec. 608.23(MH$^+$), Calc. for $C_{32}H_{35}Cl_2N_5O_3$ 607.21.

EXAMPLE 117

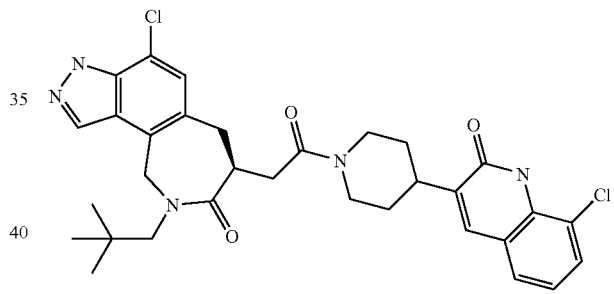

$^1$H NMR (400 MHz, MeOD) δ ppm 0.79(s, 9H), 1.46-1.70 (m, 2H), 1.73-1.85(m, 1H), 1.90-2.08(m, 2H), 2.36-2.51(m, 1H), 2.73-2.81(m, 1H), 2.97-2.06(s, 1H), 3.09-3.20(m, 4H), 3.60-3.68(m, 1H), 3.95-4.08(s, 1H), 4.21-4.27(m, 1H), 4.66-4.73(m, 2H), 5.46-5.54(m, 1H), 7.15-7.23(m, 2H), 7.55-7.62 (m, 2H), 7.79(d, J=15.86 Hz, 1H), 8.23(s, 1H); Mass spec. 608.26(MH$^+$), Calc. for $C_{32}H_{35}Cl_2N_5O_3$ 607.21.

EXAMPLE 118

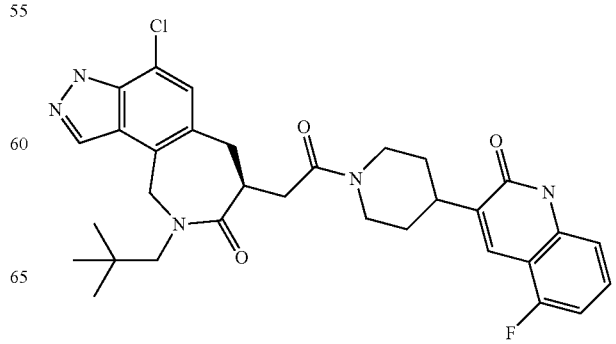

¹H NMR (400 MHz, MeOD) δ ppm 0.80(s, 9H), 1.46-1.56 (m, 1H), 1.57-1.74(m, 1H), 1.80-2.08(m, 2H), 2.35-2.50(m, 1H), 2.69-2.80(m, 1H), 2.89-3.04 (m, 1H), 3.09-3.20(m, 4H), 3.63(dd, J=19.14, 13.85 Hz, 1H), 3.95-4.07(m, 1H), 4.20-4.32(m, 1H), 4.60-4.72(m, 3H), 5.47(d, J=19.14 Hz, 1H), 6.88-6.96 (m, 1H), 7.12(t, J=8.94 Hz, 1H), 7.22(s, 1H), 7.39-7.47(m, 1H), 7.88(d, J=21.66 Hz, 1H), 8.23(s, 1H); Mass spec. 592.28(MH⁺), Calc. for $C_{32}H_{35}ClFN_5O_3$ 591.24.

EXAMPLE 119

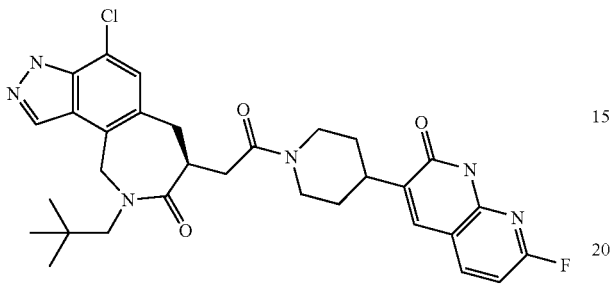

¹H NMR (400 MHz, MeOD) δ ppm 0.79(s, 9H), 1.45-1.66 (m, 2H), 1.70-1.83(m, 1H), 1.90-2.07(m, 2H), 2.38-2.50(m, 1H), 2.69-2.80(m, 1H), 2.92-3.18(m, 4H), 3.60-3.69(m, 1H), 3.95-4.07(m, 1H), 4.18-4.32(m, 1H), 4.56-4.69(m, 3H), 5.43-5.58(m, 1H), 6.41(s, 1H), 7.23(s, 1H), 7.64-7.70(m, 1H), 7.80-7.84(m, 1H), 8.23(s, 1H); Mass spec. 593.25(MH⁺), Calc. for $C_{31}H_{34}ClFN_6O_3$ 592.24.

EXAMPLE 120

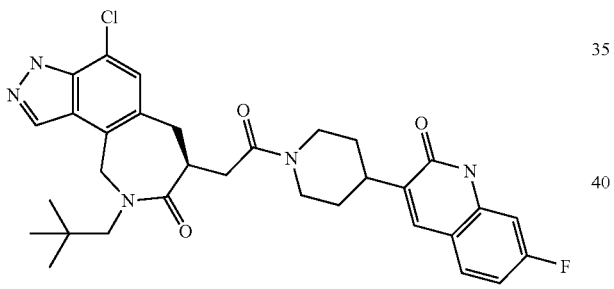

¹H NMR (400 MHz, MeOD) δ ppm 0.79(s, 9H), 1.45-1.68 (m, 2H), 1.71-1.82(m, 1H), 1.90-2.07(m, 2H), 2.37-2.49(m, 1H), 2.68-2.79(m, 1H), 2.92-3.18(m, 4H), 3.59-3.68(m, 1H), 3.94-4.06(m, 1H), 4.17-4.30(m, 1H), 4.55-4.68(m, 3H), 5.43-5.58(m, 1H) 6.95-7.04(m, 2H) 7.22(s, 1H) 7.61-7.68(m, 1H) 7.75(d, J=14.60 Hz, 1H) 8.23(s, 1H); Mass spec. 592.28 (MH⁺), Calc. for $C_{32}H_{35}ClFN_5O_3$ 592.24.

What is claimed is:

1. A compound of Formula I

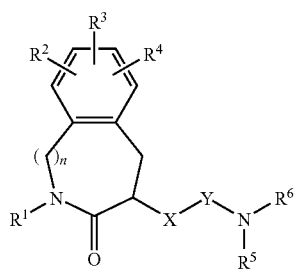

I wherein:

R¹ is $C_{1-6}$alkyl, $C_{2-6}$alkenyl, $C_{3-7}$cycloalkyl, $C_{5-7}$cycloalkenyl, $(C_{3-7}$cycloalkyl$)C_{1-6}$alkyl, $C_{1-6}$haloalkyl, $(C_{1-6}$alkoxy$)C_{1-6}$alkyl, $(Ar^1)C_{1-6}$alkyl, $(NR^7R^8)C_{1-6}$alkyl, N—(R⁹)-pyrrolidinyl or N—(R⁹)-piperidinyl;

R² is hydrogen, halo, hydroxy, $C_{1-6}$alkyl, $C_{2-6}$alkenyl, benzyloxy, or $NR^7R^8$;

R³ is hydrogen, hydroxy, halo, $C_{1-6}$alkyl, or $C_{2-6}$alkenyl;

R⁴ is hydrogen, halo or $C_{1-6}$alkyl, or $C_{2-6}$alkenyl;

R⁵ is hydrogen or $C_{1-6}$alkyl;

R⁶ is hydrogen, $C_{1-6}$alkyl,

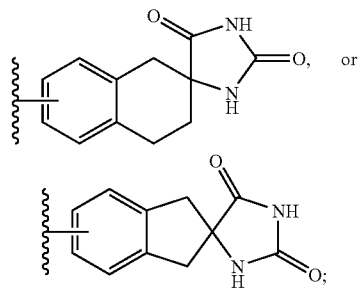

or or $NR^5R^6$ taken together is

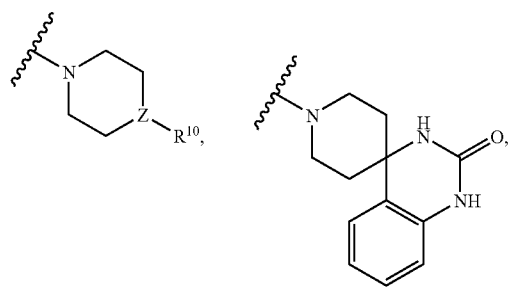

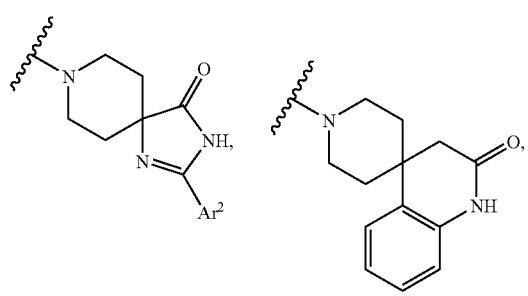

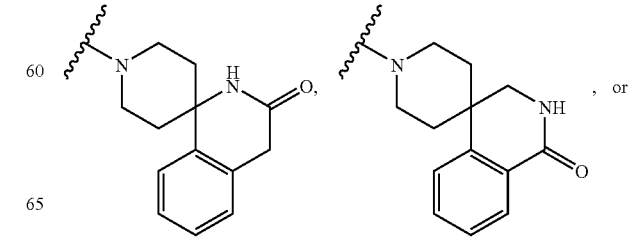

-continued

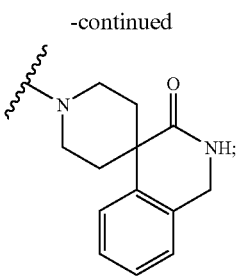

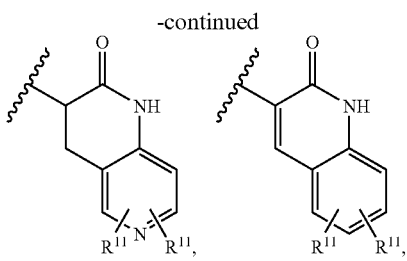

$R^7$ is hydrogen or $C_{1-6}$alkyl;

$R^8$ is hydrogen or $C_{1-6}$alkyl; or $NR^7R^8$ taken together is selected from the group consisting of pyrrolidinyl, piperidinyl, N—($R^9$)-piperazinyl, morpholinyl, and thiomorpholinyl;

$R^9$ is hydrogen, $C_{1-6}$alkyl, $C_{1-6}$alkylcarbonyl, or $C_{1-6}$alkoxycarbonyl;

$R^{10}$ is phenyl, naphthyl, pyridinyl, pyridinyl N-oxide, quinolinyl, quinolinyl N-oxide, isoquinolinyl, or isoquinolinyl N-oxide, and is substituted with 0-2 substituents selected from the group consisting of halo, $C_{1-6}$alkyl, $C_{1-6}$haloalkyl, $C_{1-6}$alkoxy, hydroxy, and phenyl;

or $R^{10}$ is selected from the group consisting of

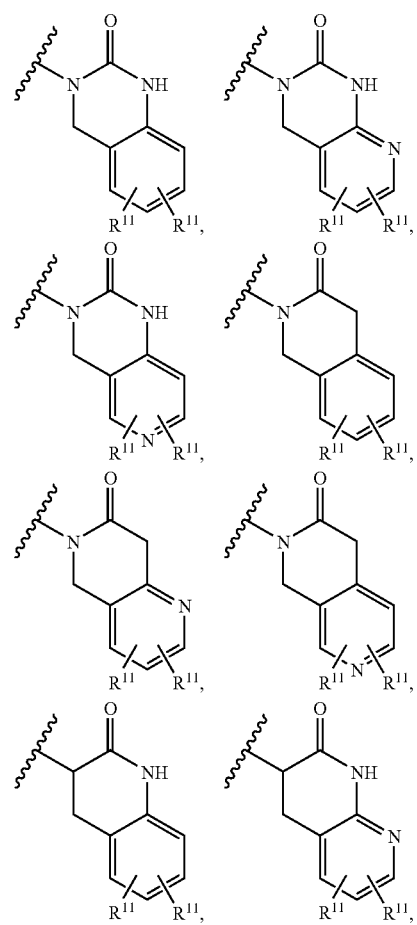

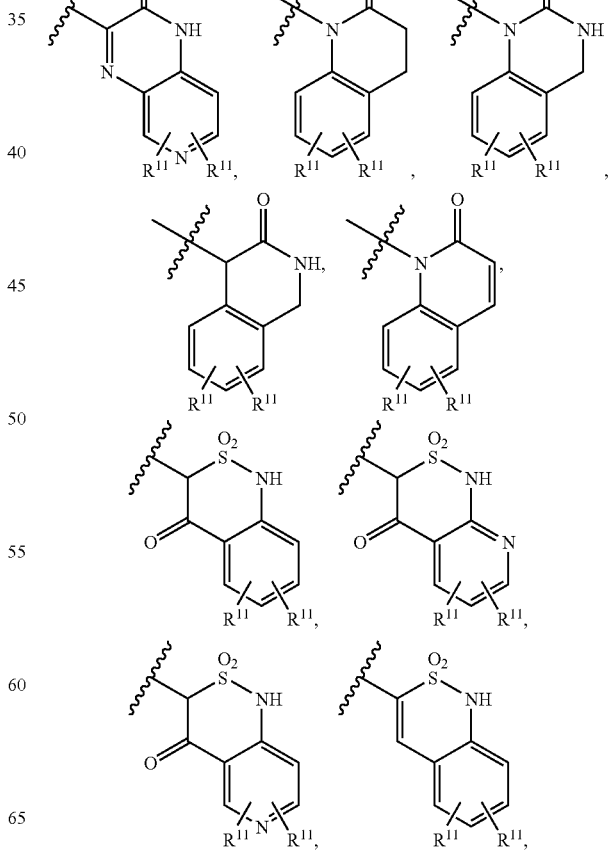

-continued

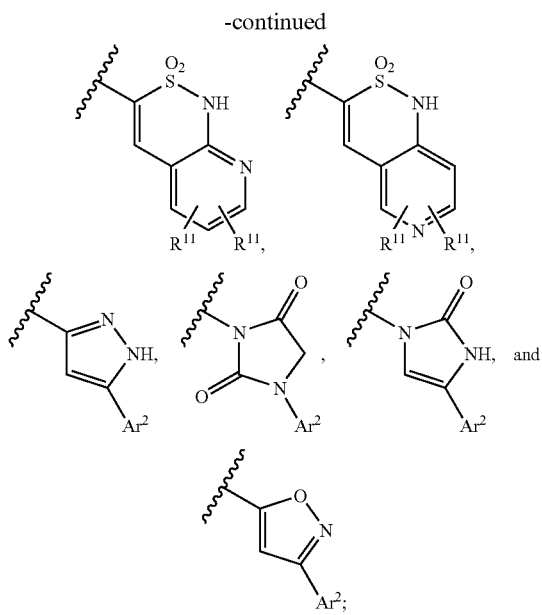

each R[11] is independently hydrogen, halo, $C_{1-6}$alkyl, $C_{1-6}$haloalkyl, or $C_{1-6}$alkoxy;

Ar[1] is phenyl, naphthyl, pyridinyl, or imidazolyl, and is substituted with 0-2 substituents selected from the group consisting of halo, $C_{1-6}$alkyl, and $C_{1-6}$haloalkyl;

Ar[2] is phenyl, naphthyl, or pyridinyl, and is substituted with 0-2 substituents selected from the group consisting of halo, $C_{1-6}$alkyl, and $C_{1-6}$haloalkyl;

X—Y is aminocarbonyl, oxycarbonyl, methylenecarbonyl, ethylene, or amino(cyano)iminomethyl;

Z is N or CH; and n is 1;

or a pharmaceutically acceptable salt thereof.

2. A compound of claim 1 where R[4] is chloro, fluoro, or methyl.

3. A compound of claim 1 where NR[5]R[6] taken together is

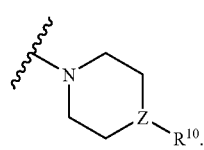

4. A compound of claim 1 where NR[5]R[6] taken together is

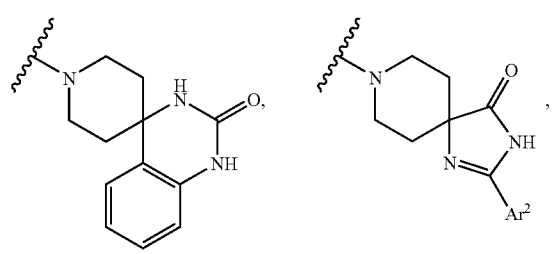

-continued

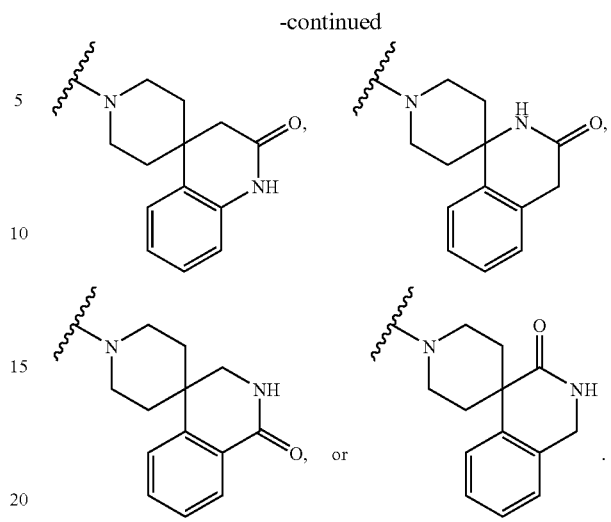

5. A compound of claim 1 where R[10] is selected from the group consisting of

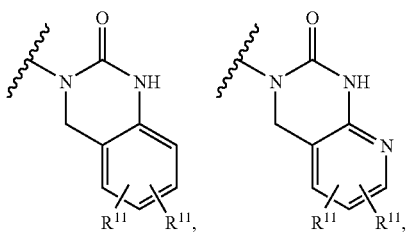

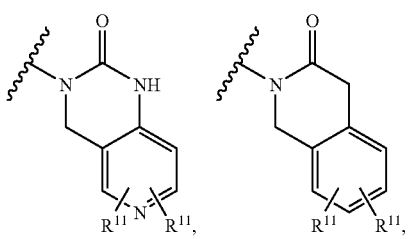

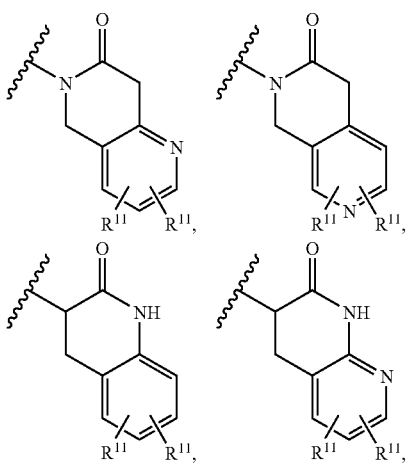

-continued

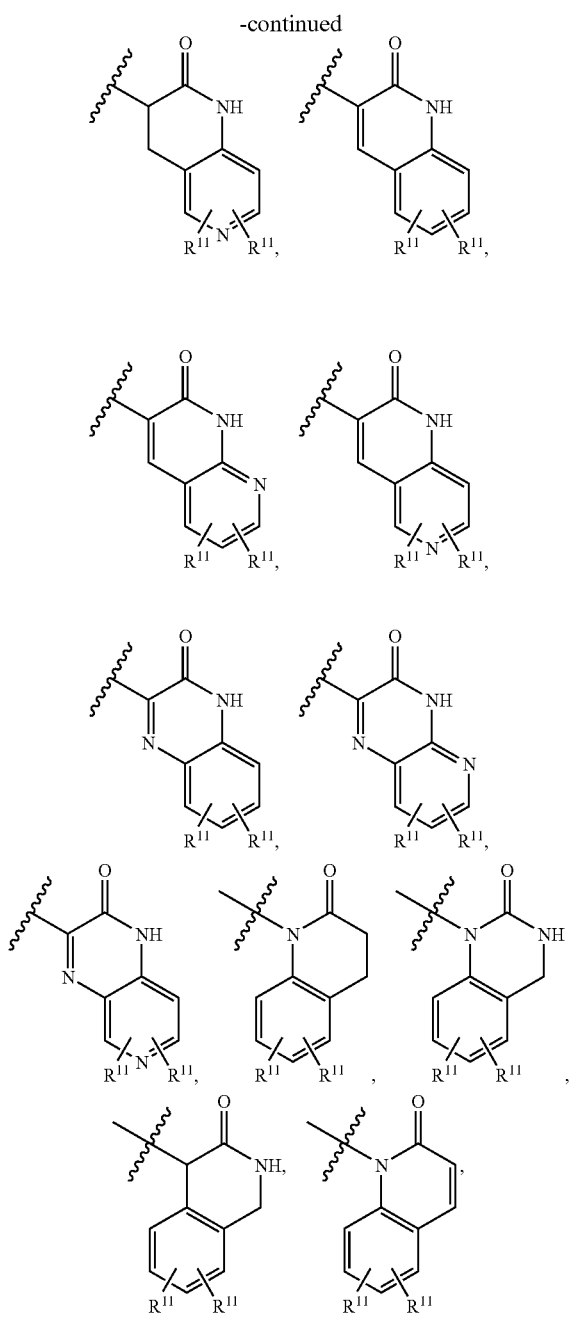

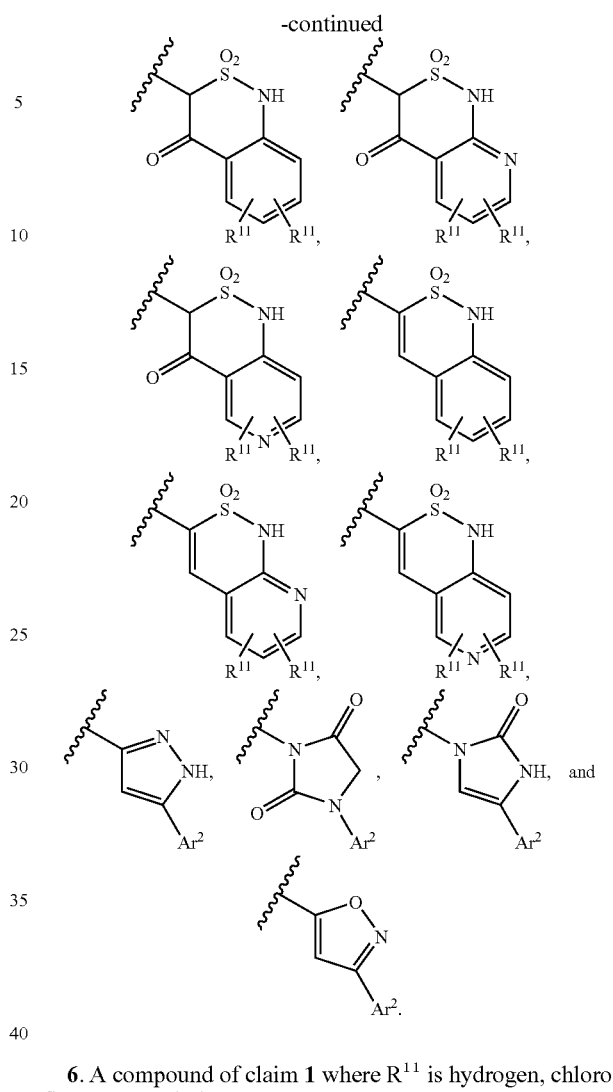

6. A compound of claim 1 where $R^{11}$ is hydrogen, chloro, fluoro, or methyl.

7. A compound of claim 1 where Z is CH.

8. A pharmaceutical composition comprising a compound of claim 1 and a pharmaceutically acceptable adjuvant, carrier, or diluent.

9. A method of treating migraine comprising the administration of a therapeutically effective amount of a compound of claim 1 to a patient.

* * * * *